United States Patent
Holmes et al.

(10) Patent No.: US 11,459,351 B1
(45) Date of Patent: Oct. 4, 2022

(54) COMPOUNDS AND METHODS FOR THE TREATMENT OF OCULAR DISORDERS

(71) Applicant: Azura Ophthalmics Ltd., Tel Aviv (IL)

(72) Inventors: Ian Holmes, Victoria (AU); Yair Alster, Tel Aviv (IL); Hila Barash, Shoham (IL); Charles Bosworth, Las Vegas, NV (US); Omer Rafaeli, Udim (IL); Robert M. Burk, Laguna Beach, CA (US); Marc Gleeson, Longueville (AU); Mark Richard Stewart, Cambridge (GB); Jonathan Dunn, Cambridge (GB); Alexander James Nicholls, Cambridge (GB)

(73) Assignee: AZURA OPHTHALMICS LTD., Tel Aviv (IL)

( * ) Notice: Subject to any disclaimer, the term of this patent is extended or adjusted under 35 U.S.C. 154(b) by 0 days.

(21) Appl. No.: 17/222,802

(22) Filed: Apr. 5, 2021

(51) Int. Cl.
*C07H 17/08* (2006.01)
*A61K 9/00* (2006.01)

(52) U.S. Cl.
CPC ........... *C07H 17/08* (2013.01); *A61K 9/0048* (2013.01)

(58) Field of Classification Search
None
See application file for complete search history.

(56) References Cited

U.S. PATENT DOCUMENTS

| | | |
|---|---|---|
| 5,846,514 A | 12/1998 | Foster et al. |
| 6,239,113 B1 | 5/2001 | Dawson et al. |
| 6,334,997 B1 | 1/2002 | Foster et al. |
| 6,569,443 B1 | 5/2003 | Dawson et al. |
| 7,056,893 B2 | 6/2006 | Roy et al. |
| 7,314,938 B2 | 1/2008 | Shen et al. |
| 7,745,460 B2 | 6/2010 | Shen et al. |
| 7,790,743 B2 | 9/2010 | Shen et al. |
| 7,928,122 B2 | 4/2011 | Shen et al. |
| 8,084,047 B2 | 12/2011 | Shen et al. |
| 8,168,655 B2 | 5/2012 | Gadek et al. |
| 8,357,506 B2 | 1/2013 | Burnet et al. |
| 8,367,701 B2 | 2/2013 | Burnier et al. |
| 8,592,450 B2 | 11/2013 | Gadek et al. |
| 8,927,574 B2 | 1/2015 | Burnier |
| 9,085,553 B2 | 7/2015 | Zeller et al. |
| 9,216,174 B2 | 12/2015 | Shen et al. |
| 9,353,088 B2 | 5/2016 | Burnier |
| 9,447,077 B2 | 9/2016 | Burnier et al. |
| 9,463,201 B2 | 10/2016 | Alster et al. |
| 9,890,141 B2 | 2/2018 | Burnier |
| 10,124,000 B2 | 11/2018 | Shen et al. |
| 10,875,845 B2 | 12/2020 | Holmes et al. |
| 2006/0099660 A1* | 5/2006 | Burnet ............... A61K 47/552 435/7.25 |
| 2009/0075978 A1 | 3/2009 | Haurand et al. |
| 2014/0031387 A1 | 1/2014 | Zeller et al. |
| 2016/0074381 A1 | 3/2016 | Shen et al. |
| 2020/0030268 A1 | 1/2020 | Amselem et al. |

FOREIGN PATENT DOCUMENTS

| | | |
|---|---|---|
| WO | WO-2017182885 A2 | 10/2017 |
| WO | WO-2018161039 A1 | 9/2018 |
| WO | WO-2020212755 A1 | 10/2020 |
| WO | WO-2022084738 A2 | 4/2022 |

OTHER PUBLICATIONS

Barabino et al. Animal Models of Dry Eye: A Critical Assessment of Opportunities and Limitations. Invest. Ophthalmol. Vis. Sci. 45:1641-1646 (2004).
Barabino et al. The Controlled-Environment Chamber: A New Mouse Model of Dry Eye. Invest. Ophthalmol. Vis. Sci. 46:2766-2771 (2005).
Berge et al. Pharmaceutical Salts. Journal of Pharmaceutical Sciences 66(1):1-19 (Jan. 1977).
Co-pending U.S. Appl. No. 17/112,371, inventors Holmes; Ian et al., filed Dec. 4, 2020.
Dursun et al. A Mouse Model of Keratoconjunctivitis Sicca. Invest. Ophthalmol. Vis. Sci. 43:632-638 (2002).
Evans. Synthesis of radiolabeled compounds. J Radioanal Chem 64(1-2):9-32 (1981).
Kabalka et al. The Synthesis of Radiolabeled Compounds via Organometallic Intermediates. Tetrahedron 45(21):6601-6621 (1989).
Knop et al. The International Workshop on Meibomian Gland Dysfunction: Report of the Subcommittee on Anatomy, Physiology, and Pathophysiology of the Meibomian Gland. IOVS 52(4):1938-1978 (2011).
Krauss et al. Improvement of Outcome Measures of Dry Eye by a Novel Integrin Antagonist in the Murine Desiccating Stress Model. Invest. Ophthalmol. Vis. Sci. 56(10):5888-5895 (2015).
Maag. Prodrugs of carboxylic acids. Prodrugs. Springer, New York, NY (pp. 703-729) (2007).
Nichols et al. The International Workshop on Meibomian Gland Dysfunction: Executive Summary. Invest. Ophthalmol. Vis. Sci. 52(4):1922-1929 (2011).
Niederkorn et al. Desiccating Stress Induces T Cell-Mediated Sjögren's Syndrome-like Lacrimal Keratoconjunctivitis. J. Immunol. 176:3950-3957 (2006).
PCT/IB2020/000288 International Search Report and Written Opinion dated Sep. 10, 2020.
PCT/IB2020/000288 Invitation to Pay Additional Fees dated Jul. 16, 2020.

(Continued)

Primary Examiner — Layla D Berry
(74) Attorney, Agent, or Firm — Wilson Sonsini Goodrich & Rosati

(57) ABSTRACT

Described herein are compositions and methods for the treatment or prevention of ocular surface disorders including meibomian gland dysfunction, blepharitis, dry eye disease and other inflammatory and/or infectious diseases of the anterior surface of the eye(s). Said compositions and methods comprise keratolytic conjugates which demonstrate keratolytic activity, and anti-inflammatory or other desirable activities. Topical administration of said compositions to the eyelid margin or surrounding areas provides therapeutic benefit to patients suffering from ocular surface disorders.

16 Claims, No Drawings

(56) References Cited

OTHER PUBLICATIONS

Pflugfelder et al. A Randomized, Double-Masked, Placebo-Controlled, Multicenter Comparison of Loteprednol Etabonate Ophthalmic Suspension, 0.5%, and Placebo for Treatment of Keratoconjunctivitis Sicca in Patients With Delayed Tear Clearance. Am J Ophthalmol 138:444-57 (2004).
Pflugfelder et al. International Dry Eye Workshop, 2007. Management and Therapy of Dry Eye Disease: Report of the Management and Therapy Subcommittee of the International Dry Eye Workshop. Ocul Surf 5:163-178 (2007).
Rautio et al. Prodrugs: design and clinical applications. Nat Rev Drug Discov 7(3):255-270 (2008).
Ravensberg et al. The Effect of a Single Inhaled Dose of a VLA-4 Antagonist on Allergen-Induced Airway Responses and Airway Inflammation in Patients With Asthma. Allergy 61:1097-1103 (2006).
Schaumberg et al. The International Workshop on Meibomian Gland Dysfunction: Report of the Subcommittee on the Epidemiology of, and Associated Risk Factors for, MGD. Invest. Ophthalmol. Vis. Sci. 52(4):1994-2005 (2011).
Blackie et al. Treatment for meibomian gland dysfunction and dry eye symptoms with a single-dose vectored thermal pulsation. Curr Opin Ophthalmol 26(4):306-13 (2015).
Lane et al. A New System, the LipiFlow, for the Treatment of Meibomian Gland Dysfunction. Cornea 31(4):396-404 (2012).
PCT/IB2021/000707 International Search Report and Written Opinion dated May 16, 2022.
Pub Chem SID 244881306 (Mar. 17, 2015).

\* cited by examiner

COMPOUNDS AND METHODS FOR THE TREATMENT OF OCULAR DISORDERS

BACKGROUND OF THE DISCLOSURE

Restasis (0.05% cyclosporine A, Allergan) was approved by the Food and Drug Administration (FDA) to increase tear production in patients whose tear production is presumed to be suppressed due to ocular inflammation associated with keratoconjunctivitis sicca. Xiidra® (lifitegrast ophthalmic solution) 5% is indicated for the treatment of signs and symptoms of dry eye disease (DED).

SUMMARY OF THE DISCLOSURE

Provided in certain embodiments herein are compounds, pharmaceutical (e.g., ophthalmic) compositions, and methods of treatment. In specific embodiments, methods of treatment provided herein include the treatment of ocular and/or periocular indications or abnormalities. In some embodiments, the ocular and/or periocular indications or abnormalities treated by or with a composition or compound provided herein are indications or abnormalities that have multifactorial etiologies and/or interactions. In certain embodiments provided herein are compounds (and compositions comprising such compounds) that have multifunctional efficacies, such as when administered in or around the eye (e.g., to the ocular surface, the eyelid, such as the eyelid margin or the inner surface of the eyelid, or the like).

In some embodiments, provided herein is a method of treating inflammation or hyperkeratosis (e.g., of the eye or skin).

In certain embodiments, methods provided herein involve the method of treating meibomian gland dysfunction (MGD).

Currently there are no approved pharmacological agents useful for the treatment of MGD. The recognition that terminal duct obstruction from hyperkeratinization of the ductal epithelium on meibomian glands is a core mechanism behind meibomian gland dysfunction (MGD) is consistent with clinical experience demonstrating that effective treatments for MGD require resolution of ductal obstruction and evacuation of glandular contents (Nichols et al, 2011; Lane et al, 2012; Blackie et al, 2015). Warm compresses and thermal/mechanical devises (e.g., LipiFlow) are used in an attempt to raise the internal temperature of the meibomian glands over the normal melting point for meibum (i.e., 32° C. to 40° C.) in an attempt to resolve terminal duct obstruction (Lane et al, 2012). Unfortunately, warm compresses are unable to achieve this benefit for severely obstructed glands which can having a melting point>40° C. Current technology for removing keratinized obstruction of the meibomian gland also includes physical removal methods (e.g., debridement and gland probing), which are quite painful to patients.

Subsequent to a period of MGD, various stages of inflammatory or bacterial disease at the ocular surface are frequently observed because meibomian gland obstruction can cause a cascade of events that include further deterioration of the glands (Knop, IOVS, 2011) from stasis of the meibum in the secretory glands, mechanical pressure and stress from glandular obstruction, and increased bacterial growth that is associated with the downstream release of bacterial lipases, toxic mediators, and/or inflammatory mediators. All these factors reduce the quality and/or quantity of meibum the glands can release which in turn can cause chronic mechanical traumatization of the conjunctival, corneal and eyelid tissues which will lead to further tissue damage and the release of inflammatory mediators. Thus, many patients suffering from MGD also have inflammatory disease affecting their conjunctiva, cornea, lacrimal gland, lids or goblet cells causing comorbid conditions such as dry eye syndrome or blepharitis for which there is an unmet medical need.

For example, literature has used the terms posterior blepharitis and MGD as if they were synonymous, but these terms are not interchangeable. Posterior blepharitis describes inflammatory conditions of the posterior lid margin, of which MGD can be one possible cause. In its earliest stages, MGD may not be associated with clinical signs characteristic of posterior blepharitis. At this stage, affected individuals may be symptomatic, but alternatively, they may be asymptomatic and the condition regarded as subclinical. As MGD progresses, symptoms develop and lid margin signs, such as changes in meibum expressibility and quality and lid margin redness, may become more visible. At this point, an MGD-related posterior blepharitis is said to be present.

In certain embodiments, provided herein are methods of treating ocular (or dermatological) disorders associated with keratosis (e.g., lid keratosis, surface ocular keratosis, and/or gland blockage—such as in MGD), microbial infiltration/infection (e.g., bacterial infiltration/infection), and/or inflammation (such as inflammation associated keratosis or not associated with keratosis). In certain instances, disorders of the skin and/or eye (and/or surround tissue/skin) are difficult to differentially diagnose and/or have multiple etiologies. For example, in some instances, it can be difficult to distinguish between ocular disorders that involve (1) inflammation only, (2) inflammation associated with keratolytic activity, (3) inflammation associated with both keratolytic activity (e.g., inducing keratosis) and microbial infiltration, (4) keratolytic activity, but not inflammation and/or microbial infiltration, or various other combinations. In some instances, compounds and compositions provided herein can be used in such ocular and/or dermatological indications without the need for differential diagnosis (which can be difficult, e.g., because of similar symptom scores, etc.). Further, many ocular and/or dermatological disorders involve multiple etiologies, such inflammation, microbial infiltration, keratolytic activity, or various combinations thereof. As a result, therapeutic agents, such as those described herein, that target multiple etiologies are beneficial in providing therapeutic efficacy, such as by targeting both an underlying condition (e.g., keratolytic activity and/or microbial infiltration) and a symptom, such as inflammation or dry eye.

As such, provided herein are compounds, compositions, methods, and formulations for the treatment of ocular (e.g., periocular) or dermatological disorders, such as those having abnormalities having multifactorial etiologies. In specific embodiments, ocular disorders include, by way of non-limiting example, surface disorders, such as MGD, dry eye and associated inflammatory and bacterial disease.

Provided in some embodiments herein is a compound, or a pharmaceutically acceptable salt or solvate thereof, having the structure of Formula (I):

Formula (I)

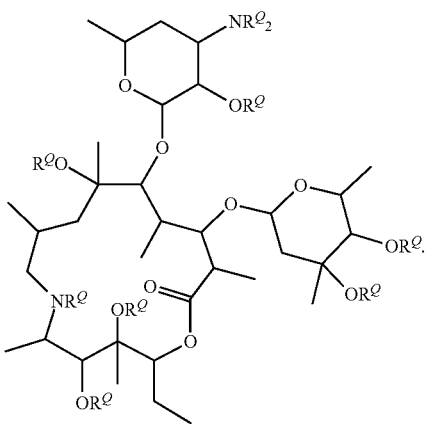

In some embodiments, each $R^Q$ is independently H, $R^N$, substituted or unsubstituted alkyl, or substituted or unsubstituted heteroalkyl, wherein at least one $R^Q$ is $R^N$. In some embodiments, $R^N$ is D-$L^a$-. In some embodiments, D is a keratolytic agent. In some embodiments, $L^a$ is a linker.

In some embodiments, each $R^Q$ is independently H, $R^N$, substituted or unsubstituted alkyl, or substituted or unsubstituted heteroalkyl, wherein one $R^Q$ is $R^N$. In some embodiments, each $R^Q$ is independently H, $R^N$, substituted alkyl, or unsubstituted alkyl. In specific embodiments, at least one $R^Q$ is $R^N$. In some embodiments, each $R^Q$ is independently H, $R^N$, or unsubstituted alkyl, wherein one $R^Q$ is $R^N$. In some embodiments, the unsubstituted alkyl is methyl, ethyl, or propyl. In some embodiments, each $R^Q$ is independently H, $R^N$, or unsubstituted heteroalkyl, wherein one $R^Q$ is $R^N$. In some embodiments, each $R^Q$ is independently H, methyl, or $R^N$, wherein one $R^Q$ is $R^N$.

In some embodiments, alkyl is optionally substituted with one or more selected from the group consisting of —OH, —SH, substituted or unsubstituted alkyl (alkylene), unsubstituted or substituted aryl, substituted or unsubstituted heteroalkyl, —NHCOMe, —O(C=O)CH$_2$OH, —O(C=O)CH(CH$_3$)OH, —O(C=O)alkyl, and —(C=O)Oalkyl (e.g., where alkyl is methyl, ethyl, propyl, isopropyl, or t-butyl). In some embodiments, the alkyl is substituted with one or more selected from the group consisting of alkyl, heterocycloalkyl, —NHCOMe, —O(C=O)alkyl, and —(C=O)Oalkyl (e.g., where alkyl is methyl, ethyl, propyl, isopropyl, or t-butyl). In some embodiments, the heterocycloalkyl is dithiolane oxide.

In some embodiments, provided herein is a compound, or a pharmaceutically acceptable salt thereof, having the structure of Formula (I-A):

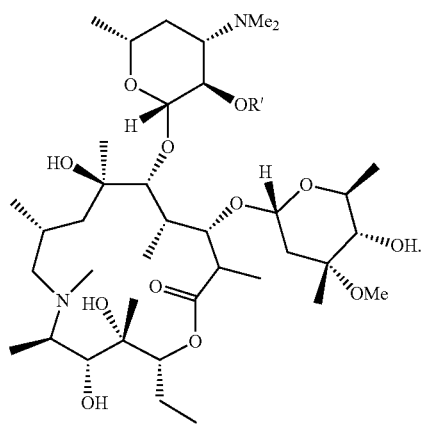

In some embodiments, R' is D-$L^a$-. In some embodiments, D is a keratolytic agent. In some embodiments, $L^a$ is a linker.

In some embodiments, $L^a$ comprises one or more linker groups, each linker group being selected from the group consisting of a bond, —O—, —S—, halo, alkyl (alkylenyl), heteroalkyl (heteroalkylenyl), disulfide, ester, and carbonyl (>C=O). In some embodiments, each linker group is selected from the group consisting of a bond, —O—, —S—, halo, alkyl (alkylenyl), heteroalkyl (heteroalkylenyl), and ester. In some embodiments, $L^a$ comprises one or more linker groups, each linker group being selected from the group consisting of a bond, alkyl (alkylenyl), heteroalkyl (heteroalkylenyl), ester, and carbonyl (>C=O). In some embodiments, each linker group is selected from the group consisting of a bond, halo, alkyl (alkylenyl), heteroalkyl (heteroalkylenyl), and ester. In some embodiments, each linker group is selected from alkyl (alkylene) and heteroalkyl (heteroalkylene), the alkyl (alkylene) or heteroalkyl (heteroalkylene) being optionally substituted.

In some embodiments, $L^a$ is alkyl (alkylene) substituted with oxo and one or more of alkyl and heteroalkyl. In some embodiments, the alkyl or heteroalkyl is substituted with one or more halo, alkyl, or haloalkyl. In some embodiments, the alkyl or heteroalkyl is substituted with one or more alkyl or haloalkyl.

In some embodiments, $L^a$ comprises one or more linker group, each linker group being independently selected from a bond, —O—, —S—, halo, (C=O), —(C=O)alkyl-, —(C=O)heteroalkyl-, —(C=O)O—, —(C=O)Oalkyl-, —(C=O)Oheteroalkyl-, —(C=O)S—, —(C=O)Salkyl-, —(C=O)Sheteroalkyl-, alkylene, or heteroalkylene, where each alkyl, heteroalkyl, alkylene, or heteroalkyl is independently optionally substituted. In some embodiments, $L^a$ comprises (C=O), —(C=O)alkyl-, —(C=O)heteroalkyl-, —(C=O)O—, —(C=O)Oalkyl-, —(C=O)Oheteroalkyl-, —(C=O)OalkylO-, —(C=O)OheteroalkylO-, —(C=O)S—, —(C=O)Salkyl-, —(C=O)Sheteroalkyl-, alkylene, and heteroalkylene. In some embodiments, $L^a$ comprises one or more linker group, each linker group being independently selected from a bond, (C=O), —(C=O)alkyl-, —(C=O)heteroalkyl-, —(C=O)O—, —(C=O)Oalkyl-, —(C=O)Oheteroalkyl-, —(C=O)S—, —(C=O)Salkyl-, —(C=O)Sheteroalkyl-, alkylene, or heteroalkylene, where each alkyl, heteroalkyl, alkylene, or heteroalkyl is independently optionally substituted. In some embodiments, $L^a$ comprises (C=O), —(C=O)alkyl-, —(C=O)heteroalkyl-, —(C=O)O—, —(C=O)Oalkyl-, —(C=O)Oheteroalkyl-, —(C=O)OalkylO-, —(C=O)OheteroalkylO-, —(C=O)S—, —(C=O)Salkyl-, —(C=O)Sheteroalkyl-, alkylene, and heteroalkylene. In some embodiments, L' comprises —O—, (C=O), —(C=O)alkyl-, —(C=O)O—, —(C=O)Oalkyl-, and/or —(C=O)OalkylO-. In some embodiments, L' is a bond.

In some embodiments, the linker comprises the structure of Formula (A):

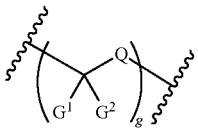

Formula (A)

wherein:

Q is a bond, —O—, —S—, or optionally substituted amino;

each $G^1$ and $G^2$ is independently hydrogen, halo, alkyl, heteroalkyl, or cycloalkyl, wherein the alkyl or cycloalkyl is optionally substituted; and g is 1-20.

In some embodiments, the compound comprises more than one linker of Formula (A). In some embodiments, Q is a bond or —O—. In some embodiments, Q is a bond and each $G^1$ and $G^2$ is independently hydrogen, alkyl, or cycloalkyl, wherein the alkyl or cycloalkyl are each optionally substituted. In some embodiments, Q is —O— and each $G^1$ and $G^2$ is independently hydrogen, alkyl, or cycloalkyl, wherein the alkyl or cycloalkyl are optionally substituted. In some embodiments, Q is a bond or —O— and each $G^1$ is hydrogen and each $G^2$ is independently alkyl or haloalkyl. In some embodiments, Q is a bond or —O— and each $G^1$ is hydrogen and each $G^2$ is methyl. In some embodiments, Q is a bond or —O— and each $G^1$ and $G^2$ is hydrogen. In some embodiments, Q is a bond and each $G^1$ is hydrogen and each $G^2$ is methyl. In some embodiments, Q is a bond and each $G^1$ and $G^2$ is hydrogen. In some embodiments, Q is —O—, each $G^1$ is hydrogen, and each $G^2$ is methyl. In some embodiments, Q is —O— and each $G^1$ and $G^2$ is hydrogen.

In some embodiments, g is 1-20. In some embodiments, g is 1-10. In some embodiments, g is 1-5. In some embodiments, g is 2. In some embodiments, g is 1.

In some embodiments, g is 1 or 2, Q is a bond and each $G^1$ is hydrogen, and each $G^2$ is methyl. In some embodiments, g is 1 or 2, Q is a bond, and each $G^1$ and $G^2$ is hydrogen. In some embodiments, g is 1 or 2, Q is —O—, each $G^1$ is hydrogen, and each $G^2$ is methyl. In some embodiments, g is 1 or 2, Q is —O—, and each $G^1$ and $G^2$ is hydrogen.

In some embodiments, the linker comprises one or more bond, oxo, —O—, methylene,

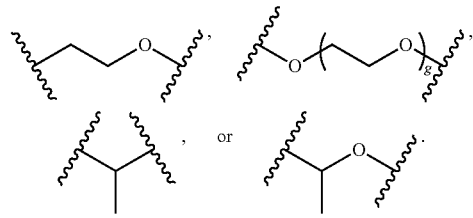

In some embodiments, g is 1-20. In some embodiments, g is 1-10. In some embodiments, g is 1-8. In some embodiments, g is 1, 2, 3, 4, 5, 6, 7, or 8.

In some embodiments, the linker comprises one or more of:

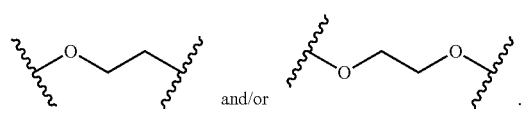 [SMILES: *CCO* ; *OCCO*]

In some embodiments, the linker comprises one or more —O—, oxo, methylene,

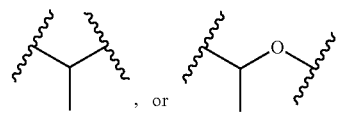

In some embodiments, the linker comprises one or more oxo, one or more —O—, and:

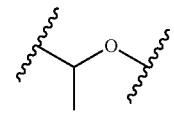

In some embodiments, the linker comprises one or more oxo, one or more —O—, and:

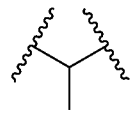

In some embodiments, L is a bond.

In some embodiments, any linker or L provided herein is attached to the rest of a molecule provided herein to form a ketal. In some embodiments, any linker or L provided herein is attached to the rest of a molecule provided herein to form an ester.

In some embodiments, D comprises a radical of one or more keratolytic group (e.g., each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc)).

In some embodiments, D comprises a radical of one or more keratolytic group, each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc).

In some embodiments, D comprises a thiol radical of one or more keratolytic group, each thiol radical of the one or more keratolytic group being independently selected from the group consisting of a thiol radical of thioglycolic acid (TGA), a thiol radical of thiolactic acid (TLac), a thiol radical of dihydrolipoic acid (diHLip), a thiol radical of N-acetyl cysteine (NAC), a thiol radical of cysteine (Cys), a thiol radical of glutathione (GSH), a thiol radical of captopril (Cap), and a thiol radical of bucillamine (Buc).

In some embodiments, the (e.g., thiol) radical of the keratolytic agent comprises a (e.g., thiol) radical of one or more keratolytic group, each (e.g., thiol) radical of the one or more keratolytic group being independently selected from the group consisting of [Lac-Lac]., [Lac-NAC]., [Cys-Cys]., [diHLip-NAC-NAC]., [diHLip-NAC]., [diHLip-Cap-Cap].,

[diHLip-Cap]., [diHLip-Cys-Cys]., [diHLip-Cys]., [diHLip-Lipox-Lipox]., and [diHLip-Lipox]..

In some embodiments, D is substituted (e.g., straight or branched) alkyl, substituted (e.g., straight or branched) heteroalkyl, or substituted heterocycloalkyl (e.g., (N—) substituted with alkyl further substituted with oxo and thiol). In some embodiments, the substituted alkyl is substituted with one or more (alkyl) substituent, at least one (alkyl) substituent being independently selected from the group consisting of —SH, substituted unsaturated cycloalkyl (e.g., being substituted with one or more $C_1$-$C_4$ alkyl), and substituted or unsubstituted disulfide containing heterocycloalkyl (e.g., dithiolane oxide). In some embodiments, the substituted alkyl being substituted with one or more (alkyl) substituent, at least one (alkyl) substituent being independently selected from the group consisting of —SH, substituted unsaturated cycloalkyl (e.g., being substituted with one or more $C_1$-$C_4$ alkyl), and dithiolanyl oxide. In some embodiments, the substituted heteroalkyl being substituted with one or more (heteroalkyl) substituent, at least one (heteroalkyl) substituent being independently selected from the group consisting of —SH, —COOH, and thioalkyl. In some embodiments, the substituted alkyl, substituted heteroalkyl, or substituted heterocycloalkyl are further optionally substituted.

In some embodiments, D is substituted (e.g., straight or branched) alkyl, substituted (e.g., straight or branched) heteroalkyl, or substituted heterocycloalkyl (e.g., (N—) substituted with alkyl further substituted with oxo and thiol). In some embodiments, the substituted alkyl being substituted with one or more (alkyl) substituent, at least one (alkyl) substituent being independently selected from the group consisting of —SH and dithiolanyl oxide. In some embodiments, the substituted heteroalkyl being substituted with one or more (heteroalkyl) substituent, at least one (heteroalkyl) substituent being independently selected from the group consisting of —SH, —COOH, and thioalkyl. In some embodiments, the substituted alkyl, substituted heteroalkyl, or substituted heterocycloalkyl are further optionally substituted.

In some embodiments, D is substituted (e.g., straight or branched) alkyl, the (e.g., straight or branched) alkyl being substituted with one or more substituent, each substituent being independently selected from the group consisting of thiol, amino, acetamide, substituted unsaturated cycloalkyl (e.g., being substituted with one or more $C_1$-$C_4$ alkyl), and substituted heterocycloalkyl (e.g., dithiolanyl oxide).

In some embodiments, D is substituted alkyl, the alkyl being substituted with substituted heterocycloalkyl (e.g., dithiolanyl oxide). In some embodiments, the substituted heterocycloalkyl is substituted with one or more substituent, each substituent being independently selected from the group consisting of $C_1$-$C_3$ alkyl, oxo (e.g., or —O⁻), and —COOH.

In some embodiments, D comprises:

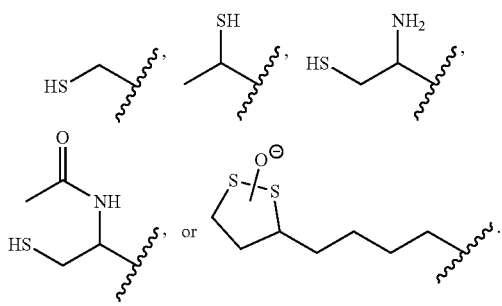

In some embodiments, D comprises:

In some embodiments, D comprises:

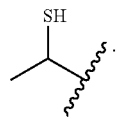

In some embodiments, D comprises:

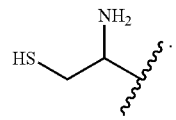

In some embodiments, D comprises:

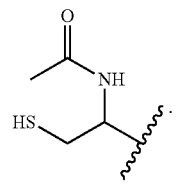

In some embodiments, D comprises:

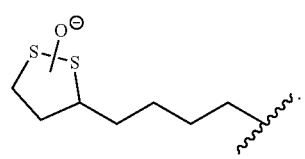

In some embodiments, D comprises:

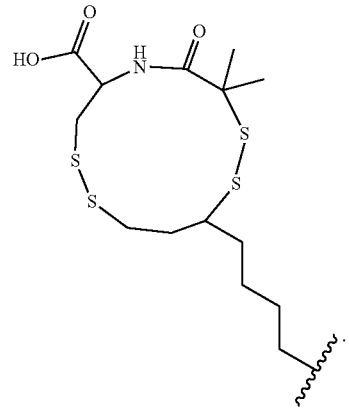 [SMILES: *CCCCC1CCSSCC(C(=O)O)NC(=O)C(C)(C)SS1]

In some embodiments, D comprises:
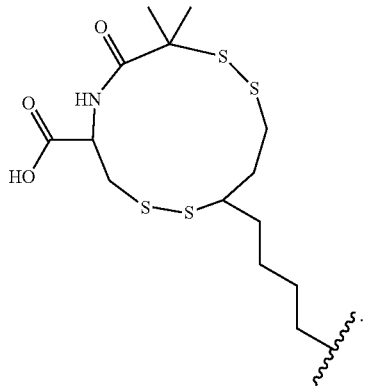 [SMILES: *CCCCC1CCSSC(C)(C)C(=O)NC(C(=O)O)CSS1]
In some embodiments, D-L$^a$- is:
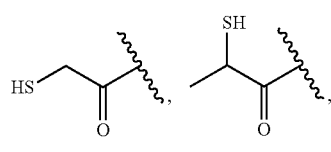
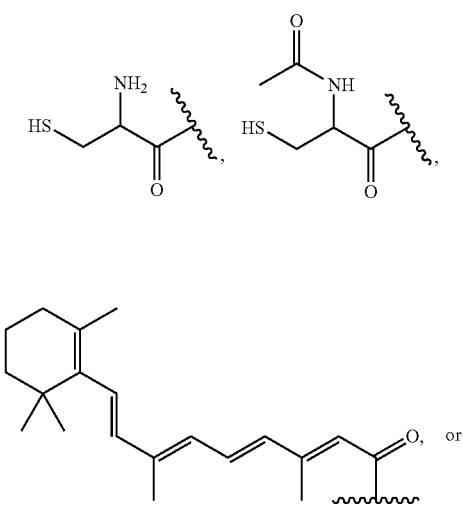
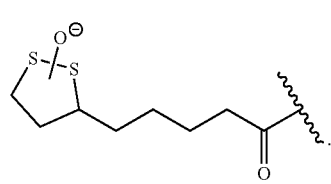
In some embodiments, D-L$^a$- is:
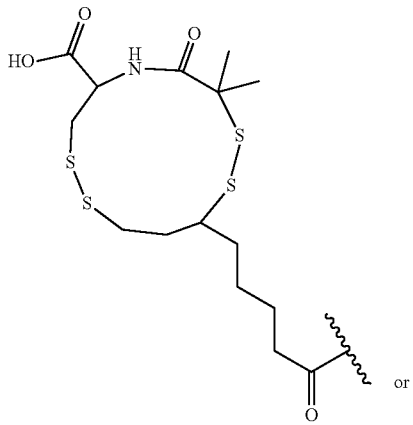 or
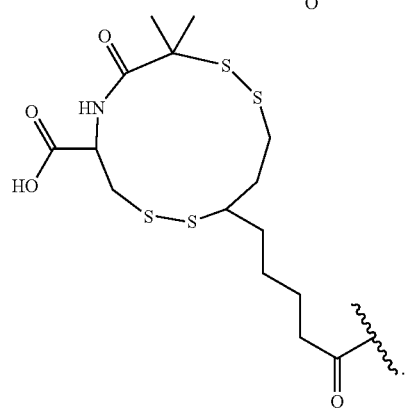
In some embodiments, D is substituted heterocycloalkyl (e.g., N-substituted with alkyl further substituted with oxo and thiol).
In some embodiments, D comprises:
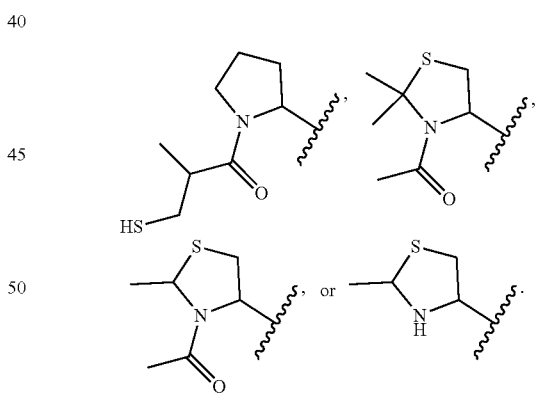
In some embodiments, D comprises:
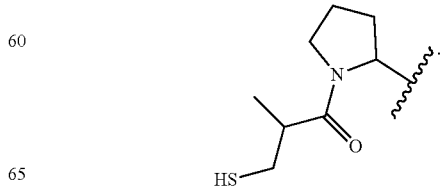

In some embodiments, D comprises:

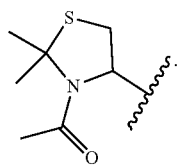 [SMILES: *C1CSC(C)(C)N1C(C)=O]

In some embodiments, D comprises:

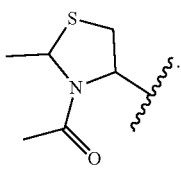 [SMILES: *C1CSC(C)N1C(C)=O]

In some embodiments, D comprises:

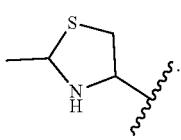 [SMILES: *C1CSC(C)N1]

In some embodiments, D-L$^a$- is:

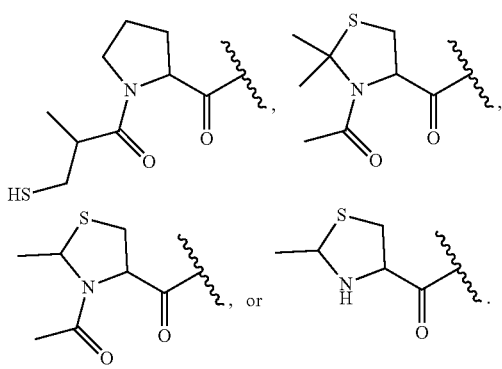

In some embodiments, D is substituted (e.g., linear or branched) heteroalkyl comprising one or more ester, one or more amide, and/or one or more disulfide (e.g., within the (e.g., linear or branched) heteroalkyl chain).

In some embodiments, D is substituted (e.g., linear or branched) heteroalkyl comprising one ester (e.g., within the (e.g., linear or branched) heteroalkyl chain).

In some embodiments, D is substituted or unsubstituted (e.g., linear or branched) heteroalkyl comprising one or two amide (e.g., within the (e.g., linear or branched) heteroalkyl chain).

In some embodiments, D is substituted or unsubstituted (e.g., linear or branched) heteroalkyl comprising one or two disulfide (e.g., within the (e.g., linear or branched) heteroalkyl chain).

In some embodiments, D is substituted or unsubstituted (e.g., linear or branched) heteroalkyl containing one disulfide (e.g., within the (e.g., linear or branched) heteroalkyl chain).

In some embodiments, D is substituted or unsubstituted (e.g., linear or branched) heteroalkyl containing one or two disulfide and one amide (e.g., within the (e.g., linear or branched) heteroalkyl chain).

In some embodiments, D is substituted (e.g., linear or branched) heteroalkyl, the (e.g., linear or branched) heteroalkyl being substituted with one or more substituent, each substituent being independently selected from the group consisting of thioalkyl, amino, carboxylic acid, $C_1$-$C_6$ alkyl, acetamide, thiol, oxo, and optionally substituted (e.g., N-attached) heterocycloalkyl (e.g., optionally substituted with carboxylic acid).

In some embodiments, D is substituted branched heteroalkyl.

In some embodiments, D comprises:

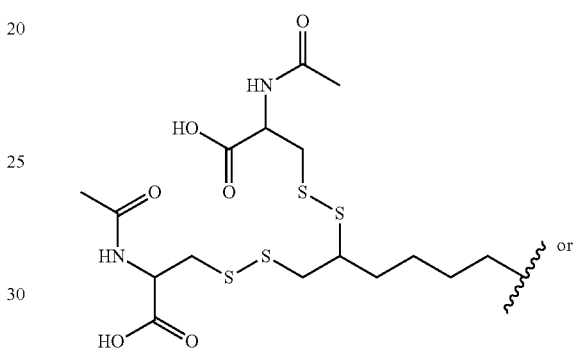

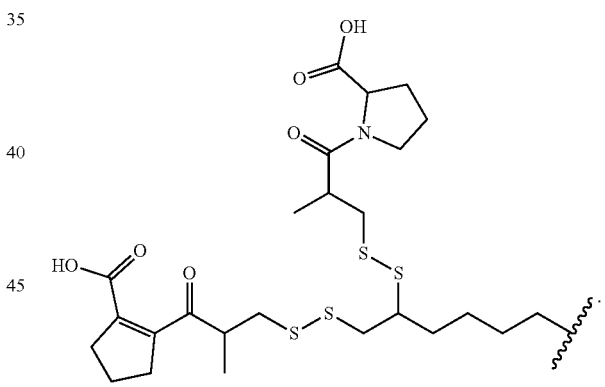

In some embodiments, D is:

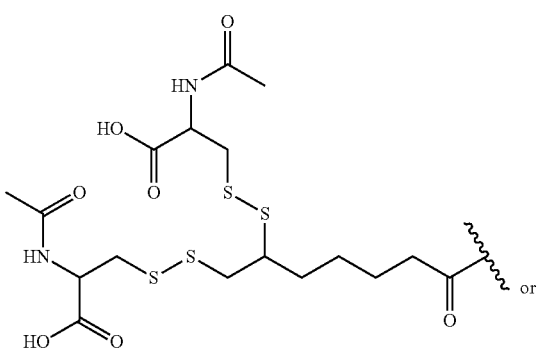

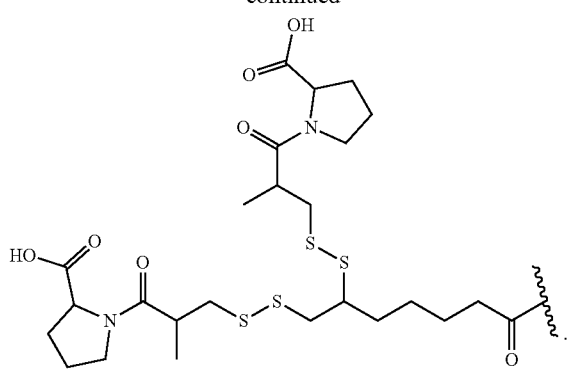
In some embodiments, D comprises:
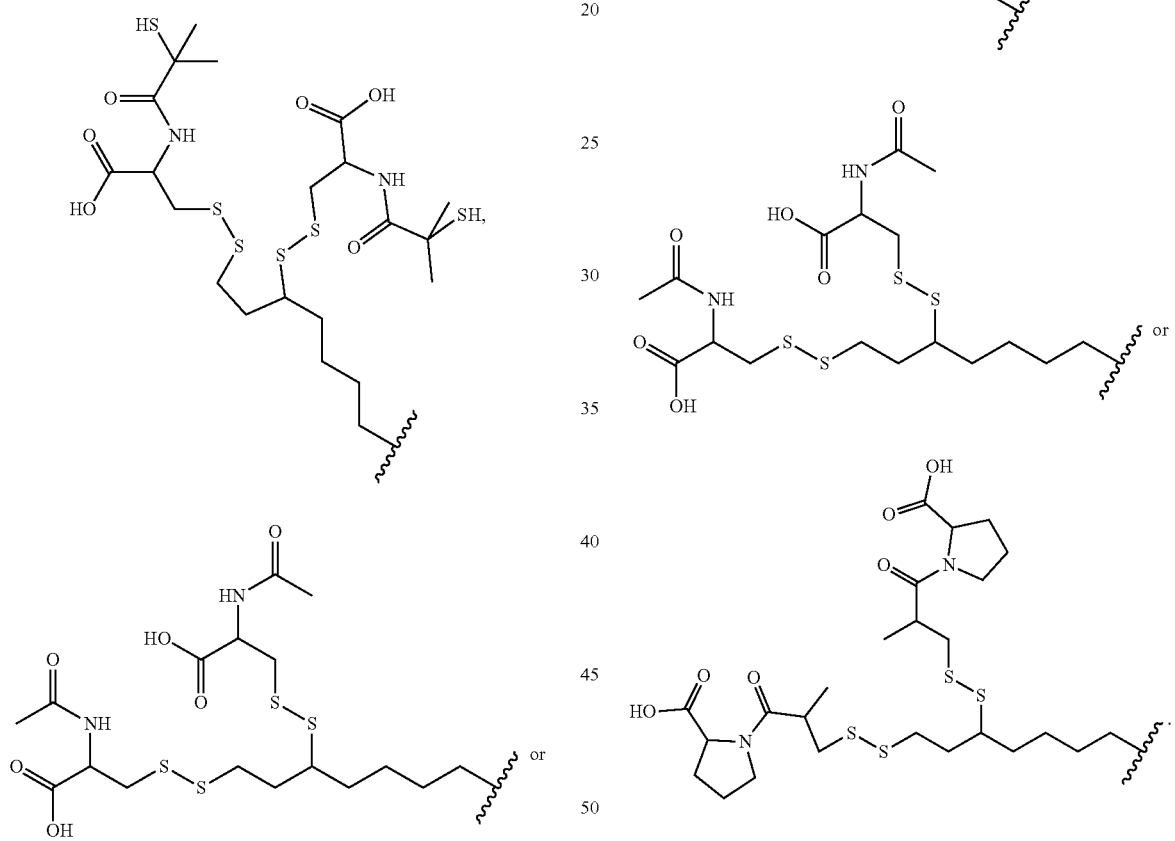
In some embodiments, D is:
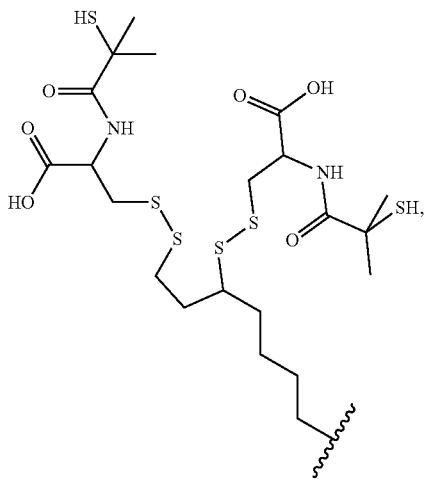
In some embodiments, D is:
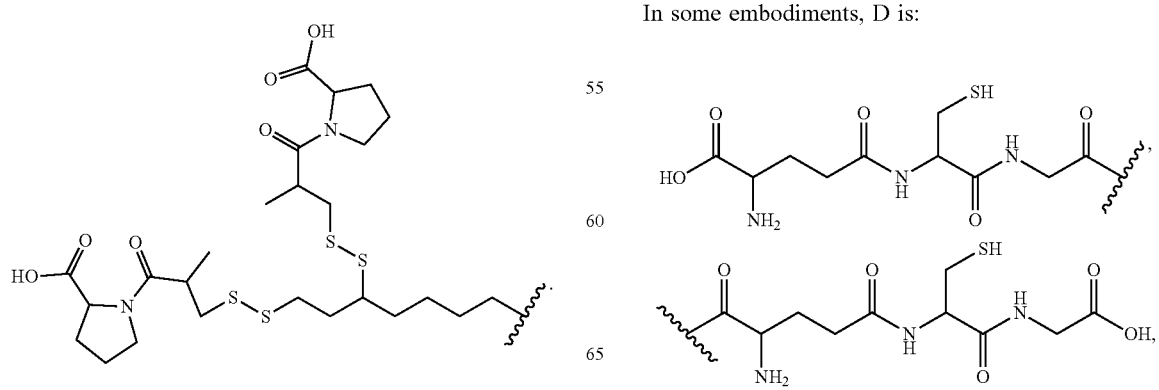

-continued
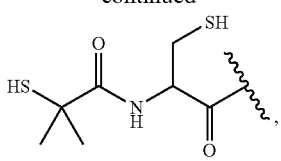
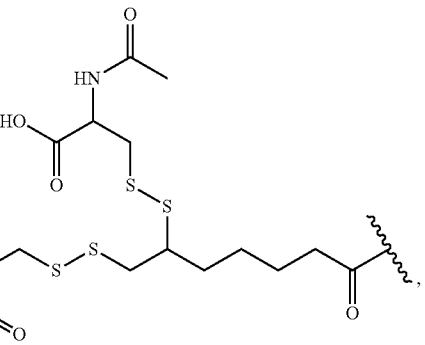
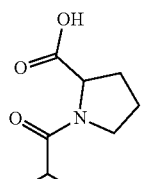
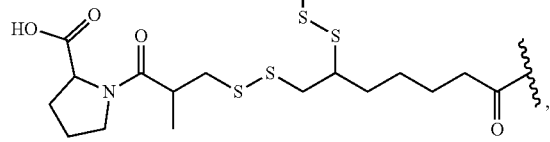
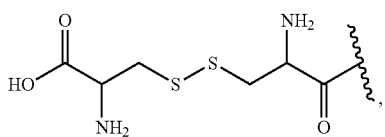, or
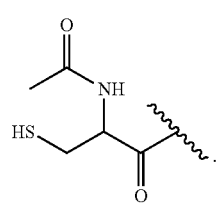.
In some embodiments, D comprises:
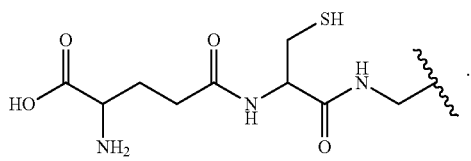 [SMILES: *CNC(=O)C(CS)NC(=O)CCC(N)C(=O)O]
In some embodiments, D comprises:
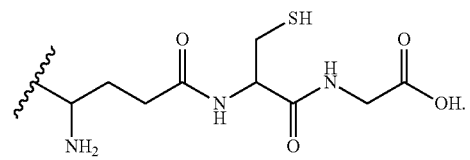
In some embodiments, D comprises:
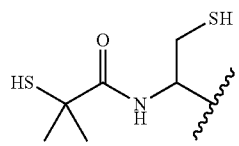
In some embodiments, D comprises:
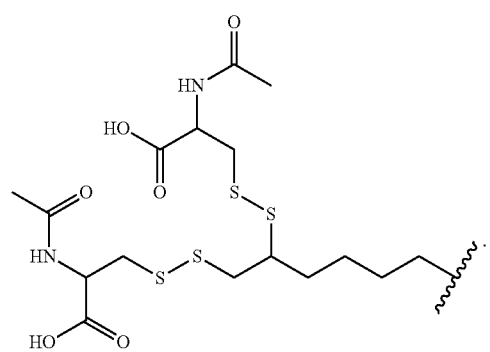 [SMILES: *CCCCC(CSSCC(NC(C)=O)C(=O)O)SSCC(NC(C)=O)C(=O)O]
In some embodiments, D comprises:
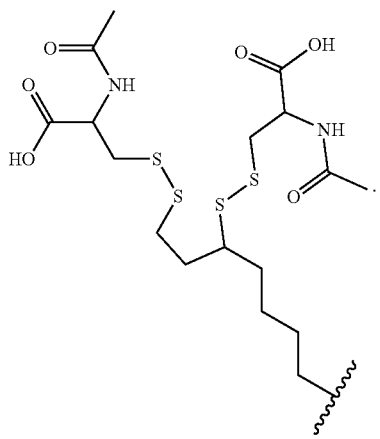 [SMILES: *CCCCC(CCSSCC(NC(C)=O)C(=O)O)SSCC(NC(C)=O)C(=O)O]

In some embodiments, D is:
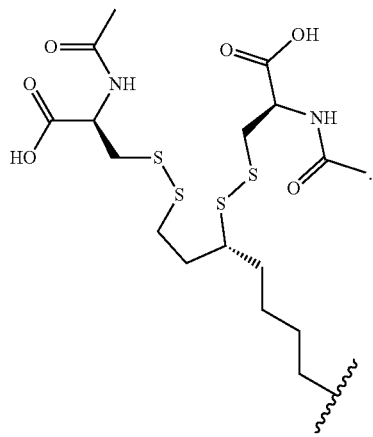 [SMILES: *CCCC[C@H](CCSSC[C@H](NC(C)=O)C(=O)O)SSC[C@H](NC(C)=O)C(=O)O]
In some embodiments, D comprises:
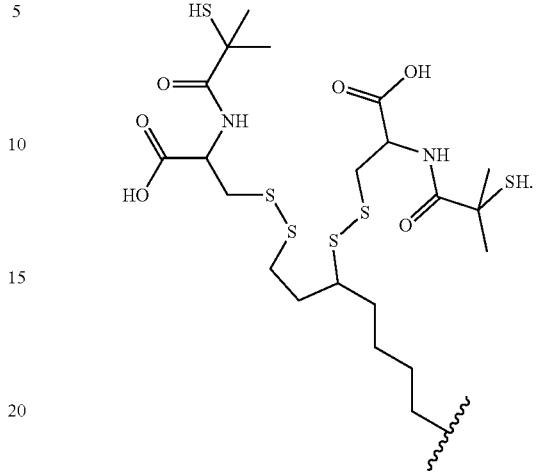
In some embodiments, D comprises:
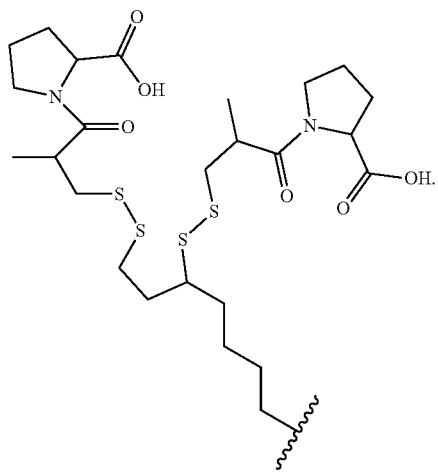 [SMILES: *CCCCC(CCSSCC(C)C(=O)N1CCCC1C(=O)O)SSCC(C)C(=O)N1CCCC1C(=O)O]
In some embodiments, D is:
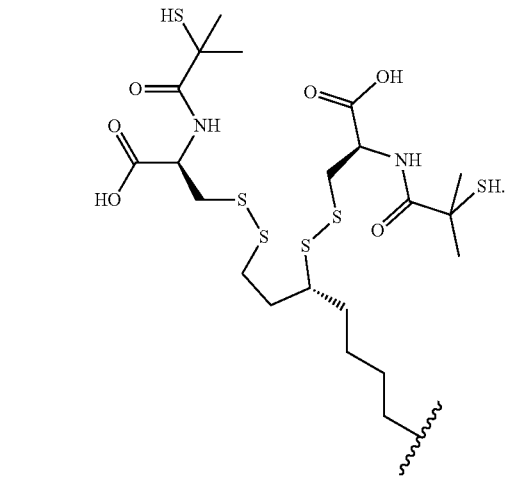
In some embodiments, D is:
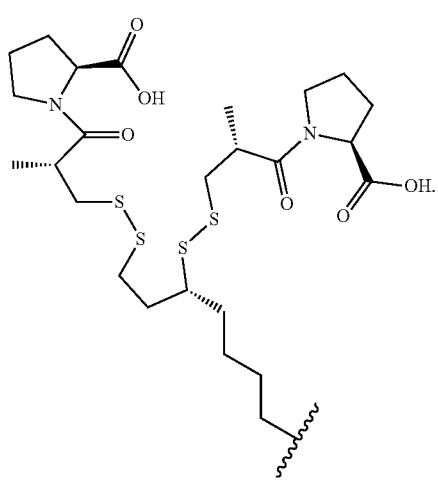 [SMILES: *CCCC[C@H](CCSSC[C@H](C)C(=O)N1CCC[C@H]1C(=O)O)SSC[C@H](C)C(=O)N1CCC[C@H]1C(=O)O]
In some embodiments, D comprises:
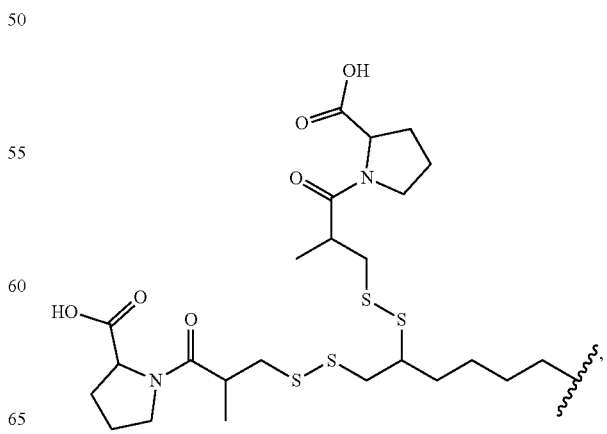

In some embodiments, D comprises:

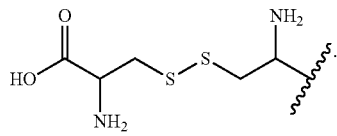

In some embodiments, D comprises:

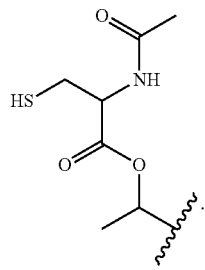

In some embodiments, D comprises:

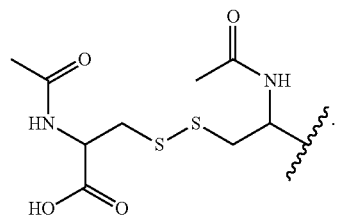 [SMILES: *C(CSSCC(NC(C)=O)C(=O)O)NC(C)=O]

In some embodiments, D comprises:

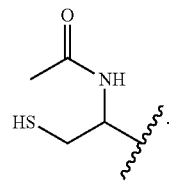

In some embodiments, D comprises: $HOCH_2$—, $HOCH(CH_3)$—, $HO(CH_2CH_2O)_4CH_2$—, $HO(CH_2CH_2O)_4CH_2CH_2$—, $HOCH_2(C=O)$—, $HOCH(CH_3)(C=O)$—, $HO(CH_2CH_2O)_4CH_2(C=O)$—, $HO(CH_2CH_2O)_4CH_2CH_2(C=O)$—, $CH_3O(C=O)$—, $CH_3CH_2O(C=O)$—, $(CH_3)_2CO(C=O)$—, $(CH_3)_3CO(C=O)$—, $CH_3(C=O)$—, $CH_3CH_2(C=O)$—, $(CH_3)_2C(C=O)$—, $(CH_3)_3C(C=O)$—, $HOCH_2(C=O)$—, $HO(CH_3)CH(C=O)$—, $HO(CH_3)CH(C=O)O(CH_3)CH(C=O)$—, $CH_3(C=O)O(CH_3)CH(C=O)$—, $CH_3O(C=O)O(CH_3)CH(C=O)$—, $CH_3O(C=O)(CH_3)CHO(C=O)$—, $CH_3CH_2O(C=O)(CH_3)CHO(C=O)$—, $HOCH_2(HOCH_2)CHCH_2O(C=O)$—, $CH_3(C=O)OCH_2(CH_3(C=O)OCH_2)CHCH_2O(C=O)$—, $(CH_3)_3C(C=O)OCH_2((CH_3)_3C(C=O)OCH_2)CHCH_2O(C=O)$—, $HO(CH_3)CH(C=O)OCH_2(HO(CH_3)CH(C=O)OCH_2)CHCH_2O(C=O)$—, $HSCH_2(C=O)$—, $HS(CH_3)CH(C=O)$—, $HSCH_2(NH_2)CH(C=O)$—, $HSCH_2(CH_3(C=O)NH)CH(C=O)$—, $HOOC(NH_2)CHCH_2(C=O)$—, $HOOC(NH_2)CHCH_2(C=O)NH(HSCH_2)CH(C=O)NHCH_2(C=O)$—, —$(C=O)CH(NH_2)CH_2CH_2(C=O)NHCH(CH_2SH)(C=O)NHCH_2COOH$, $HS(CH_3)_2C(C=O)NH(SHCH_2)CH(C=O)$—, $HOOC(NH_2)CHCH_2SSCH_2CH(NH_2)(C=O)$—, $HSCH_2(CH_3(C=O)NH)CH(C=O)OCH(CH_3)(C=O)$—,

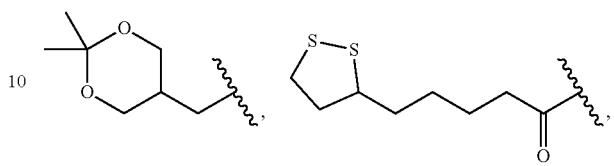

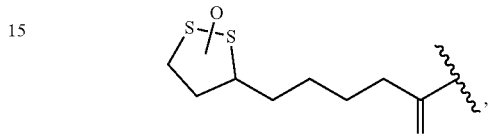

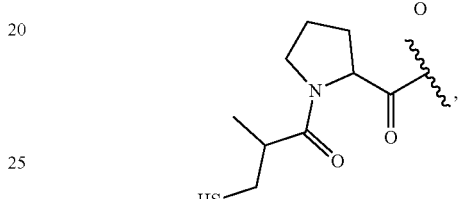

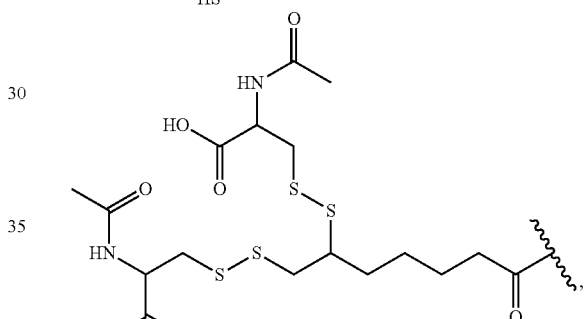

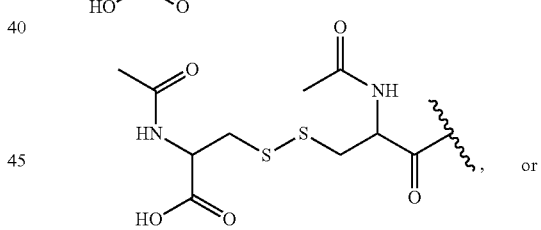 or

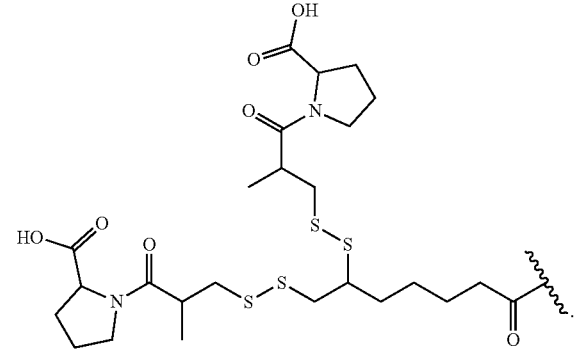 [SMILES: *C(=O)CCCCC(CSSCC(C)C(=O)N1CCCC1C(=O)O)SSCC(C)C(=O)N1CCCC1C(=O)O]

In some embodiments, D comprises: $HSCH_2(C=O)$—, $HS(CH_3)CH(C=O)$—, $HSCH_2(NH_2)CH(C=O)$—, $HSCH_2(CH_3(C=O)NH)CH(C=O)$—, $HOOC(NH_2)CHCH_2(C=O)NH(HSCH_2)CH(C=O)NHCH_2(C=O)$—, —$(C=O)CH(NH_2)CH_2CH_2(C=O)NHCH$ (CH₂SH)(C═O)NHCH₂COOH, HS(CH₃)₂C(C═O)NH(SHCH₂)CH(C═O)—, HOOC(NH₂)CHCH₂SSCH₂CH(NH₂)(C═O)—, HSCH₂(CH₃(C═O)NH)CH(C═O)OCH(CH₃)(C═O)—,
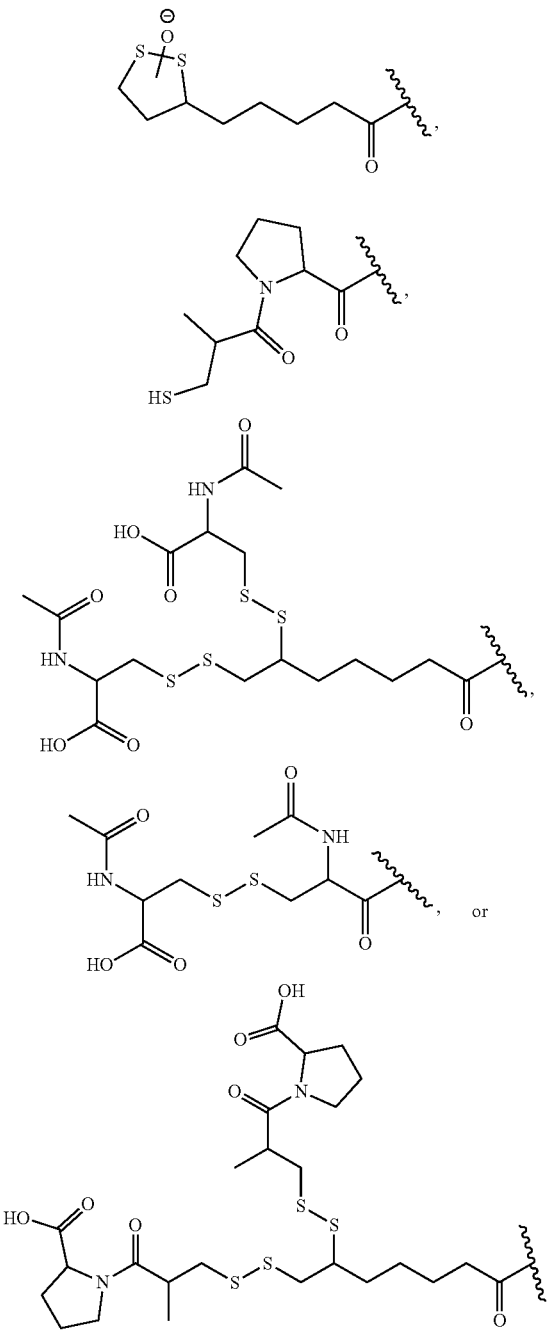
In some embodiments, D-Lᵃ is:
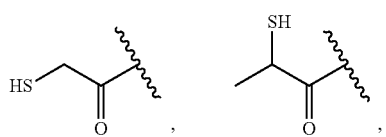
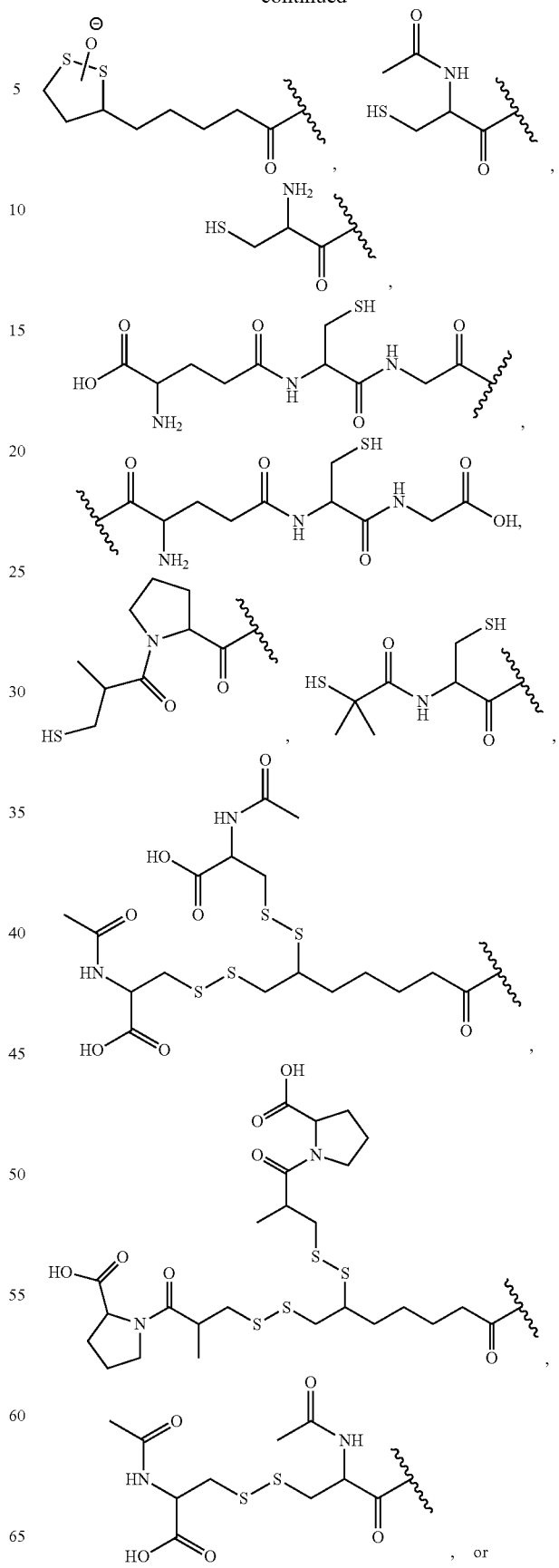
or -continued

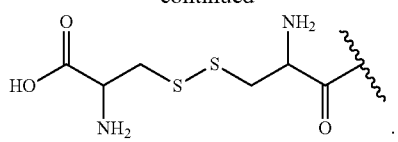

In some embodiments, D-L$^a$ is:

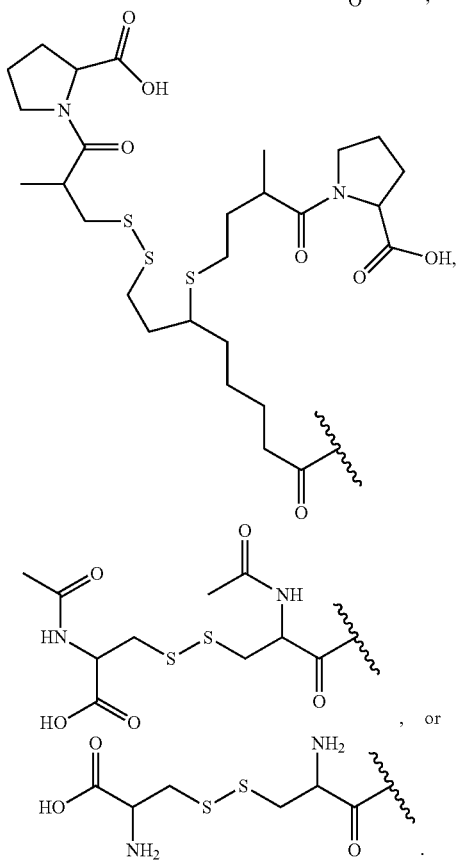

-continued

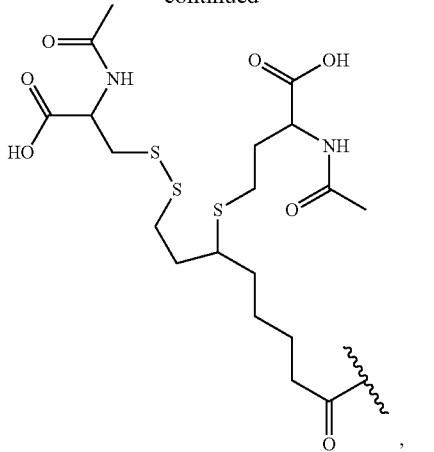

In some embodiments, D is a "keratolytic agent" radical that, upon release, hydrolysis, or other mechanism metabolizes or otherwise produces (e.g., when administered to an individual or patient, such as in or around the eye, such as the eyelid margin) an active keratolytic agent (e.g., a carboxylic acid and/or a thiol). In some instances, upon release (e.g., by hydrolysis or other mechanism), D produces a plurality of active keratolytic agents. In some instances, the active keratolytic agent comprises one or more of —SH, —OH, COOH (or COO—), or disulfide. In some embodiments, the active keratolytic agent is a carboxylic acid. In some embodiments, the active keratolytic agent is selected from the group consisting of acetic acid, glycolic acid, lactic acid, lipoic acid, pivalic acid, isobutryic acid, butyric acid, propionic acid, formic acid, and carbonic acid. In some embodiments, the active keratolytic agent is a thiol. In some embodiments, the active keratolytic agent is a carboxylic acid.

In some embodiments, one or more group of the keratolytic agent (e.g., thiol, hydroxy, carboxylic acid, amide, or amine) is protected or masked (e.g., with optionally substituted $C_1$-$C_6$ alkyl (e.g., being optionally substituted with oxo)). In some embodiments, one or more thiol of the keratolytic agent is protected or masked with acetyl. In some embodiments, one or more amine of the keratolytic agent is protected or masked with acetyl. In some embodiments, one or more carboxylic acid of the keratolytic agent is protected or masked with methyl, ethyl, propyl, isopropyl, or t-butyl. In some embodiments, one or more carboxylic acid of the keratolytic agent is protected or masked with ethyl.

In some embodiments, $L^a$ is attached to D by a bond.

In some embodiments, any L or linker provided herein comprises one or more substituted or unsubstituted alkoxy (e.g., polyethylene glycol (PEG)).

In some embodiments, any L or linker provided herein comprises a compound having a structure of Formula (B):

—X(C=O)—.

In some embodiments, X is a bond or O. In some embodiments, X is a bond. In some embodiments, X is O.

In some embodiments, any L or linker provided herein is attached to the compound having a structure of Formula (B). In some embodiments, the linker is —(C=O)(OCR$^8$R$^9$)$_z$—.

In some embodiments, the linker is —(C=O)OCH(CH$_3$)—. In some embodiments, the linker is —(C=O)(OCH$_2$CH$_2$)$_z$ and attached to the compound having a structure of Formula (B).

In some embodiments, z is an integer from 1-20. In some embodiments, z is an integer from 1-10.

In some embodiments, z is an integer from 1-5. In some embodiments, z is 1, 2, 3, 4, 5, 6, 7, 8, 9, or 10. In some embodiments, z is 4. In some embodiments, z is 8.

In some embodiments, the linker is —(C=O)(OCH$_2$CH$_2$)$_z$ and attached to —O(C=O)—. In some embodiments, the linker is —(C=O)(OCH$_2$CH$_2$)$_4$ and attached to —O(C=O)—. In some embodiments, the linker is —(C=O)(OCH$_2$CH$_2$)$_8$ and attached to —O(C=O)—.

In some embodiments, the compound having the structure of Formula (B) is attached to a keratolytic agent provided herein (e.g., as described elsewhere herein). In some embodiments, the compound having the structure of Formula (B) is attached to and includes at least a portion of a keratolytic agent provided herein (e.g., as described elsewhere herein).

In some embodiments, the compound having the structure of Formula (B) is attached to any R or R' provided herein (e.g., as described elsewhere herein).

In certain instances, provided herein is a combination of an anti-inflammatory and/or anti-microbial moiety (e.g., having a structure of any formula provided herein, minus the R') with a keratolytic moiety (e.g., being represented by and/or having a structure of D). In certain embodiments, such moieties are radicals connected by a linker that is a bond, with the keratolytic moiety being hydrolyzable to produce both (1) an anti-inflammatory and/or anti-microbial agent and (2) one or more active keratolytic agent. In some embodiments, such moieties are radicals connected by a hydrolyzable linker, with the hydrolyzable linker being hydrolyzable, such that both (1) an anti-inflammatory and/or anti-microbial agent and (2) one or more active keratolytic agent are released (e.g., in vivo, such as after therapeutic (e.g., topical) delivery to the eye and/or skin).

In some embodiments, a compound provided herein comprises a first radical (e.g., a first radical of Formula I (or any other formula provided herein)) that is dimerized with a second radical (e.g., a second radical of Formula I (or any other formula provided herein)). In some embodiments, each radical of Formula I (or any other formula provided herein) is dimerized through an —SH group thereof (e.g., forming an S—S linkage).

In some embodiments, provided herein is a compound, or a pharmaceutically acceptable salt or solvate (e.g., or a stereoisomer) thereof, having the structure of Formula (Ia):

Formula (Ia)

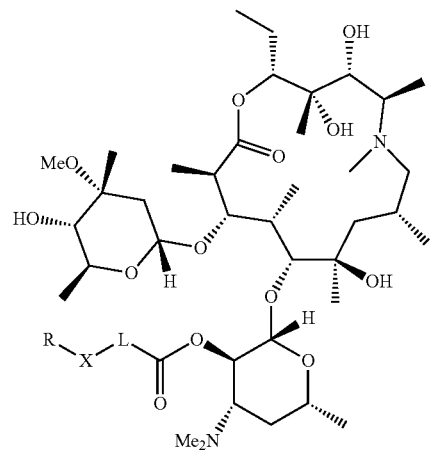

In some embodiments, L is bond, —(C=O)(OCR$^8$R$^9$)$_z$—, or —(C=O)(OCR$^8$R$^9$)$_z$O—. In some embodiments, L is bond, —(C=O)O(CR$^8$R$^9$)$_z$—, or —(C=O)O(CR$^8$R$^9$)$_z$O—. In some embodiments, each R$^8$ and R$^9$ is independently H, halogen, $C_1$-$C_3$-alkyl, $C_1$-$C_3$-haloalkyl, $C_1$-$C_3$-alkoxy, $C_3$-$C_5$-cycloalkyl, or R$^8$ and R$^9$ are taken together with the atoms to which they are attached to form a $C_3$-$C_5$-cycloalkyl. In some embodiments, z is 1-6. In some embodiments, X is absent or —O—. In some embodiments, R is substituted (e.g., straight or branched) alkyl, substituted (e.g., straight or branched) heteroalkyl, or substituted heterocycloalkyl (e.g., (N—) substituted with alkyl further substituted with oxo and thiol). In some embodiments, the substituted alkyl is substituted with one or more (alkyl) substituent, at least one (alkyl) substituent being independently selected from the group consisting of —SH, substituted or unsubstituted (e.g., unsaturated) cycloalkyl, and substituted heteroalkyl (e.g., dithiolanyl oxide). In some embodiments, the substituted alkyl is substituted with one or more (alkyl) substituent, at least one (alkyl) substituent being independently selected from the group consisting of —SH, substituted or unsubstituted (e.g., unsaturated) cycloalkyl, and dithiolanyl oxide. In some embodiments, the substituted alkyl is substituted with one or more (alkyl) substituent, at least one (alkyl) substituent being independently selected from the group consisting of —SH and dithiolanyl oxide. In some embodiments, the substituted heteroalkyl is substituted with one or more (heteroalkyl) substituent, at least one (heteroalkyl) substituent being independently selected from the group consisting of —SH, —COOH, and thioalkyl. In some embodiments, the substituted alkyl, substituted heteroalkyl, or substituted heterocycloalkyl are further optionally substituted.

In some embodiments, L is bond. In some embodiments, L is —(C=O)(OCR$^8$R$^9$)$_z$— or —(C=O)(OCR$^8$R$^9$)$_z$O—. In some embodiments, L is —(C=O)(OCR⁸R⁹)_z—. In some embodiments, L is —(C=O)(OCR⁸R⁹)_zO—. In some embodiments z is 1-3. In some embodiments, z is 1. In some embodiments, each R⁸ and R⁹ is independently H or $C_1$-$C_3$-alkyl. In some embodiments, each R⁸ is H and each R⁹ is $C_1$-$C_3$-alkyl. In some embodiments, each R⁸ is H and each R⁹ is $CH_3$. In some embodiments, R⁸ and R⁹ are H. In some embodiments, L is —(C=O)OCH($CH_3$)—. In some embodiments, L is —(C=O)OCH($CH_3$)O—.

In some embodiments, X is absent. In some embodiments, X is —O—.

In some embodiments, L is —(C=O)OCH($CH_3$)— or —(C=O) OCH($CH_3$)O— and X is absent or —O—.

In some embodiments, L is —(C=O)OCH($CH_3$)— and X is absent. In some embodiments, L is —(C=O)OCH($CH_3$) O— and X is absent.

In some embodiments, L is —(C=O)OCH($CH_3$)— and X is —O—. In some embodiments, L is —(C=O)OCH($CH_3$) O— and X is —O—.

In some embodiments, L is bond and X is absent.

In some embodiments, R is substituted alkyl, substituted heteroalkyl, or substituted heterocycloalkyl.

In some embodiments, R is substituted (e.g., straight or branched) alkyl, the (e.g., straight or branched) alkyl being substituted with one or more (alkyl) substituent, each (alkyl) substituent being independently selected from the group consisting of thiol, amino, acetamide, substituted unsaturated cycloalkyl (e.g., being substituted with one or more $C_1$-$C_4$ alkyl), and substituted heterocycloalkyl (e.g., dithiolanyl oxide). In some embodiments, R is substituted (e.g., straight or branched) alkyl, the (e.g., straight or branched) alkyl being substituted with thiol. In some embodiments, R is substituted (e.g., straight or branched) alkyl, the (e.g., straight or branched) alkyl being substituted with thiol and amide. In some embodiments, R is substituted (e.g., straight or branched) alkyl, the (e.g., straight or branched) alkyl being substituted with thiol and acetamide (e.g., —N(C=O) $CH_3$). In some embodiments, R is substituted (e.g., straight or branched) alkyl, the (e.g., straight or branched) alkyl being substituted with 1,2-dithiolanyl oxide. In some embodiments, R is substituted (e.g., straight or branched) alkyl, the (e.g., straight or branched) alkyl being substituted with substituted unsaturated cycloalkyl (e.g., being substituted with one or more $C_1$-$C_4$ alkyl).

In some embodiments, R is substituted alkyl. In some embodiments, R is substituted alkyl, wherein the substituted alkyl is substituted with one or more alkyl substituent, at least one alkyl substituent being independently selected from the group consisting of substituted or unsubstituted cycloalkyl and substituted heterocycloalkyl. In some embodiments, R is substituted alkyl, the alkyl being substituted with substituted heterocycloalkyl. In some embodiments, R is substituted alkyl, the alkyl being substituted with 1,2-dithiolanyl oxide. In some embodiments, R is substituted alkyl, the alkyl being substituted with substituted heterocycloalkyl (e.g., $C_5$-$C_{15}$ heterocycloalkyl (e.g., $C_{12}$ heterocycloalkyl with one or more disulfide and one or more amide within the heterocycloalkyl ring)) being substituted with one or more substituent, at least one substituent being independently selected from the group consisting of $C_1$-$C_3$ alkyl, oxo, and —COOH. In some embodiments, the substituted alkyl is further optionally substituted.

In some embodiments, L is bond, X is absent, and R is substituted (e.g., straight or branched) alkyl, the (e.g., straight or branched) alkyl being substituted with one or more (alkyl) substituent, each (alkyl) substituent being independently selected from the group consisting of thiol, amino, acetamide, substituted unsaturated cycloalkyl (e.g., being substituted with one or more $C_1$-$C_4$ alkyl), and substituted heterocycloalkyl (e.g., dithiolanyl oxide).

In some embodiments, L is bond, X is absent, and R is substituted alkyl, wherein the substituted alkyl is substituted with one or more alkyl substituent, at least one alkyl substituent being independently selected from the group consisting of substituted or unsubstituted cycloalkyl and substituted heterocycloalkyl. In some embodiments, the substituted alkyl is further optionally substituted.

In some embodiments, R is:

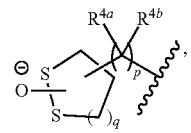

wherein:
each $R^{4a}$ and $R^{4b}$ is independently H, halogen, or substituted or unsubstituted alkyl;
p is an integer from 1-10; and
q is an integer from 1-3.
In some embodiments, q is 1 and p is an integer from 3-5.
In some embodiments, each $R^{4a}$ and $R^{4b}$ is H.
In some embodiments, R is:

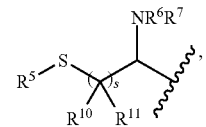

wherein:
$R_5$ is —$SR^{1c}$;
$R^{1c}$ is:
  substituted alkyl or substituted heteroalkyl,
    wherein the alkyl is substituted with one or more alkyl substituent, each alkyl substituent being independently selected from the group consisting of carboxylic acid, —SH, thioalkyl, acetamide, amino, oxo, and optionally substituted heterocycloalkyl, and the heteroalkyl is substituted with one or more heteroalkyl substituent, each heteroalkyl substituent being independently selected from the group consisting of oxo, carboxylic acid, amino, thioalkyl, thiol, acetamide, and $C_1$-$C_3$ alkyl;
$R^6$ and $R^7$ are each independently H, substituted or unsubstituted alkyl, or substituted or unsubstituted heteroalkyl;
each $R^{10}$ and $R^{11}$ is independently H, halogen, $C_1$-$C_3$-alkyl, $C_1$-$C_3$-haloalkyl, $C_1$-$C_3$-alkoxy, $C_3$-$C_5$-cycloalkyl, or two of $R^{10}$ and $R^{11}$ are taken together with the atoms to which they are attached to form a $C_3$-$C_5$-cycloalkyl; and
s is an integer from 1-10.
In some embodiments, $R^6$, $R^7$, $R^{10}$ and $R^{11}$ are each H, and s is 1-3.
In some embodiments, $R^{1c}$ is heteroalkyl substituted with carboxylic acid. In some embodiments, $R^{1c}$ is alkyl substituted with one or more alkyl substituent, each alkyl substituent being independently selected from the group consisting of carboxylic acid and acetamide.

In some embodiments, R⁵ is:
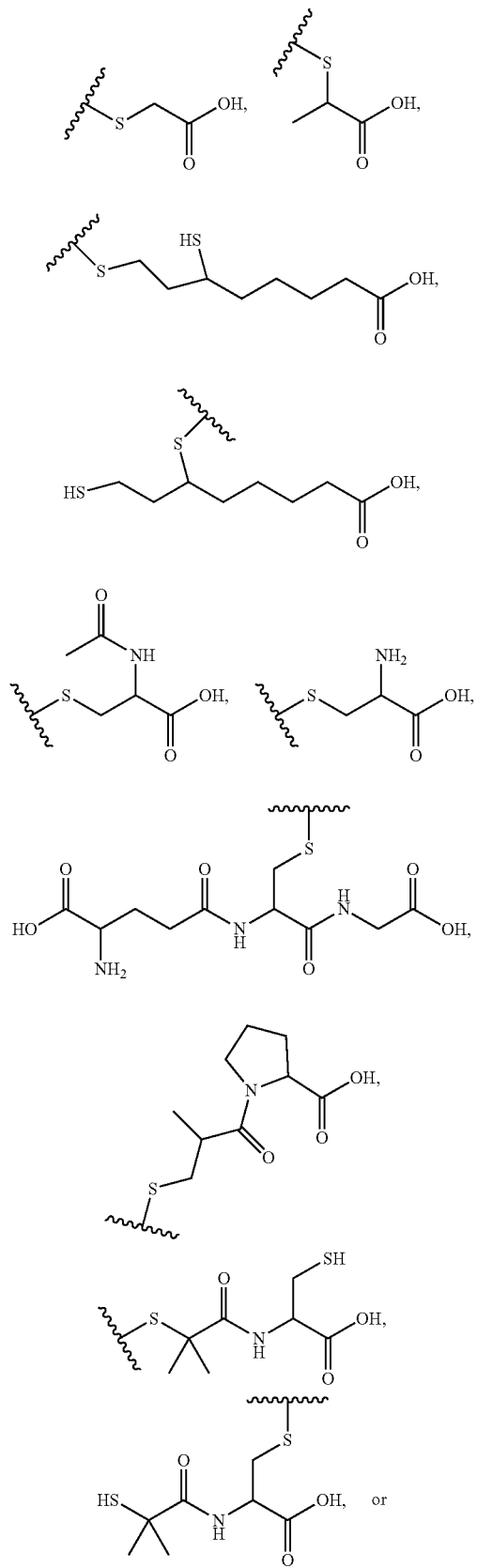
-continued
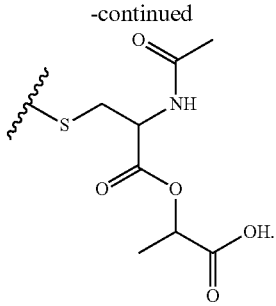
In some embodiments, R is:
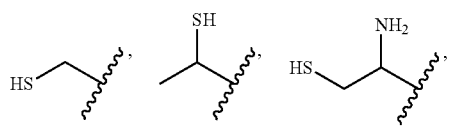
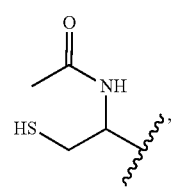
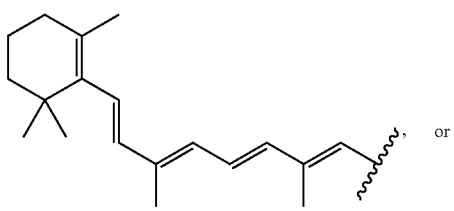
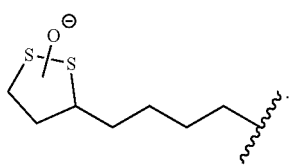
In some embodiments, R is:
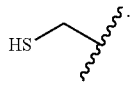
In some embodiments, R is:
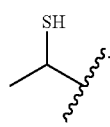

In some embodiments, R is:

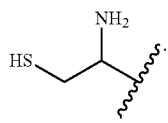

In some embodiments, R is:

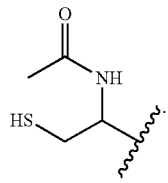

In some embodiments, R is:

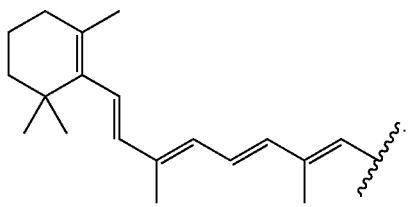 [SMILES: */C=C(C)/C=C/C=C(C)/C=C/C1=C(C)CCCC1(C)C]

In some embodiments, R is:

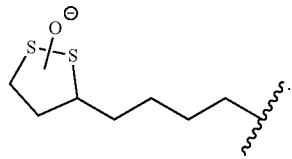

In some embodiments, R is:

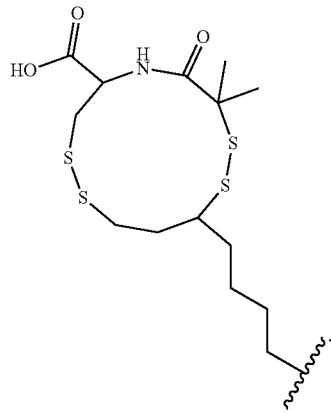 [SMILES: *CCCCC1CCSSCC(C(=O)O)NC(=O)C(C)(C)SS1]

In some embodiments, R is:

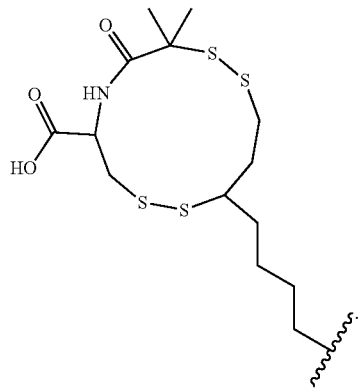 [SMILES: *CCCCC1CCSSC(C)(C)C(=O)NC(C(=O)O)CSS1]

In some embodiments, R is substituted (e.g., linear or branched) heteroalkyl comprising one or more ester, one or more amide, and/or one or more disulfide (e.g., within the (e.g., linear or branched) heteroalkyl chain).

In some embodiments, R is substituted (e.g., linear or branched) heteroalkyl comprising one ester (e.g., within the (e.g., linear or branched) heteroalkyl chain).

In some embodiments, R is substituted or unsubstituted (e.g., linear or branched) heteroalkyl comprising one or two amide (e.g., within the (e.g., linear or branched) heteroalkyl chain).

In some embodiments, R is substituted or unsubstituted (e.g., linear or branched) heteroalkyl comprising one or two disulfide (e.g., within the (e.g., linear or branched) heteroalkyl chain).

In some embodiments, R is substituted or unsubstituted (e.g., linear or branched) heteroalkyl containing one disulfide (e.g., within the (e.g., linear or branched) heteroalkyl chain).

In some embodiments, R is substituted or unsubstituted (e.g., linear or branched) heteroalkyl containing one or two disulfide and one amide (e.g., within the (e.g., linear or branched) heteroalkyl chain).

In some embodiments, R is substituted (e.g., linear or branched) heteroalkyl, the (e.g., linear or branched) heteroalkyl being substituted with one or more (heteroalkyl) substituent, each (heteroalkyl) substituent being independently selected from the group consisting of thioalkyl, amino, carboxylic acid, $C_1$-$C_6$ alkyl, thiol, oxo, and optionally substituted (e.g., N-attached) heterocycloalkyl (e.g., optionally substituted with carboxylic acid). In some embodiments, R is substituted linear heteroalkyl, the linear heteroalkyl being substituted with thioalkyl, amino, and carboxylic acid. In some embodiments, R is substituted linear heteroalkyl, the linear heteroalkyl being substituted with thioalkyl, thiol, and $C_1$-$C_4$ alkyl. In some embodiments, R is substituted branched heteroalkyl, the branched heteroalkyl being substituted with one or more carboxylic acid. In some embodiments, R is substituted branched heteroalkyl, the branched heteroalkyl being substituted with one or more $C_1$-$C_4$ alkyl, one or more oxo, and one or more N-attached pyrrolidine substituted with carboxylic acid. In some embodiments, R is substituted linear heteroalkyl, the linear heteroalkyl being substituted with amino and carboxylic acid. In some embodiments, R is substituted linear heteroalkyl, the linear heteroalkyl being substituted with thioalkyl.

In some embodiments, R is substituted linear heteroalkyl, the linear heteroalkyl being substituted with acetamide and carboxylic acid.

In some embodiments, R is substituted heteroalkyl, wherein the substituted heteroalkyl is substituted with one or more heteroalkyl substituent, each heteroalkyl substituent being independently selected from the group consisting of —COOH, substituted heterocycloalkyl, acetamide, alkoxy, oxo, thiol, $C_1$-$C_3$ alkyl, and thioalkyl. In some embodiments, R is substituted heteroalkyl, the heteroalkyl being substituted with —COOH, —$CH_2SH$, and/or optionally substituted N-attached heterocycloalkyl. In some embodiments, the substituted heteroalkyl is further optionally substituted. In some embodiments, the substituted heteroalkyl is further substituted with one or more other substituent, each substituent being independently selected from the group consisting of acetamide, amino, $C_1$-$C_6$ alkyl, thiol, and oxo.

In some embodiments, R is substituted heteroalkyl, the heteroalkyl being substituted with one or more substituent, each substituent being independently selected from the group consisting of —COOH and acetamide.

In some embodiments, R is substituted heteroalkyl, the heteroalkyl being substituted with one or more substituent, each substituent being independently selected from the group consisting of oxo and acetamide (e.g., wherein the heteroalkyl chain comprises a disulfide bond and —O—).

In some embodiments, R is substituted heteroalkyl, the heteroalkyl being substituted with one or more substituent, each substituent being independently selected from the group consisting of $C_1$-$C_3$ alkyl, oxo, and substituted N-attached heterocycloalkyl (e.g., optionally substituted with —COOH).

In some embodiments, R is substituted heteroalkyl, the heteroalkyl being substituted with one or more substituent, each substituent being independently selected from the group consisting of $C_1$-$C_3$ alkyl, oxo, —COOH, and thiol (e.g., wherein the branched heteroalkyl chain comprises two disulfide bonds and two —NH—).

In some embodiments, R is substituted heteroalkyl comprising one or more ester, amide, or disulfide bond within the heteroalkyl chain.

In some embodiments, R is substituted heteroalkyl, the heteroalkyl being substituted with —COOH, —$CH_2SH$, and/or optionally substituted N-attached heterocycloalkyl, and being further substituted with one or more other substituent, each substituent being independently selected from the group consisting of acetamide, amino, $C_1$-$C_6$ alkyl, thiol, and oxo.

In some embodiments, R is substituted heteroalkyl comprising two disulfide bonds within the heteroalkyl chain, the heteroalkyl being substituted with —COOH or substituted N-attached heterocycloalkyl. In some embodiments, the heteroalkyl is further substituted with one or more other substituent, each substituent being independently selected from the group consisting of acetamide and $C_1$-$C_6$ alkyl.

In some embodiments, R is substituted heteroalkyl comprising one disulfide bond within the heteroalkyl chain, the heteroalkyl being substituted with acetamide, —COOH, and —SH.

In some embodiments, R is heterocycloalkyl N-substituted with alkyl, the alkyl being further substituted with oxo and/or thiol.

In some embodiments, L is bond, X is absent, and R is substituted (e.g., linear or branched) heteroalkyl, the (e.g., linear or branched) heteroalkyl being substituted with one or more (heteroalkyl) substituent, each (heteroalkyl) substituent being independently selected from the group consisting of thioalkyl, amino, carboxylic acid, $C_1$-$C_6$ alkyl, acetamide, thiol, oxo, and optionally substituted (e.g., N-attached) heterocycloalkyl (e.g., optionally substituted with carboxylic acid).

In some embodiments, L is bond, X is absent, and R is substituted heteroalkyl, wherein the substituted heteroalkyl is substituted with one or more heteroalkyl substituent, at least one heteroalkyl substituent being independently selected from the group consisting of —COOH, substituted heterocycloalkyl, and thioalkyl. In some embodiments, the substituted heteroalkyl is further optionally substituted.

In some embodiments, R is:

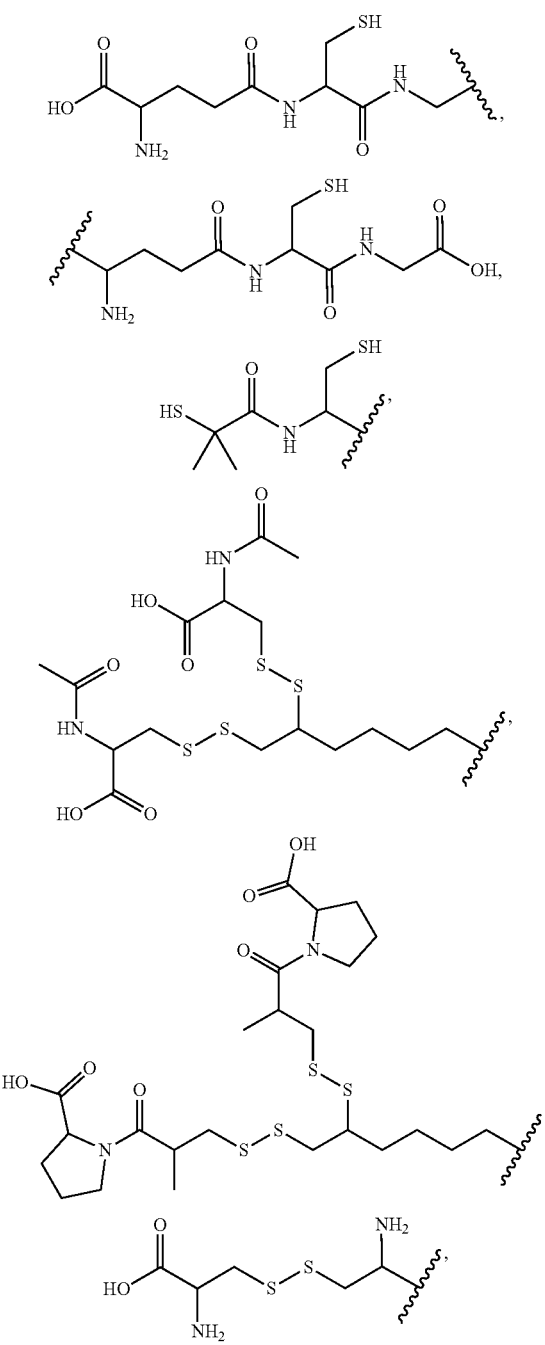

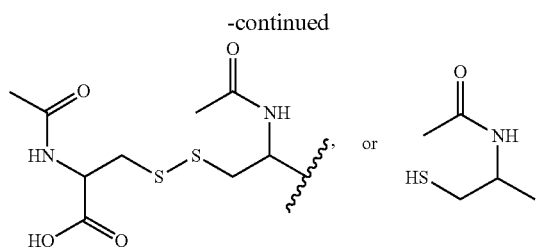
In some embodiments, R is:
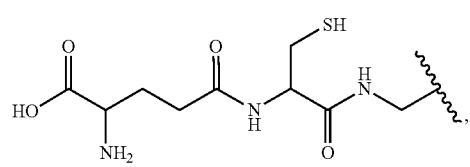 [SMILES: *CNC(=O)C(CS)NC(=O)CCC(N)C(=O)O]
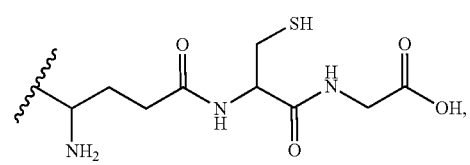
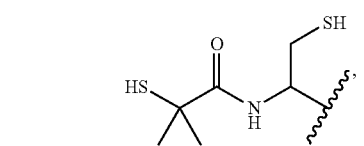
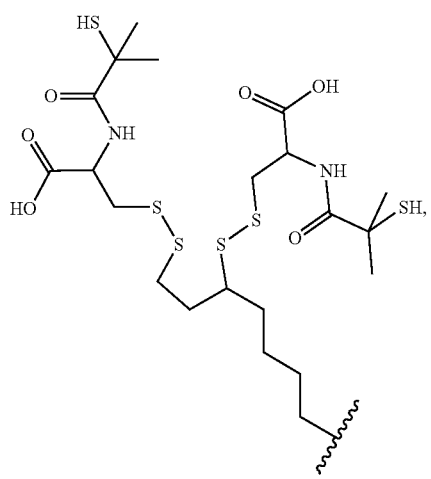
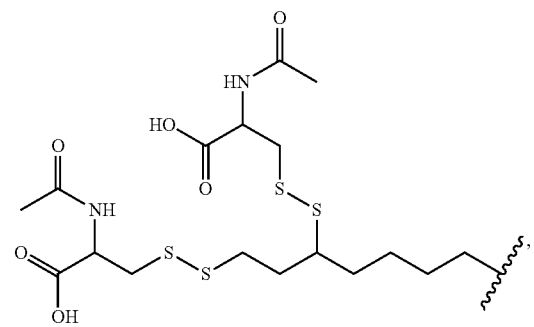
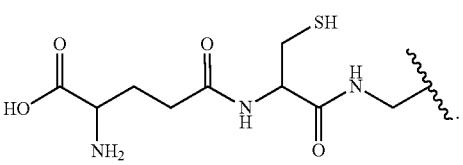
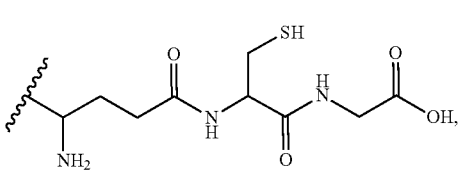 [SMILES: *C(N)CCC(=O)NC(CS)C(=O)NCC(=O)O]
In some embodiments, R is:
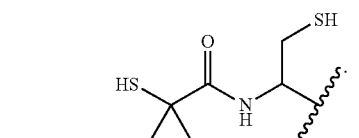
In some embodiments, R is:
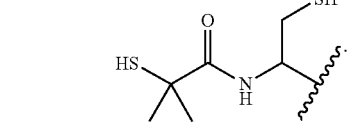
In some embodiments, R is:
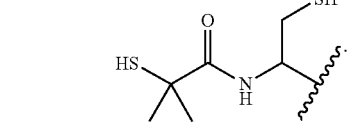

In some embodiments, R is:
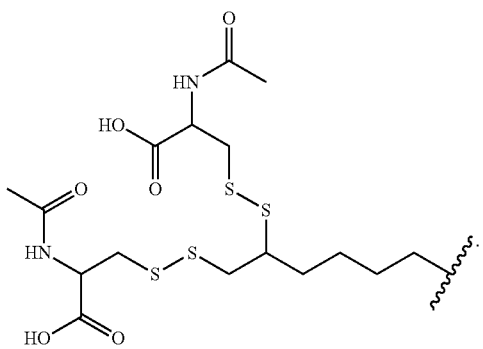 [SMILES: *CCCCC(CSSCC(NC(C)=O)C(=O)O)SSCC(NC(C)=O)C(=O)O]
In some embodiments, R is:
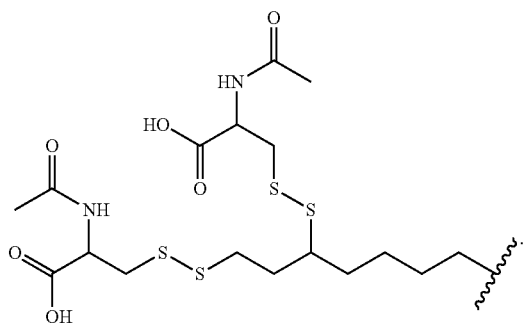 [SMILES: *CCCCC(CCSSCC(NC(C)=O)C(=O)O)SSCC(NC(C)=O)C(=O)O]
In some embodiments, R is:
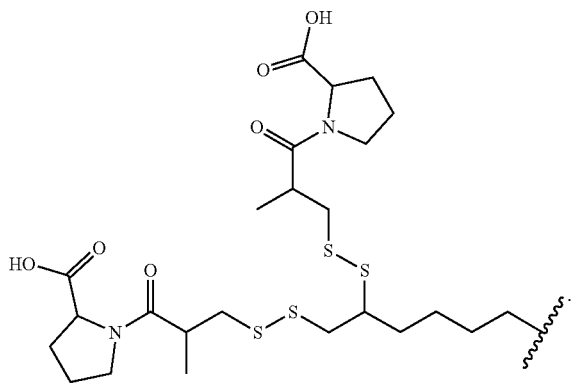 [SMILES: *CCCCC(CSSCC(C)C(=O)N1CCCC1C(=O)O)SSCC(C)C(=O)N1CCCC1C(=O)O]
In some embodiments, R is:
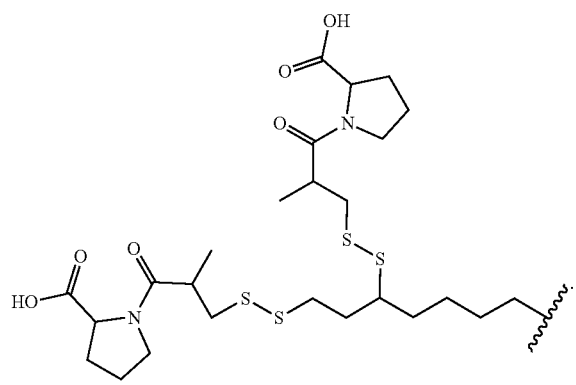 [SMILES: *CCCCC(CCSSCC(C)C(=O)N1CCCC1C(=O)O)SSCC(C)C(=O)N1CCCC1C(=O)O]
In some embodiments, R is:
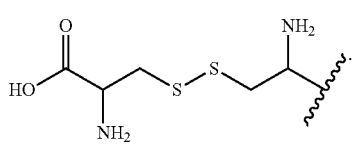 [SMILES: *C(N)CSSCC(N)C(=O)O]
In some embodiments, R is:
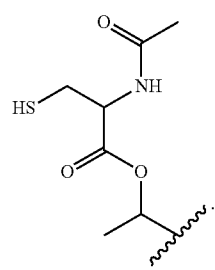
In some embodiments, R is:
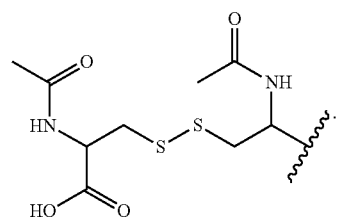 [SMILES: *C(CSSCC(NC(C)=O)C(=O)O)NC(C)=O]
In some embodiments, R is:
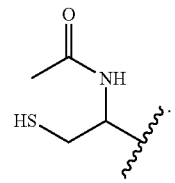 [SMILES: *C(CS)NC(C)=O]
In some embodiments, R is:
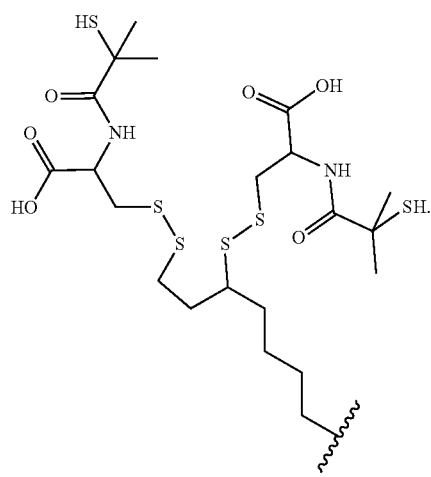 [SMILES: *CCCCC(CCSSCC(NC(=O)C(C)(C)S)C(=O)O)SSCC(NC(=O)C(C)(C)S)C(=O)O]

In some embodiments, R is substituted branched heteroalkyl.
In some embodiments, R is:
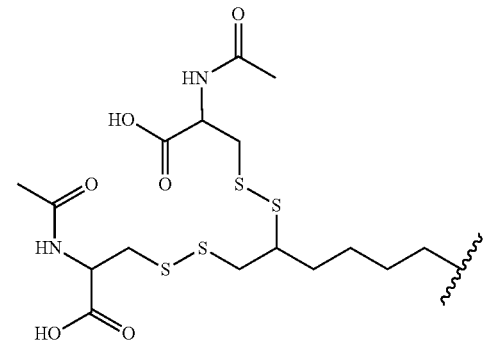
or
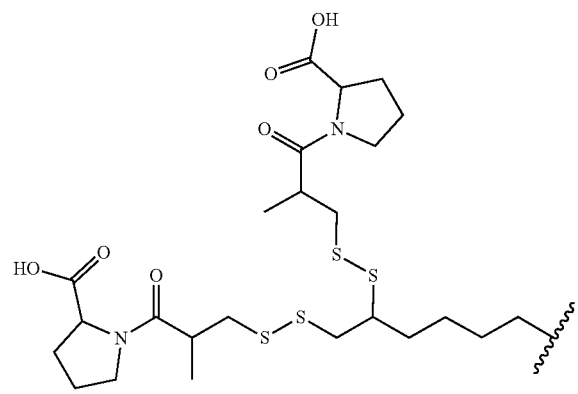
In some embodiments, R is:
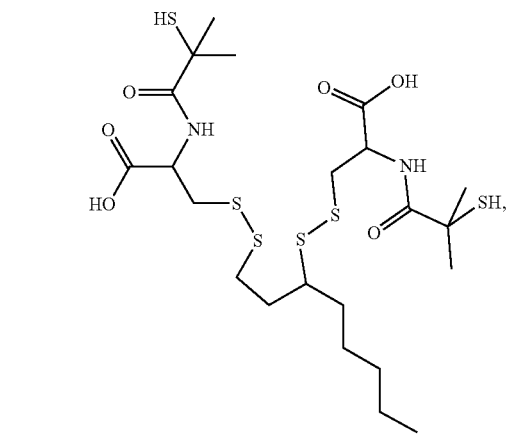
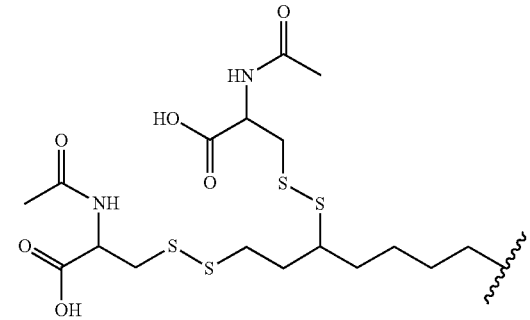
or
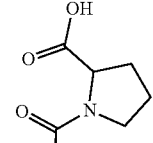
-continued
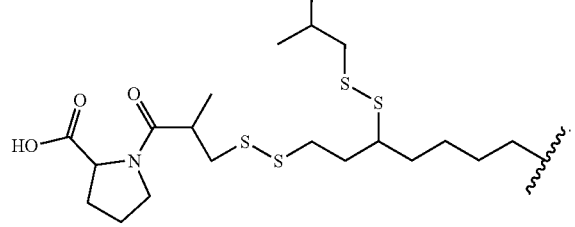
In some embodiments, R-X-L is:
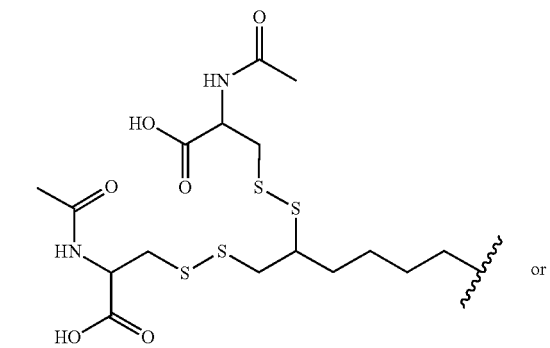
or
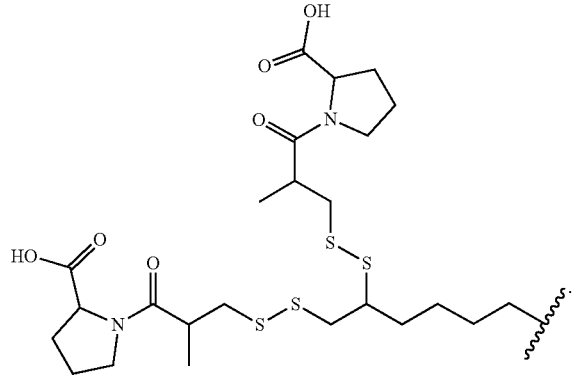
In some embodiments, R-X-L is:
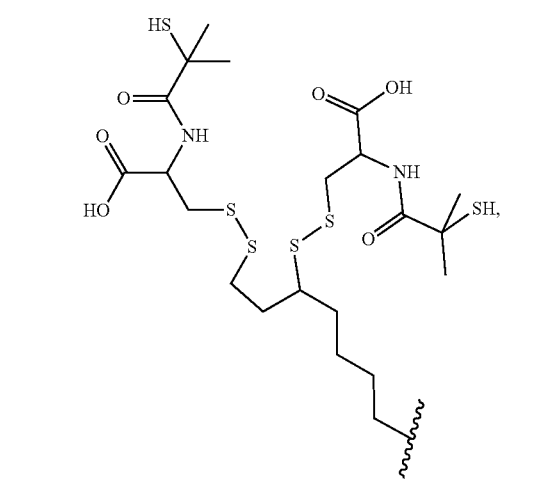

-continued
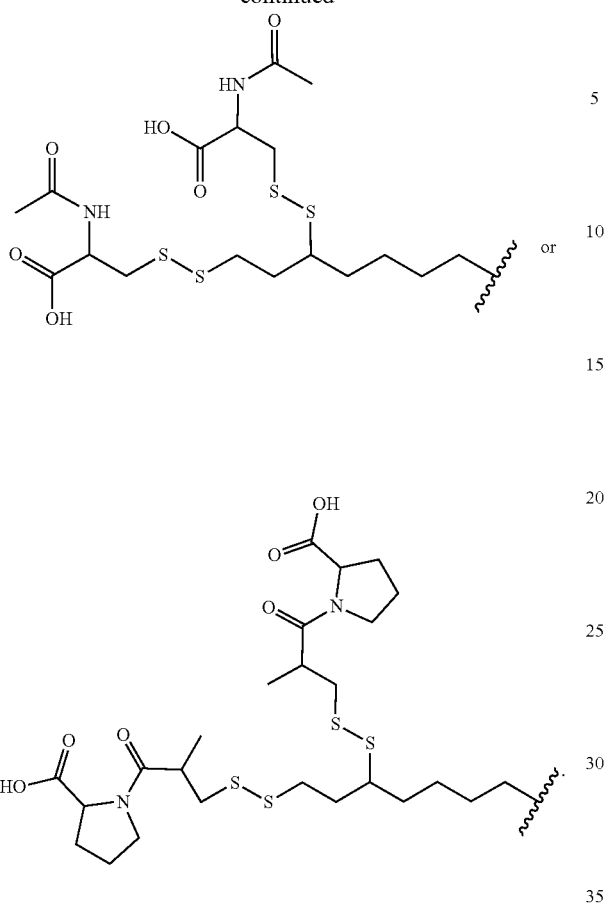
or
In some embodiments, R-X-L is:
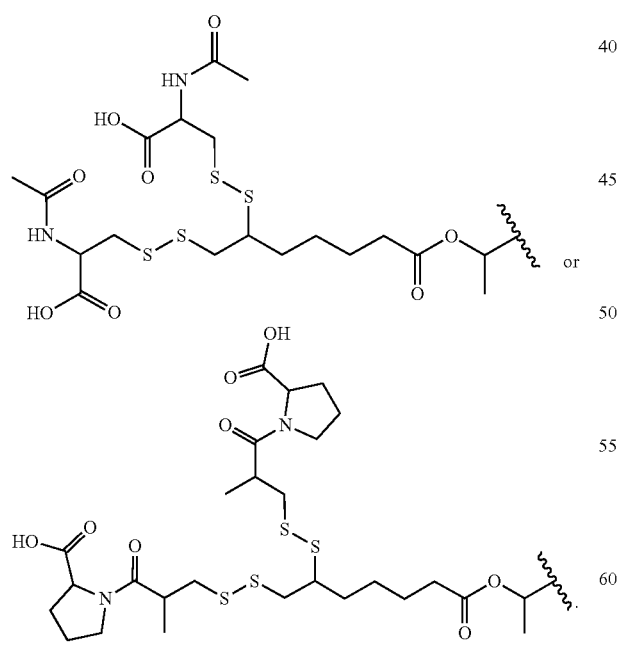
In some embodiments, R is substituted heterocycloalkyl (e.g., N-substituted with alkyl further substituted with oxo and/or thiol).
In some embodiments, R is:
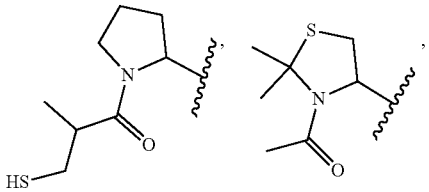
In some embodiments, R is:
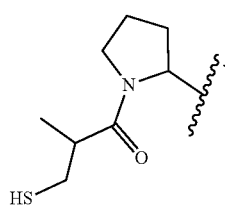 [SMILES: *C1CCCN1C(=O)C(C)CS]
In some embodiments, R is:
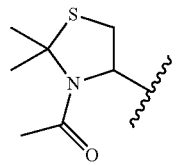
In some embodiments, R is:
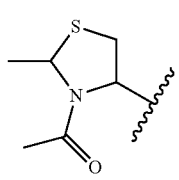
In some embodiments, R is:
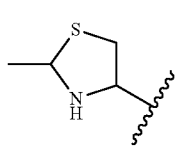

In some embodiments, R-X-L is

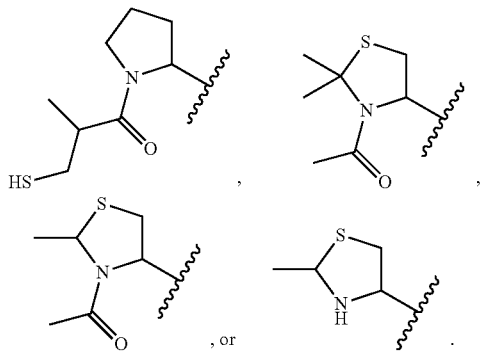

, or

.

In some embodiments, R comprises a radical of one or more keratolytic group (e.g., each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc)).

In some embodiments, R comprises a radical of one or more keratolytic group, each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc).

In some embodiments, R comprises a thiol radical of one or more keratolytic group, each thiol radical of the one or more keratolytic group being independently selected from the group consisting of a thiol radical of thioglycolic acid (TGA), a thiol radical of thiolactic acid (TLac), a thiol radical of dihydrolipoic acid (diHLip), a thiol radical of N-acetyl cysteine (NAC), a thiol radical of cysteine (Cys), a thiol radical of glutathione (GSH), a thiol radical of captopril (Cap), and a thiol radical of bucillamine (Buc).

In some embodiments, the (e.g., thiol) radical of the keratolytic agent comprises a (e.g., thiol) radical of one or more keratolytic group, each (e.g., thiol) radical of the one or more keratolytic group being independently selected from the group consisting of [Lac-Lac]., [Cys-Cys]., [diHLip-NAC]., [diHLip-NAC]., [diHLip-Cap-Cap]., [diHLip-Cap]., [diHLip-Cys-Cys]., [diHLip-Cys]., [diHLip-Lipox-Lipox]., and [diHLip-Lipox]..

In some embodiments, R is:

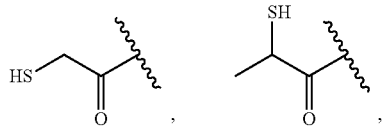

,

-continued

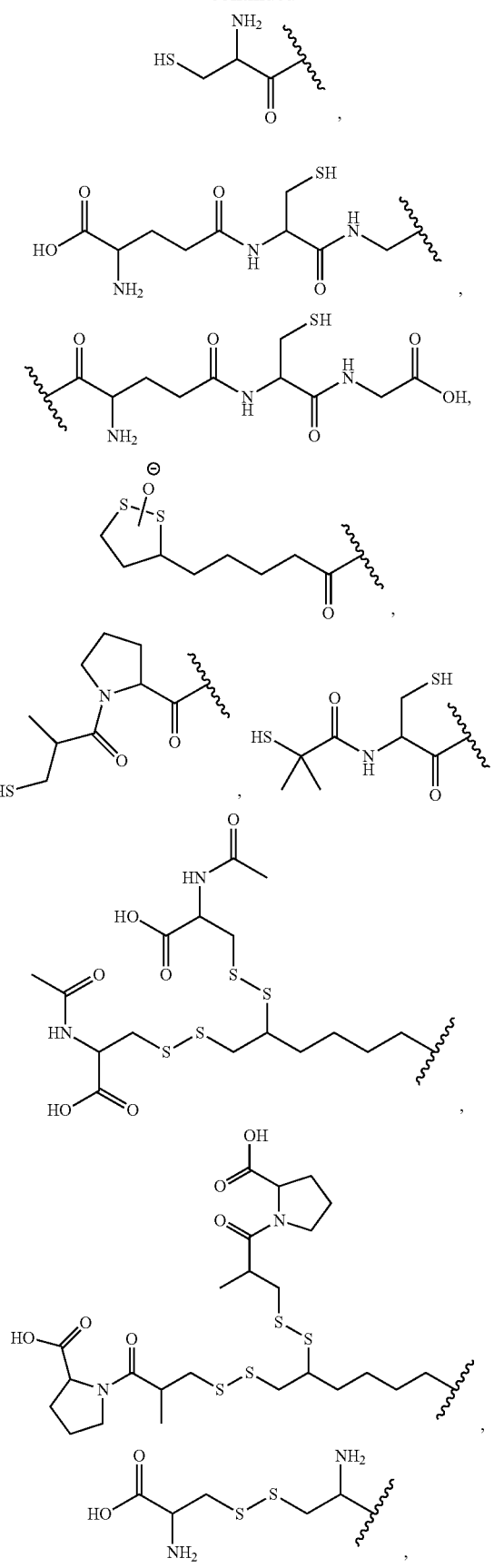

,

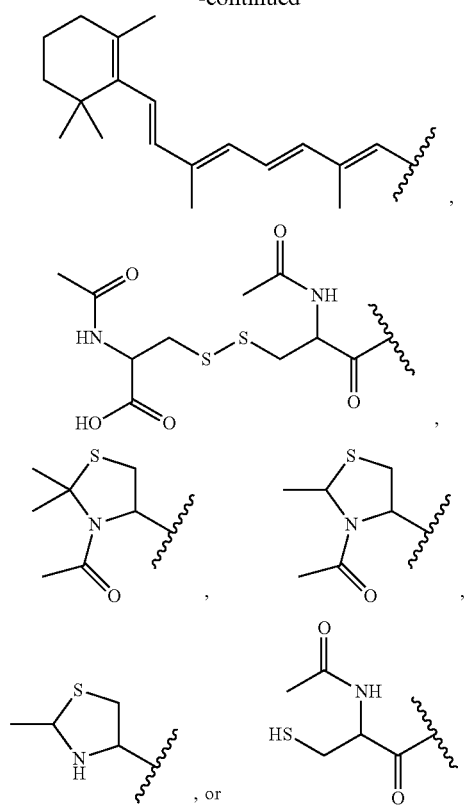
In some embodiments, R-X-L- is:
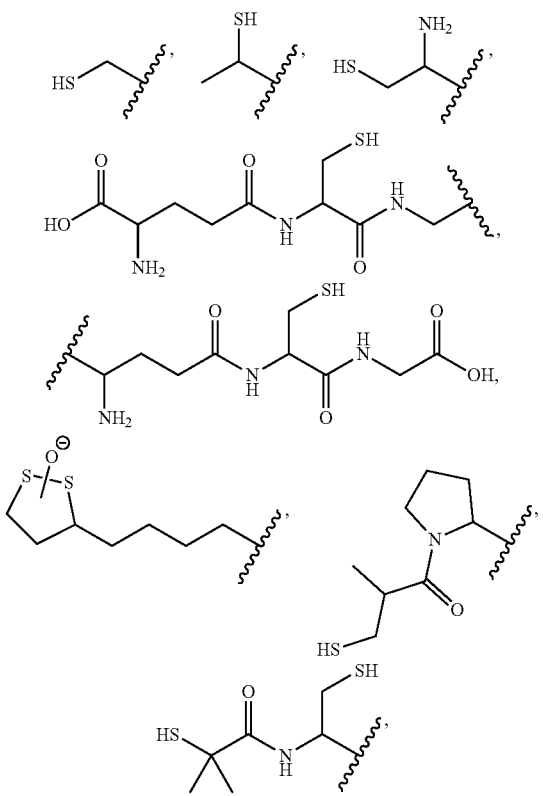
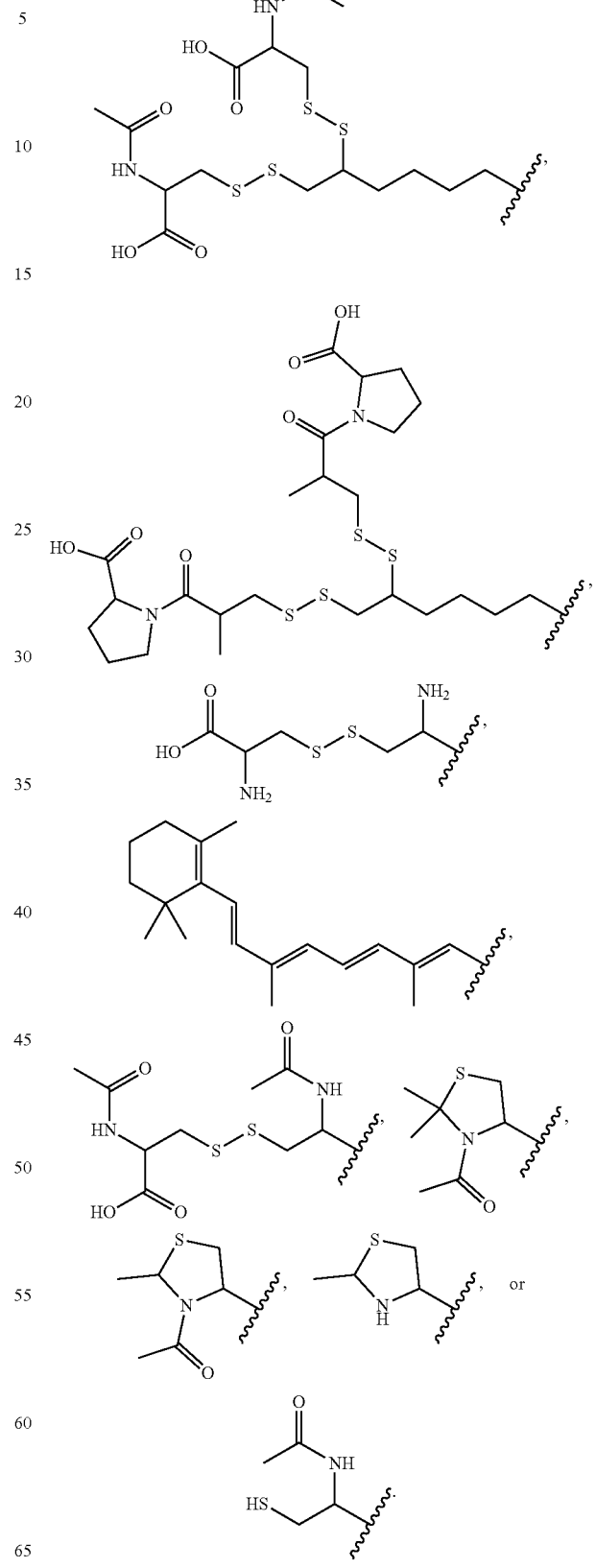

In some embodiments, R-X-L- is:
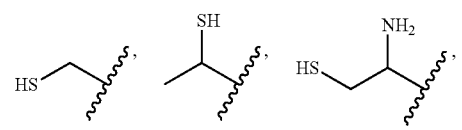
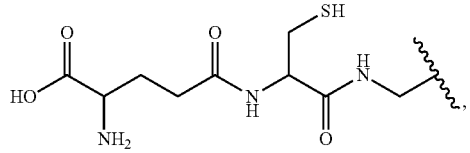
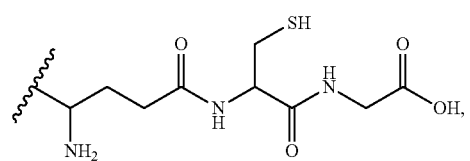
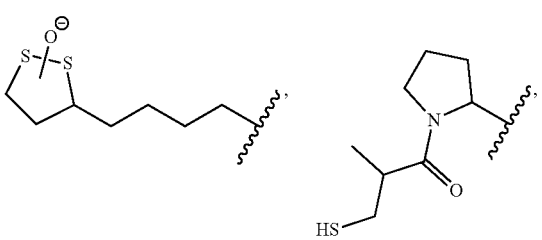
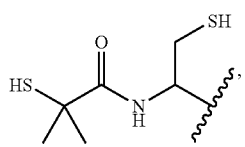
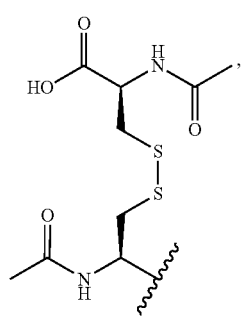
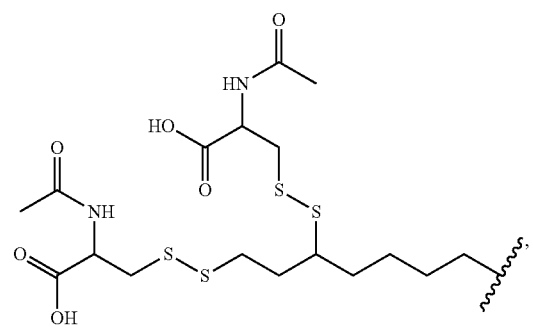
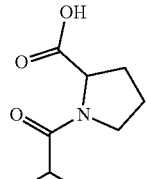
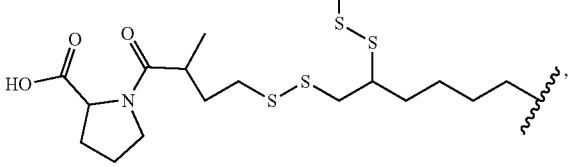
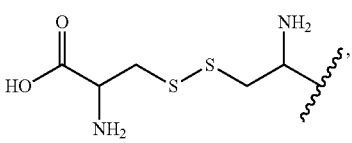
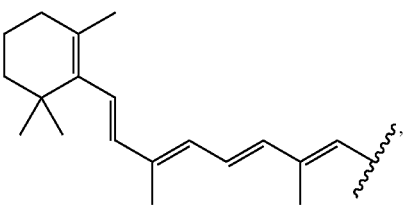
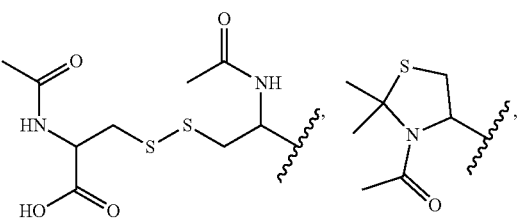
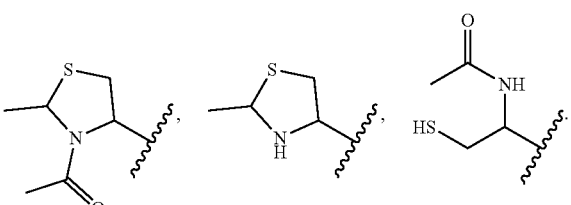
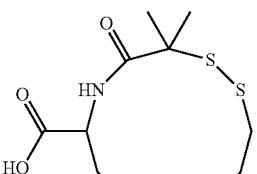
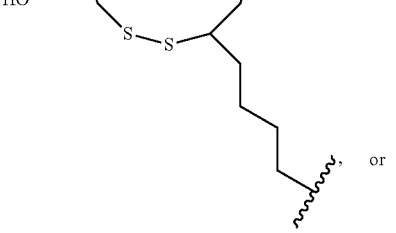

-continued

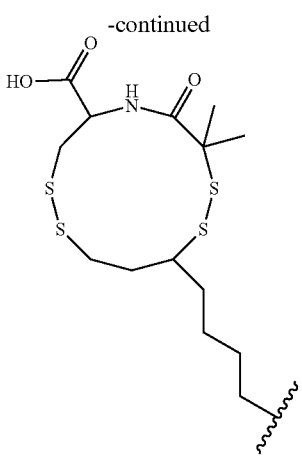

In some embodiments, the compound is other than a compound having the structure:

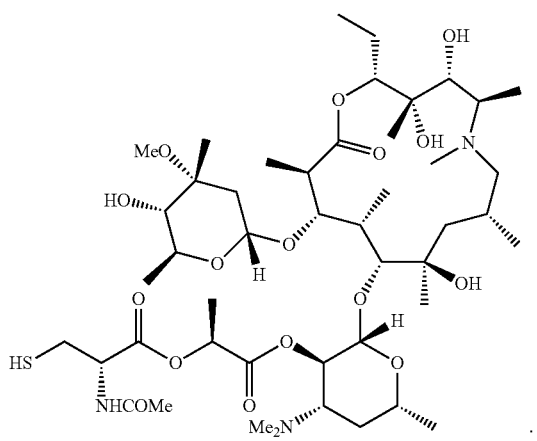

Provided in some embodiments herein is a compound, or a pharmaceutically acceptable salt or solvate (e.g., or a stereoisomer) thereof, having the structure of Formula (Ib):

Formula (Ib)

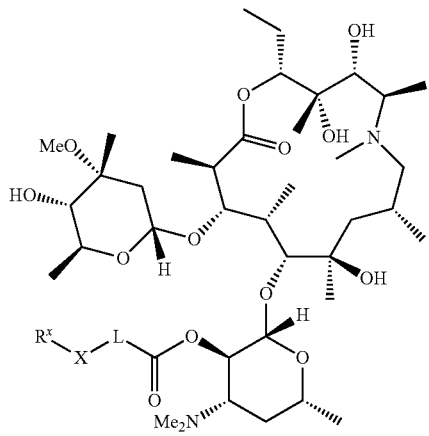

In some embodiments, L is bond, —(C=O)(OCR$^8$R$^9$)$_z$—, or —(C=O)(OCR$^8$R$^9$)$_z$O—. In some embodiments, each R$^8$ and R$^9$ is independently H, halogen, C$_1$-C$_3$-alkyl, C$_1$-C$_3$-haloalkyl, C$_1$-C$_3$-alkoxy, C$_3$-C$_5$-cycloalkyl, or R$^8$ and R$^9$ are taken together with the atoms to which they are attached to form a C$_3$-C$_5$-cycloalkyl. In some embodiments, z is 1-6. In some embodiments, X is absent or —O—.

In some embodiments, R$^x$ is:

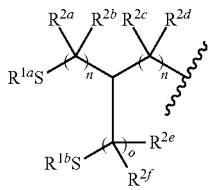

In some embodiments, R$^{1a}$ and R$^{1b}$ are each independently —H or —SR$^{1c}$. In some embodiments, each R$^{1c}$ is independently substituted or unsubstituted (e.g., straight or branched) alkyl (e.g., substituted with one or more (alkyl) substituent, each (alkyl) substituent being independently selected from the group consisting of carboxylic acid, —SH, thioalkyl, acetamide, amino, oxo, optionally substituted heterocycloalkyl (e.g., N-attached pyrrolidinyl substituted with —COOH)) or substituted or unsubstituted (e.g., straight or branched) heteroalkyl (e.g., substituted with one or more (heteroalkyl) substituent, each (heteroalkyl) substituent being independently selected from the group consisting of carboxylic acid, amino, thioalkyl, thiol, acetamide, and C$_1$-C$_3$ alkyl). In some embodiments, each R$^{2a}$, R$^{2b}$, R$^{2c}$, R$^{2d}$, R$^{2e}$, and R$^{2f}$ is independently H, halogen, C$_1$-C$_3$-alkyl, C$_1$-C$_3$-haloalkyl, C$_1$-C$_3$-alkoxy, C$_3$-C$_5$-cycloalkyl, or two of R$^{2a}$ and R$^{2b}$, R$^{2c}$ and R$^{2d}$, or R$^{2e}$ and R$^{2f}$ are taken together with the atoms to which they are attached to form a C$_3$-C$_5$-cycloalkyl. In some embodiments, m is an integer from 1-10. In some embodiments, n and o are each independently an integer from 0-3. In some embodiments, n and o are each independently an integer from 1-3.

In some embodiments, L, R$^8$, R$^9$, X, and z are each described elsewhere herein.

In some embodiments, n and o are each independently 0, 1, or 2. In some embodiments, n is 1 or 1. In some embodiments, n is 2. In some embodiments, o is 0 or 1. In some embodiments, o is 0. In some embodiments, o is 0 and n is 2.

In some embodiments, n and o are each independently 0 or 1. In some embodiments, n is 0 or 1.

In some embodiments, n is 1. In some embodiments, o is 0 or 1. In some embodiments, o is 0. In some embodiments, o is 0 and n is 1.

In some embodiments, m is 3-5. In some embodiments, m is 4. In some embodiments, o is 0 and m is 4. In some embodiments, n is 2 and m is 4. In some embodiments, o is 0, n is 2, and m is 4.

In some embodiments, m is 3-5. In some embodiments, m is 4. In some embodiments, n is 0 and m is 4. In some embodiments, n is 1 and m is 4. In some embodiments, o is 0, n is 1, and m is 4.

In some embodiments, each R$^{2a}$, R$^{2b}$, R$^{2c}$, R$^{2d}$, R$^{2e}$, and R$^{2f}$ is independently H, halogen, C$_1$-C$_3$alkyl, or C$_1$-C$_3$haloalkyl. In some embodiments, each R$^{2a}$, R$^{2b}$, R$^{2c}$, R$^{2d}$, R$^{2e}$, and R$^{2f}$ is independently H, halogen, C$_1$-C$_3$alkyl, or C$_1$-C$_3$haloalkyl, at least one of R$^{2a}$, R$^{2b}$, R$^{2c}$, R$^{2d}$, R$^{2e}$, and R$^{2f}$ being halogen, C$_1$-C$_3$alkyl, or C$_1$-C$_3$haloalkyl. In some embodiments, each R$^{2a}$, R$^{2b}$, R$^{2c}$, R$^{2d}$, R$^{2e}$, and R$^{2f}$ is H.

In some embodiments, $R^x$ is:

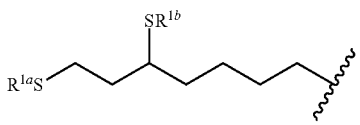

In some embodiments, $R^x$ is:

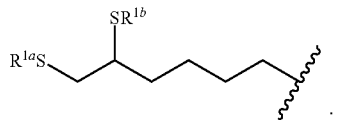

In some embodiments, $R^{1a}$ and $R^{1b}$ are each independently —H or —$SR^{1c}$. In some embodiments, each $R^{1c}$ is independently substituted or unsubstituted (e.g., straight or branched) alkyl (e.g., substituted with one or more (alkyl) substituent, each (alkyl) substituent being independently selected from the group consisting of carboxylic acid, —SH, thioalkyl, acetamide, amino, oxo, optionally substituted heterocycloalkyl (e.g., N-attached pyrrolidinyl substituted with —COOH)) or substituted or unsubstituted (e.g., straight or branched) heteroalkyl (e.g., substituted with one or more (heteroalkyl) substituent, each (heteroalkyl) substituent being independently selected from the group consisting of carboxylic acid, amino, thioalkyl, thiol, acetamide, and $C_1$-$C_3$ alkyl).

In some embodiments, $R^{1a}$ is —H or —$SR^{1c}$ and $R^{1b}$ is —$SR^{1c}$, or $R^{1a}$ is —$SR^{1c}$ and $R^{1b}$ is —H or —$SR^{1c}$. In some embodiments, $R^{1a}$ is —H or —$SR^{1c}$ and $R^{1b}$ is —$SR^{1c}$. In some embodiments, $R^{1a}$ is —H and $R^{1b}$ is —$SR^{1c}$. In some embodiments, $R^{1a}$ is —$SR^{1c}$ and $R^{1b}$ is —H or —$SR^{1c}$. In some embodiments, $R^{1a}$ is —$SR^{1c}$ and $R^{1b}$ is —$SR^{1c}$. In some embodiments, $R^{1a}$ and $R^{1b}$ are each —$SR^{1c}$.

In some embodiments, $R^{1a}$ and $R^{1b}$ each independently comprise a radical of one or more keratolytic group (e.g., each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc)).

In some embodiments, $R^{1a}$ and $R^{1b}$ are each independently a radical of one or more keratolytic group, each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc).

In some embodiments, $R^{1a}$ and $R^{1b}$ each independently comprise a (thiol) radical of one or more keratolytic group, each (thiol) radical of the one or more keratolytic group being independently selected from the group consisting of a (thiol) radical of thioglycolic acid (TGA), a (thiol) radical of thiolactic acid (TLac), a (thiol) radical of dihydrolipoic acid (diHLip), a (thiol) radical of N-acetyl cysteine (NAC), a (thiol) radical of cysteine (Cys), a (thiol) radical of glutathione (GSH), a (thiol) radical of captopril (Cap), and a (thiol) radical of bucillamine (Buc).

In some embodiments, $R^{1a}$ and $R^{1b}$ are each independently a thiol radical of one or more keratolytic group, each thiol radical of the one or more keratolytic group being independently selected from the group consisting of a thiol radical of thioglycolic acid (TGA), a thiol radical of thiolactic acid (TLac), a thiol radical of dihydrolipoic acid (diHLip), a thiol radical of N-acetyl cysteine (NAC), a thiol radical of cysteine (Cys), a thiol radical of glutathione (GSH), a thiol radical of captopril (Cap), and a thiol radical of bucillamine (Buc).

In some embodiments, the (e.g., thiol) radical of the keratolytic agent comprises a (e.g., thiol) radical of one or more keratolytic group, each (e.g., thiol) radical of the one or more keratolytic group being independently selected from the group consisting of [Lac-Lac]., [Lac-NAC]., [Cys-Cys]., [diHLip-NAC-NAC]., [diHLip-NAC]., [diHLip-Cap-Cap]., [diHLip-Cap]., [diHLip-Cys-Cys]., [diHLip-Cys]., [diHLip-Lipox-Lipox]., and [diHLip-Lipox]..

In some embodiments, the thiol radical of the keratolytic group is the point of attachment of $R^{1a}$ and/or $R^{1b}$ to the rest of the molecule. In some embodiments, (the thiol radical of) $R^{1a}$ and/or $R^{1b}$ each independently attach to the rest of the molecule to form a disulfide bond.

In some embodiments, $R^{1a}$ and $R^{1b}$ are each independently —H or:

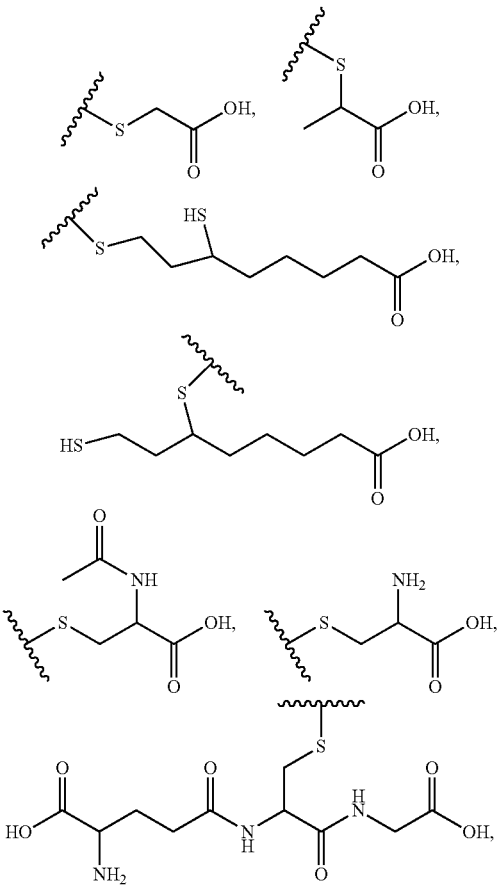

-continued

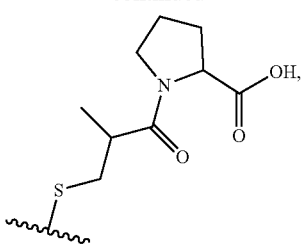

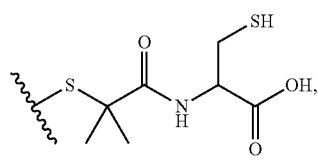

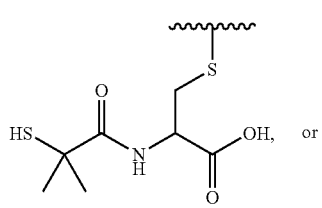 or

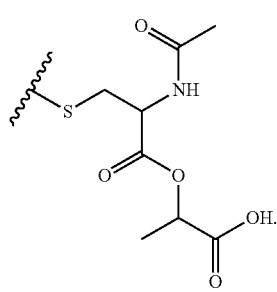

In some embodiments, $R^{1a}$ and $R^{1b}$ are the same. In some embodiments, $R^{1a}$ and $R^{1b}$ are each —$SR^{1c}$ and the same. In some embodiments, $R^{1a}$ and $R^{1b}$ are different. In some embodiments, $R^{1a}$ and $R^{1b}$ are each $SR^{1c}$ and different.

In some embodiments, L is bond, X is absent, and $R^x$ is:

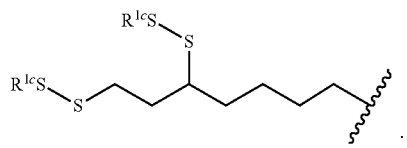

In some embodiments, L is —(C=O)OCH(CH$_3$)—, X is absent, and $R^x$ is:

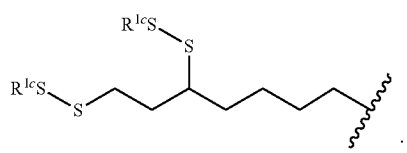

In some embodiments, L is —(C=O)OCH(CH$_3$)—, X is absent, and $R^x$ is:

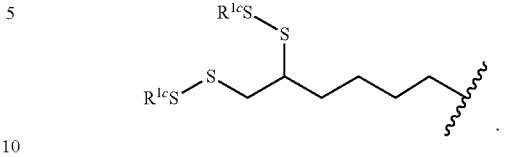

In some embodiments, each $R^{1c}$ is independently substituted or unsubstituted (e.g., straight or branched) alkyl or substituted or unsubstituted (e.g., straight or branched) heteroalkyl. In some embodiments, each $R^{1c}$ is independently substituted (e.g., straight or branched) alkyl or substituted (e.g., straight or branched) heteroalkyl. In some embodiments, each $R^{1c}$ is independently substituted (e.g., straight or branched) alkyl. In some embodiments, each $R^{1c}$ is (the same) substituted (e.g., straight or branched) alkyl. In some embodiments, each $R^{1c}$ is (a different) substituted (e.g., straight or branched) alkyl.

In some embodiments, each $R^{1c}$ is independently substituted (e.g., straight or branched) heteroalkyl. In some embodiments, each $R^{1c}$ is (the same) substituted (e.g., straight or branched) heteroalkyl. In some embodiments, each $R^{1c}$ is (a different) substituted (e.g., straight or branched) heteroalkyl.

In some embodiments, one of $R^{1c}$ is substituted (e.g., straight or branched) alkyl and the other is substituted (e.g., straight or branched) heteroalkyl.

In some embodiments, each $R^{1c}$ is the same. In some embodiments, each $R^{1c}$ is different.

In some embodiments, each $R^{1c}$ is independently substituted (e.g., straight or branched) alkyl, the substituted alkyl being substituted with one or more (alkyl) substituent, each (alkyl) substituent being independently selected from the group consisting of carboxylic acid, —SH, thioalkyl (e.g., —CH$_2$SH), acetamide (e.g., —NH(C=O)CH$_3$), amino, oxo, and optionally substituted heterocycloalkyl (e.g., N-attached pyrrolidinyl substituted with —COOH).

In some embodiments, the optionally substituted heterocycloalkyl is:

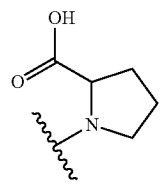

In some embodiments, each $R^{1c}$ is independently substituted (e.g., straight or branched) heteroalkyl, the substituted heteroalkyl being substituted with one or more (heteroalkyl) substituent, each (heteroalkyl) substituent being independently selected from the group consisting of carboxylic acid, amino, thioalkyl (e.g., —CH$_2$SH), thiol, acetamide (e.g., —NH(C=O)CH$_3$), and C$_1$-C$_3$ alkyl.

In some embodiments, $R^{1c}$ is:

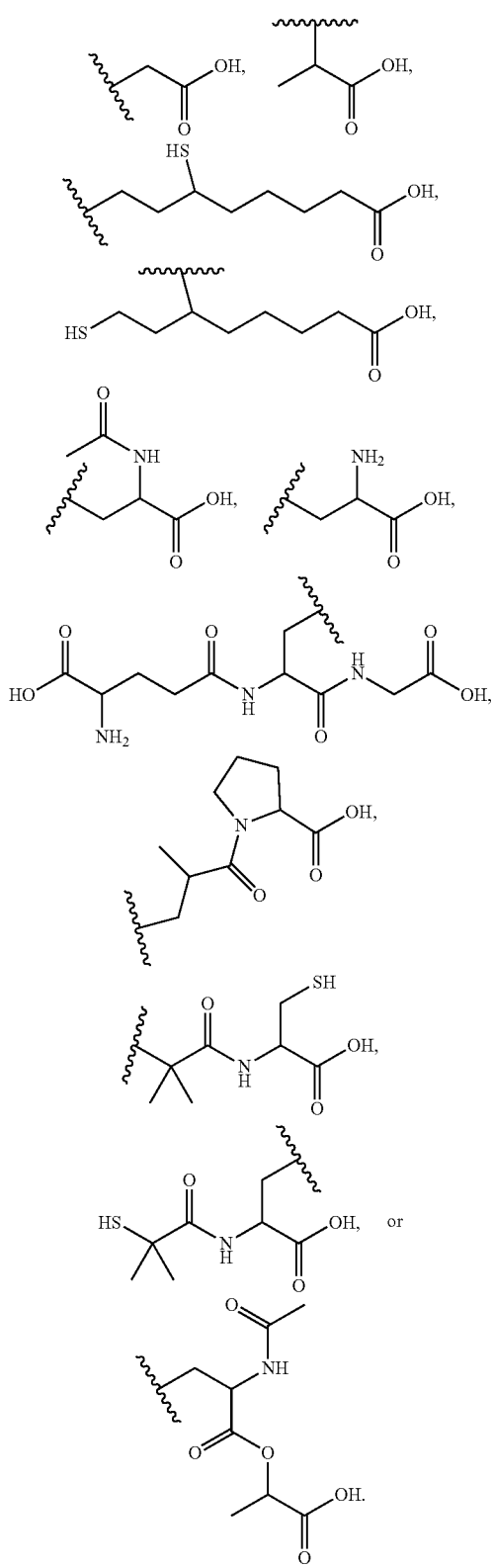

In some embodiments, $R^{1a}$, $R^{1b}$, and each $R^{1c}$ each independently comprise one or more substituent that is a carboxylic acid or an ester. In some embodiments, $R^{1a}$, $R^{1b}$, and each $R^{1c}$ each independently comprise one or more substituent that is a carboxylic acid (e.g., —(C=O)OH). In some embodiments, $R^{1a}$ comprises one or more substituent that is a carboxylic acid (e.g., —(C=O)OH). In some embodiments, $R^{1b}$ comprises one or more substituent that is a carboxylic acid (e.g., —(C=O)OH). In some embodiments, each $R^{1c}$ independently comprises one or more substituent that is a carboxylic acid (e.g., —(C=O)OH). In some embodiments, $R^{1a}$, $R^{1b}$, and each $R^{1c}$ each independently comprise one or more substituent that is an ester (e.g., —(C=O)O—$C_1$-$C_4$alkyl). In some embodiments, $R^{1a}$ comprises one or more substituent that is an ester (e.g., —(C=O)O—$C_1$-$C_4$alkyl). In some embodiments, $R^{1b}$ comprises one or more substituent that is an ester (e.g., —(C=O)O—$C_1$-$C_4$alkyl). In some embodiments, each $R^{1c}$ independently comprises one or more substituent that is an ester (e.g., —(C=O)O—$C_1$-$C_4$alkyl).

In some embodiments, the —(C=O)OH of $R^{1a}$, $R^{1b}$, and/or $R^{1c}$ is optionally esterified (e.g., —(C=O)OH or —(C=O)O—$C_1$-$C_4$alkyl). In some embodiments, the $C_1$-$C_4$alkyl is methyl, ethyl, propyl, isopropyl, butyl, or t-butyl.

Provided in some embodiments herein is a compound, or a pharmaceutically acceptable salt or solvate (e.g., or a stereoisomer) thereof, having the structure of Formula (Ic):

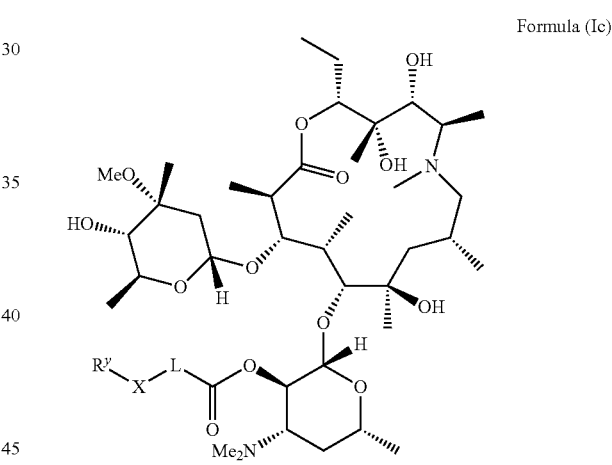

Formula (Ic)

In some embodiments, L is bond, —(C=O)(OCR$^8$R$^9$)$_z$—, or —(C=O)(OCR$^8$R$^9$)$_z$O—. In some embodiments, each $R^8$ and $R^9$ is independently H, halogen, $C_1$-$C_3$-alkyl, $C_1$-$C_3$-haloalkyl, $C_1$-$C_3$-alkoxy, $C_3$-$C_5$-cycloalkyl, or $R^8$ and $R^9$ are taken together with the atoms to which they are attached to form a $C_3$-$C_5$-cycloalkyl. In some embodiments, z is 1-6. In some embodiments, X is absent or —O—.

In some embodiments, $R^y$ is:

In some embodiments, each $R^{4a}$ and $R^{4b}$ is independently H, halogen, or substituted or unsubstituted alkyl. In some embodiments, p is an integer from 1-10. In some embodiments, q is an integer from 1-3.

In some embodiments, L, $R^8$, $R^9$, z, and X are each described elsewhere herein.

In some embodiments, $R^y$ is:

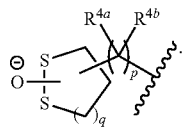

In some embodiments, each $R^{4a}$ and $R^{4b}$ is independently H, halogen, or substituted or unsubstituted alkyl. In some embodiments, p is an integer from 1-10. In some embodiments, q is an integer from 1-3.

In some embodiments, q is 1 or 2. In some embodiments, q is 1. In some embodiments, p is an integer from 3-5. In some embodiments, p is 4. In some embodiments, q is 1 and p is 4.

In some embodiments, each $R^{4a}$ and $R^{4b}$ is independently H or substituted or unsubstituted alkyl.

In some embodiments, each $R^{4a}$ and $R^{4b}$ is independently H, halogen, $C_1$-$C_3$alkyl, or $C_1$-$C_3$haloalkyl. In some embodiments, each $R^{4a}$ and $R^{4b}$ is H.

In some embodiments, q is 1, p is an integer from 3-5, and each $R^{4a}$ and $R^{4b}$ is independently H, halogen, $C_1$-$C_3$alkyl, or $C_1$-$C_3$haloalkyl. In some embodiments, q is 1, p is 4, and each $R^{4a}$ and $R^{4b}$ is H.

In some embodiments, L is —(C═O)OCH(CH$_3$)—, X is absent, and $R^y$ is:

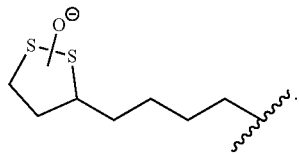

In some embodiments, provided herein is a compound, or a pharmaceutically acceptable salt or solvate (e.g., or a stereoisomer) thereof, having the structure of Formula (Id):

Formula (Id)

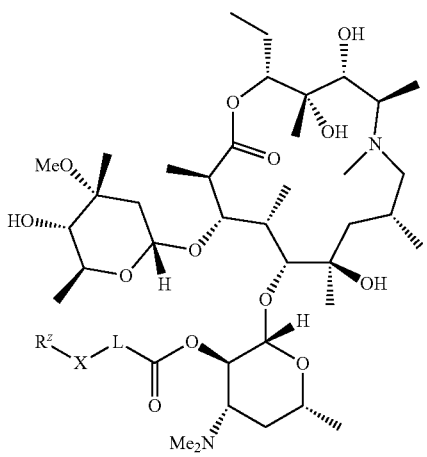

In some embodiments, L is bond, —(C═O)(OCR$^8$R$^9$)$_z$—, or —(C═O)(OCR$^8$R$^9$)$_z$O—. In some embodiments, each $R^8$ and $R^9$ is independently H, halogen, $C_1$-$C_3$-alkyl, $C_1$-$C_3$-haloalkyl, $C_1$-$C_3$-alkoxy, $C_3$-$C_5$-cycloalkyl, or $R^8$ and $R^9$ are taken together with the atoms to which they are attached to form a $C_3$-$C_5$-cycloalkyl. In some embodiments, z is 1-6. In some embodiments, X is absent or —O—.

In some embodiments, $R^z$ is:

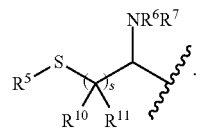

In some embodiments, $R^5$ is —$SR^{1c}$. In some embodiments, $R^{1c}$ is substituted or unsubstituted (e.g., straight or branched) alkyl (e.g., substituted with one or more (alkyl) substituent, each (alkyl) substituent being independently selected from the group consisting of carboxylic acid, —SH, thioalkyl, acetamide, amino, oxo, optionally substituted heterocycloalkyl (e.g., N-attached pyrrolidinyl substituted with —COOH)) or substituted or unsubstituted (e.g., straight or branched) heteroalkyl (e.g., substituted with one or more (heteroalkyl) substituent, each (heteroalkyl) substituent being independently selected from the group consisting of carboxylic acid, amino, thioalkyl, thiol, acetamide, and $C_1$-$C_3$ alkyl). In some embodiments, $R^6$ and $R^7$ are each independently H, substituted or unsubstituted alkyl, or substituted or unsubstituted heteroalkyl. In some embodiments, each $R^{10}$ and $R^{11}$ is independently H, halogen, $C_1$-$C_3$-alkyl, $C_1$-$C_3$-haloalkyl, $C_1$-$C_3$-alkoxy, $C_3$-$C_5$-cycloalkyl, or two of $R^{10}$ and $R^{11}$ are taken together with the atoms to which they are attached to form a $C_3$-$C_5$-cycloalkyl. In some embodiments, s is an integer from 1-10.

In some embodiments, L, $R^8$, $R^9$, X, and z are each described elsewhere herein.

In some embodiments, $R^5$ is —$SR^{1c}$. In some embodiments, $R^{1c}$ is substituted or unsubstituted (e.g., straight or branched) alkyl (e.g., substituted with one or more (alkyl) substituent, each (alkyl) substituent being independently selected from the group consisting of carboxylic acid, —SH, thioalkyl, acetamide, amino, oxo, optionally substituted heterocycloalkyl (e.g., N-attached pyrrolidinyl substituted with —COOH)) or substituted or unsubstituted (e.g., straight or branched) heteroalkyl (e.g., substituted with one or more (heteroalkyl) substituent, each (heteroalkyl) substituent being independently selected from the group consisting of carboxylic acid, amino, thioalkyl, thiol, acetamide, and $C_1$-$C_3$ alkyl). In some embodiments, $R^6$ and $R^7$ are each independently H, substituted or unsubstituted alkyl, or substituted or unsubstituted heteroalkyl. In some embodiments, each $R^{10}$ and $R^{11}$ is independently H, halogen, $C_1$-$C_3$-alkyl, $C_1$-$C_3$-haloalkyl, $C_1$-$C_3$-alkoxy, $C_3$-$C_5$-cycloalkyl, or two or more of $R^{10}$ and $R^{11}$ are taken together with the atoms to which they are attached to form a $C_3$-$C_5$-cycloalkyl. In some embodiments, s is an integer from 1-10.

In some embodiments $R^{1c}$ is substituted alkyl or substituted heteroalkyl.

In some embodiments $R^{1c}$ is substituted alkyl, the alkyl being substituted with one or more alkyl substituent, each alkyl substituent being independently selected from the group consisting of carboxylic acid, —SH, thioalkyl, acetamide, amino, oxo, and optionally substituted heterocycloalkyl. In some embodiments, $R^{1c}$ is alkyl substituted with one or more alkyl substituent, each alkyl substituent being independently selected from the group consisting of carboxylic acid and acetamide.

In some embodiments $R^{1c}$ is substituted heteroalkyl, the heteroalkyl being substituted with one or more heteroalkyl substituent, each heteroalkyl substituent being independently selected from the group consisting of oxo, carboxylic acid, amino, thioalkyl, thiol, acetamide, and $C_1$-$C_3$ alkyl. In some embodiments, $R^{1c}$ is heteroalkyl substituted with carboxylic acid.

In some embodiments, $R^{1c}$ is substituted heteroalkyl, the heteroalkyl being substituted with —COOH and oxo. In some embodiments, $R^{1c}$ is substituted heteroalkyl, the heteroalkyl being substituted with oxo and acetamide. In some embodiments, $R^{1c}$ is substituted heteroalkyl, the heteroalkyl being substituted with $C_1$-$C_3$ alkyl, oxo, and substituted N-attached heterocycloalkyl. In some embodiments, $R^{1c}$ is substituted heteroalkyl, the heteroalkyl being substituted with —COOH, $C_1$-$C_3$ alkyl, oxo, and thiol.

In some embodiments, $R^6$ and $R^7$ are each independently H or substituted or unsubstituted alkyl (e.g., $C_1$-$C_3$ alkyl optionally substituted with oxo). In some embodiments, $R^6$ and $R^7$ are each independently H or $C_1$-$C_3$ alkyl optionally substituted with oxo. In some embodiments, $R^6$ and $R^7$ are each independently H or —(C=O)CH$_3$. In some embodiments, $R^6$ is H and $R^7$ is H or —(C=O)CH$_3$. In some embodiments, $R^6$ is H and $R^7$ is —(C=O)CH$_3$. In some embodiments, $R^6$ and $R^7$ are H.

In some embodiments, each $R^{10}$ and $R^{11}$ is independently H, halogen, $C_1$-$C_3$alkyl, or $C_1$-$C_3$haloalkyl.

In some embodiments, each $R^{10}$ and $R^{11}$ is H.

In some embodiments, s is 1-3. In some embodiments, s is 1. In some embodiments, s is 1 and $R^{10}$ and $R^{11}$ are H.

In some embodiments, $R^6$, $R^7$, $R^{10}$ and $R^{11}$ are each H, and s is 1-3.

In some embodiments, $R^5$ comprises a radical of one or more keratolytic group (e.g., each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc)).

In some embodiments, $R^5$ is a radical of one or more keratolytic group, each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc).

In some embodiments, $R^5$ comprises a (thiol) radical of one or more keratolytic group, each (thiol) radical of the one or more keratolytic group being independently selected from the group consisting of a (thiol) radical of thioglycolic acid (TGA), a (thiol) radical of thiolactic acid (TLac), a (thiol) radical of dihydrolipoic acid (diHLip), a (thiol) radical of N-acetyl cysteine (NAC), a (thiol) radical of cysteine (Cys), a (thiol) radical of glutathione (GSH), a (thiol) radical of captopril (Cap), and a (thiol) radical of bucillamine (Buc).

In some embodiments $R^5$ is a thiol radical of one or more keratolytic group, each thiol radical of the one or more keratolytic group being independently selected from the group consisting of a thiol radical of thioglycolic acid (TGA), a thiol radical of thiolactic acid (TLac), a thiol radical of dihydrolipoic acid (diHLip), a thiol radical of N-acetyl cysteine (NAC), a thiol radical of cysteine (Cys), a thiol radical of glutathione (GSH), a thiol radical of captopril (Cap), and a thiol radical of bucillamine (Buc).

In some embodiments, the (e.g., thiol) radical of the keratolytic agent comprises a (e.g., thiol) radical of one or more keratolytic group, each (e.g., thiol) radical of the one or more keratolytic group being independently selected from the group consisting of [Lac-Lac]., [Lac-NAC]., [Cys-Cys]., [diHLip-NAC-NAC]., [diHLip-NAC]., [diHLip-Cap-Cap]., [diHLip-Cap]., [diHLip-Cys-Cys]., [diHLip-Cys]., [diHLip-Lipox-Lipox]., and [diHLip-Lipox]..

In some embodiments, the thiol radical of the keratolytic group is the point of attachment of $R^5$ to the rest of the molecule. In some embodiments, $R^5$ attaches to the rest of the molecule to form a disulfide bond.

In some embodiments, $R^5$ is:

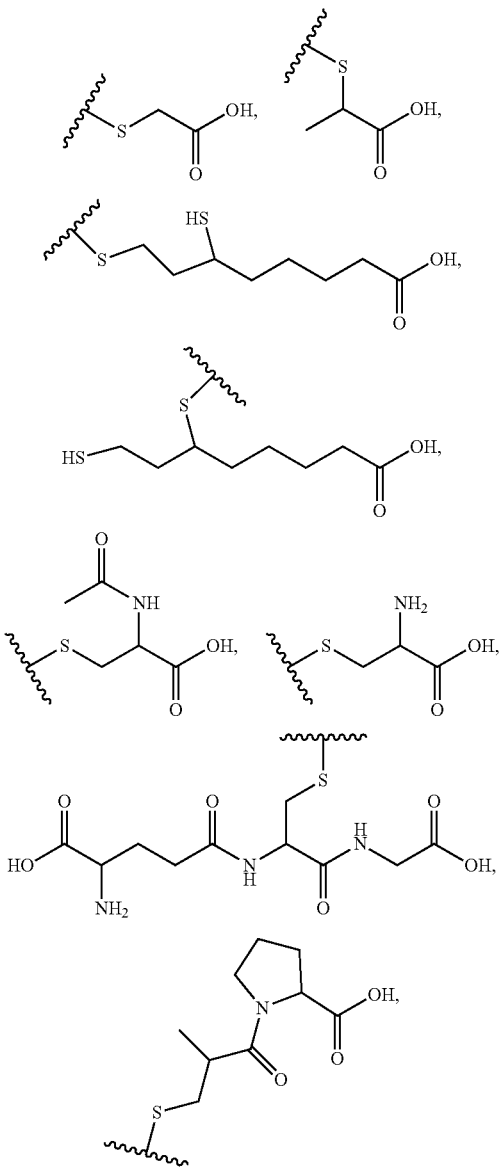

-continued

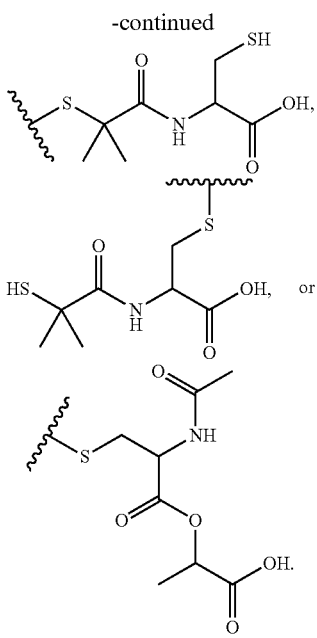

In some embodiments, $R^5$ comprises one or more substituent that is a carboxylic acid or an ester. In some embodiments, $R^5$ comprises one or more substituent that is a carboxylic acid (e.g., —(C=O)OH). In some embodiments, $R^5$ comprises one or more substituent that is an ester (e.g., —(C=O)O—$C_1$-$C_4$alkyl).

In some embodiments, the —(C=O)OH of $R^5$ is optionally esterified (e.g., —(C=O)OH or —(C=O)O—$C_1$-$C_4$alkyl). In some embodiments, the $C_1$-$C_4$alkyl is methyl, ethyl, propyl, isopropyl, butyl, or t-butyl.

In some embodiments, $R^z$ is:

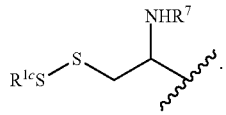

In some embodiments, $R^7$ is H or —(C=O)$CH_3$. In some embodiments, $R^7$ is H. In some embodiments, $R^7$ is —(C=O)$CH_3$.

In some embodiments, $R^{1c}$ is described elsewhere herein.

In some embodiments, provided herein is a pharmaceutical composition comprising any compound provided herein, such as a compound represented by any one of Formula (I), Formula (I-A), Formula (Ia), Formula (Ib), Formula (Ic), Formula (Id), Table 1, or a pharmaceutically acceptable salt thereof, and at least one pharmaceutically acceptable excipient. In some embodiments, the pharmaceutical composition is suitable for ophthalmic administration. In some embodiments, the pharmaceutical composition is suitable for topical ophthalmic administration. In some embodiments, topical ophthalmic administration is administration in and/or around the eye, such as to the eyelid margin.

In some embodiments, topical ophthalmic administration is administration to the ocular surface and the inner surface to the eyelid.

In some embodiments, a compound or a pharmaceutical composition comprising any compound provided herein, such as a compound of any one of Formula (I), Formula (I-A), Formula (Ia), Formula (Ib), Formula (Ic), Formula (Id), Table 1, or a pharmaceutically acceptable salt thereof, is substantially hydrolytically stable (e.g., stable in an aqueous composition (e.g., solution), such as a buffer solution or ophthalmically acceptable aqueous composition). In some embodiments, the compound or the pharmaceutical composition is formulated in an aqueous vehicle. In some embodiments, the compound or the pharmaceutical composition is formulated and stored in an aqueous vehicle. In some instances, compositions or formulations provided herein are chemically and/or physically stable in an aqueous composition.

In some embodiments, a compound provided herein, such as a compound of any one of Formula (I), Formula (I-A), Formula (Ia), Formula (Ib), Formula (Ic), Formula (Id), Table 1, or a pharmaceutically acceptable salt thereof, is reduced to one or more keratolytic agent (e.g., a free form of a radical of Formula (I), Formula (I-A), Formula (Ia), Formula (Ib), Formula (Ic), Formula (Id), or Table 1, such as wherein R is a negative charge or H) and/or hydrolyzed to an active pharmaceutical agent (e.g., a free form of a radical of Formula (I), Formula (I-A), Formula (Ia), Formula (Ib), Formula (Ic), Formula (Id), or Table 1, such as wherein R is a negative charge or H). In some embodiments, the compound or pharmaceutical composition is reduced to one or more keratolytic agent in an ocular space. In some embodiments, the compound or pharmaceutical composition is reduced to one or more keratolytic agent by a reductase in an ocular space.

In some embodiments, a compound provided herein, such as a compound of any one of Formula (I), Formula (I-A), Formula (Ia), Formula (Ib), Formula (Ic), Formula (Id), Table 1, or a pharmaceutically acceptable salt thereof, is hydrolyzed to an active pharmaceutical agent (e.g., a free form of a radical of Formula (I), Formula (I-A), Formula (Ia), Formula (Ib), Formula (Ic), Formula (Id), or Table 1, such as wherein R is a negative charge or H) and a keratolytic agent. In some embodiments, the compound or pharmaceutical composition is hydrolyzed to an active pharmaceutical agent and a keratolytic agent in an ocular space. In some embodiments, the compound or pharmaceutical composition is hydrolyzed to an active pharmaceutical agent and a keratolytic agent by an esterase in an ocular space. In some embodiments, the active pharmaceutical agent is an anti-bacterial agent. In some embodiments the anti-bacterial agent is azithromycin. In some embodiments, the keratolytic agent is a carboxylic acid. In some embodiments, the carboxylic acid is selected from the group consisting of acetic acid, glycolic acid, lactic acid, lipoic acid, pivalic acid, isobutryic acid, butyric acid, propionic acid, formic acid, and carbonic acid. In some embodiments, the active keratolytic agent is a thiol.

In some embodiments, a compound or a pharmaceutical composition comprising any compound provided herein, such as a compound of any one of Formula (I), Formula (I-A), Formula (Ia), Formula (Ib), Formula (Ic), Formula (Id), Table 1, or a pharmaceutically acceptable salt thereof. In certain embodiments, the composition further comprises an amount of a free form of a radical of any of Formula (I), Formula (I-A), Formula (Ia), Formula (Ib), Formula (Ic), Formula (Id), Table 1, or the like (such as wherein the free form is the radical, wherein R is a negative charge or an H). In some embodiments, a composition provided herein comprises a (e.g., weight or molar) ratio of a compound provided herein to a free form of a radical of Formula (I), Formula (I-A), Formula (Ia), Formula (Ib), Formula (Ic), Formula (Id), Table 1, or a pharmaceutically acceptable salt thereof (e.g., wherein R is a negative charge or an H) is about 1:99 to about 100:0 (e.g., the amount of the free form of the radical relative to the overall amount of free form of the radical plus the conjugate is between 0% (weight or molar) and 99%). In some embodiments, the relative amount of the free form of the radical is 0% to about 50%, such 0% to about 20%, 0% to about 10%, about 0.1% to about 10%, about 0.1% to about 5%, less than 5%, less than 2.5%, less than 2%, or the like (percentages being weight/weight or mole/mole percentages). In some instances, such aqueous compositions are pre-manufactured or are manufactured at the time of application in order to maintain high concentrations of the compound relative to the free form of a radical thereof. In some embodiments, such concentrations of the compound are present in the composition for at least 45 minutes in an aqueous composition (such as in an aqueous composition, e.g., a HEPES buffer, such as under the conditions described herein, such as in Table 2). Table 2 of the Examples illustrate good stability of the compositions provided herein and such recitations are incorporated in the disclosure hereof. Further, in some instances, compounds provided herein release free form of a radical of a compound of Formula (I), Formula (I-A), Formula (Ia), Formula (Ib), Formula (Ic), Formula (Id), or Table 1, (e.g., wherein R is a negative charge or H), such as when administered to an individual (e.g., ocular (e.g., periocular) or dermatological administration). In more specific instances, when administered to an individual at a location with esterases and/or reductases present, rapid release of active (free) forms of a radical of Formula (I), Formula (I-A), Formula (Ia), Formula (Ib), Formula (Ic), Formula (Id), or Table 1, (e.g., wherein R is a negative charge or H) (and, a keratolytic agent and/or agent that further produces active keratolytic agent(s) (e.g., by further hydrolysis and/or reduction thereof)).

In some embodiments, provided herein a compound or a pharmaceutical composition comprising any compound provided herein, such as a compound of any one of Formula (I), Formula (I-A), Formula (Ia), Formula (Ib), Formula (Ic), Formula (Id), Table 1, or a pharmaceutically acceptable salt thereof, has keratolytic effects (e.g., reduces disulfide (S—S) bonds) (e.g., in any environment provided herein).

Provided in some embodiments herein is a method of treating inflammation and/or hyperkeratosis, the method comprising administering to an individual (e.g., in need thereof) any compound provided herein (e.g., of any Formula or Table provided herein) (e.g., in a therapeutically effective amount). In specific embodiments, the inflammation and/or hyperkeratosis is inflammation and/or hyperkeratosis of the eye, periocular structures (e.g., eyelid), and/or skin.

Provided in some embodiments herein is a method of treating a dermal or an ocular disease or disorder in an individual, comprising administering to the individual in need thereof a composition comprising any compound provided herein, such as a compound represented by any one of Formula (I), Formula (I-A), Formula (Ia), Formula (Ib), Formula (Ic), Formula (Id), Table 1, or a pharmaceutically acceptable salt thereof. In some embodiments, the dermal or the ocular disease or disorder is associated with keratosis, microbial infiltration, microbial infection, inflammation, or any combination thereof.

Provided in some embodiments herein is a method of treating a dermatological or an ophthalmic disease or disorder in an individual in need of thereof, comprising administering to the individual in need thereof a composition comprising any compound provided herein, such as a compound represented by any one of Formula (I), Formula (I-A), Formula (Ia), Formula (Ib), Formula (Ic), Formula (Id), Table 1, or a pharmaceutically acceptable salt thereof. In some embodiments, the dermatological or ophthalmic disease or disorder is inflammation or hyperkeratosis of the eyes or skin (e.g., the ocular surface). In some embodiments, the dermatological or ophthalmic dermatological disease or disorder is selected from the group consisting of meibomian gland dysfunction (MGD), dry eye disease (DED), ocular manifestations of graft versus host disease, vernal keratoconjunctivitis, atopic keratoconjunctivitis, Cornelia de Lange Syndrome, evaporative eye disease, aqueous deficiency dry eye, blepharitis, and seborrheic blepharitis.

In some embodiments, the dermatological or ophthalmic disease or disorder is inflammation or hyperkeratosis (e.g., of the eyes or skin), such as, for example, meibomian gland dysfunction (MGD), dry eye disease (DED), ocular manifestations of graft versus host disease, vernal keratoconjunctivitis, atopic keratoconjunctivitis, Cornelia de Lange Syndrome, evaporative eye disease, aqueous deficiency dry eye, blepharitis, seborrheic blepharitis, or any combination thereof.

In some embodiments, the ophthalmic disease or disorder is selected from dry eye, lid wiper epitheliopathy (LWE), contact lens discomfort (CLD), contact lens discomfort, dry eye syndrome, evaporative dry eye syndrome, aqueous deficiency dry eye syndrome, blepharitis, keratitis, meibomian gland dysfunction, conjunctivitis, lacrimal gland disorder, inflammation of the anterior surface of the eye, infection of the anterior surface of the eye, infection of the lid, demodex lid infestation, lid wiper epitheliopathy and autoimmune disorder of the anterior surface of the eye.

In some embodiments, provided herein is a method of treating an ocular (e.g., periocular) or dermatological indication (e.g., associated with keratolytic activity, inflammation, and/or microbial infiltration), the method comprising administering a therapeutically effective amount of a compound or composition provided herein. In some embodiments, a composition provided herein (e.g., used in a method provided herein) comprises a compound provided herein in a therapeutically effective amount (e.g., at a concentration effective to treat keratosis/keratolytic activity, inflammation, and/or microbial infiltration), in the eye, surrounding tissue, or skin. In some embodiments, a (e.g., pharmaceutical and/or ophthalmic) composition provided herein comprises about 0.1 wt. % to about 10 wt. % of a compound provided herein.

In some embodiments, ocular and/or dermatological disorders include, for example, inflammatory conditions of the eyelids (e.g., hordeolum (stye), blepharitis, and chalazion), ocular surface (e.g., dry eye disease and anterior uveitis) and posterior eye (e.g., posterior and pan-uveitis), abnormalities of the periocular glands (e.g., meibomian gland dysfunction (MGD)), allergic-type conditions, (e.g., eczema, atopic dermatitis, atopic keratoconjunctivitis refractory to topical steroid treatment, and vernal keratoconjunctivitis), surgical complications (e.g., corneal transplant rejection, post-corneal transplant glaucoma, cataracts secondary to phakic corneal transplant, fungal infections in keratoplasty patients, and post-LASIK dry eye and/or poor refractive outcomes), corneal abnormalities (e.g., inflammatory corneal ulceration, rheumatoid corneal ulcers, and Thygeson's superficial punctate keratitis), conjunctival abnormalities (e.g., iridocyclitis, ligneous conjunctivitis), ocular complications from systemic treatments and/or autoimmune diseases (e.g., pauciarticular juvenile rheumatoid arthritis, graft versus host disease, and sjogren's syndrome) and/or infectious disease of the anterior surface of the eye.

In some embodiments, provided herein are compositions and methods for the treatment of ocular and periocular abnormalities that have multifactorial etiologies and interactions.

INCORPORATION BY REFERENCE

All publications, patents, and patent applications mentioned in this specification are herein incorporated by reference for the specific purpose identified herein.

DETAILED DESCRIPTION

Certain Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The terms "treat," "treating," or "treatment" as used herein, include reducing, alleviating, abating, ameliorating, relieving, or lessening the symptoms associated with a disease, disease sate, or indication (e.g., addiction, such as opioid addiction, or pain) in either a chronic or acute therapeutic scenario. Also, treatment of a disease or disease state described herein includes the disclosure of use of such compound or composition for the treatment of such disease, disease state, or indication.

"Amino" refers to the —$NH_2$ radical.
"Cyano" refers to the —CN radical.
"Nitro" refers to the —$NO_2$ radical.
"Oxo" refers to the =O radical.
"Alkyl" generally refers to a straight or branched hydrocarbon chain radical consisting solely of carbon and hydrogen atoms, such as having from one to fifteen carbon atoms (e.g., $C_1$-$C_{15}$ alkyl). Unless otherwise state, alkyl is saturated or unsaturated (e.g., an alkenyl, which comprises at least one carbon-carbon double bond). Disclosures provided herein of an "alkyl" are intended to include independent recitations of a saturated "alkyl," unless otherwise stated. Alkyl groups described herein are generally monovalent, but may also be divalent (which may also be described herein as "alkylene" or "alkylenyl" groups). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. In general, alkyl groups are each independently substituted or unsubstituted. Each recitation of "alkyl" provided herein, unless otherwise stated, includes a specific and explicit recitation of an unsaturated "alkyl" group. Similarly, unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is optionally substituted as described for "alkyl" groups.

"Alkylene" or "alkylene chain" generally refers to a straight or branched divalent alkyl group linking the rest of the molecule to a radical group, such as having from one to twelve carbon atoms, for example, methylene, ethylene, propylene, i-propylene, n-butylene, and the like. Unless stated otherwise specifically in the specification, an alkylene chain is optionally substituted as described for alkyl groups herein.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system can contain hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" or "aryl-alkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" or "cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl or cycloalkyl is saturated (i.e., containing single C—C bonds, no double or triple bonds between two carbons) or unsaturated (i.e., containing one or more double bonds or triple bonds). Examples of saturated cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carboxylic acid," "COOH," or "(C=O)OH" refers to a radical of the formula —COOH. Each recitation of "carboxylic acid," "COOH," or "(C=O)OH" provided herein, unless otherwise stated, includes a specific and explicit recitation of an esterified "carboxylic acid," "COOH," or "(C=O)OH" group (e.g., or radical thereof). In some embodiments, the esterified carboxylic acid group (or radical thereof) is (C=O)O—$C_1$-$C_4$alkyl, wherein alkyl is as defined hereinabove. In some embodiments, "carboxylic acid," "COOH," or "(C=O)OH" is COOH. In some embodiments, "carboxylic acid," "COOH," or "(C=O)OH" is (C=O)O—$C_1$-$C_4$alkyl.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkenyl" refers to a radical of the formula —$R^c$-carbocyclyl where $R^c$ is an alkenylene chain as defined above. The alkenylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Halo" or "halogen" refers to fluoro, bromo, chloro, or iodo substituents.

"Haloalkyl" refers to an alkyl radical, as defined above, that is substituted by one or more halogen radicals, as defined above, for example, trihalomethyl, dihalomethyl, halomethyl, and the like. In some embodiments, the haloalkyl is a fluoroalkyl, such as, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

The term "heteroalkyl" refers to an alkyl group as defined above in which one or more skeletal carbon atoms of the alkyl are substituted with a heteroatom (with the appropriate number of substituents or valencies—for example, —CH$_2$— may be replaced with —NH— or —O—). For example, each substituted carbon atom is independently substituted with a heteroatom, such as wherein the carbon is substituted with a nitrogen, oxygen, sulfur, or other suitable heteroatom. In some instances, each substituted carbon atom is independently substituted for an oxygen, nitrogen (e.g. —NH—, —N(alkyl)-, or —N(aryl)- or having another substituent contemplated herein), or sulfur (e.g. —S—, —S(=O)—, or —S(=O)$_2$—). In some embodiments, a heteroalkyl is attached to the rest of the molecule at a carbon atom of the heteroalkyl. In some embodiments, a heteroalkyl is attached to the rest of the molecule at a heteroatom of the heteroalkyl. In some embodiments, a heteroalkyl is a $C_1$-$C_{18}$ heteroalkyl. In some embodiments, a heteroalkyl is a $C_1$-$C_{12}$ heteroalkyl. In some embodiments, a heteroalkyl is a $C_1$-$C_6$ heteroalkyl. In some embodiments, a heteroalkyl is a $C_1$-$C_4$ heteroalkyl. Representative heteroalkyl groups include, but are not limited to —OCH$_2$OMe, or —CH$_2$CH$_2$OMe. In some embodiments, heteroalkyl includes alkoxy, alkoxyalkyl, alkylamino, alkylaminoalkyl, aminoalkyl, heterocycloalkyl, heterocycloalkyl, and heterocycloalkylalkyl, as defined herein. Unless stated otherwise specifically in the specification, a heteroalkyl group is optionally substituted as defined above for an alkyl group.

"Heteroalkylene" refers to a divalent heteroalkyl group defined above which links one part of the molecule to another part of the molecule. Unless stated specifically otherwise, a heteroalkylene is optionally substituted, as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl).

Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

In general, optionally substituted groups are each independently substituted or unsubstituted. Each recitation of an optionally substituted group provided herein, unless otherwise stated, includes an independent and explicit recitation of both an unsubstituted group and a substituted group (e.g., substituted in certain embodiments, and unsubstituted in certain other embodiments). Unless otherwise stated, substituted groups may be substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Pharmaceutically acceptable salt" includes both acid and base addition salts. A pharmaceutically acceptable salt of any one of the pharmacological agents described herein is intended to encompass any and all pharmaceutically suitable salt forms. Exemplary pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Compositions

The meibomian glands are large sebaceous glands located in the eyelids, and unlike skin, are unassociated with hair. The meibomian glands produce the lipid layer of the tear film that protects it against evaporation of the aqueous phase. The meibomian gland orifice is located on the epithelial side of the lid margin, and can be a few hundred microns from the mucosal side. The glands are located on both upper and lower eyelids, with higher amounts of the glands on the upper eyelid. A single meibomian gland is composed of clusters of secretory acini that are arranged circularly around a long central duct and connected to it by short ductules. The terminal part of the central duct is lined by an ingrowth of the epidermis that covers the free lid margin and forms a short excretory duct that opens as an orifice at the posterior part of the lid margin just anterior to the mucocutaneous junction near the inner lid border. The oily secretion composed of lipids is synthesized within the secretory acini. The lipid secretion is a liquid at near body temperature and is delivered to the skin of the lid margin as a clear fluid, called "meibum." It forms shallow reservoirs on the upper and lower lid margins, and consists of a complex mixture of cholesterol, wax, cholesteryl esters, phospholipids, with small amounts of triglycerides, triacylglycerols, and hydrocarbons. The separate meibomian glands are arranged in parallel, and in a single row throughout the length of the tarsal plates in the upper and lower lids. The extent of the glands corresponds roughly to the dimensions of the tarsal plates.

The term "keratinized obstruction" as used herein refers to a blockage of the meibomian gland, regardless of the location of the blockage. In some embodiments, the blockage is complete, whereas in other embodiments, the blockage is partial. Regardless of the degree of blockage, such keratinized obstruction leads to meibomian gland dysfunction. In some embodiments, the keratinized obstruction is composed of keratinized material and lipids. In some embodiments, the keratinized obstruction is a blockage at the meibomian gland orifice and excretory duct. In some embodiments, the keratinized obstruction is caused by keratinization of the epithelium at the lid margin and meibomian gland. In certain instances, the keratin obstruction is influenced by the migration or aberrant differentiation of stem cells. In some embodiments, the keratinized obstruction results in reduced delivery of oil to the lid margin and tear film, and stasis inside the meibomian gland that causes increased pressure, resultant dilation, acinar atrophy, and low secretion. In certain instances, keratinization of the meibomian gland causes degenerative gland dilation and atrophy.

Ocular surface diseases is a group of diseases including, but not limited to, dry eye syndrome (including evaporative DES and/or aqueous deficiency DES), blepharitis, keratitis, meibomian gland dysfunction, conjunctivitis, lacrimal gland disorder, contact lens related conditions and inflammatory, infectious, or autoimmune diseases or disorders of the anterior surface of the eye. The term, "meibomian gland dysfunction," as used herein, refers to chronic, diffuse abnormality of the meibomian glands, that is characterized by terminal duct obstruction or qualitative or quantitative changes in the glandular secretion, or both. MGD may result in alteration of the tear film, eye irritation symptoms, inflammation, or ocular surface disease. The most prominent aspects of MGD are obstruction of the meibomian gland orifices and terminal ducts and changes in the meibomian gland secretions.

In some instances, meibomian gland dysfunction (MGD) is a chronic, diffuse abnormality of the meibomian glands, which can be characterized by terminal duct obstruction and/or qualitative/quantitative changes in the glandular secretion. Terminal duct obstruction is caused by hyperkeratinization of the ductal epithelium (Nichols et al, Inv. Oph. & Vis. Sci. (2011); 52(4):1922-1929). These alterations in both meibum quality and expression may result in alteration of the tear film, symptoms of eye irritation, and ocular surface disease such as evaporative dry eye. The principal clinical consequence of MGD is evaporative dry eye syndrome and large population based studies (i.e., Bankok Study and the Shihpai Eye Study) estimate that over 60% of patients with dry eye symptoms also have MGD (Schaumberg et al, Investigative Ophthalmology and Visual Science. (2011); 52(4):1994-2005).

MGD is a leading contributor of dry eye syndrome. The occurrence of dry eye syndrome is widespread and affects about 20 million patients in the United States alone. Dry eye syndrome is a disorder of the ocular surface resulting from either inadequate tear production or excessive evaporation of moisture from the surface of the eye. Tears are important to corneal health because the cornea does not contain blood vessels, and relies on tears to supply oxygen and nutrients. Tears and the tear film are composed of lipids, water, and mucus, and disruption of any of these can cause dry eye. An inadequate amount of lipids flowing from the meibomian glands as caused by a keratinized obstruction, may cause excessive evaporation, thereby causing dry eye syndrome.

In some embodiments, altered meibomian gland secretion is detected by physically expressing the meibomian glands by applying digital pressure to the tarsal plates. In subjects without MGD, the meibum is a pool of clear oil. In MGD, both the quality and expressibility of the expressed material is altered. The altered meibum is also known as meibomian excreta and is made up of a mixture of altered secretions and keratinized epithelial material. In MGD, the quality of expressed lipid varies in appearance from a clear fluid, to a viscous fluid containing particulate matter and densely opaque, toothpaste-like material. The meibomian orifices may exhibit elevations above surface level of the lid, which is referred to as plugging or pouting, and is due to obstruction of the terminal ducts and extrusion of a mixture of meibomian lipid and keratinized material.

Obstructive MGD is characterized by all or some of the following: 1) chronic ocular discomfort, 2) anatomic abnormalities around the meibomian gland orifice (which is one or more of the following: vascular engorgement, anterior or posterior displacement of the mucocutaneous junction, irregularity of the lid margin) and 3) obstruction of the meibomian glands (obstructive findings of the gland orifices by slit lamp biomicroscopy (pouting, plugging or ridge), decreased meibum expression by moderate digital pressure).

Current methods for assessing and monitoring MGD symptoms include, but are not limited to patient questionnaires, meibomian gland expression, tear stability break up time, and determining the number of patent glands as seen by digital expression.

In some embodiments, the symptoms of a patient are assessed by asking the patient a series of questions. Questionnaires allow the assessment of a range of symptoms associated with ocular discomfort. In some embodiments, the questionnaire is the SPEED questionnaire. The SPEED questionnaire assesses frequency and severity of a patient's dry eye symptoms. It examines the occurrence of symptoms on the current day, past 72 hours and past three months. A SPEED score is tallied based on the patient's answers to the questions, to give a range of severity of the patient's symptoms. The SPEED questionnaire includes questions such as the following: 1) what dry eye symptoms are you experiencing, and when do they occur? 2) how frequently do you experience dryness, grittiness, or scratchiness in your eyes? 3) how often do you experience soreness or irritation of the eyes? 4) how often do you experience burning or watering of the eyes? 5) how often do you experience eye fatigue? and 6) how severe are the symptoms?

Meibomian gland expressibility is optionally determined to assess the meibomian gland function. In normal patients, meibum is a clear to light yellow oil. Meibum is excreted from the glands when digital pressure is placed on the glands. Changes in meibomian gland expressibility are one potential indicator of MGD. In some embodiments, during expression, quantifying the amount of physical force applied during expression is monitored in addition to assessing lipid volume and lipid quantity.

Tear stability break up time (TBUT) is a surrogate marker for tear stability. Tear film instability is a core mechanism in dry eye and MGD. Low TBUT implies a possibility of lipid layer compromise and MGD. TBUT is optionally measured by examining fluorescein breakup time, as defined as the time to initial breakup of the tear film after a blink. Fluorescein is optionally applied by wetting a commercially available fluorescein-impregnated strip with saline, and applied to the inferior fornix or bulbar conjuctiva. The patient is then asked to blink several times and move the eyes. The break up is then analyzed with a slit lamp, a cobalt blue filter, and a beam width of 4 mm. The patient is instructed to blink, and the time from upstroke of the last blink to the first tear film break or dry spot formation is recorded as a measurement.

Other methods for assessing MGD symptoms, include but are not limited to, Schirmer test, ocular surface staining, lid morphology analysis, meibography, meibometry, interferometry, evaporimetry, tear lipid composition analysis, fluorophotometry, meiscometry, osmolarity analysis, indices of tear film dynamics, evaporation and tear turnover.

Current treatments for MGD include lid warming, lid massage, lid hygiene, lid expression and meibomian gland probing. Pharmacological methods, prior to those described herein, have not been used.

Lid hygiene is considered the primary treatment for MGD and consists of three components: 1) application of heat, 2) mechanical massage of eyelids and 3) cleansing the eyelid. Eyelid warming procedures improve meibomian gland secretion by melting the pathologically altered meibomian lipids. Warming is achieved by warm compresses or devices. Mechanical lid hygiene includes the use of scrubs, mechanical expression and cleansing with various solutions of the eyelashes and lid margins. Lid margins are optionally also cleansed with hypoallergenic bar soap, dilute infant shampoo or commercial lid scrubs. Physical expression of meibomian glands is performed in a physician's office or is performed by the patient at home. The technique varies from gentle massage of the lids against the eyeball to forceful squeezing of the lids either against each other or between a rigid object on the inner lid surface and a finger, thumb, or rigid object (such as a glass rod, cotton swab, or metal paddle) on the outer lid surface. The rigid object on the inner lid surface protects the eyeball from forces transferred through the eyelid during expression and to offer a stable resistance, to increase the amount of force that is applied to the glands.

Eyelid warming is limited because the warming melts the lipids, but does not address movement of the keratinized material. Further, eyelid warming induces transient visual degradation due to corneal distortion. Mechanical lid hygiene is also limited because the force needed to remove an obstruction can be significant, resulting in significant pain to the patient. The effectiveness of mechanical lid hygiene is limited by the patient's ability to tolerate the associated pain during the procedure. Other treatments for MGD are limited.

Physical opening of meibomian glands obstruction by meibomian gland expression is an acceptable method to improve meibomian gland secretion and dry eye symptoms. In addition probing of the meibomian gland canal has been used to open the obstructed canal. Both methods, expression and probing, are limited, however, by the pain induced by the procedure, the possible physical insult to the gland and canal structures and their short lived effect estimated at days and weeks. Therefore, methods are needed to improve patient comfort, which will not cause harm to the meibomian glands and canals, that will reduce the dependency on frequent office visits and improve secretion of meibum.

U.S. Pat. No. 9,463,201 entitled, "Compositions and methods for the treatment of meibomian gland dysfunction" describes a method for treating meibomian gland dysfunction involving the topical administration of a therapeutically-effective amount of at least one keratolytic agent in an ophthalmically-acceptable carrier. The patent includes keratolytic agents that are inorganic selenium (Se) compounds such as selenium disulfide ($SeS_2$) or organoselenium compounds such as Ebselen (2-Phenyl-1,2-benzoselenazol-3-one). This agent would treat the underlying cause of MGD, but not a "plus" inflammatory disease as described by the DEWS report on MGD.

The role of inflammation in the etiology of MGD is controversial. The terms posterior blepharitis and MGD are not synonymous. Posterior blepharitis describes inflammatory conditions of the posterior lid margin and has various causes, of which MGD can be one possible cause (Nichols et al 2011). In its earliest stages, MGD is not associated with clinical signs characteristic of posterior blepharitis. As MGD progresses, an MGD-related posterior blepharitis is said to be present. MGD-related posterior blepharitis affects the meibomian glands and meibomian gland orifices. MGD-related posterior blepharitis is characterized by flora changes, esterase and lipase release, lipid changes, and eyelid inflammation.

Hyperkeratinization of the meibomian gland epithelium (thickening of the lining of the glands) may lead to obstruction and a decrease in the quantity of meibomian gland secretions and may be responsible for MGD-related posterior blepharitis. Diagnosis of MGD-related posterior blepharitis includes meibomian gland expression with demonstration of an altered quality of expressed secretions, and/or by a loss of gland functionality (decreased or absent expressibility). The TFOS report on Meibomian Gland Disease specifically notes that anterior blepharitis and exacerbated inflammatory ocular surface disease are "plus" diseases to MGD which are managed by topical, ocular steroids (Nichols et al 2011). Since these "plus" conditions can be present in various levels of severity from early to late MGD there is a need for treatments and/or combinations of treatments that can target both the underlying non-inflammatory pathophysiology of MGD and inflammation associated with these comorbid conditions.

MGD-related inflammatory eye disease may comprise a different mechanism than blepharitis-related MGD. MGD-related inflammatory eye disease is characterized by an inflammatory cascade involving activation and migration of T lymphocytes to the inflamed tissue. T lymphocyte infiltration may result in lacrimal gland stimulation and upregulation of cytokines. Exemplary cytokines that may be involved in MGD-related inflammatory eye disease include, but are not limited to, interleukin-1, interleukin-4, interleukin-6, inteleukin-8, interferon gamma, macrophage inflammatory protein 1 alpha, and tumor necrosis factor alpha. Kinase pathways including the mitogen activated protein kinase (MAPK) pathway are also activated in the inflammatory cascade. The inflammatory process results in loss of mucin-producing goblet cells and destruction of the ocular surface that can lead to further damage.

Dry eye syndrome, also known as keratoconjunctivitis sicca (KCS), is considered a self-sustaining disease that is progressively disconnected from its initial cause. Dry eye syndrome is associated with inflammation at the ocular surface and periocular tissue. Inflammation is characterized by the activation and migration of T lymphocytes to the inflamed tissue including in the conjunctiva and lacrimal glands. Inflammatory cytokines, chemokines, and matrix metalloproteinase have also been identified as being increased.

Animal models of dry eye disease have been established and reviewed (Barabino, et al, (Invest. Ophthalmol. Vis. Sci. 2004, 45:1641-1646)). Barabino, et al, (Invest. Ophthalmol. Vis. Sci. 2005, 46:2766-2771) described a model wherein exposure of normal mice to a low-humidity environment in a controlled-environment chamber leads to significant alterations in tear secretion, goblet cell density, and acquisition of dry eye-related ocular surface signs. However, no single animal model adequately accounts for the immune, endocrine, neuronal and environmental factors which contribute to dry eye pathogenesis.

Anti-inflammatory agents may be used to treat ocular surface diseases or disorders including dry eye syndrome. Corticosteroids are an effective anti-inflammatory therapy in dry eye disease. For example, in a 4-week, double-masked, randomized study in 64 patients with dry eye and delayed tear clearance, loteprednol etabonate 0.5% ophthalmic suspension (Lotemax [Bausch and Lomb, Rochester, N.Y.]), QID, was found to be more effective than its vehicle in improving some signs and symptoms (Pflugfelder et al, Am J Ophthalmol (2004); 138:444-57). The TFOS 2007 report on dry eye disease went so far as to conclude that, "In the US Federal Regulations, ocular corticosteroids receiving "class labeling" are indicated for the treatment " . . . of steroid responsive inflammatory conditions of the palpebral and bulbar conjunctiva, cornea and anterior segment of the globe such as allergic conjunctivitis, acne rosacea, superficial punctate keratitis, herpes zoster keratitis, iritis, cyclitis, selected infective conjunctivitis, when the inherent hazard of steroid use is accepted to obtain an advisable diminution in edema and inflammation." KCS, in some instances, is included in this list of steroid-responsive inflammatory conditions (Therapy Subcommittee of the International Dry Eye WorkShop, 2007. Management and Therapy of Dry Eye Disease: Report of the Management and Therapy Subcommittee of the International Dry Eye WorkShop (2007). 2007; 5: 163-178)." While the US FDA does not agree with this conclusion, short courses of steroids, especially Lotemax, can be used to treat inflammation associated with dry eye disease.

Other anti-inflammatory agents include nonsteroidal anti-inflammatory drugs (NSAIDs). NSAIDs inhibit the activity of cyclooxygenases including cyclooxygenase-1 (COX-1) and cyclooxygenase-2 (COX-2), which are enzymes involved in the synthesis of prostaglandins and thromboxanes from arachidonic acid. Prostaglandin and thromboxane signaling are involved in inflammation and immune modulation. In some cases, NSAIDs are used for treating dry eye disease by treating the inflammation at the ocular surface.

Treatment of dry eye is also accomplished through agents that enhance tear fluid and mucin production. For example, agonists of the $P2Y_2$ receptor have been shown to increase tear fluid and mucin secretion. The mechanism is thought to involve $P2Y_2$ signaling to raise intracellular calcium and open chloride channels in the apical membrane. The $P2Y_2$ receptor belongs to the family of purinergic receptors, which have been classified into P1 receptors and P2 receptors on the basis of their native agonism by purine nucleosides and purine and pyrimidine nucleotides, respectively. P2 receptors are further distinguished physiologically into two types: P2X receptors and P2Y receptors. The P2Y receptors are involved in diver signaling including platelet aggregation, immunity, lipid metabolism, and bone activity. Several studies have also demonstrated the presence of P2X and P2Y receptors in ocular tissues, including the retina, ciliary body, and lens. These studies indicate that $P2Y_2$ receptors appear to be the main subtype of purinergic receptor located at the ocular surface. $P2Y_2$ receptors have also been demonstrated to be localized in ocular tissues in the conjunctival epithelial goblet and serous cells and meibomian gland acinus and ductal epithelial cells of the rhesus macaque.

Azithromycin

Azithromycin is a macrolide antibiotic with a 15-membered ring. Its chemical name is (2R,3S,4R,5R,8R,10R,11R,12S,13S,14R)-13-[(2,6-dideoxy-3-C-methyl-3-O-methylα-L-ribo-hexopyranosyl)oxy]-2-ethyl-3,4,10-trihydroxy-3,5,6,8,10,12,14-heptamethyl11-[[3,4,6-trideoxy-3-(dimethylamino)-b-D-xylo-hexopyranosyl]oxy]-1-oxa-6-azacyclopentadecan-15-one having a molecular weight of 749, and an empirical formula is $C_{38}H_{72}N_2O_{12}$. The structural formula is:

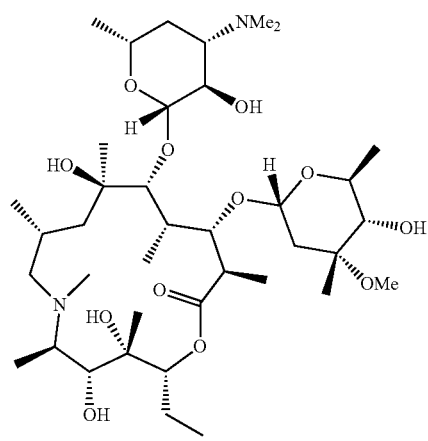 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2O)[C@](C)(O)C[C@@H](C)CN(C)[C@H](C)[C@@H](O)[C@]1(C)O]

Azithromycin acts by binding to the 50S ribosomal subunit of susceptible microorganisms and interfering with microbial protein synthesis. In the topical ophthalmic setting, Azithromycin is formulated as a 1% solution of pH 6.3 comprising benzalkonium chloride. Azithromycin is indicated for the treatment of bacterial conjunctivitis caused by susceptible isolates of the following microorganisms: *Haemophilus influenzae, Staphylococcus aureus, Streptococcus mitis* group, or *Streptococcus pneumoniae*. Further information about azithromycin ophthalmic solution can be found in, for example, U.S. Pat. Nos. 6,239,113, 6,569,443, or 7,056,893.

Described herein are compounds (e.g., keratolytic conjugates and/or dual acting-agents) which address simultaneously the non-inflammatory keratolytic blockage component of meibomian gland dysfunction and the inflammation associated dry eye disease including aqueous deficiency. In some embodiments, a compound provided herein is useful as either an acute therapy (e.g., by a trained specialist or physician) or as a chronic therapy (e.g., in the hands of a patient, or alternatively, by a trained specialist or physician). A compound provided herein is tested, in some embodiments, using the assays and methods described herein (e.g., as described in the examples). In some embodiments, a compound provided herein represents a significant advance in the art as the first-order metabolites obtained from metabolism of the agents are operative against both the keratolytic and the inflammatory component of dry eye disease.

Provided in some embodiments herein is a compound, having the structure of Formula (I):

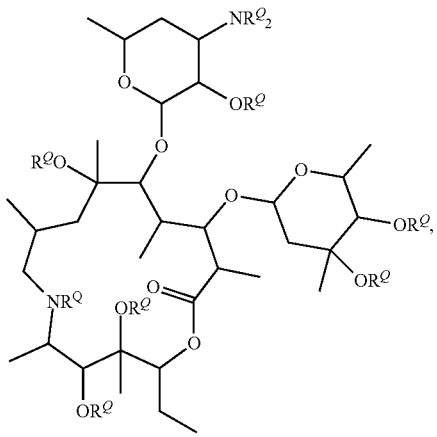

Formula (I)

wherein, each $R^Q$ is independently H, $R^N$, substituted or unsubstituted alkyl, or substituted or unsubstituted heteroalkyl, wherein at least one $R^Q$ is $R^N$;

$R^N$ is D-$L^a$-;

D is a keratolytic agent; and $L^a$ is a linker, or a stereoisomer thereof, or a pharmaceutically acceptable salt or solvate thereof.

In some embodiments, the compound has a structure represented by:

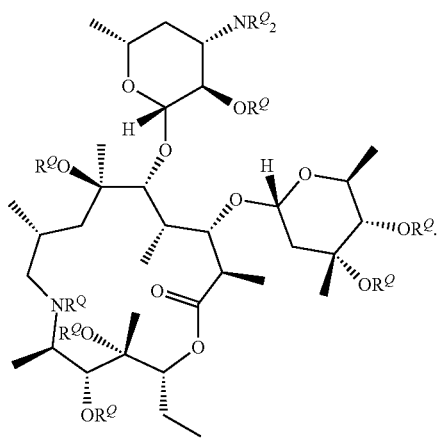

In some embodiments, provide herein is a compound, having the structure of Formula (I-A):

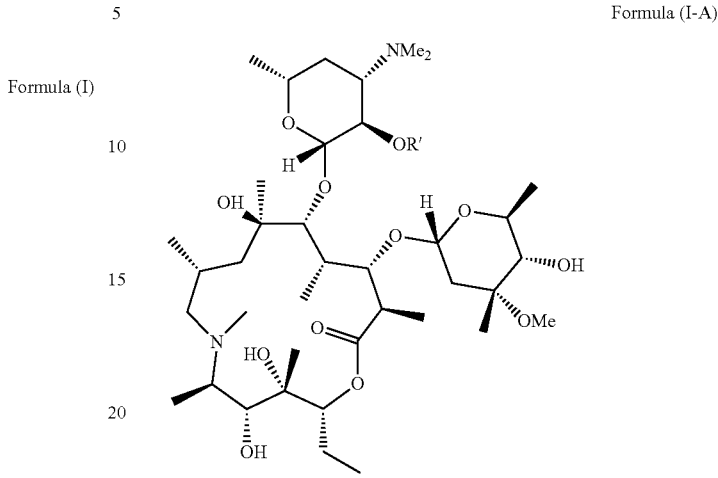

Formula (I-A)

wherein,

R' is D-$L^a$-;

D is a keratolytic agent; and $L^a$ is a linker, or a stereoisomer thereof, or a pharmaceutically acceptable salt or solvate thereof.

In some embodiments, $L^a$ comprises one or more linker group, each linker group being independently selected from the group consisting of a bond, —O—, —S—, alkyl (alkylenyl), heteroalkyl (heteroalkylenyl), disulfide, ester, and carbonyl (>C=O). In some embodiments, the keratolytic agent comprises one or more groups of the group (e.g., keratolytic group, such as a group conferring keratolytic activity), each group (e.g., keratolytic group) being independently selected from the group consisting of thiol, disulfide, selenium (e.g., selenide, diselenide), carboxylic acid or a group which can be metabolized to a carboxylic acid.

In some embodiments, R' is alkyl or heteroalkyl substituted with at least one oxo, and further optionally substituted.

In some embodiments, R' is:

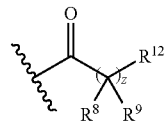

wherein:

z is 1-6;

each $R^8$ and $R^9$ is independently H, halogen, $C_1$-$C_3$-alkyl, $C_1$-$C_3$-haloalkyl, $C_1$-$C_3$-alkoxy, $C_3$-$C_5$-cycloalkyl, or $R^8$ and $R^9$ are taken together with the atoms to which they are attached to form a $C_3$-$C_5$-cycloalkyl; and $R^{12}$ is H, alkyl, aryl or heteroalkyl, the alkyl, aryl, or heteroalkyl being optionally substituted, or a stereoisomer thereof, or a pharmaceutically acceptable salt or solvate thereof.

In some embodiments, the alkyl or heteroalkyl of $R^{12}$ is substituted with one or more substituent, each substituent being independently selected from the group consisting of alkyl, heteroalkyl, hydroxyl, thiol, thioether, disulfide, seleno, selenol, sulfone, amide, halo, oxo, heterocyclyl, and cycloalkyl, wherein the heterocyclyl and cycloalkyl is optionally substituted (e.g., with one or more substituent selected from the group consisting of alkyl, heteroalkyl, hydroxyl, thiol, thioether, disulfide, selenol, sulfone, amide, halo, and oxo).

In some embodiments, z is described elsewhere herein.

In some embodiments, each $R^8$ and $R^9$ is described elsewhere herein.

In some embodiments, provided herein is a compound having the structure of Formula (Ia):

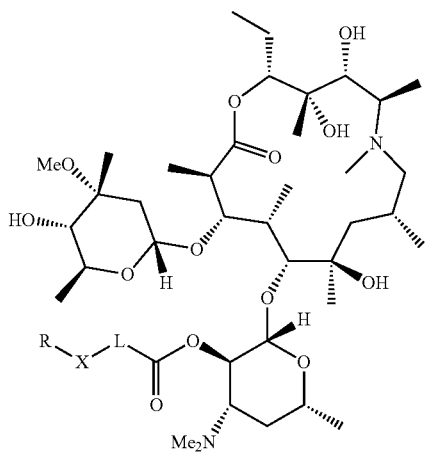

Formula (Ia)

or a pharmaceutically acceptable salt or solvate (e.g., or a stereoisomer) thereof,
wherein,
L is bond, —(C=O)(OCR$^8$R$^9$)$_z$—, or —(C=O)(OCR$^8$R$^9$)$_z$O—;
each $R^8$ and $R^9$ is independently H, halogen, $C_1$-$C_3$-alkyl, $C_1$-$C_3$-haloalkyl, $C_1$-$C_3$-alkoxy, $C_3$-$C_5$-cycloalkyl, or $R^8$ and $R^9$ are taken together with the atoms to which they are attached to form a $C_3$-$C_5$-cycloalkyl;
z is 1-6;
X is absent or —O—; and
R is substituted alkyl, substituted heteroalkyl, or substituted heterocycloalkyl,
wherein the substituted alkyl is substituted with one or more alkyl substituent, at least one alkyl substituent being independently selected from the group consisting of substituted or unsubstituted cycloalkyl and substituted heterocycloalkyl, and the substituted heteroalkyl is substituted with one or more heteroalkyl substituent, at least one heteroalkyl substituent being independently selected from the group consisting of —COOH, substituted heterocycloalkyl, and thioalkyl, the substituted alkyl or substituted heteroalkyl being further optionally substituted.

In some embodiments, provided herein is a compound having the structure of Formula (Ia):

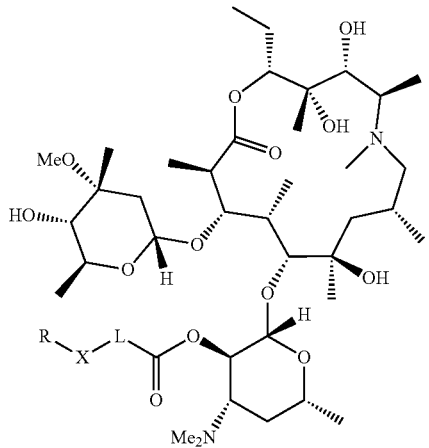

Formula (Ia)

or a pharmaceutically acceptable salt or solvate (e.g., or a stereoisomer) thereof,
wherein,
L is bond, —(C=O)(OCR$^8$R$^9$)$_z$—, or —(C=O)(OCR$^8$R$^9$)$_z$O—;
each $R^8$ and $R^9$ is independently H, halogen, $C_1$-$C_3$-alkyl, $C_1$-$C_3$-haloalkyl, $C_1$-$C_3$-alkoxy, $C_3$-$C_5$-cycloalkyl, or $R^8$ and $R^9$ are taken together with the atoms to which they are attached to form a $C_3$-$C_5$-cycloalkyl;
z is 1-6;
X is absent or —O—; and
R is substituted (e.g., straight or branched) alkyl, substituted (e.g., straight or branched) heteroalkyl, or substituted heterocycloalkyl (e.g., (N—) substituted with alkyl further substituted with oxo and thiol), the substituted alkyl being substituted with one or more (alkyl) substituent, at least one (alkyl) substituent being independently selected from the group consisting of —SH, substituted or unsubstituted (e.g., unsaturated) cycloalkyl, and dithiolanyl oxide, or the substituted heteroalkyl being substituted with one or more (heteroalkyl) substituent, at least one (heteroalkyl) substituent being independently selected from the group consisting of —SH, —COOH, and thioalkyl, the substituted alkyl, substituted heteroalkyl, or substituted heterocycloalkyl being further optionally substituted.

In some embodiments, L is bond. In some embodiments, L is —(C=O)(OCR$^8$R$^9$)$_z$— or —(C=O)(OCR$^8$R$^9$)$_z$O—. In some embodiments, L is —(C=O)(OCR$^8$R$^9$)$_z$—. In some embodiments, L is —(C=O)(OCR$^8$R$^9$)$_z$O—. In some embodiments z is 1-3. In some embodiments, z is 1. In some embodiments, each $R^8$ and $R^9$ is independently H or $C_1$-$C_3$-alkyl. In some embodiments, each $R^8$ is H and each $R^9$ is $C_1$-$C_3$-alkyl. In some embodiments, each $R^8$ is H and each $R^9$ is $CH_3$. In some embodiments, $R^8$ and $R^9$ are H. In some embodiments, L is —(C=O)OCH(CH$_3$)—. In some embodiments, L is —(C=O)OCH(CH$_3$)O—.

In some embodiments, X is absent. In some embodiments, X is —O—.

In some embodiments, L is —(C=O)OCH(CH$_3$)— or —(C=O) OCH(CH$_3$)O— and X is absent or —O—.

In some embodiments, L is —(C=O)OCH(CH$_3$)— and X is absent.

In some embodiments, L is —(C═O)OCH(CH₃)— and X is —O—.

In some embodiments, L is bond and X is absent.

In some embodiments, R is substituted (e.g., straight or branched) alkyl, the (e.g., straight or branched) alkyl being substituted with one or more (alkyl) substituent, each (alkyl) substituent being independently selected from the group consisting of hydroxy, optionally substituted alkoxy (e.g., optionally substituted with oxo and hydroxy or oxo and $C_1$-$C_3$ alkoxy)), oxo, optionally substituted alkyl (e.g., optionally substituted with alkoxy further optionally substituted with oxo, $C_1$-$C_4$ alkyl, and/or hydroxy), optionally substituted heterocycloalkyl (e.g., optionally substituted dioxane (e.g., 1,3 dioxanyl optionally substituted with methyl), dithiolanyl, or dithiolanyl oxide), hydroxyalkyl, thiol, acetamide, substituted unsaturated cycloalkyl (e.g., being substituted with one or more $C_1$-$C_4$ alkyl), and amino.

In some embodiments, R is substituted (e.g., straight or branched) alkyl, the (e.g., straight or branched) alkyl being substituted with one or more (alkyl) substituent, each (alkyl) substituent being independently selected from the group consisting of thiol, amino, acetamide, substituted unsaturated cycloalkyl (e.g., being substituted with one or more $C_1$-$C_4$ alkyl), and substituted heterocycloalkyl (e.g., dithiolanyl oxide).

In some embodiments, R is substituted alkyl, the alkyl being substituted with substituted heterocycloalkyl.

In some embodiments, R is substituted alkyl. In some embodiments, R is substituted alkyl, wherein the substituted alkyl is substituted with one or more alkyl substituent, at least one alkyl substituent being independently selected from the group consisting of substituted or unsubstituted cycloalkyl and substituted heterocycloalkyl. In some embodiments, R is substituted alkyl, the alkyl being substituted with substituted heterocycloalkyl. In some embodiments, R is substituted alkyl, the alkyl being substituted with 1,2-dithiolanyl oxide. In some embodiments, R is substituted alkyl, the alkyl being substituted with substituted $C_5$-$C_{15}$ heterocycloalkyl (e.g., $C_{12}$ heterocycloalkyl with one or more disulfide and one or more amide within the heterocycloalkyl ring) being substituted with one or more substituent, at least one substituent being independently selected from the group consisting of $C_1$-$C_3$ alkyl, oxo, and —COOH. In some embodiments, the substituted alkyl is further optionally substituted.

In some embodiments, L is bond, X is absent, and R is substituted (e.g., straight or branched) alkyl, the (e.g., straight or branched) alkyl being substituted with one or more (alkyl) substituent, each (alkyl) substituent being independently selected from the group consisting of thiol, amino, acetamide, substituted unsaturated cycloalkyl (e.g., being substituted with one or more $C_1$-$C_4$ alkyl), and substituted heterocycloalkyl (e.g., dithiolanyl oxide).

In some embodiments, R is:

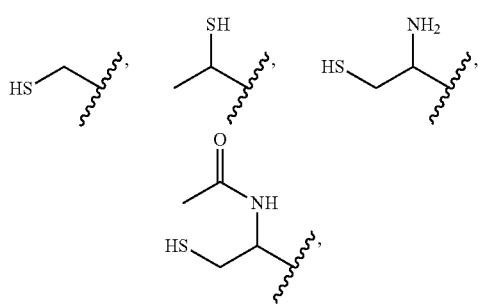

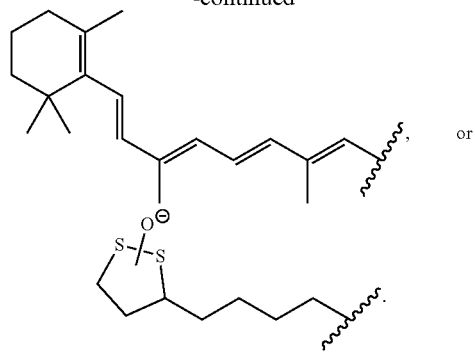

In some embodiments, R is:

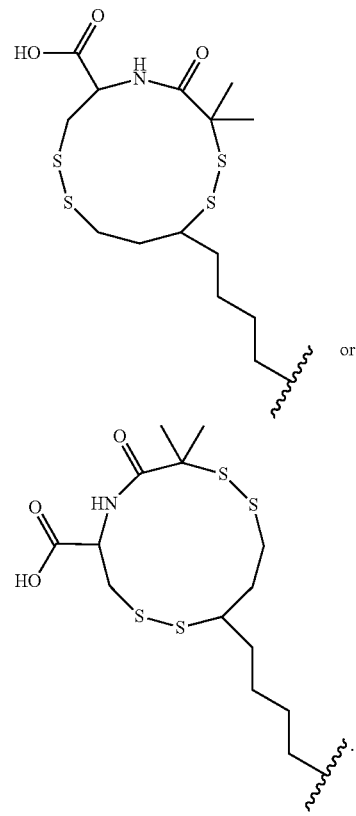

In some embodiments, R is substituted or unsubstituted (e.g., linear or branched) heteroalkyl comprising one or more —C—O—C— (e.g., within the (e.g., linear or branched) heteroalkyl chain).

In some embodiments, R is substituted or unsubstituted (e.g., linear or branched) heteroalkyl comprising one or more ester, one or more carbonate, one or more amide, and/or one or more disulfide (e.g., within the (e.g., linear or branched) heteroalkyl chain).

In some embodiments, R is substituted (e.g., linear or branched) heteroalkyl comprising one or more ester, one or more amide, and/or one or more disulfide (e.g., within the (e.g., linear or branched) heteroalkyl chain).

In some embodiments, R is substituted or unsubstituted (e.g., linear or branched) heteroalkyl comprising one carbonate (e.g., within the (e.g., linear or branched) heteroalkyl chain).

In some embodiments, R is substituted or unsubstituted (e.g., linear or branched) heteroalkyl comprising one or two ester (e.g., within the (e.g., linear or branched) heteroalkyl chain).

In some embodiments, R is substituted or unsubstituted (e.g., linear or branched) heteroalkyl comprising one ester (e.g., within the (e.g., linear or branched) heteroalkyl chain).

In some embodiments, R is substituted or unsubstituted (e.g., linear or branched) heteroalkyl comprising one ester and one carbonate (e.g., within the (e.g., linear or branched) heteroalkyl chain).

In some embodiments, R is substituted or unsubstituted (e.g., linear or branched) heteroalkyl comprising one or two ester and one amide (e.g., within the (e.g., linear or branched) heteroalkyl chain).

In some embodiments, R is substituted or unsubstituted (e.g., linear or branched) heteroalkyl comprising one ester and one amide (e.g., within the (e.g., linear or branched) heteroalkyl chain).

In some embodiments, R is substituted or unsubstituted (e.g., linear or branched) heteroalkyl comprising one or two amide (e.g., within the (e.g., linear or branched) heteroalkyl chain).

In some embodiments, R is substituted or unsubstituted (e.g., linear or branched) heteroalkyl comprising one or two disulfide (e.g., within the (e.g., linear or branched) heteroalkyl chain).

In some embodiments, R is substituted or unsubstituted (e.g., linear or branched) heteroalkyl containing one disulfide (e.g., within the (e.g., linear or branched) heteroalkyl chain).

In some embodiments, R is substituted or unsubstituted (e.g., linear or branched) heteroalkyl comprising one or two disulfide and one ester (e.g., within the (e.g., linear or branched) heteroalkyl chain).

In some embodiments, R is substituted or unsubstituted (e.g., linear or branched) heteroalkyl containing one or two disulfide and one amide (e.g., within the (e.g., linear or branched) heteroalkyl chain).

In some embodiments, R is substituted (e.g., linear or branched) heteroalkyl, the (e.g., linear or branched) heteroalkyl being substituted with one or more (heteroalkyl) substituent, each (heteroalkyl) substituent being independently selected from the group consisting of optionally substituted $C_1$-$C_6$ alkyl, acetamide, hydroxy, heterocycloalkyl, thiol, thioalkyl, amino, and carboxylic acid.

In some embodiments, R is substituted (e.g., linear or branched) heteroalkyl, the (e.g., linear or branched) heteroalkyl being substituted with one or more (heteroalkyl) substituent, each (heteroalkyl) substituent being independently selected from the group consisting of thioalkyl, amino, carboxylic acid, $C_1$-$C_6$ alkyl, acetamide, thiol, oxo, and optionally substituted (e.g., N-attached) heterocycloalkyl (e.g., optionally substituted with carboxylic acid).

In some embodiments, R is substituted (e.g., linear or branched) heteroalkyl, the (e.g., linear or branched) heteroalkyl being substituted with substituted $C_1$-$C_6$ alkyl, the $C_1$-$C_6$ alkyl being substituted with heteroalkyl being further optionally substituted with one or more additional substituent, each additional substituent being independently selected from the group consisting of hydroxy, carboxylic acid, optionally substituted N-substituted pyrrolidinyl (e.g., optionally substituted with carboxylic acid)).

In some embodiments, R is substituted (e.g., linear or branched) heteroalkyl, the (e.g., linear or branched) heteroalkyl being substituted with heterocycloalkyl. In some embodiments, R is substituted (e.g., linear or branched) heteroalkyl, the (e.g., linear or branched) heteroalkyl being substituted with 1,2-dithiolane, 1,2-dithiolane oxide, optionally substituted dioxane (e.g., optionally substituted with one or more $C_1$-$C_6$ alkyl), (e.g., N-substituted) pyrrolidine (e.g., substituted with alkyl further substituted with oxo, thiol, and $C_1$-$C_3$ alkyl), or substituted (e.g., N-attached) pyrrolidine (e.g., substituted with carboxylic acid).

In some embodiments, R is substituted (e.g., linear or branched) heteroalkyl, the (e.g., linear or branched) heteroalkyl being substituted with acetamide and carboxylic acid.

In some embodiments, R is substituted heteroalkyl, the heteroalkyl being substituted with —COOH, —CH$_2$SH, and/or optionally substituted N-attached heterocycloalkyl, and being further substituted with one or more other substituent, each substituent being independently selected from the group consisting of acetamide, amino, $C_1$-$C_6$ alkyl, thiol, and oxo.

In some embodiments, R is substituted heteroalkyl comprising two disulfide bonds within the heteroalkyl chain, the heteroalkyl being substituted with —COOH or substituted N-attached heterocycloalkyl, and being further substituted with one or more other substituent, each substituent being independently selected from the group consisting of acetamide and $C_1$-$C_6$ alkyl.

In some embodiments, R is substituted heteroalkyl comprising one disulfide bond within the heteroalkyl chain, the heteroalkyl being substituted with acetamide, —COOH, and —SH.

In some embodiments, L is bond, X is absent, and R is substituted (e.g., linear or branched) heteroalkyl, the (e.g., linear or branched) heteroalkyl being substituted with one or more (heteroalkyl) substituent, each (heteroalkyl) substituent being independently selected from the group consisting of thioalkyl, amino, carboxylic acid, $C_1$-$C_6$ alkyl, acetamide, thiol, oxo, and optionally substituted (e.g., N-attached) heterocycloalkyl (e.g., optionally substituted with carboxylic acid).

In some embodiments, R is:

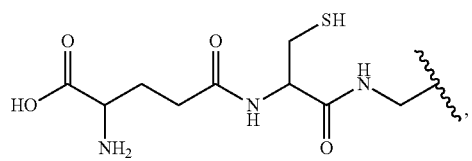

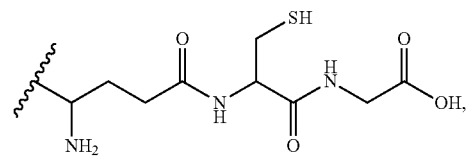

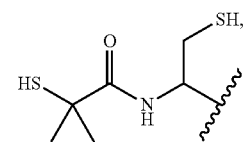

89
-continued
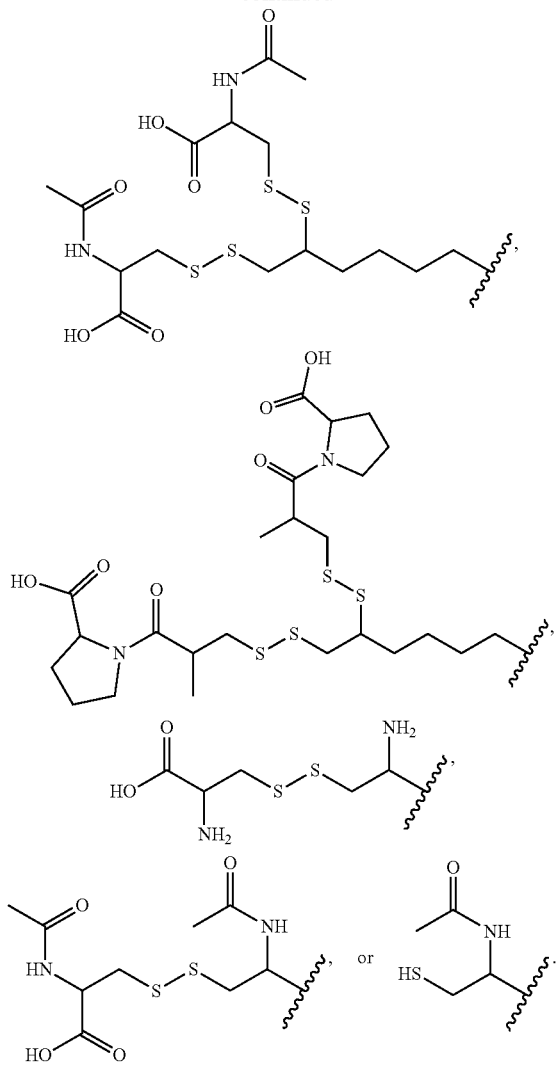
In some embodiments, R is substituted branched heteroalkyl.
In some embodiments, R is:
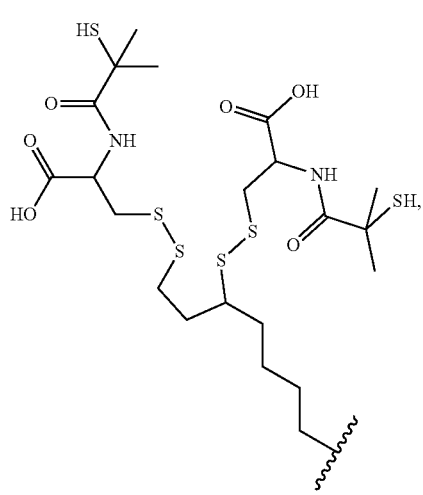
90
-continued
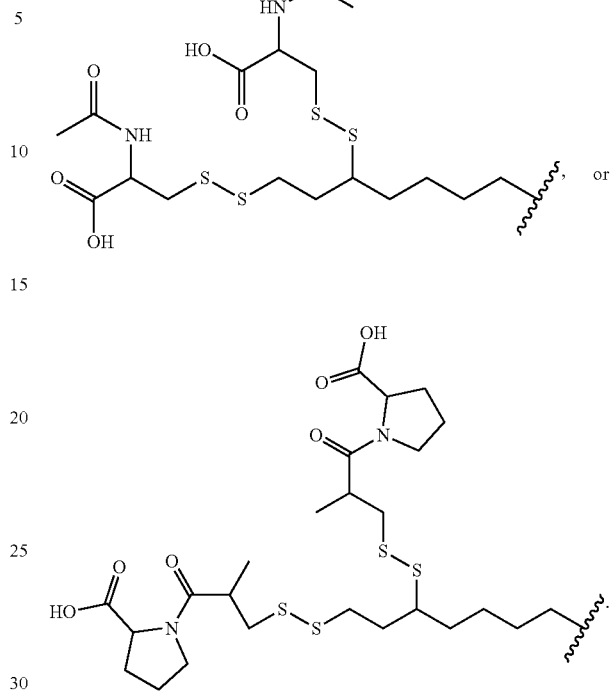
In some embodiments, R is:
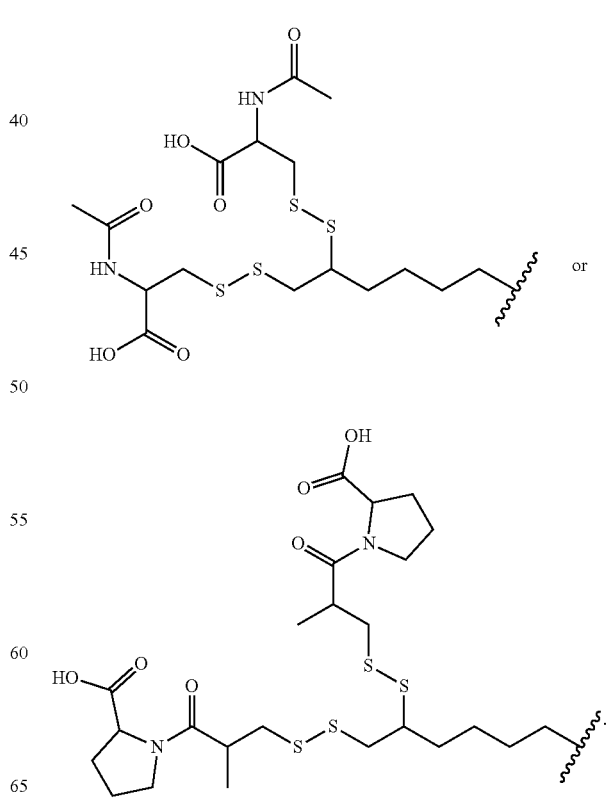

In some embodiments, R-X-L is:

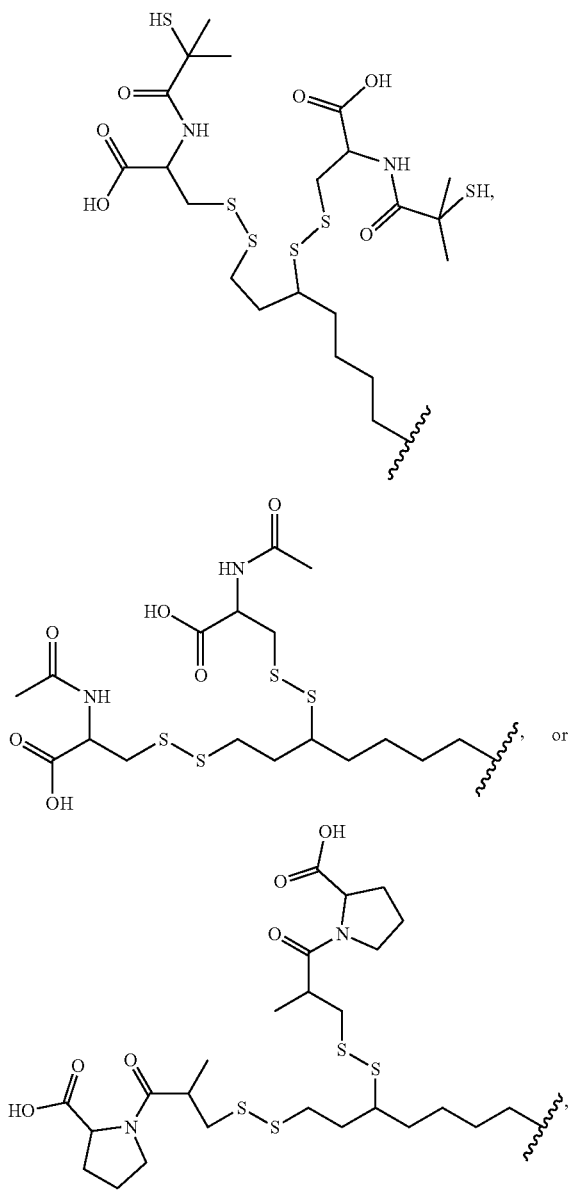

In some embodiments, R-X-L is:

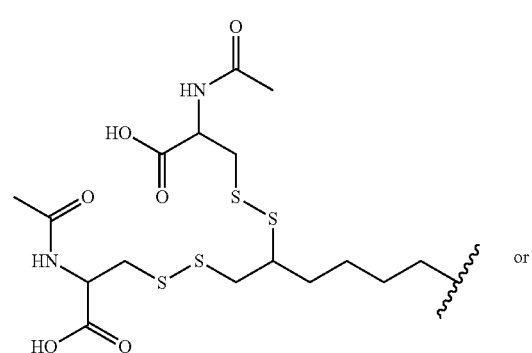

-continued

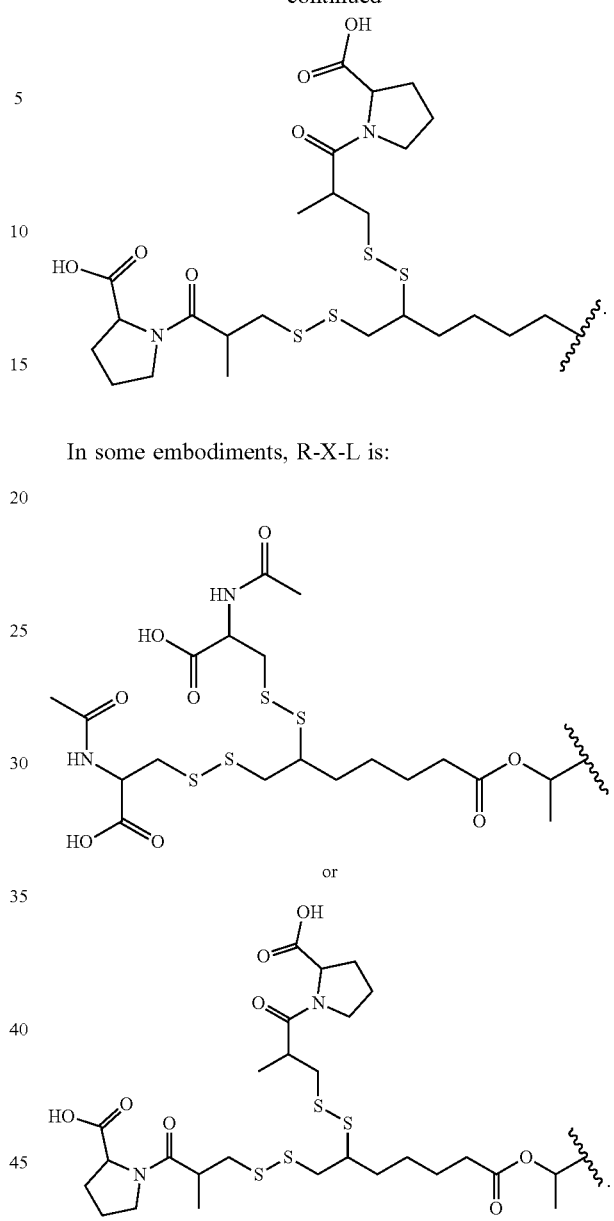

In some embodiments, R-X-L is:

In some embodiments, R is substituted heterocycloalkyl (e.g., N-substituted with alkyl further substituted with oxo and thiol).

In some embodiments, R is heterocycloalkyl N-substituted with alkyl, the alkyl being further substituted with oxo and/or thiol.

In some embodiments, R is:

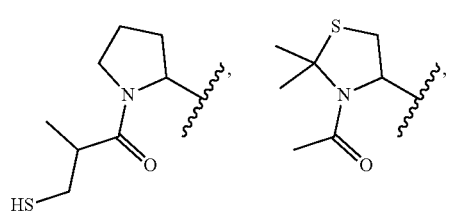

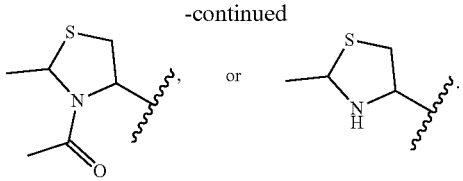

In some embodiments, R comprises a radical of one or more keratolytic group (e.g., each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc)).

In some embodiments, R comprises a radical of one or more keratolytic group, each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc).

In some embodiments, R comprises a thiol radical of one or more keratolytic group, each thiol radical of the one or more keratolytic group being independently selected from the group consisting of a thiol radical of thioglycolic acid (TGA), a thiol radical of thiolactic acid (TLac), a thiol radical of dihydrolipoic acid (diHLip), a thiol radical of N-acetyl cysteine (NAC), a thiol radical of cysteine (Cys), a thiol radical of glutathione (GSH), a thiol radical of captopril (Cap), and a thiol radical of bucillamine (Buc).

In some embodiments, the (e.g., thiol) radical of the keratolytic agent comprises a (e.g., thiol) radical of one or more keratolytic group, each (e.g., thiol) radical of the one or more keratolytic group being independently selected from the group consisting of [Lac-Lac]., [Lac-NAC]., [Cys-Cys]., [diHLip-NAC-NAC]., [diHLip-NAC]., [diHLip-Cap-Cap]., [diHLip-Cap]., [diHLip-Cys-Cys]., [diHLip-Cys]., [diHLip-Lipox-Lipox]., and [diHLip-Lipox]..

In some embodiments, the (e.g., thiol) radical of the keratolytic agent comprises a (e.g., thiol) radical of one or more keratolytic group, each (e.g., thiol) radical of the one or more keratolytic group being independently selected from the group consisting of [Lac-Lac]., [Cys-Cys]., [diHLip-NAC-NAC]., [diHLip-NAC]., [diHLip-Cap-Cap]., [diHLip-Cap]., [diHLip-Cys-Cys]., [diHLip-Cys]., [diHLip-Lipox-Lipox]., and [diHLip-Lipox]..

Unless stated otherwise, a radical (or .) is molecule having unpaired electrons. In some embodiments, the radical is a radical of a heteroatom (e.g., —O., —N., or —S.). In some embodiments, the radical (e.g., the molecule having unpaired electron) is paired with another unpaired electron of another molecule to form paired electrons. In some embodiments, a radical of a keratolytic agent provided herein is paired with any compound provided herein. In some embodiments, a first radical of a keratolytic agent provided herein is paired with a second radical of a keratolytic provided herein.

In some embodiments, the radical of the keratolytic group is the point of attachment of R to the rest of the molecule. In some embodiments, (the thiol radical of) R each independently attach to the rest of the molecule to form a disulfide bond.

In some embodiments, R is:

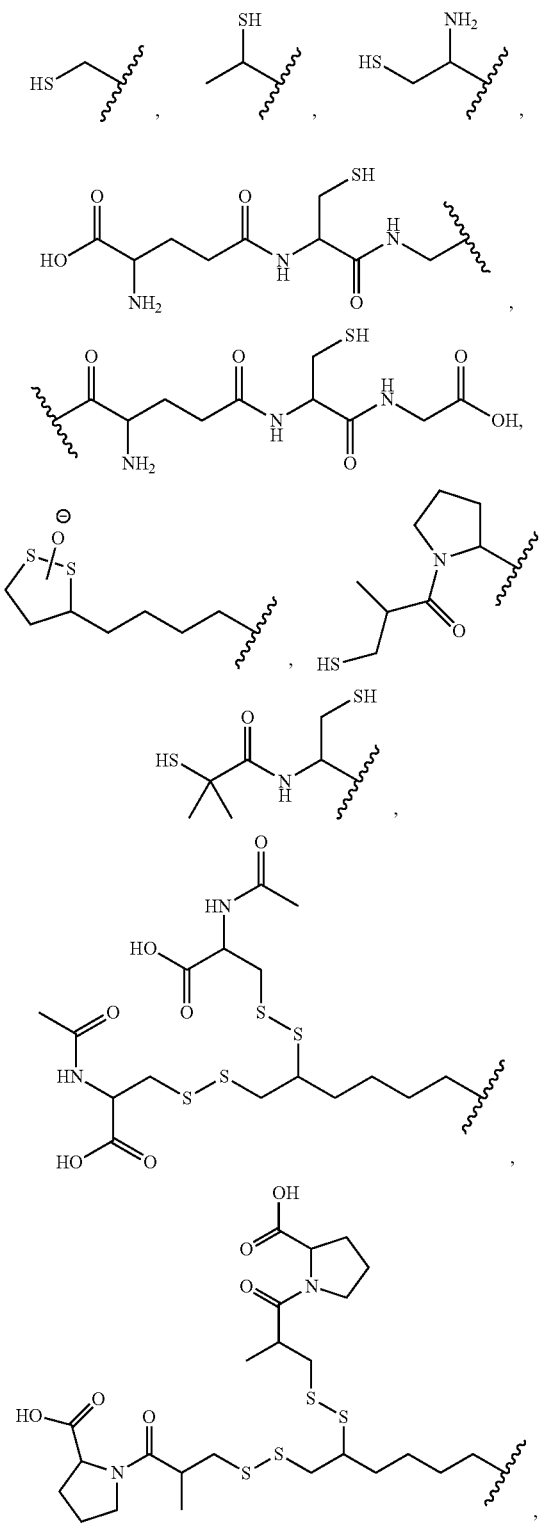

95
-continued
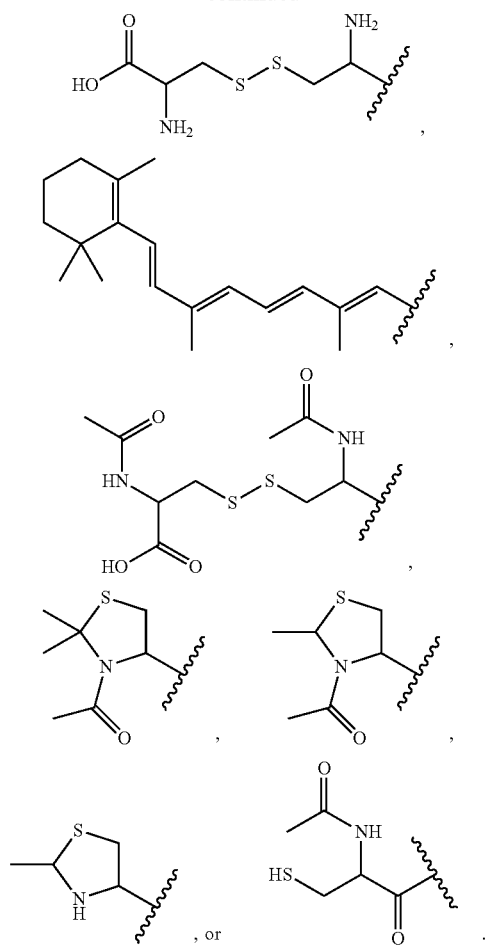
In some embodiments, R is:
96
-continued
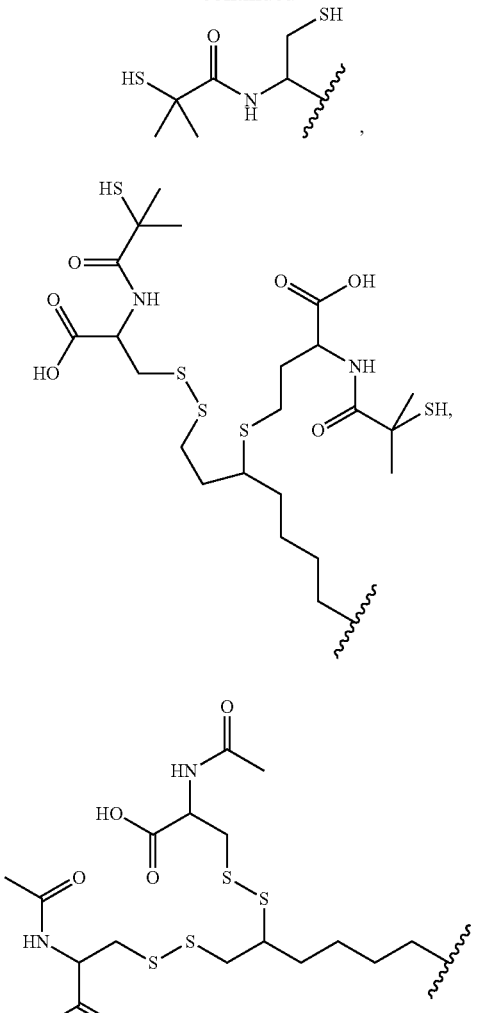
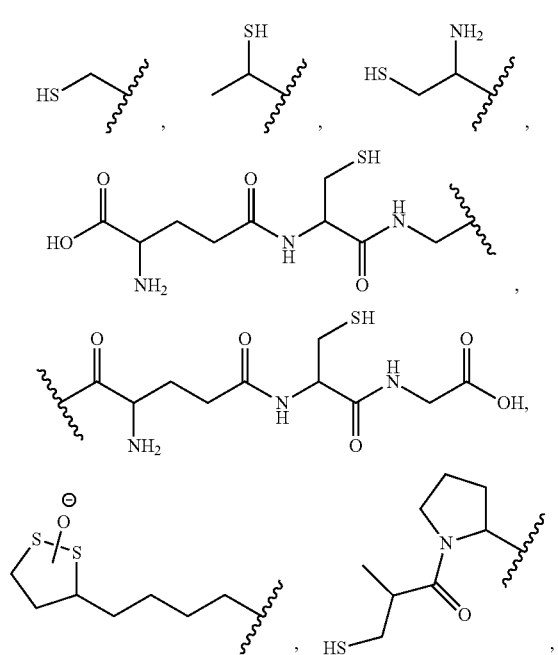

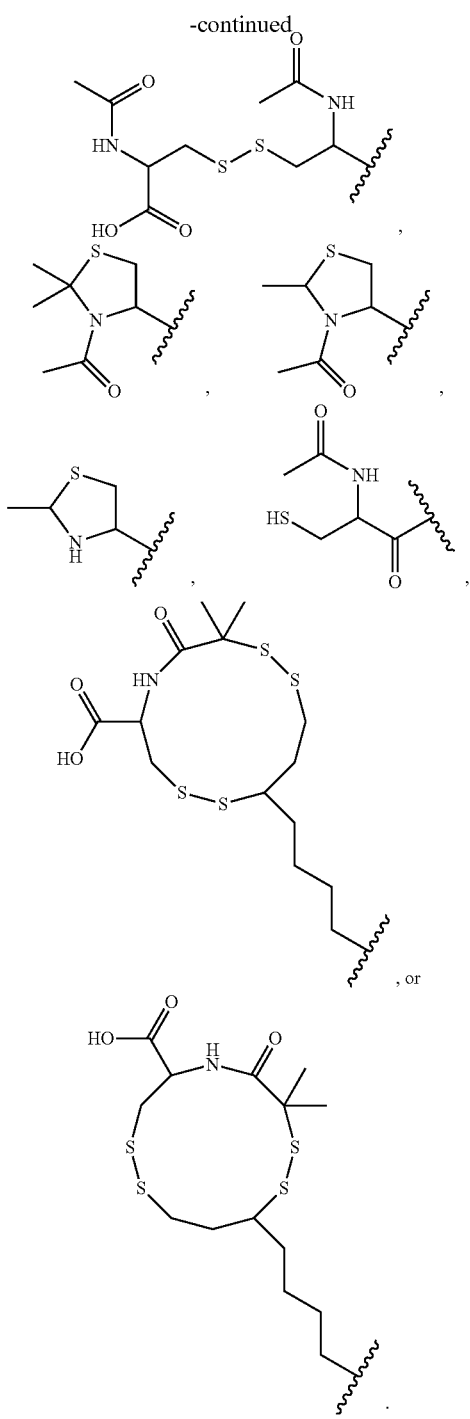

In some embodiments, R is the radical recited in Compound 1.
In some embodiments, R is the radical recited in Compound 2.
In some embodiments, R is the radical recited in Compound 3.
In some embodiments, R is the radical recited in Compound 4.
In some embodiments, R is the radical recited in Compound 5.
In some embodiments, R is the radical recited in Compound 6.
In some embodiments, R is the radical recited in Compound 7.
In some embodiments, R is the radical recited in Compound 8.
In some embodiments, R is the radical recited in Compound 9.
In some embodiments, R is the radical recited in Compound 10.
In some embodiments, R is the radical recited in Compound 11.
In some embodiments, R is the radical recited in Compound 12.
In some embodiments, R is the radical recited in Compound 13.
In some embodiments, R is the radical recited in Compound 14.
In some embodiments, R is the radical recited in Compound 15.
In some embodiments, R is the radical recited in Compound 16.
In some embodiments, R is the radical recited in Compound 17.
In some embodiments, R is the radical recited in Compound 18.
In some embodiments, R is the radical recited in Compound 19.
In some embodiments, R is the radical recited in Compound 20.
In some embodiments, R is the radical recited in Compound 24.
In some embodiments, R is the radical recited in Compound 25.
In some embodiments, R is the radical recited in Compound 26.
In some embodiments, R is the radical recited in Compound 28.
In some embodiments, R is the radical recited in Compound 29.
In some embodiments, R is the radical recited in Compound 31.
In some embodiments, R is the radical recited in Compound 32.
In some embodiments, R is the radical recited in Compound 33.
In some embodiments, R is the radical recited in Compound 34.
In some embodiments, R is the radical recited in Compound 35.
In some embodiments, R is the radical recited in Compound 36.
In some embodiments, R is the radical recited in Compound 37.
In some embodiments, R is the radical recited in Compound 38.
In some embodiments, R is the radical recited in Compound 40.
In some embodiments, R is the radical recited in Compound 41.
In some embodiments, R is the radical recited in Compound 42.
In some embodiments, R is the radical recited in Compound 43.
In some embodiments, R is the radical recited in Compound 44.
In some embodiments, R is the radical recited in Compound 45.

In some embodiments, R is the radical recited in Compound 46.
In some embodiments, R is the radical recited in Compound 47.
In some embodiments, R is the radical recited in Compound 48.
In some embodiments, R is the radical recited in Compound 49.
In some embodiments, R is the radical recited in Compound 50.
In some embodiments, R is the radical recited in Compound 51.
In some embodiments, the compound is other than a compound having the structure:

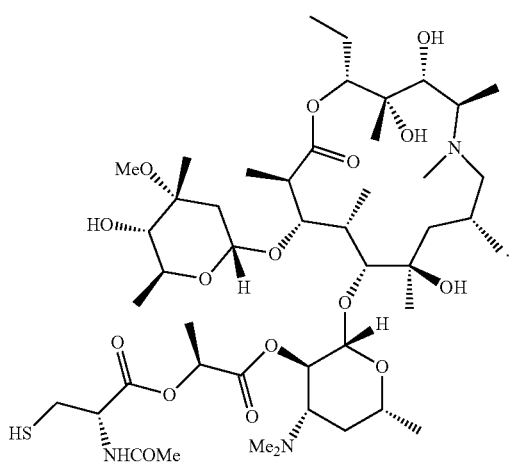

Provided in some embodiments herein is a compound having the structure of Formula (Ib):

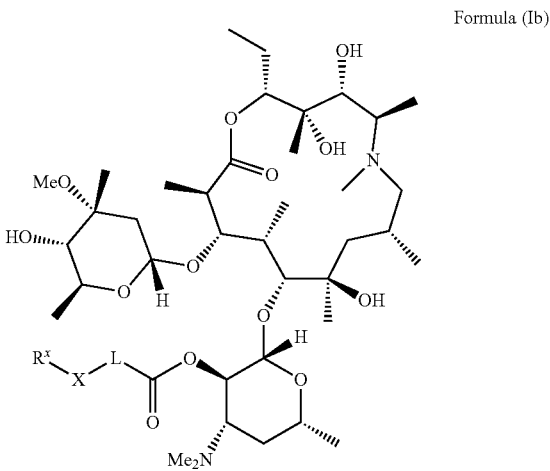

Formula (Ib)

or a pharmaceutically acceptable salt or solvate (e.g., or a stereoisomer) thereof,
wherein:
L is bond, —(C=O)(OCR$^8$R$^9$)$_z$—, or —(C=O)(OCR$^8$R$^9$)$_z$O—;
each R$^8$ and R$^9$ is independently H, halogen, $C_1$-$C_3$-alkyl, $C_1$-$C_3$-haloalkyl, $C_1$-$C_3$-alkoxy, $C_3$-$C_5$-cycloalkyl, or R$^8$ and R$^9$ are taken together with the atoms to which they are attached to form a $C_3$-$C_5$-cycloalkyl;
z is 1-6;
X is absent or —O—; and R$^x$ is:

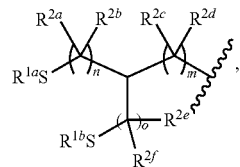

R$^{1a}$ and R$^{1b}$ are each independently —H or —SR$^{1c}$;
each R$^{1C}$ is independently substituted or unsubstituted (e.g., straight or branched) alkyl (e.g., substituted with one or more (alkyl) substituent, each (alkyl) substituent being independently selected from the group consisting of carboxylic acid, —SH, thioalkyl, acetamide, amino, oxo, optionally substituted heterocycloalkyl (e.g., N-attached pyrrolidinyl substituted with —COOH)) or substituted or unsubstituted (e.g., straight or branched) heteroalkyl (e.g., substituted with one or more (heteroalkyl) substituent, each (heteroalkyl) substituent being independently selected from the group consisting of carboxylic acid, amino, thioalkyl, thiol, acetamide, and $C_1$-$C_3$ alkyl);
each R$^{2a}$, R$^{2b}$, R$^{2c}$, R$^{2d}$, R$^{2e}$, and R$^{2f}$ is independently H, halogen, $C_1$-$C_3$-alkyl, $C_1$-$C_3$-haloalkyl, $C_1$-$C_3$-alkoxy, $C_3$-$C_5$-cycloalkyl, or two of R$^{2a}$ and R$^{2b}$, R$^{2c}$ and R$^{2d}$, or R$^{2e}$ and R$^{2f}$ are taken together with the atoms to which they are attached to form a $C_3$-$C_5$-cycloalkyl;
m is an integer from 1-10; and
n and o are each independently an integer from 0-3.

Provided in some embodiments herein is a compound having the structure of Formula (Ib):

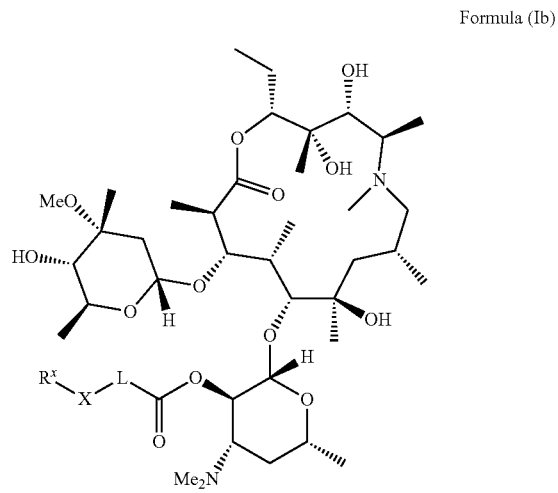

Formula (Ib)

or a pharmaceutically acceptable salt or solvate (e.g., or a stereoisomer) thereof,
wherein:
L is bond, —(C=O)(OCR$^8$R$^9$)$_z$—, or —(C=O)(OCR$^8$R$^9$)$_z$O—;
each R$^8$ and R$^9$ is independently H, halogen, $C_1$-$C_3$-alkyl, $C_1$-$C_3$-haloalkyl, $C_1$-$C_3$-alkoxy, $C_3$-$C_5$-cycloalkyl, or $R^8$ and $R^9$ are taken together with the atoms to which they are attached to form a $C_3$-$C_5$-cycloalkyl;

z is 1-6;

X is absent or —O—; and $R^x$ is:

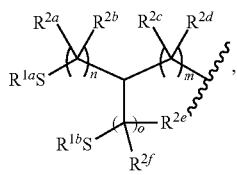

$R^{1a}$ and $R^{1b}$ are each independently —H or —$SR^{1c}$;

each $R^{1c}$ is independently substituted or unsubstituted (e.g., straight or branched) alkyl (e.g., substituted with one or more (alkyl) substituent, each (alkyl) substituent being independently selected from the group consisting of carboxylic acid, —SH, thioalkyl, acetamide, amino, oxo, optionally substituted heterocycloalkyl (e.g., N-attached pyrrolidinyl substituted with —COOH)) or substituted or unsubstituted (e.g., straight or branched) heteroalkyl (e.g., substituted with one or more (heteroalkyl) substituent, each (heteroalkyl) substituent being independently selected from the group consisting of carboxylic acid, amino, thioalkyl, thiol, acetamide, and $C_1$-$C_3$ alkyl);

each $R^{2a}$, $R^{2b}$, $R^{2c}$, $R^{2d}$, $R^{2e}$, and $R^{2f}$ is independently H, halogen, $C_1$-$C_3$-alkyl, $C_1$-$C_3$-haloalkyl, $C_1$-$C_3$-alkoxy, $C_3$-$C_5$-cycloalkyl, or two of $R^{2a}$ and $R^{2b}$, $R^{2c}$ and $R^{2d}$, or $R^{2e}$ and $R^{2f}$ are taken together with the atoms to which they are attached to form a $C_3$-$C_5$-cycloalkyl;

m is an integer from 1-10; and n and o are each independently an integer from 1-3.

In some embodiments, o is 0.

In some embodiments, o is 0, and $R^x$ is:

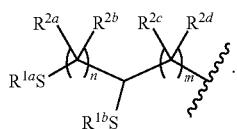

In some embodiments, o is 0 and n is 2.

In some embodiments, o is 0, n is 2, and $R^x$ is:

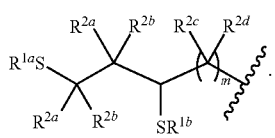

In some embodiments, o is 0 and n is 1.

In some embodiments, o is 0, n is 1, and $R^x$ is:

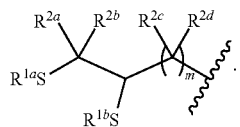

In some embodiments, m is an integer from 3-5.

In some embodiments, each $R^{2a}$, $R^{2b}$, $R^{2c}$, $R^{2d}$, $R^{2e}$, and $R^{2f}$ is independently H, halogen, $C_1$-$C_3$alkyl, or $C_1$-$C_3$haloalkyl. In some embodiments, each $R^{2a}$, $R^{2b}$, $R^{2c}$, $R^{2d}$, $R^{2e}$, and $R^{2f}$ is H.

In some embodiments, $R^x$ is:

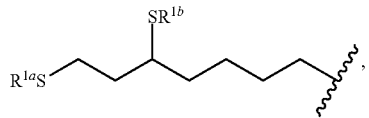

wherein:

$R^{1a}$ and $R^{1b}$ are each independently —H or —$SR^{1c}$; and
each $R^{1c}$ is independently substituted or unsubstituted (e.g., straight or branched) alkyl (e.g., substituted with one or more (alkyl) substituent, each (alkyl) substituent being independently selected from the group consisting of carboxylic acid, —SH, thioalkyl, acetamide, amino, oxo, optionally substituted heterocycloalkyl (e.g., N-attached pyrrolidinyl substituted with —COOH)) or substituted or unsubstituted (e.g., straight or branched) heteroalkyl (e.g., substituted with one or more (heteroalkyl) substituent, each (heteroalkyl) substituent being independently selected from the group consisting of carboxylic acid, amino, thioalkyl, thiol, acetamide, and $C_1$-$C_3$ alkyl).

In some embodiments, $R^x$ is:

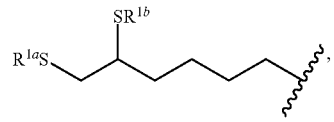

wherein:

$R^{1a}$ and $R^{1b}$ are each independently —H or —$SR^{1c}$; and
each $R^{1c}$ is independently substituted or unsubstituted (e.g., straight or branched) alkyl (e.g., substituted with one or more (alkyl) substituent, each (alkyl) substituent being independently selected from the group consisting of carboxylic acid, —SH, thioalkyl, acetamide, amino, oxo, optionally substituted heterocycloalkyl (e.g., N-attached pyrrolidinyl substituted with —COOH)) or substituted or unsubstituted (e.g., straight or branched) heteroalkyl (e.g., substituted with one or more (heteroalkyl) substituent, each (heteroalkyl) substituent being independently selected from the group consisting of carboxylic acid, amino, thioalkyl, thiol, acetamide, and $C_1$-$C_3$ alkyl).

In some embodiments, $R^{1a}$ is —H or —$SR^{1c}$ and $R^{1b}$ is —$SR^{1c}$, or $R^{1a}$ is —$SR^{1c}$ and $R^{1b}$ is —H or —$SR^{1c}$. In some embodiments, $R^{1a}$ and $R^{1b}$ are each —$SR^{1c}$.

In some embodiments, $R^{1a}$ and $R^{1b}$ each independently comprise a radical of one or more keratolytic group (e.g., each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc)).

In some embodiments, $R^{1a}$ and $R^{1b}$ are each independently a radical of one or more keratolytic group, each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc).

In some embodiments, $R^{1a}$ and $R^{1b}$ each independently comprise a (thiol) radical of one or more keratolytic group, each (thiol) radical of the one or more keratolytic group being independently selected from the group consisting of a (thiol) radical of thioglycolic acid (TGA), a (thiol) radical of thiolactic acid (TLac), a (thiol) radical of dihydrolipoic acid (diHLip), a (thiol) radical of N-acetyl cysteine (NAC), a (thiol) radical of cysteine (Cys), a (thiol) radical of glutathione (GSH), a (thiol) radical of captopril (Cap), and a (thiol) radical of bucillamine (Buc).

In some embodiments, $R^{1a}$ and $R^{1b}$ are each independently a thiol radical of one or more keratolytic group, each thiol radical of the one or more keratolytic group being independently selected from the group consisting of a thiol radical of thioglycolic acid (TGA), a thiol radical of thiolactic acid (TLac), a thiol radical of dihydrolipoic acid (diHLip), a thiol radical of N-acetyl cysteine (NAC), a thiol radical of cysteine (Cys), a thiol radical of glutathione (GSH), a thiol radical of captopril (Cap), and a thiol radical of bucillamine (Buc).

In some embodiments, the (e.g., thiol) radical of the keratolytic agent comprises a (e.g., thiol) radical of one or more keratolytic group, each (e.g., thiol) radical of the one or more keratolytic group being independently selected from the group consisting of [Lac-Lac]., [Lac-NAC]., [Cys-Cys]., [diHLip-NAC-NAC]., [diHLip-NAC]., [diHLip-Cap-Cap]., [diHLip-Cap]., [diHLip-Cys-Cys]., [diHLip-Cys]., [diHLip-Lipox-Lipox]., and [diHLip-Lipox]•.

Unless stated otherwise, a radical (or .) is molecule having unpaired electrons. In some embodiments, the radical is a radical of a heteroatom (e.g., —O., —N., or —S.). In some embodiments, the radical (e.g., the molecule having unpaired electron) is paired with another unpaired electron of another molecule to form paired electrons. In some embodiments, a radical of a keratolytic agent provided herein is paired with any compound provided herein. In some embodiments, a first radical of a keratolytic agent provided herein is paired with a second radical of a keratolytic provided herein.

In some embodiments, the thiol radical of the keratolytic group is the point of attachment of $R^{1a}$ and/or $R^{1b}$ to the rest of the molecule. In some embodiments, $R^{1a}$ and/or $R^{1b}$ attach to the rest of the molecule to form a disulfide bond.

In some embodiments, $R^{1a}$ and $R^{1b}$ are each independently —H or:

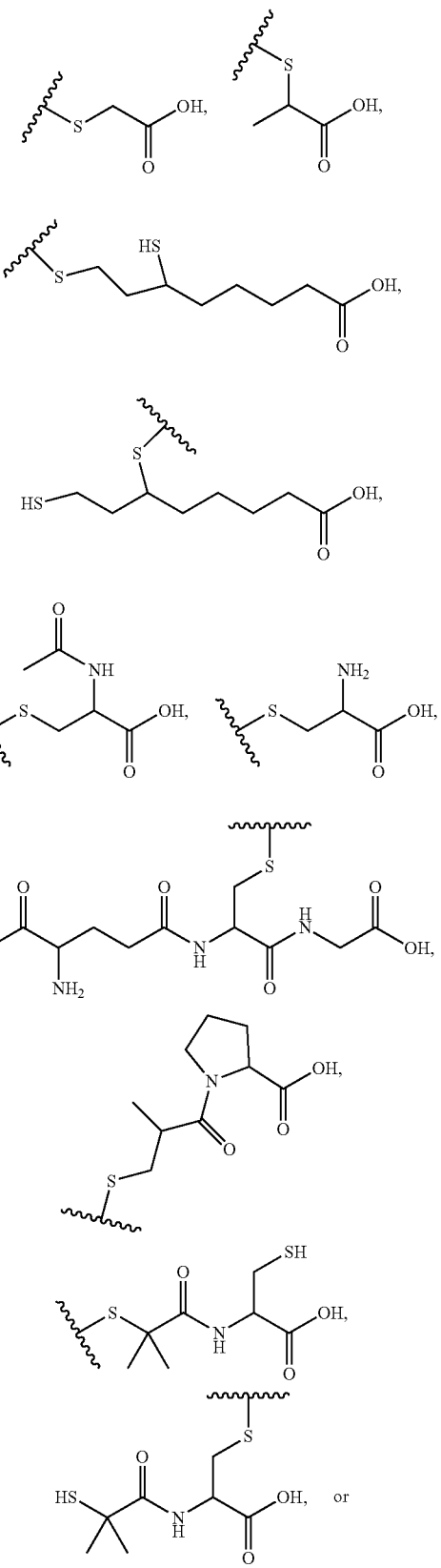

-continued

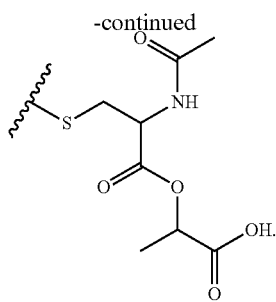

In some embodiments, $R^{1a}$ and $R^{1b}$ are the same. In some embodiments, $R^{1a}$ and $R^{1b}$ are different.

In some embodiments, $R^x$ is:

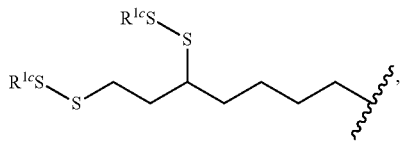

wherein:
each $R^{1c}$ is independently substituted or unsubstituted (e.g., straight or branched) alkyl (e.g., substituted with one or more (alkyl) substituent, each (alkyl) substituent being independently selected from the group consisting of carboxylic acid, —SH, thioalkyl, acetamide, amino, oxo, optionally substituted heterocycloalkyl (e.g., N-attached pyrrolidinyl substituted with —COOH)) or substituted or unsubstituted (e.g., straight or branched) heteroalkyl (e.g., substituted with one or more (heteroalkyl) substituent, each (heteroalkyl) substituent being independently selected from the group consisting of carboxylic acid, amino, thioalkyl, thiol, acetamide, and $C_1$-$C_3$ alkyl).

In some embodiments, $R^x$ is:

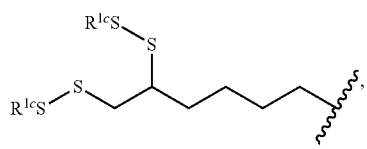

wherein:
each $R^{1c}$ is independently substituted or unsubstituted (e.g., straight or branched) alkyl (e.g., substituted with one or more (alkyl) substituent, each (alkyl) substituent being independently selected from the group consisting of carboxylic acid, —SH, thioalkyl, acetamide, amino, oxo, optionally substituted heterocycloalkyl (e.g., N-attached pyrrolidinyl substituted with —COOH)) or substituted or unsubstituted (e.g., straight or branched) heteroalkyl (e.g., substituted with one or more (heteroalkyl) substituent, each (heteroalkyl) substituent being independently selected from the group consisting of carboxylic acid, amino, thioalkyl, thiol, acetamide, and $C_1$-$C_3$ alkyl).

In some embodiments, each $R^{1c}$ is independently substituted or unsubstituted (e.g., straight or branched) alkyl or substituted or unsubstituted (e.g., straight or branched) heteroalkyl. In some embodiments, each $R^{1c}$ is independently substituted (e.g., straight or branched) alkyl or substituted (e.g., straight or branched) heteroalkyl.

In some embodiments, each $R^{1c}$ is independently substituted (e.g., straight or branched) alkyl, the substituted alkyl being substituted with one or more (alkyl) substituent, each (alkyl) substituent being independently selected from the group consisting of carboxylic acid, —SH, thioalkyl, acetamide, amino, oxo, and optionally substituted heterocycloalkyl (e.g., N-attached pyrrolidinyl substituted with —COOH).

In some embodiments, each $R^{1c}$ is independently substituted (e.g., straight or branched) heteroalkyl, the substituted heteroalkyl being substituted with one or more (heteroalkyl) substituent, each (heteroalkyl) substituent being independently selected from the group consisting of carboxylic acid, amino, thioalkyl, thiol, acetamide, and $C_1$-$C_3$ alkyl.

In some embodiments, $R^{1a}$, $R^{1b}$, and each $R^{1c}$ each independently comprise one or more substituent that is a carboxylic acid or an ester. In some embodiments, $R^{1a}$, $R^{1b}$, and each $R^{1c}$ each independently comprise one or more substituent that is a carboxylic acid (e.g., —(C=O)OH). In some embodiments, $R^{1a}$ comprises one or more substituent that is a carboxylic acid (e.g., —(C=O)OH). In some embodiments, $R^{1b}$ comprises one or more substituent that is a carboxylic acid (e.g., —(C=O)OH). In some embodiments, each $R^1$ independently comprises one or more substituent that is a carboxylic acid (e.g., —(C=O)OH). In some embodiments, $R^{1a}$, $R^{1b}$, and each $R^{1c}$ each independently comprise one or more substituent that is an ester (e.g., —(C=O)O—$C_1$-$C_4$alkyl). In some embodiments, $R^{1a}$ comprises one or more substituent that is an ester (e.g., —(C=O)O—$C_1$-$C_4$alkyl). In some embodiments, $R^{1b}$ comprises one or more substituent that is an ester (e.g., —(C=O)O—$C_1$-$C_4$alkyl). In some embodiments, each $R^{1c}$ independently comprises one or more substituent that is an ester (e.g., —(C=O)O—$C_1$-$C_4$alkyl).

In some embodiments, the —(C=O)OH of $R^{1a}$, $R^{1b}$, and/or $R^{1c}$ is optionally esterified (e.g., —(C=O)OH or —(C=O)O—$C_1$-$C_4$alkyl). In some embodiments, the $C_1$-$C_4$alkyl is methyl, ethyl, propyl, isopropyl, butyl, or t-butyl.

Provided in some embodiments herein is a compound having the structure of Formula (Ic):

Formula (Ic)

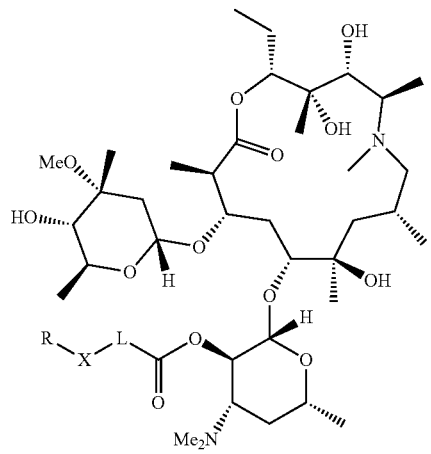

or a pharmaceutically acceptable salt or solvate (e.g., or a stereoisomer) thereof,
wherein:
L is bond, —(C=O)(OCR$^8$R$^9$)$_z$—, or —(C=O)(OCR$^8$R$^9$)$_z$O—;
each $R^8$ and $R^9$ is independently H, halogen, $C_1$-$C_3$-alkyl, $C_1$-$C_3$-haloalkyl, $C_1$-$C_3$-alkoxy, $C_3$-$C_5$-cycloalkyl, or $R^8$ and $R^9$ are taken together with the atoms to which they are attached to form a $C_3$-$C_5$-cycloalkyl;
z is 1-6;

X is absent or —O—; and
$R^y$ is:

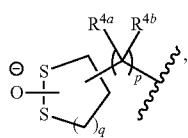

each $R^{4a}$ and $R^{4b}$ is independently H, halogen, or substituted or unsubstituted alkyl;
p is an integer from 1-10; and
q is an integer from 1-3.

In some embodiments, q is 1.

In some embodiments, p is an integer from 3-5. In some embodiments, p is 4. In some embodiments, q is 1 and p is 4.

In some embodiments, q is 1 and p is an integer from 3-5.

In some embodiments, each $R^{4a}$ and $R^{4b}$ is independently H or substituted or unsubstituted alkyl.

In some embodiments, each $R^{4a}$ and $R^{4b}$ is independently H, halogen, $C_1$-$C_3$alkyl, or $C_1$-$C_3$haloalkyl. In some embodiments, each $R^{4a}$ and $R^{4b}$ is H.

In some embodiments, $R^y$ is:

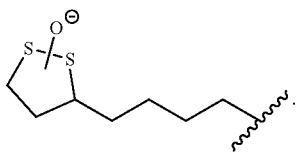

In some embodiments, the sulfoxide of any compound provided herein is racemic. In some embodiments, the sulfoxide of any compound provided herein is an enantiomer. In some embodiments, the sulfoxide of any compound provided herein is has a stereochemistry that is (R) or (S).

In some embodiments, provided herein is a compound having the structure of Formula (Id):

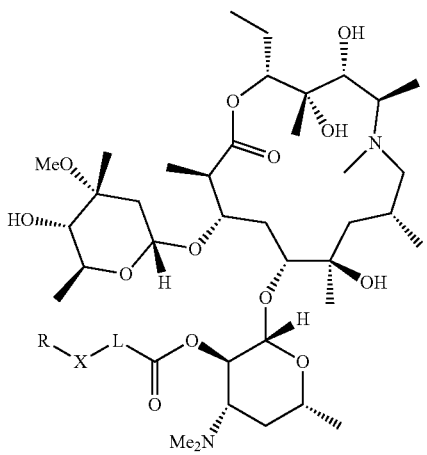

Formula (Id)

or a pharmaceutically acceptable salt or solvate (e.g., or a stereoisomer) thereof,
wherein:
L is bond, —(C=O)(OCR$^8$R$^9$)$_z$—, or —(C=O)(OCR$^8$R$^9$)$_z$O—;
each $R^8$ and $R^9$ is independently H, halogen, $C_1$-$C_3$-alkyl, $C_1$-$C_3$-haloalkyl, $C_1$-$C_3$-alkoxy, $C_3$-$C_5$-cycloalkyl, or $R^8$ and $R^9$ are taken together with the atoms to which they are attached to form a $C_3$-$C_5$-cycloalkyl;
z is 1-6;
X is absent or —O—; and
$R^z$ is:

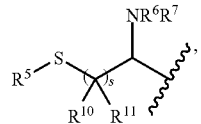

$R^5$ is —SR1c;
$R^{1c}$ is substituted or unsubstituted (e.g., straight or branched) alkyl (e.g., substituted with one or more (alkyl) substituent, each (alkyl) substituent being independently selected from the group consisting of carboxylic acid, —SH, thioalkyl, acetamide, amino, oxo, optionally substituted heterocycloalkyl (e.g., N-attached pyrrolidinyl substituted with —COOH)) or substituted or unsubstituted (e.g., straight or branched) heteroalkyl (e.g., substituted with one or more (heteroalkyl) substituent, each (heteroalkyl) substituent being independently selected from the group consisting of carboxylic acid, amino, thioalkyl, thiol, acetamide, and $C_1$-$C_3$ alkyl);
$R^6$ and $R^7$ are each independently H, substituted or unsubstituted alkyl, or substituted or unsubstituted heteroalkyl;
each $R^{10}$ and $R^{11}$ is independently H, halogen, $C_1$-$C_3$-alkyl, $C_1$-$C_3$-haloalkyl, $C_1$-$C_3$-alkoxy, $C_3$-$C_5$-cycloalkyl, or two of $R^{10}$ and $R^{11}$ are taken together with the atoms to which they are attached to form a $C_3$-$C_5$-cycloalkyl; and
s is an integer from 1-10.

In some embodiments, $R^6$ and $R^7$ are each independently H or substituted or unsubstituted alkyl (e.g., $C_1$-$C_3$ alkyl optionally substituted with oxo). In some embodiments, $R^6$ and $R^7$ are each independently H or $C_1$-$C_3$ alkyl optionally substituted with oxo. In some embodiments, $R^6$ and $R^7$ are each independently H or —(C=O)CH$_3$. In some embodiments, $R^6$ is H and $R^7$ is H or —(C=O)CH$_3$. In some embodiments, $R^6$ is H and $R^7$ is —(C=O)CH$_3$. In some embodiments, $R^6$ and $R^7$ are H.

In some embodiments, each $R^{10}$ and $R^{11}$ is independently H, halogen, $C_1$-$C_3$alkyl, or $C_1$-$C_3$haloalkyl.

In some embodiments, each $R^{10}$ and $R^{11}$ is H.

In some embodiments, s is 1-3. In some embodiments, s is 1. In some embodiments, s is 1 and $R^{10}$ and $R^{11}$ are H.

In some embodiments, $R^6$, $R^7$, $R^{10}$ and $R^{11}$ are each H, and s is 1-3.

In some embodiments $R^{1c}$ is substituted alkyl or substituted heteroalkyl.

In some embodiments, $R^{1c}$ is heteroalkyl substituted with carboxylic acid.

In some embodiments, $R^{1c}$ is alkyl substituted with one or more alkyl substituent, each alkyl substituent being independently selected from the group consisting of carboxylic acid and acetamide.

In some embodiments $R^{1c}$ is substituted heteroalkyl, the heteroalkyl being substituted with one or more heteroalkyl substituent, each heteroalkyl substituent being independently selected from the group consisting of oxo, carboxylic acid, amino, thioalkyl, thiol, acetamide, and $C_1$-$C_3$ alkyl. In some embodiments, $R^{1c}$ is heteroalkyl substituted with carboxylic acid.

In some embodiments, $R^{1c}$ is substituted heteroalkyl, the heteroalkyl being substituted with —COOH and oxo. In some embodiments, $R^{1c}$ is substituted heteroalkyl, the heteroalkyl being substituted with oxo and acetamide. In some embodiments, $R^{1c}$ is substituted heteroalkyl, the heteroalkyl being substituted with $C_1$-$C_3$ alkyl, oxo, and substituted N-attached heterocycloalkyl. In some embodiments, $R^{1c}$ is substituted heteroalkyl, the heteroalkyl being substituted with —COOH, $C_1$-$C_3$ alkyl, oxo, and thiol.

In some embodiments, $R^5$ comprises a radical of one or more keratolytic group (e.g., each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc)).

In some embodiments, $R^5$ is a radical of one or more keratolytic group, each radical of the one or more keratolytic group being independently selected from the group consisting of a radical of glycolic acid (GA), a radical of thioglycolic acid (TGA), a radical of lactic acid (Lac), a radical of thiolactic acid (TLac), a radical of lipoic acid (Lip), a radical of lipoic acid sulfoxide (Lipox), a radical of dihydrolipoic acid (diHLip), a radical of N-acetyl cysteine (NAC), a radical of cysteine (Cys), a radical of glutathione (GSH), a radical of captopril (Cap), and a radical of bucillamine (Buc).

In some embodiments, $R^5$ comprises a (thiol) radical of one or more keratolytic group, each (thiol) radical of the one or more keratolytic group being independently selected from the group consisting of a (thiol) radical of thioglycolic acid (TGA), a (thiol) radical of thiolactic acid (TLac), a (thiol) radical of dihydrolipoic acid (diHLip), a (thiol) radical of N-acetyl cysteine (NAC), a (thiol) radical of cysteine (Cys), a (thiol) radical of glutathione (GSH), a (thiol) radical of captopril (Cap), and a (thiol) radical of bucillamine (Buc).

In some embodiments $R^5$ is a thiol radical of one or more keratolytic group, each thiol radical of the one or more keratolytic group being independently selected from the group consisting of a thiol radical of thioglycolic acid (TGA), a thiol radical of thiolactic acid (TLac), a thiol radical of dihydrolipoic acid (diHLip), a thiol radical of N-acetyl cysteine (NAC), a thiol radical of cysteine (Cys), a thiol radical of glutathione (GSH), a thiol radical of captopril (Cap), and a thiol radical of bucillamine (Buc).

In some embodiments, the (e.g., thiol) radical of the keratolytic agent comprises a (e.g., thiol) radical of one or more keratolytic group, each (e.g., thiol) radical of the one or more keratolytic group being independently selected from the group consisting of [Lac-Lac]., [Lac-NAC]., [Cys-Cys]., [diHLip-NAC-NAC]., [diHLip-NAC]., [diHLip-Cap-Cap]., [diHLip-Cap]., [diHLip-Cys-Cys]., [diHLip-Cys]., [diHLip-Lipox-Lipox]., and [diHLip-Lipox]..

In some embodiments, the thiol radical of the keratolytic group is the point of attachment of $R^5$ to the rest of the molecule. In some embodiments, $R^5$ attaches to the rest of the molecule to form a disulfide bond.

In some embodiments, $R^5$ is:

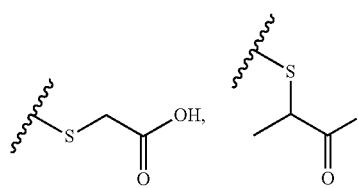

-continued

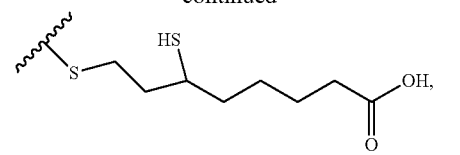

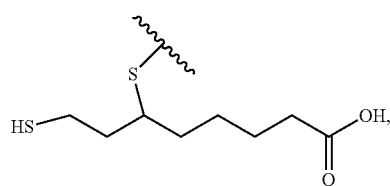

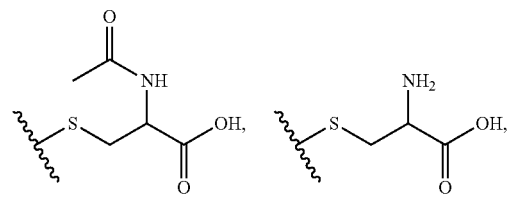

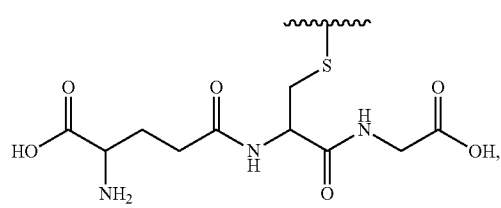

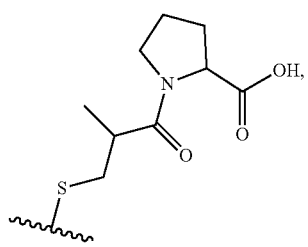

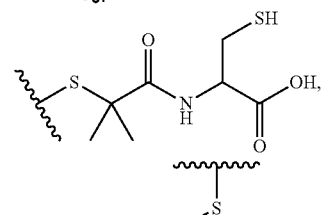

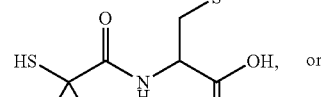

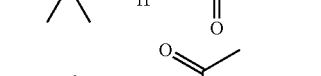 or

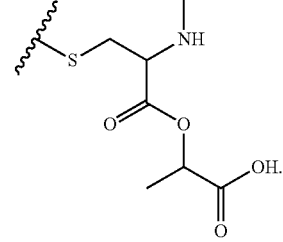

In some embodiments, $R^z$ is:

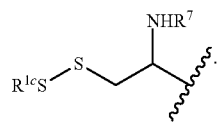

In some embodiments, $R^7$ is H or —(C=O)CH$_3$. In some embodiments, $R^7$ is H. In some embodiments, $R^7$ is —(C=O)CH$_3$.

In some embodiments, each $R^{1c}$ is independently substituted or unsubstituted (e.g., straight or branched) alkyl or substituted or unsubstituted (e.g., straight or branched) heteroalkyl. In some embodiments, each $R^{1c}$ is independently substituted (e.g., straight or branched) alkyl or substituted (e.g., straight or branched) heteroalkyl.

In some embodiments, each $R^{1c}$ is independently substituted (e.g., straight or branched) alkyl, the substituted alkyl being substituted with one or more (alkyl) substituent, each (alkyl) substituent being independently selected from the group consisting of carboxylic acid, —SH, thioalkyl, acetamide, amino, oxo, and optionally substituted heterocycloalkyl (e.g., N-attached pyrrolidinyl substituted with —COOH).

In some embodiments, each $R^{1c}$ is independently substituted (e.g., straight or branched) heteroalkyl, the substituted heteroalkyl being substituted with one or more (heteroalkyl) substituent, each (heteroalkyl) substituent being independently selected from the group consisting of carboxylic acid, amino, thioalkyl, thiol, acetamide, and $C_1$-$C_3$ alkyl.

In some embodiments, $R^5$ and each $R^{1c}$ each independently comprise one or more substituent that is a carboxylic acid or an ester. In some embodiments, $R^5$ and each $R^{1c}$ each independently comprise one or more substituent that is a carboxylic acid (e.g., —(C=O)OH). In some embodiments, $R^5$ and each $R^{1c}$ each independently comprise one or more substituent that is an ester (e.g., —(C=O)O—$C_1$-$C_4$alkyl).

In some embodiments, the —(C=O)OH of $R^5$ and/or $R^{1c}$ is optionally esterified (e.g., —(C=O)OH or —(C=O)O—$C_1$-$C_4$alkyl). In some embodiments, the $C_1$-$C_4$alkyl is methyl, ethyl, propyl, isopropyl, butyl, or t-butyl.

Provided in some embodiments herein is a compound, a stereoisomer thereof, or a pharmaceutically acceptable salt of the compound or the stereoisomer, having a structure provided in Table 1.

TABLE 1

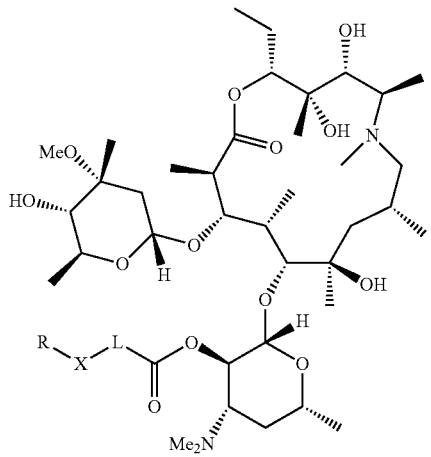

| Compound | R | X | L |
|---|---|---|---|
| 1 | HS⌇ | absent | bond |
| 2 | SH (dashed)—CH—CH$_3$⌇ | absent | bond |
| 3 | SH—CH—CH$_3$⌇ | absent | bond |
| 4 | HS—CH$_2$—CH(NH$_2$)—⌇ | absent | bond |

TABLE 1-continued

| Compound | R | X | L |
|---|---|---|---|
| 5 | (N-acetyl cysteine, HS-CH2-CH(NHAc)-) | absent | bond |
| 6 | (1,2-dithiolane 1-oxide with pentyl linker) | absent | bond |
| 7 | (1,2-dithiolane 1-oxide with pentyl linker, alternate stereochemistry) | absent | bond |
| 8 | (1,2-dithiolane 2-oxide with pentyl linker) | absent | bond |
| 9 | (1,2-dithiolane 2-oxide with pentyl linker, alternate stereochemistry) | absent | bond |
| 10 | (glutathione-derived) | absent | bond |

TABLE 1-continued

| Compound | R | X | L |
|---|---|---|---|
| 11 | (4-amino-glutamyl-cysteinyl-glycine structure with SH and NH₂, COOH) | absent | bond |
| 12 | (2-mercapto-2-methylpropanoyl-cysteine structure with SH) | absent | bond |
| 13 | (2-mercapto-2-methylpropanoyl-cysteine structure with SH) | absent | bond |
| 14 | (2-methyl-3-mercaptopropanoyl-pyrrolidine structure) | absent | bond |
| 15 | (bis-N-acetylcysteine trisulfide structure with hexyl chain) | absent | bond |

TABLE 1-continued

| Compound | R | X | L |
|---|---|---|---|
| 16 | (structure shown) | absent | bond |
| 17 | (structure shown) | absent | bond |
| 18 | (structure shown) | absent | bond |

TABLE 1-continued
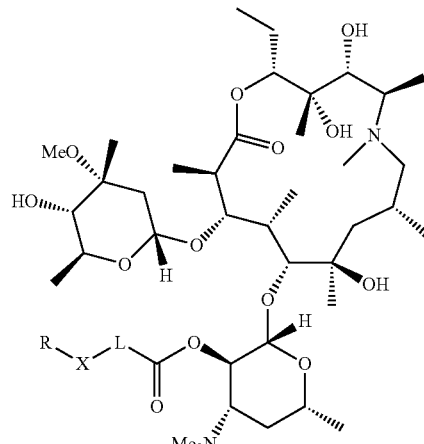
| Compound | R | X | L |
|---|---|---|---|
| 19 | HOOC-CH(NH₂)-CH₂-S-S-CH₂-CH(NH₂)-⁓ | absent | bond |
| 20 | HS-CH₂-⁓ | absent | —(C=O)OCH(CH₃)O— |
| 21 | HS-CH₂-⁓ | absent | —(C=O)OCH₂O— |
| 22 | HS-CH₂-CH(NH₂)-⁓ | absent | —(C=O)OCH(CH₃)O— |
| 23 | lipoic acid S-oxide group | absent | —(C=O)OCH(CH₃)O— |
| 24 | lipoic acid S-oxide group | —O— | —(C=O)OCH₂O— |
| 25 | lipoic acid S-oxide group | —O— | —(C=O)OCH(CH₂CH₃)O— |

TABLE 1-continued

| Compound | R | X | L |
|---|---|---|---|
| 26 | [structure: 1,2-dithiolane 1-oxide with pentyl chain] | absent | —(C=O)OC(CH₃)₂O— |
| 27 | [structure: Fmoc-protected cysteine with S-tBu] | absent | bond |
| 28 | [structure: H₂N-CH(CH₂-S-tBu)-] | absent | bond |
| 29 | [structure: Ac-NH-CH(CH₂-S-tBu)-] | absent | bond |

TABLE 1-continued
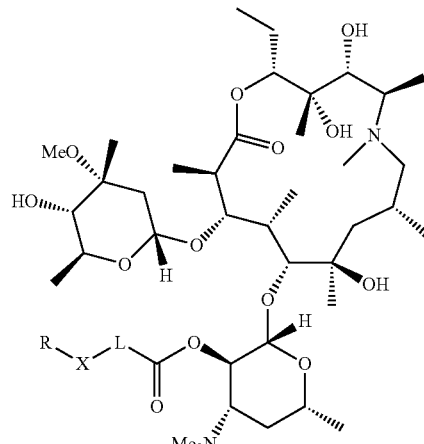
| Compound | R | X | L |
|---|---|---|---|
| 30 | 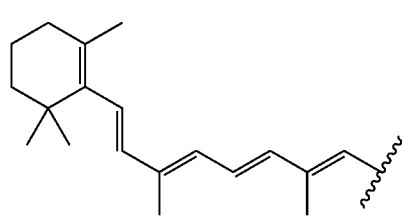 [SMILES: */C=C(C)/C=C/C=C(C)/C=C/C1=C(C)CCCC1(C)C] | absent | bond |
| 31 | 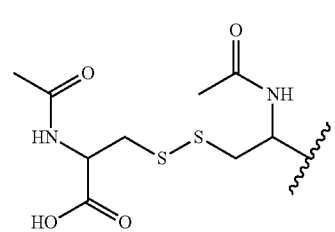 [SMILES: *C(CSSCC(NC(C)=O)C(=O)O)NC(C)=O] | absent | bond |
| 32 | 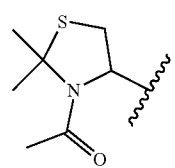 [SMILES: *C1CSC(C)(C)N1C(C)=O] | absent | bond |
| 33 | 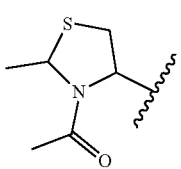 [SMILES: *C1CSC(C)N1C(C)=O] | absent | bond |
| 34 |  | absent | bond |

TABLE 1-continued
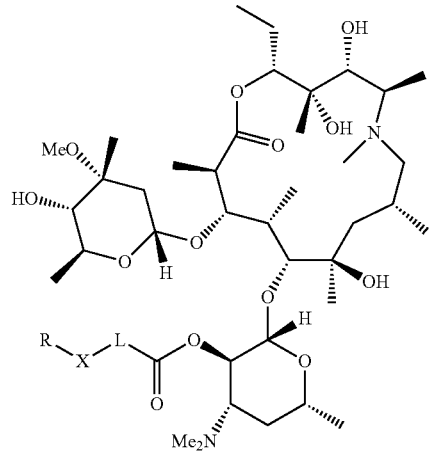
| Compound | R | X | L |
|---|---|---|---|
| 35 | 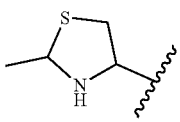 | absent | bond |
| 36 | 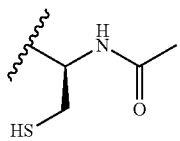 | absent | —(C=O)(O(CH$_2$)$_2$)$_4$O— |
| 37 | 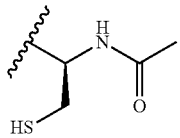 [SMILES: *[C@H](CS)NC(C)=O] | absent | —(C=O)(O(CH$_2$)$_2$)$_8$O— |
| 38 | 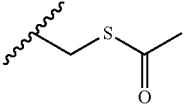 [SMILES: *CSC(C)=O] | absent | bond |
| 39 | 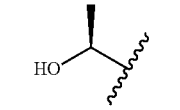 [SMILES: *[C@H](C)O] | absent | bond |
| 40 | 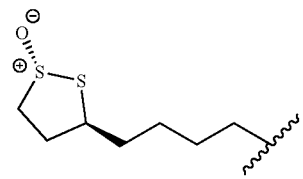 [SMILES: *CCCC[C@H]1CC[S@+]([O-])S1] | absent | bond |
| 41 | 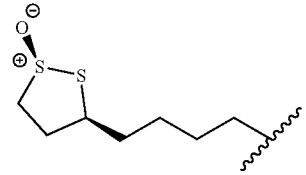 [SMILES: *CCCC[C@H]1CC[S@@+]([O-])S1] | absent | bond |

TABLE 1-continued
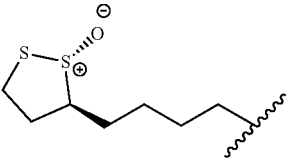 [SMILES: *CCCC[C@H]1CCS[S@+]1[O-]]
| Compound | R | X | L |
|---|---|---|---|
| 42 | 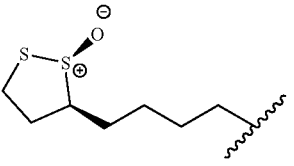 [SMILES: *CCCC[C@H]1CCS[S@@+]1[O-]] | absent | bond |
| 43 | 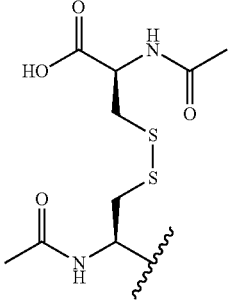 [SMILES: *[C@H](CSSC[C@H](NC(C)=O)C(=O)O)NC(C)=O] | absent | bond |
| 44 | 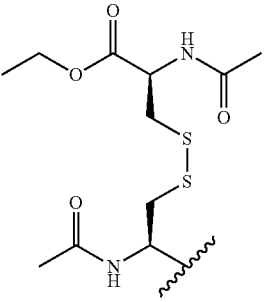 [SMILES: *[C@H](CSSC[C@H](NC(C)=O)C(=O)OCC)NC(C)=O] | absent | bond |
| 45 |  | absent | bond |

TABLE 1-continued

| Compound | R | X | L |
|---|---|---|---|
| 46 | | absent | bond |
| 47 | | absent | bond |

TABLE 1-continued
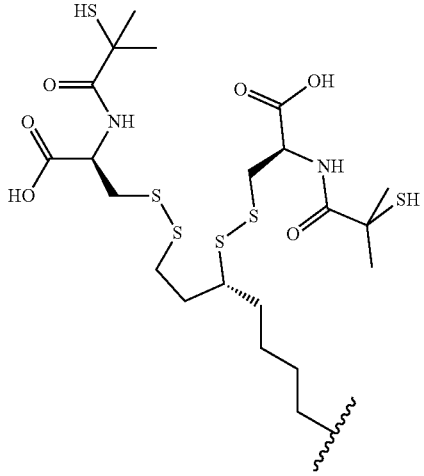 [SMILES: *CCCC[C@H](CCSSC[C@H](NC(=O)C(C)(C)S)C(=O)O)SSC[C@H](NC(=O)C(C)(C)S)C(=O)O]
| Compound | R | X | L |
|---|---|---|---|
| 48 | 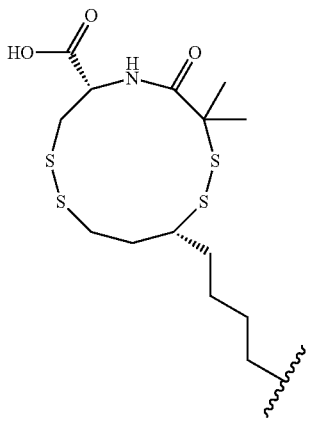 [SMILES: *CCCC[C@@H]1CCSSC[C@H](C(=O)O)NC(=O)C(C)(C)SS1] | absent | bond |
| 49 | | absent | bond |

TABLE 1-continued

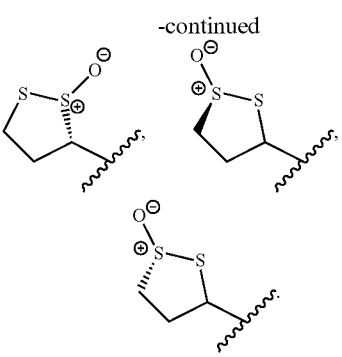

| Compound | R | X | L |
|---|---|---|---|
| 50 | 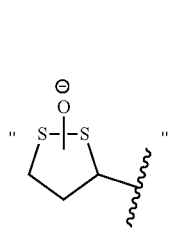 | absent | bond |
| 51 | | absent | bond |

Each recitation of

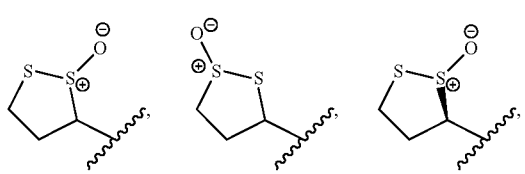

provided herein, unless otherwise stated, includes a specific and explicit recitation of:

and

The compounds used in the reactions described herein are made according to organic synthesis techniques starting from commercially available chemicals and/or from compounds described in the chemical literature or the present disclosure. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," $2^{nd}$ Ed., Academic Press, New York, 1983; H. O. House, "Modern Synthetic Reactions", $2^{nd}$ Ed., W. A. Benjamin, Inc. Menlo Park, Calif. 1972; T. L. Gilchrist, "Heterocyclic Chemistry", $2^{nd}$ Ed., John Wiley & Sons, New York, 1992; J. March, "Advanced Organic Chemistry: Reactions, Mechanisms and Structure", $4^{th}$ Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" $2^{nd}$ Edition (1999) Wiley-VCH, ISBN: 0-471-19031-4; March, J. "Advanced Organic Chemistry: Reactions, Mechanisms, and Structure" $4^{th}$ Edition (1992) John Wiley & Sons, ISBN: 0-471-60180-2; Otera, J. (editor) "Modern Carbonyl Chemistry" (2000) Wiley-VCH, ISBN: 3-527-2987 I -1; Patai, S. "Patai's 1992 Guide to the Chemistry of Functional Groups" (1992) Interscience ISBN: 0-471-93022-9; Solomons, T. W. G. "Organic Chemistry" $7^{th}$ Edition (2000) John Wiley & Sons, ISBN: 0-471-19095-0; Stowell, J. C., "Intermediate Organic Chemistry" $2^{nd}$ Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of chemicals prepared by the Chemical Abstract Service of the American Chemical Society, which are available in most public and university libraries, as well as through on-line databases (contact the American Chemical Society, Washington, D.C. for more details). Chemicals not commercially available in catalogs are optionally prepared by custom chemical synthesis houses, where many of the standard chemical supply houses (e.g., those listed above) provide custom synthesis services. A reference for the preparation and selection of pharmaceutical salts of the keratolytic conjugate described herein is P. H. Stahl & C. G. Wermuth "Handbook of Pharmaceutical Salts", Verlag Helvetica Chimica Acta, Zurich, 2002.

In some embodiments, a compound provided herein is a compound represented by any one of Formula (I), Formula (I-A), Formula (Ia), Formula (Ib), Formula (Ic), Formula (Id), or Table 1. In some embodiments, a compound provided herein is administered as a pure chemical. In other embodiments, a compound provided herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, $21^{st}$ Ed. Mack Pub. Co., Easton, Pa. (2005)).

Provided in some embodiments herein is a pharmaceutical composition comprising at least one keratolytic conjugate together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

In some embodiments, a compound provided herein (e.g., such as a compound represented by any one of Formula (I), Formula (I-A), Formula (Ia), Formula (Ib), Formula (Ic), Formula (Id), or Table 1) is substantially pure, in that it contains less than, for example, about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, $21^{st}$ Ed. Mack Pub. Co., Easton, Pa. (2005)).

In some embodiments provided herein is a pharmaceutical composition comprising a compound provided herein (e.g., such as a compound represented by any one of Formula (I), Formula (I-A), Formula (Ia), Formula (Ib), Formula (Ic), Formula (Id), or Table 1) and at least one pharmaceutically acceptable excipient. In some embodiments, the pharmaceutical composition is suitable for ophthalmic administration. In some embodiments, the pharmaceutical composition is suitable for topical ophthalmic administration. In some embodiments, topical ophthalmic administration is administration in and/or around the eye, such as to the eyelid margin. In some embodiments, topical ophthalmic administration is administration to the ocular surface and the inner surface to the eyelid.

In some embodiments, a keratolytic conjugate provided herein (such as a compound represented by any one of Formula (I), Formula (I-A), Formula (Ia), Formula (Ib), Formula (Ic), Formula (Id), or Table 1) is formulated as a solution or suspension for topical administration to the eye.

In some embodiments, a keratolytic conjugate provided herein (such as a compound represented by any one of Formula (I), Formula (I-A), Formula (Ia), Formula (Ib), Formula (Ic), Formula (Id), or Table 1) is formulated for administration by injection. In some instances, the injection formulation is an aqueous formulation. In some instances, the injection formulation is a non-aqueous formulation. In some instances, the injection formulation is an oil-based formulation, such as sesame oil, or the like.

In some embodiments, the dose of the composition comprising at least one keratolytic conjugate as provided herein differ, depending upon the patient's (e.g., human) condition, that is, general health status, age, and other factors.

Pharmaceutical compositions provided in some embodiments herein are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. The optimal dose depends upon the body mass, weight, or blood volume of the patient.

In other embodiments, the topical compositions described herein are combined with a pharmaceutically suitable or acceptable carrier (e.g., a pharmaceutically suitable (or acceptable) excipient, physiologically suitable (or acceptable) excipient, or physiologically suitable (or acceptable) carrier). Exemplary excipients are described, for example, in *Remington: The Science and Practice of Pharmacy* (Gennaro, 21$^{st}$ Ed. Mack Pub. Co., Easton, Pa. (2005)).

Methods of Treatment Utilizing Keratolytic Conjugates

In some embodiments provided herein is a method of treating a dermatological or ophthalmic disease or disorder in a patient in need of thereof, comprising administering to the patient any compound provided herein, or a pharmaceutically acceptable salt thereof, or a (e.g., pharmaceutical) composition comprising any compound provided herein, or a pharmaceutically acceptable salt thereof, such as a compound represented by any one of Formula (I), Formula (I-A), Formula (Ia), Formula (Ib), Formula (Ic), Formula (Id), or Table 1. In some embodiments provided herein the pharmaceutical composition is in the form of a solution or suspension suitable for topical ophthalmic administration. In some embodiments, topical ophthalmic administration is administration in and/or around the eye, such as to the eyelid margin. In some embodiments, topical ophthalmic administration is administration to the ocular surface and the inner surface to the eyelid.

In some embodiments, the dermatological or ophthalmic disease or disorder is inflammation or hyperkeratosis (e.g., of the eyes or skin). In some embodiments, the dermatological or ophthalmic disease or disorder is inflammation or hyperkeratosis of the eyes or skin (e.g., the ocular surface). In some embodiments, the dermatological or ophthalmic dermatological disease or disorder is selected from the group consisting of meibomian gland dysfunction (MGD), dry eye disease (DED), ocular manifestations of graft versus host disease, vernal keratoconjunctivitis, atopic keratoconjunctivitis, Cornelia de Lange Syndrome, evaporative eye disease, aqueous deficiency dry eye, blepharitis, and seborrheic blepharitis. In some embodiments, the dermatological or ophthalmic disease or disorder is inflammation or hyperkeratosis (e.g., of the eyes or skin), such as, for example, meibomian gland dysfunction (MGD), dry eye disease (DED), ocular manifestations of graft versus host disease, vernal keratoconjunctivitis, atopic keratoconjunctivitis, Cornelia de Lange Syndrome, evaporative eye disease, aqueous deficiency dry eye, blepharitis, seborrheic blepharitis, or any combination thereof.

In some embodiments, the ophthalmic disease or disorder is selected from the group consisting of dry eye, lid wiper epitheliopathy (LWE), contact lens discomfort (CLD), dry eye syndrome, evaporative dry eye syndrome, aqueous deficiency dry eye syndrome, blepharitis, keratitis, meibomian gland dysfunction, conjunctivitis, lacrimal gland disorder, contact lens related conditions and inflammation of the anterior surface of the eye, infection of the anterior surface of the eye, and autoimmune disorder of the anterior surface of the eye.

Provided herein is a method for treating an ocular surface disorder in an individual in need thereof comprising topical administration of a keratolytic conjugate to the individual in need thereof. In some embodiments, administration occurs with the assistance of a health-care provider (e.g., this category includes both acute and maintenance uses of the keratolytic conjugate). An acute use, in some embodiments, requires a stronger keratolytic conjugate (either in terms of concentration of the agent or the inherent activity of the agent). A maintenance use, in some embodiments, allows for the use of lower concentrations of the agent, or agents with lower inherent activity. A maintenance use, in some embodiments, involves a patient at a routine visit to the health care provider. Both acute uses and maintenance uses optionally involve use of an eye-protecting device or apparatus. In some embodiments, the acute use is performed by the health care provider, and the maintenance use is performed by the patient or non-health care provider. In some embodiments, administration does not occur with the active assistance of a health care provider (e.g., but rather involves the patient applying the keratolytic conjugate to his/her own eyelid margin). In some embodiments, such administration occurs over an extended period of time (e.g., one way of describing this patient-administered multi-administration mode is as a chronic use). In some embodiments, different or second formulations of the keratolytic conjugate are used for chronic or patient-administered uses. In some embodiments the different or second formulation utilizes a lower concentration of the keratolytic conjugate. In some embodiments, the second or different formulation utilizes a keratolytic conjugate that has a lower activity than the first formulation.

It should be understood that the present methods also include the physical removal of an obstruction in an meibomian gland (e.g., followed by chronic and/or maintenance administration of a keratolytic conjugate provided herein).

In some embodiments provided herein is a method for treating meibomian gland dysfunction in a patient in need thereof, comprising topically administering to the patient a composition comprising a therapeutically-effective amount of at least one keratolytic conjugate in an ophthalmically-acceptable carrier. In some embodiments, the topical administration of the composition comprising a therapeutically-effective amount of at least one keratolytic conjugate in an ophthalmically-acceptable carrier results in enhanced meibum production.

In some embodiments, the topical administration of the composition comprising a therapeutically-effective amount of at least one keratolytic conjugate in an ophthalmically-acceptable carrier occurs until the keratinized obstruction is relieved. In some embodiments, the topical administration of the composition comprising a therapeutically-effective amount of at least one keratolytic conjugate in an ophthalmically-acceptable carrier occurs periodically after relieving of the keratinized obstruction. In some embodiments, the topical administration of the composition comprising a therapeutically-effective amount of at least one keratolytic conjugate in an ophthalmically-acceptable carrier is a single administration. In some embodiments, the topical administration of the composition comprising a therapeutically-effective amount of at least one keratolytic conjugate in an ophthalmically-acceptable carrier is a periodic administration. In some embodiments, the topical administration of the composition comprising a therapeutically-effective amount of at least one keratolytic conjugate in an ophthalmically-acceptable carrier occurs once a day. In some embodiments, the topical administration of the composition comprising a therapeutically-effective amount of at least one keratolytic conjugate in an ophthalmically-acceptable carrier occurs twice a day. In some embodiments, the topical administration of the composition comprising a therapeutically-effective amount of at least one keratolytic conjugate in an ophthalmically-acceptable carrier occurs more than twice a day.

In some embodiments, the composition for topical administration comprises a therapeutically-effective amount of at least one keratolytic conjugate in an ophthalmically-acceptable carrier is a solution. In some embodiments, the composition for topical administration comprises a therapeutically-effective amount of at least one keratolytic conjugate in an ophthalmically-acceptable carrier is a solution suitable for topical administration as eye drops. In some embodiments, the composition for topical administration comprises a therapeutically-effective amount of at least one keratolytic conjugate in an ophthalmically-acceptable carrier is a gel, ocular insert, spray, or other topical ocular delivery method. In some embodiments, the composition for topical administration comprises a therapeutically-effective amount of at least one keratolytic conjugate in an ophthalmically-acceptable carrier is a semi-solid. In some embodiments, the composition for topical administration comprises a therapeutically-effective amount of at least one keratolytic conjugate in an ophthalmically-acceptable carrier is homogenous. In some embodiments, the composition for topical administration comprises a therapeutically-effective amount of at least one keratolytic conjugate in an ophthalmically-acceptable carrier is a dispersion. In some embodiments, the composition for topical administration comprises a therapeutically-effective amount of at least one keratolytic conjugate in an ophthalmically-acceptable carrier is hydrophilic. In some embodiments, the composition for topical administration comprises a therapeutically-effective amount of at least one keratolytic conjugate in an ophthalmically-acceptable carrier and an oleaginous base. In some embodiments, the composition for topical administration comprises a therapeutically-effective amount of at least one keratolytic conjugate in an ophthalmically-acceptable carrier and at least one ophthalmically-acceptable excipient.

In some embodiments provided herein is a method for treating MGD in a patient in need thereof comprising topical administration of a composition comprising a keratolytic conjugate. In some embodiments, the topical administration of the composition comprising a keratolytic conjugate occurs once a week. In some embodiments, the topical administration of the composition comprising a keratolytic conjugate occurs twice a week. In some embodiments, the topical administration of the composition comprising a keratolytic conjugate occurs every other day. In some embodiments, the topical administration of the composition comprises a keratolytic conjugate occurs every day. In some embodiments, the topical administration of the composition comprises a keratolytic conjugate occurs several times a day.

In some embodiments, the method comprises administering a compound or formulation provided herein in an acute treatment scenario. In some embodiments, the method comprises treatment of a patient naïve to treatment. In some embodiments, the method comprises administering a compound or formulation provided herein in a chronic treatment scenario. In some embodiments, the method comprises administering a compound or formulation provided herein in a maintenance therapy scenario. In an acute treatment scenario, the administered dosage of keratolytic conjugate may be higher than the administered dosage of keratolytic conjugate employed in a chronic treatment scenario or a maintenance therapy scenario. In an acute treatment scenario, the keratolytic conjugate may be different from the keratolytic conjugate employed in a chronic treatment scenario. In some embodiments, the course of therapy begins in the initial phase of therapy as an acute treatment scenario and later transitions into a chronic treatment scenario or a maintenance therapy scenario. In some embodiments, the meibomian gland opening pharmacological agent administered in the acute treatment scenario is a keratolytic agent and/or keratoplastic agent, and the pharmacological agent administered in the chronic treatment scenario or a maintenance therapy scenario is a keratolytic conjugate.

In some embodiments, an initial treatment is administered (e.g., by a physician or healthcare professional) to an individual to initially open a blockage of the meibomian gland, such as by placing a more highly concentrated formulation of one of the keratolytic conjugate provided herein. In the event the higher concentration formulations are required, the application thereof may require ocular shielding or other activity to minimize the impact of irritation or disruption of the ocular surface or surrounding tissues. Following such a procedure, a patient may be given a different formulation of keratolytic conjugate to take home to apply periodically to the lid margin to maintain the patency of the meibomian gland. Such application may occur twice daily, once a day, weekly or monthly, depending on the formulation activity and the therapeutic product profile of the formulation.

Provided in some embodiments of the methods of treatment described herein is the location of the topical administration of the composition. In some embodiments, the composition comprising a keratolytic conjugate is administered such that no irritation to eye occurs. In some embodiments, the composition comprising a keratolytic conjugate is administered to the eye lid margin.

In some embodiments of the methods of treatment provided herein is the use of a protective element provided to the eye to avoid irritation to the eye. Although the formulations described herein are generally non-irritating, in some embodiments (e.g., high concentration of agent or when used on a sensitive eye) a protective element provides an additional layer of safety and comfort for the patient. In some embodiments, the composition comprising a keratolytic conjugate is administered while an eye shield is placed on the eye to reduce contact of the pharmacological agent with the cornea and/or conjunctiva such that reduced irritation to eye occurs. In some embodiments, the eye shield is a contact lens or an eye covering. In some embodiments, the eye covering comprises a self-adhesive. In some embodiments, the composition comprising a keratolytic conjugate is administered while the lid is pulled away from the globe to reduce contact of the pharmacological agent with the cornea and/or conjunctiva such that reduced irritation to eye occurs.

While exemplary embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

I. Chemical Synthesis

Solvents, reagents and starting materials were purchased from commercial vendors and used as received unless otherwise described. All reactions were performed at room temperature unless otherwise stated. Starting materials were purchased from commercial sources or synthesized according to the methods described herein or using literature procedures or the present disclosure.

Abbreviations

The following abbreviations are used in the Examples and other parts of the description:
AcOH: Acetic acid
$CDCl_3$: Deuterochloroform
COMU: (1-Cyano-2-ethoxy-2-oxoethylideneaminooxy)dimethylamino-morpholino-carbenium hexafluorophosphate
CV: Column Volume
DBU: 1,8-Diazabicyclo[5,4,0]undec-7-ene
DCM: Dichloromethane
DIPEA: N,N-Diisopropylethylamine
$D_2O$: Deuterium oxide
DMF: N,N-Dimethylformamide
DMSO-D6: Deuterated dimethyl sulfoxide
DPBS: Dulbecco's phosphate-buffered saline
EtOAc: Ethyl acetate
h: Hour(s)
HCl: Hydrochloric acid
LCMS: Liquid chromatography-mass spectrometry
M: Molar
MeCN; Acetonitrile
MeOH: Methanol
$MgSO_4$: Magnesium sulfate
mins: Minute(s)
$N_2$: Nitrogen
$Na_2SO_4$: Sodium sulfate
$NH_4Cl$: ammonium chloride
r.t.: Room temperature
Rt: Retention time
s: Second
sat.: Saturated
TEA: Triethylamine
THF: Tetrahydrofuran
vac: Vacuum Analytical Methods:
Method A: Waters Sunfire C18 3.5 µm, 50×4.6 mm; A=water+0.1% formic acid; B=MeCN; 45° C.; % B: 0.0 min 5% 2.25 mL/min, 1.0 min 37.5% 2.2 mL/min, 3.0 min 95% 2.2 mL/min, 3.5 min 95% 2.3 mL/min, 3.51 min 0% 2.3 mL/min, 4.0 min 0% 2.25 mL/min.
Method B: Waters Sunfire C18 5 µm, 100×4.6 mm; A=water+0.1% formic acid; B=MeCN+0.1% formic acid; 45° C.; % B: 0.0 min 5%, 0.50 min 5%, 7.5 min 95%, 10.0 min 95%, 10.1 min 5%, 13.0 min 5%; 1.5 mL/min.
Method C: Phenomenex Luna C18 (2) 3 µm, 50×4.6 mm; A=water+0.1% formic acid; B=MeOH+0.1% formic acid; 45° C.; % B: 0.0 min 5% 2.25 mL/min, 1.0 min 37.5% 2.2 mL/min, 3.0 min 95% 2.2 mL/min, 3.5 min 95% 2.3 mL/min, 3.51 min 5% 2.3 mL/min, 4.0 min 5% 2.25 mL/min.
Method D: Waters Sunfire C18 3.5 µm, 50×4.6 mm; A=water+0.1% formic acid; B=MeCN; 45° C.; % B: 0.0 min 5% 2.25 mL/min, 1.0 min 20% 2.2 mL/min, 3.0 min 50% 2.2 mL/min, 3.25 min 95% 2.2 mL/min, 3.50 min 95% 2.3 mL/min, 3.51 min 100% 2.30 mL/min, 4.0 min 100% 2.25 mL/min.
Method E: Phenomenex Gemini NX C18 5 µm, 150×4.6 mm; A=water+0.1% formic acid; B=MeOH; 40° C.; % B: 0.0 min 5%, 0.5 min 5%, 7.5 min 95%, 10.0 min 95%, 10.1 min 5%, 13.0 min 5%; 1.5 mL/min.
Method F: Waters CSH C18 1.7 µm, 100×2.1 mm; A=water+0.1% formic acid; B=MeCN; 45° C.; % B: 0.05 min 5% 0.35 mL/min, 5.00 min 95% 0.35 mL/min, 6.60 min 5% 0.35 mL/min. 8.00 min end.

Chemical Synthesis Example 1

Method 1:

Step 1: Methyl 2-((tert-butyldiphenylsilyl)oxy)acetate

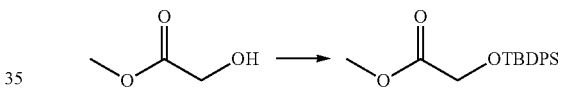

To a stirred solution of methyl glycolate (0.77 mL, 10.0 mmol) in anhydrous DMF (14 mL) were added imidazole (803 mg, 11.8 mmol) and tert-butylchlorodiphenylsilane (3.12 mL, 12.0 mmol) and the mixture stirred at room temperature for 3 hours. The solvent was evaporated in vacuo and the residue diluted with DCM and washed with ice-cold water. The organic layer was dried ($MgSO_4$) and the solvent evaporated in vacuo to give the crude product which was purified by flash chromatography (Biotage SP1; 100 g SNAP cartridge) eluting with isohexane→10% EtOAc-isohexane to yield the title compound as a colourless oil (3.26 g, 99%). LCMS (Method A): Rt=3.50 min; [M+Na]+=351.2. $^1$H-NMR (400 MHz, $CDCl_3$) δ 7.67-7.69 (m, 4H), 7.37-7.43 (m, 6H), 4.24 (s, 2H), 3.68 (s, 3H), 1.09 (t, J=3.0 Hz, 9H)

Step 2: 2-((tert-Butyldiphenylsilyl)oxy)acetic acid

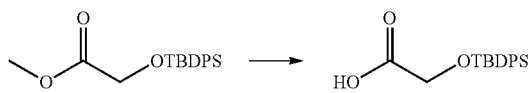

To a stirred solution of methyl 2-((tert-butyldiphenylsilyl) oxy) (1.00 g, 3.04 mmol) in THF (2.75 mL) and water (0.92 mL) was added 0.75 M lithium hydroxide$_{(aq)}$ (4.06 mL, 3.05 mmol) and the mixture stirred at room temperature for 20 hours. The reaction mixture was diluted with water (10 mL) and extracted with $Et_2O$ (3×20 mL). The aqueous phase was acidified to pH3 with 5 M HCl$_{(aq)}$ and the solution extracted with EtOAc (3×20 mL). The combined organics were dried (MgSO$_4$), filtered and the solvent evaporated in vacuo. The crude product was purified by flash chromatography (Biotage SP1; 25 g SNAP cartridge) eluting with isohexane 4 EtOAc to yield the title compound as a colourless oil (0.65 g, 68%). LCMS (Method A): Rt=2.77 mis; [M–H]–=313.3. $^1$H-NMR (400 MHz, CDCl$_3$) δ 7.61-7.66 (m, 4H), 7.39-7.47 (m, 6H), 4.22 (s, 2H), 1.08-1.12 (m, 9H)

Step 3: (2S,3R,4S,6R)-4-(Dimethylamino)-2-(((2R, 3S,4R,5R,8R,10R,11R,12S,13S,14R)-2- ethyl-3,4, 10-trihydroxy-13-(((2R,4R,5S,6S)-5-hydroxy-4-methoxy-4,6-dimethyltetrahydro-2H-pyran-2-yl) oxy)-3,5,6,8,10,12,14-heptamethyl-15-oxo-1-oxa-6-azacyclopentadecan-11-yl)oxy)-6-methyltetrahydro-2H-pyran-3-yl 2-((tert-butyldiphenylsilyl)oxy) acetate combined, diluted with DCM and neutralised with sat. NaHCO$_{3(aq)}$. The organic layer was separated and the aqueous phase extracted with DCM. The combined organics were washed with sat. brine solution, dried (MgSO$_4$) and evaporated in vacuo to yield the title compound as a colourless gum (40 mg, 12%). LCMS (Method A): Rt=1.72 min; [M+H]+=1046.0

Step 4: (2S,3R,4S,6R)-4-(Dimethylamino)-2-(((2R, 3S,4R,5R,8R,10R,11R,12S,13S,14R)-2- ethyl-3,4, 10-trihydroxy-13-(((2R,4R,5S,6S)-5-hydroxy-4-methoxy-4,6-dimethyltetrahydro-2H-pyran-2-yl) oxy)-3,5,6,8,10,12,14-heptamethyl-15-oxo-1-oxa-6-azacyclopentadecan-11-yl)oxy)-6-methyltetrahydro-2H-pyran-3-yl 2-hydroxyacetate

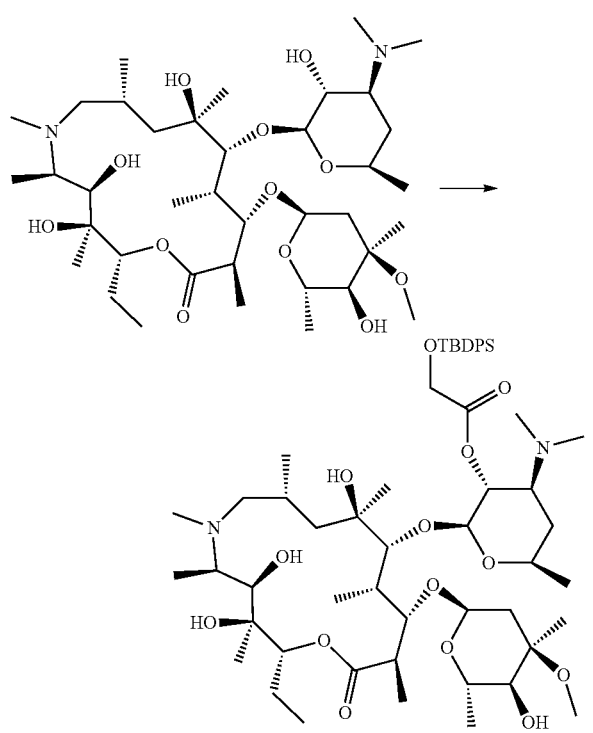

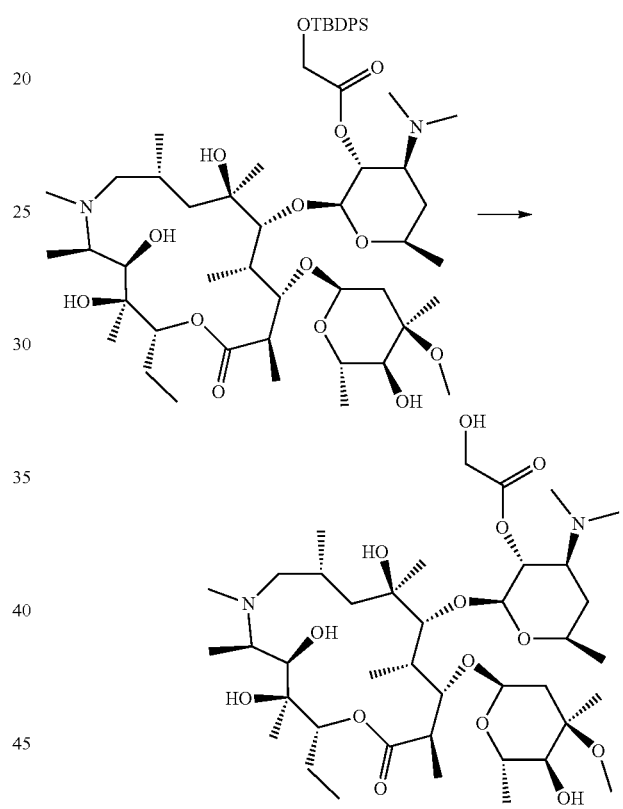

To a solution of 2-((tert-butyldiphenylsilyl)oxy)acetic acid (97 mg, 0.308 mmol) and azithromycin dihydrate (291 mg, 0.370 mmol) in toluene (15 mL) at room temperature was added TEA (155 μL, 1.11 mmol), 4-(dimethylamino) pyridine (286 mg, 2.34 mmol) and 2,4,6-trichlorobenzoyl chloride (162 μL, 1.05 mmol). The mixture was stirred at room temperature for 121 hours. The resulting mixture was diluted with DCM (10 mL), sat. NaHCO$_{3(aq)}$ (10 mL) and H$_2$O (10 mL) and the layers separated. The aqueous phase was extracted with DCM (3×10 mL). The combined organics were dried (MgSO$_4$), filtered, and the solvent evaporated in vacuo. The crude product was purified by flash chromatography (Biotage SP1; 10 g SNAP cartridge) eluting with 4:1 isohexane-acetone (1% TEA)→acetone (1% TEA) and further purified by flash chromatography (Biotage SP1; 10 g SNAP cartridge) eluting with isohexane→acetone (1% TEA). The crude product was then purified by reversed-phase preparative HPLC. Fractions containing product were To a stirred solution of (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5- hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 2-((tert-butyldiphenylsilyl)oxy)acetate (40 mg, 0.0383 mmol) in anhydrous THF (1 mL) under N$_2$ was added 1 M tetrabutylammonium fluoride hydrate (115 μL, 0.115 mmol) in THF. The reaction was stirred at room temperature for 2 hours then quenched with sat. NaHCO$_{3(aq)}$ and extracted with EtOAc. The organic layer was washed with sat. brine solution and the layers separated. The organic phase was dried (MgSO$_4$), filtered and the solvent evaporated in vacuo. The crude product was purified by flash chromatography (Biotage SP1; 10 g SNAP cartridge) eluting with isohexane (2% TEA)→acetone (2% TEA) to yield the title compound as a white solid (12 mg, 39%). LCMS (Method B): Rt=3.04 min; [M+H]+=807.9.

Method 2:

(2S,3R,4S,6R)-4-(Dimethylamino)-2-(((2R,3S,4R,
5R,8R,10R,11R,12S,13S,14R)-2-ethyl-3,4,10-trihy-
droxy-13-(((2R,4R,5S,6S)-5-hydroxy-4-methoxy-4,
6-dimethyltetrahydro-2H-pyran-2-yl)oxy)-3,5,6,8,
10,12,14-heptamethyl-15-oxo-1-oxa-6-
azacyclopentadecan-11-yl)oxy)-6-methyltetrahydro-
2H-pyran-3-yl (S)-2-hydroxypropanoate

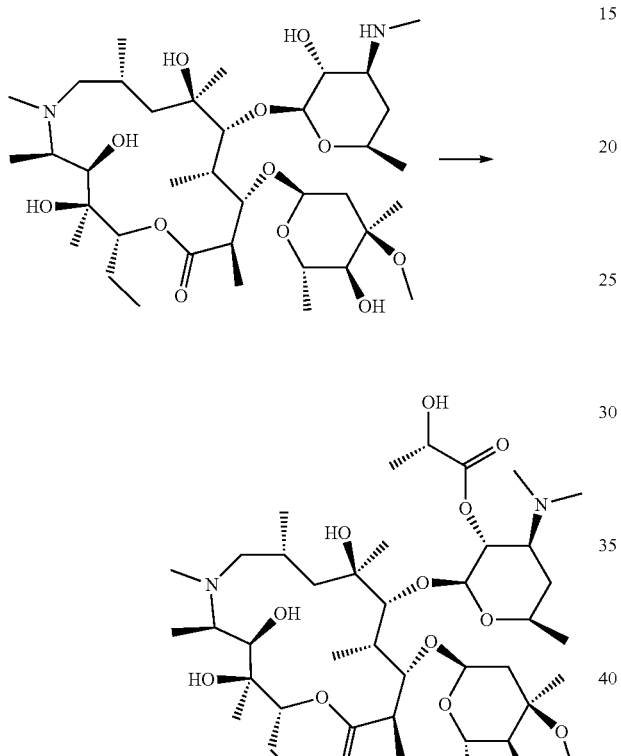

This reaction was performed using a flow setup: A solution of L-(+)-lactic acid (0.24 mL, 3.18 mmol) and DIPEA (0.67 mL, 3.82 mmol) in DCM (10 mL) (flow rate: 2.0 mL/min) and a solution of triphosgene (0.15 g, 0.510 mmol) in DCM (6 mL) (flow rate: 1.2 mL/min) were introduced to a T-shape mixer 1 at r.t. with syringe pumps. The resultant mixture was passed through reaction tube 1 (inner diameter: 0.8 mm, length: 54 mm, volume: 27 mL, reaction time: 0.5 s) at r.t. The resultant mixture and a solution of azithromycin dihydrate (1.00 g, 1.27 mmol) in DCM (10 mL) (flow rate: 2.0 mL/min) were introduced to T-shape mixer 2 at r.t. The resultant mixture was passed through reaction tube 2 (inner diameter: 0.8 mm, length: 742 mm, volume: 373 µL, reaction time: 4.3 s) at r.t. After 55 s the resultant mixture was collected, diluted with DCM (25 mL), and washed with sat. NH$_4$Cl$_{(aq)}$ (8×30 mL). The combined organics were washed with sat. brine solution (20 mL), dried (MgSO$_4$), filtered and the solvent evaporated in vacuo. The crude product was purified by flash chromatography (Biotage SP1; 25 g Sfar cartridge) eluting with 8:2 isohexane-acetone (1% TEA)→ acetone (1% TEA) to yield (2S,3R,4S,6R)-4-(dimethyl-amino)-2-(((2R,3S,4R,5R,8R,10R,11R,12S,13S,14R)-2-ethyl-3,4,10-trihydroxy-13-(((2R,4R,5S,6S)-5- hydroxy-4-methoxy-4,6-dimethyltetrahydro-2H-pyran-2-yl)oxy)-3,5,6,8,10,12,14-heptamethyl-15-oxo-1-oxa-6-azacyclopent-adecan-11-yl)oxy)-6-methyltetrahydro-2H-pyran-3-yl (S)-2-hydroxypropanoate (227 mg, 22%) as a white solid. LCMS (Method D): Rt=1.73 mins; [M+H]+=821.6.

Chemical Synthesis Example 2

Method A:

(2S,3R,4S,6R)-4-(Dimethylamino)-2-(((2R,3S,4R,
5R,8R,10R,11R,12S,13S,14R)-2-ethyl-3,4,10-trihy-
droxy-13-(((2R,4R,5S,6S)-5-hydroxy-4-methoxy-4,
6-dimethyltetrahydro-2H-pyran-2-yl)oxy)-3,5,6,8,
10,12,14-heptamethyl-15-oxo-1-oxa-6-
azacyclopentadecan-11-yl)oxy)-6-methyltetrahydro-
2H-pyran-3-yl 5-((3R)-2-oxido-1,2-dithiolan-3-yl)
pentanoate and (2S,3R,4S,6R)-4-(Dimethylamino)-
2-(((2R,3S,4R,5R,8R,10R,11R,12S,13S,14R)-2-
ethyl-3,4,10-trihydroxy-13-(((2R,4R,5S,6S)-5-
hydroxy-4-methoxy-4,6-dimethyltetrahydro-2H-
pyran-2-yl)oxy)-3,5,6,8,10,12,14-heptamethyl-15-
oxo-1-oxa-6-azacyclopentadecan-11-yl)oxy)-6-
methyltetrahydro-2H-pyran-3-yl 5-((3R)-1-oxido-1,
2-dithiolan-3-yl)pentanoate

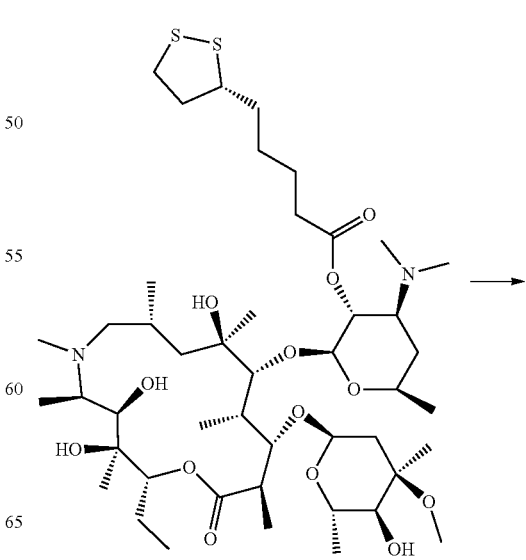

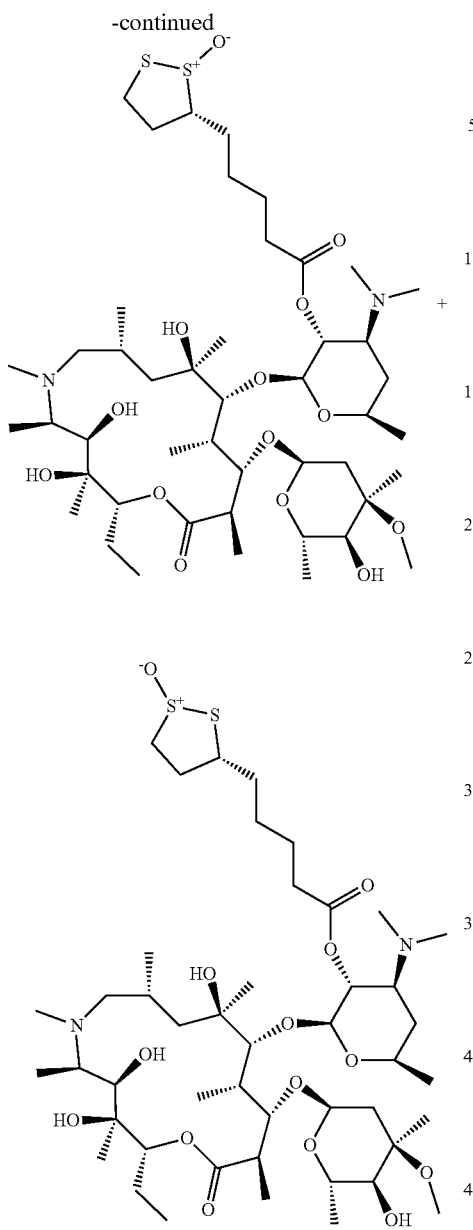

(2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((R)-1,2-dithiolan-3-yl)pentanoate (1.50 g, 1.60 mmol) had been stored in vacuo at 30° C. in the dark (vac oven) for a period of 2 weeks. Over this time approximately 10% of the various sulfoxide isomers had formed. The crude material was purified by flash chromatography (Biotage SP1; 25 g SNAP cartridge) eluting with isohexane→3:1 isohexane-acetone (1% TEA)→acetone to yield (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((3R)-2-oxido-1,2-dithiolan-3-yl)pentanoate and (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((3R)-1-oxido-1,2-dithiolan-3-yl)pentanoate (103 mg, 3%) as a white solid. LCMS (Method A): Rt=1.60 mins; [M+H]+=953.7.

Method B:

(2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((3R)-2-oxido-1,2-dithiolan-3-yl)pentanoate and (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((3R)-1-oxido-1,2-dithiolan-3-yl)pentanoate

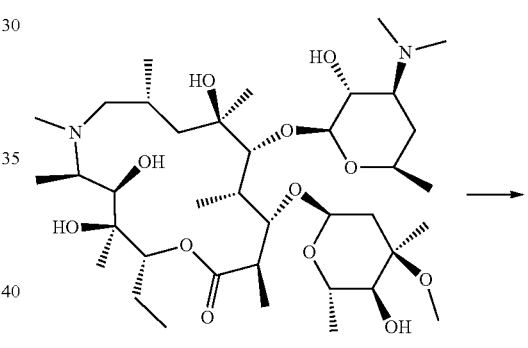

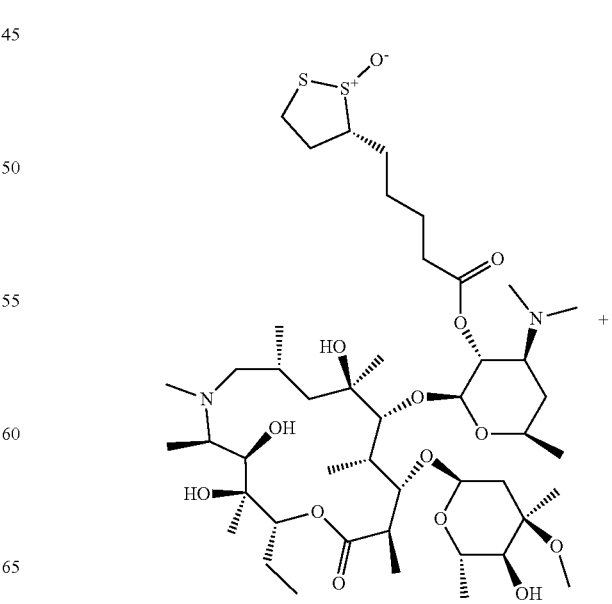

-continued

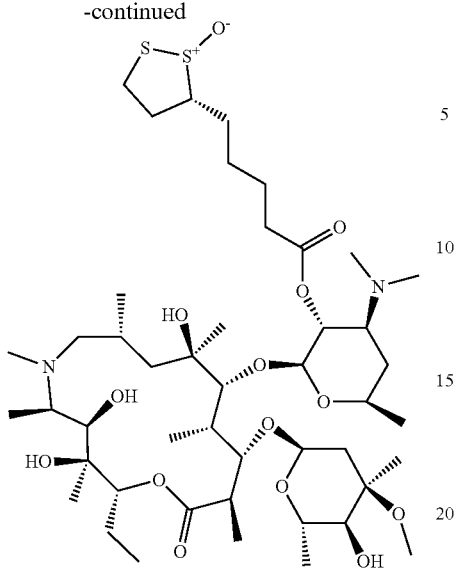

A mixture of 5-((3R)-1-oxido-1,2-dithiolan-3-yl)pentanoic acid and 5-((3R)-2-oxido-1,2-dithiolan-3-yl)pentanoic acid (0.73 g, 3.27 mmol), azithromycin (1.87 g, 2.50 mmol), and 1-cyano-2-ethoxy-2-oxoethylidenaminooxy)dimethylamino-morpholino-carbenium hexafluorophosphate (3.74 g, 8.74 mmol) were dissolved in anhydrous DCM (25 mL). DIPEA (2.5 mL, 14.3 mmol) was added and the mixture stirred at 30° C. for 20 h. The mixture was diluted with DCM (40 mL) and the solution washed successively with sat. $NH_4Cl_{(aq)}$ (2×60 mL) and sat. brine solution (50 mL). The organic phase was dried ($MgSO_4$), filtered and the solvent evaporated in vacuo. The crude product was purified by flash chromatography eluting with isohexane (1% TEA)→3:1 isohexane-acetone (1% TEA) to yield the title mixture (1.45 g, 58%) as a viscous orange oil. LCMS (Method A): $R_t$=2.14 min; [M+H]$^+$=953.6.

Chemical Synthesis Example 3

Step 1: (R)-2,2-Dimethylthiazolidine-4-carboxylic acid

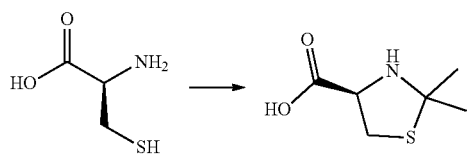

A suspension of L-cysteine (2.00 g, 16.0 mmol) in anhydrous acetone (50 mL) was stirred at reflux under an atmosphere of nitrogen for 18 hours. The reaction mixture was cooled to r.t., filtered through a celite cartridge, concentrated to ~50% of its original volume then left to stand at r.t. After 4 hours the mother liquor was decanted. The solid was further washed with acetone (10 mL) then dried in vacuo to yield (R)-2,2-dimethylthiazolidine-4-carboxylic acid (2.29 g, 89%) as a white solid. LCMS (Method A): Rt=0.53 mins; [M+H]$^+$=162.1. $^1$H-NMR (400 MHz, D$_2$O) δ 4.47 (dd, J=8.0, 7.3 Hz, 1H), 3.50 (dd, J=12.1, 8.0 Hz, 1H), 3.35 (dd, J=12.4, 7.3 Hz, 1H), 1.70 (s, 3H), 1.69 (3s, 3H).

Step 2: (R)-3-Acetyl-2,2-dimethylthiazolidine-4-carboxylic acid

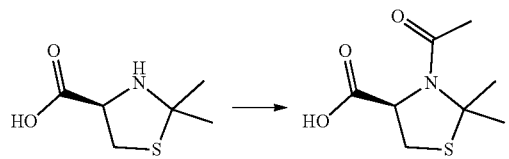

(R)-2,2-Dimethylthiazolidine-4-carboxylic acid (500 mg, 3.10 mmol) was dissolved in acetone (30 mL). Acetic anhydride (0.60 mL, 6.20 mmol) was added in one portion and the mixture stirred at r.t. for 10 minutes. DBU (0.93 mL, 6.20 mmol) was added in one portion. The reaction mixture was stirred at r.t. for 16 hours. The mixture was diluted with sat. $NH_4Cl_{(aq)}$ (50 mL) and EtOAc (30 mL) and the layers separated. The aqueous phase was extracted with EtOAc (2×30 mL) and the combined organics dried ($MgSO_4$), filtered and the solvent evaporated in vacuo. The aqueous phase was acidified with 2M HCl and the solution extracted with EtOAc (3×30 mL). The combined organics were dried ($MgSO_4$), filtered and the solvent evaporated in vacuo. (R)-3-Acetyl-2,2-dimethylthiazolidine-4-carboxylic acid (350 mg, 56%) was obtained as a white solid. LCMS (Method E), Rt=5.70 mins; [M−H]$^-$=204.3. $^1$H-NMR (400 MHz, acetone-D6) δ 11.52 (br s, 1H), 5.09 (dd, J=6.0, 0.9 Hz, 1H), 3.41 (dd, J=11.9, 6.0 Hz, 1H), 3.30 (dd, J=11.9, 1.4 Hz, 1H), 2.02 (s, 3H), 1.83 (s, 3H), 1.79 (s, 3H).

Step 3: (2S,3R,4S,6R)-4-(Dimethylamino)-2-(((2R,3S,4R,5R,8R,10R,11R,12S,13S,14R)-2- ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (R)-3-acetyl-2,2-dimethylthiazolidine-4-carboxylate

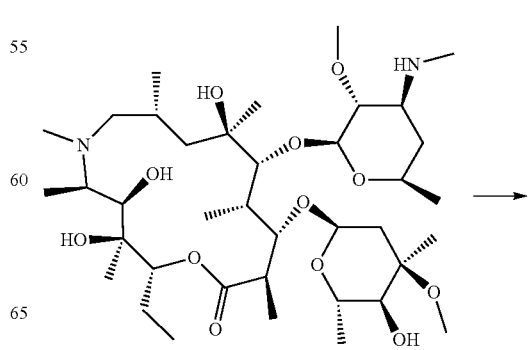

-continued

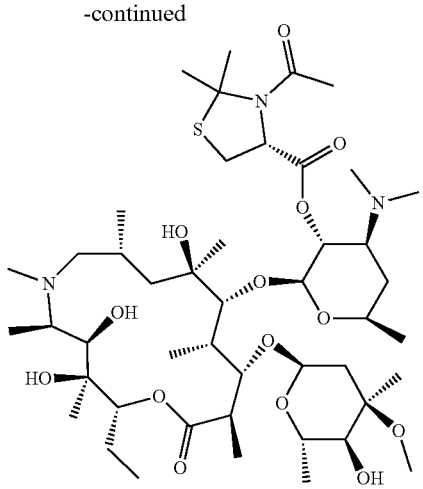

(R)-3-Acetyl-2,2-dimethylthiazolidine-4-carboxylic acid (100 mg, 0.490 mmol), azithromycin (380 mg, 0.490 mmol) and COMU (737 mg, 1.72 mmol) were dissolved in anhydrous THF (10 mL). DIPEA (0.50 mL, 2.95 mmol) was added and the mixture stirred at r.t. under $N_2$ for 18 hours. The mixture was diluted with EtOAc (50 mL) and the solution washed with sat $NH_4Cl_{(aq)}$ (3×20 mL), dried ($MgSO_4$), filtered and the solvent evaporated in vacuo. The crude product was purified by flash chromatography (Biotage SP1; 25 g Sfar cartridge) eluting with isohexane→3:1 isohexane-acetone (1% TEA). (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (R)-3-acetyl-2,2-dimethylthiazolidine-4-carboxylate (250 mg, 54%) was obtained as a white solid. LCMS (Method E), Rt=5.43 mins; [M+H]$^+$=934.9. $^1$H-NMR (400 MHz, CDCl$_3$) δ 5.07 (d, J=4.8 Hz, 1H), 4.74 (dd, J=10.5, 7.3 Hz, 1H), 4.68 (td, J=6.2, 2.4 Hz, 1H), 4.58 (d, J=7.3 Hz, 1H), 4.26 (q, J=2.3 Hz, 1H), 4.11-4.21 (m, 1H), 4.00-4.07 (m, 1H), 3.63-3.70 (m, 2H), 3.49-3.54 (m, 1H), 3.30-3.38 (m, 3H), 3.22-3.26 (m, 1H), 3.05 (t, J=9.8 Hz, 1H), 2.84 (s, 1H), 2.62-2.79 (m, 2H), 2.48-2.57 (m, 1H), 2.33 (d, J=15.6 Hz, 3H), 2.23-2.29 (m, 1H), 2.20 (d, J=10.1 Hz, 4H), 2.12 (d, J=10.1 Hz, 1H), 1.87-2.06 (m, 6H), 1.85 (d, J=6.9 Hz, 2H), 1.35-1.75 (m, 4H), 1.29-1.34 (m, 4H), 1.25 (t, J=5.7 Hz, 4H), 1.21 (d, J=6.9 Hz, 3H), 1.13-1.16 (m, 1H), 1.06-1.10 (m, 4H), 0.85-0.94 (m, 6H).

Chemical Synthesis Example 4

Step 1: 3-Acetyl-2-methylthiazolidine-4-carboxylic acid

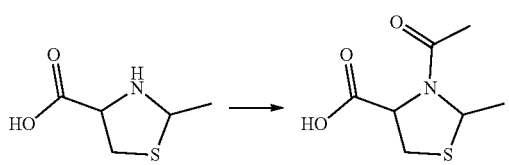

To a solution of 2-methyl-1,3-thiazolidine-4-carboxylic acid (300 mg, 2.04 mmol) in anhydrous acetone (30 mL) under an atmosphere of nitrogen, was added acetic anhydride (0.39 mL, 4.08 mmol) followed by DBU (0.61 mL, 4.08 mmol). The reaction mixture was stirred at r.t. for 17 hours. Water (30 mL) was added and the mixture stirred for 10 minutes. The mixture was extracted with EtOAc (2×30 mL) and the combined organics washed with sat. brine solution (30 mL), dried ($MgSO_4$), filtered and the solvent evaporated in vacuo to yield 3-acetyl-2-methylthiazolidine-4-carboxylic acid (212 mg, 55%) as a yellow oil. LCMS (Method C): Rt 1.27, 1.31 mins; [M+H]+=no obvious mass ion. 1H-NMR (400 MHz, CDCl$_3$) δ 8.48 (br s, 2H), 5.08-5.41 (m, 1H), 4.70-4.90 (m, 1H), 3.02-3.49 (m, 2H), 2.00-2.18 (m, 3H), 1.48-1.69 (m, 3H).

Step 2: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 3-acetyl-2-methylthiazolidine-4-carboxylate

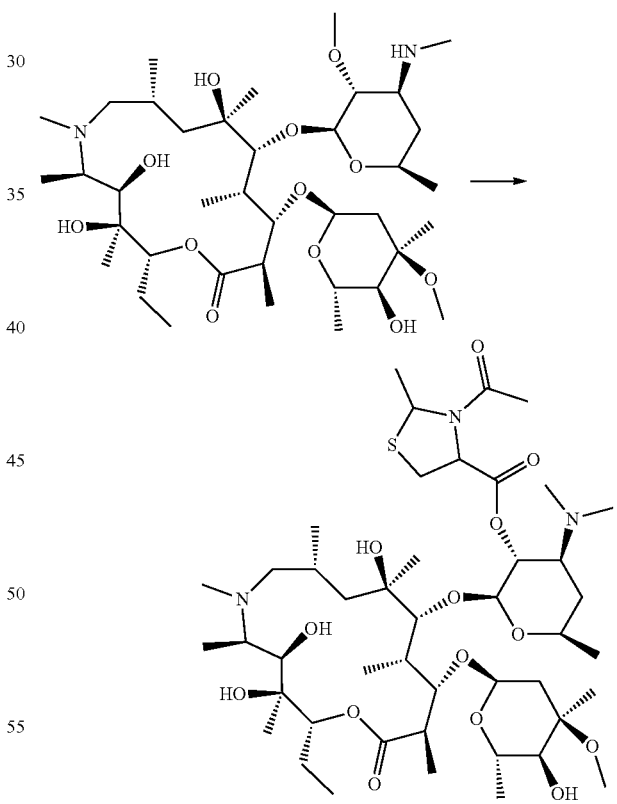

3-Acetyl-2-methyl-thiazolidine-4-carboxylic acid (50 mg, 0.264 mmol), azithromycin (204 mg, 0.264 mmol) and COMU (396 mg, 0.925 mmol) were dissolved in anhydrous THF (20 mL). DIPEA (0.28 mL, 1.59 mmol) was added and the mixture stirred at r.t. under $N_2$ for 18 hours. The mixture was diluted with EtOAc (50 mL), washed with sat. $NH_4Cl_{(aq)}$ (3×20 mL), dried ($MgSO_4$), and the crude product purified by flash chromatography (Biotage SP1; 25 g Sfar cartridge) eluting with isohexane→3:1 isohexane-acetone (1% TEA) to yield (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 3-acetyl-2-methyl-thiazolidine-4-carboxylate (104 mg, 43%) as an off-white solid. LCMS (Method C): Rt=1.96 mins; [M+H]$^+$=920.7.

Chemical Synthesis Example 5

Step 1: (2S,3R,4S,6R)-4-(Dimethylamino)-2-(((2R,3S,4R,5R,8R,10R,11R,12S,13S,14R)-2- ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl N-(((9H-fluoren-9-yl)methoxy)carbonyl)-S-(tert-butyl)-L-cysteinate

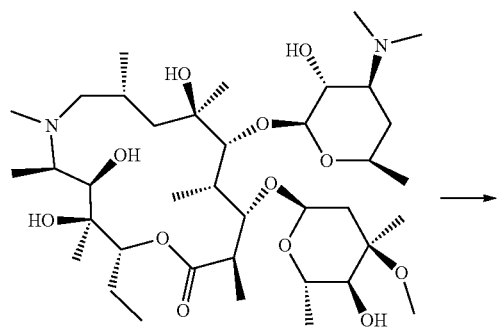

Azithromycin (1.88 g, 2.50 mmol), COMU (3.75 g, 8.76 mmol) and DIPEA (2.60 mL, 15.0 mmol) were dissolved in anhydrous DCM (50 mL). N-Fmoc-(R)-2-amino-3-(S-tert-butyl)propanoic acid (1.00 g, 2.50 mmol) was added and the mixture stirred at 30° C. for 20 hours. The solution was diluted with DCM (10 mL) and the solution washed with sat. NH$_4$Cl$_{(aq)}$ (2×30 mL). The organic phase was dried (MgSO$_4$), filtered and the solvent evaporated in vacuo. The crude product was purified by flash chromatography (Biotage Isolera four; 50 g Sfar cartridge), eluting with 95:5 isohexane-acetone (1% TEA)→65:35 isohexane-acetone (1% TEA) to yield (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5- hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl N-(((9H-fluoren-9-yl)methoxy)carbonyl)-S-(tert-butyl)-L-cysteinate (1.35 g, 45%) as a yellow oil. LCMS (Method A): Rt=2.02 mins; [M+H]+=1131.3.

Step 2: (2S,3R,4S,6R)-4-(Dimethylamino)-2-(((2R,3S,4R,5R,8R,10R,11R,12S,13S,14R)-2- ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl S-(tert-butyl)-L-cysteinate

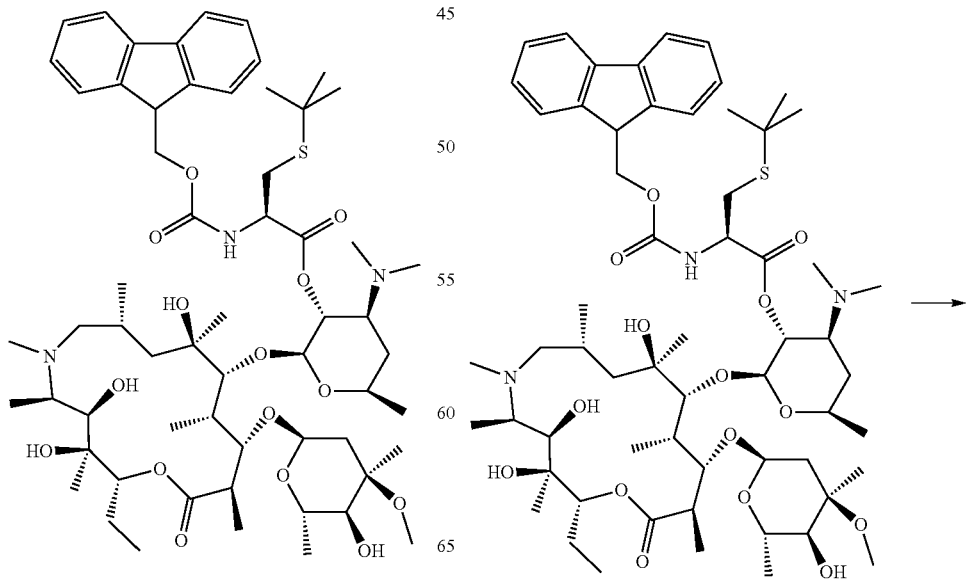

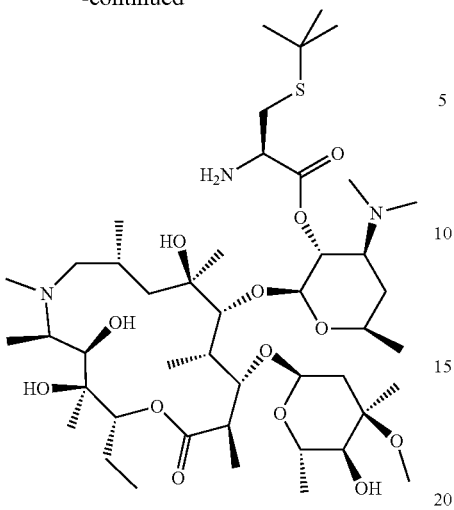

(2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl N-(((9H-fluoren-9-yl)methoxy)carbonyl)-S-(tert-butyl)-L-cysteinate (1.35 g, 1.19 mmol) was dissolved in DMF (20 mL). Piperidine (5.00 mL, 50.6 mmol) was added and the mixture stirred at r.t. for 90 minutes. The solvent was evaporated in vacuo and then dried in a vac. oven at 40° C. for 16 hours. Crude (2S,3R,4S,6R)-4-(Dimethylamino)-2-(((2R,3S,4R,5R,8R,10R,11R,12S,13S,14R)-2-ethyl-3,4,10- trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl S-(tert-butyl)-L-cysteinate (3.14 g) was obtained as a yellow solid which was purified no further. LCMS (Method A): R$_t$=1.57 min; [M+H]$^+$=909.0.

Step 3: (2S,3R,4S,6R)-4-(Dimethylamino)-2-(((2R,3S,4R,5R,8R,10R,11R,12S,13S,14R)-2- ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl N-acetyl-S-(tert-butyl)-L-cysteinate

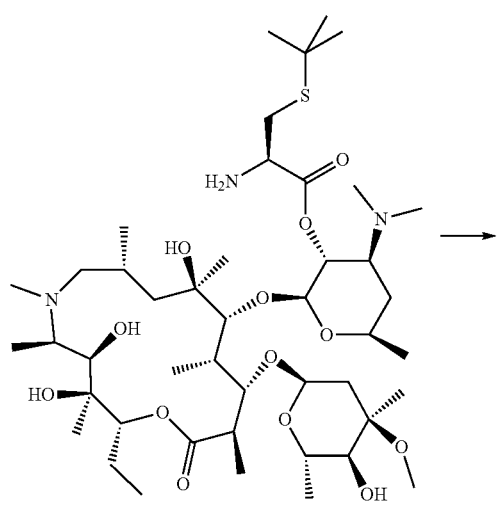

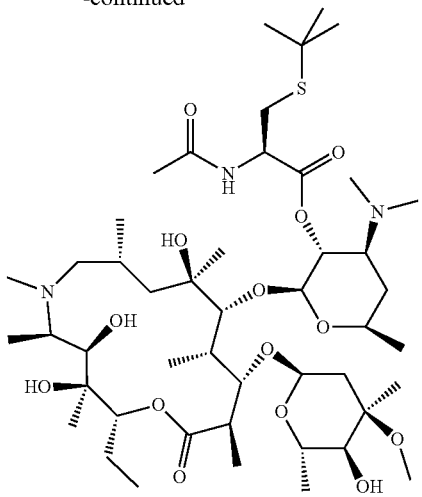

Crude (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl S-(tert-butyl)-L-cysteinate (1.00 g) was dissolved in anhydrous acetone (18 mL). DBU (0.160 mL, 1.10 mmol) was added in one portion and the mixture stirred at r.t. for 10 mins. Acetic anhydride (0.100 mL, 1.10 mmol) was added dropwise over 2 mins. The mixture was stirred at r.t. for 18 h. The solvent was evaporated in vacuo and the residue diluted with EtOAc (25 mL) and sat. NH$_4$Cl$_{(aq)}$ (25 mL). The mixture was stirred at r.t. for 10 minutes and the layers separated. The organic phase was dried (MgSO$_4$), filtered and the solvent evaporated in vacuo. The crude product was purified by flash chromatography (Biotage Isolera four; 50 g Sfar cartridge), eluting with 9:1 isohexane-acetone (1% TEA)→6:4 isohexane-acetone (1% TEA) to yield 2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl N-acetyl-S-(tert-butyl)-L-cysteinate (650 mg, 56%) as a white solid. LCMS (Method A): Rt=1.60 mins; [M+H]+=950.8.

157

Step 4: (2S,3R,4S,6R)-4-(Dimethylamino)-2-(((2R, 3S,4R,5R,8R,10R,11R,12S,13S,14R)-2- ethyl-3,4, 10-trihydroxy-13-(((2R,4R,5S,6S)-5-hydroxy-4-methoxy-4,6-dimethyltetrahydro-2H-pyran-2-yl) oxy)-3,5,6,8,10,12,14-heptamethyl-15-oxo-1-oxa-6-azacyclopentadecan-11-yl)oxy)-6-methyltetrahydro-2H-pyran-3-yl N-acetyl-S-((2-nitrophenyl)thio)-L-cysteinate

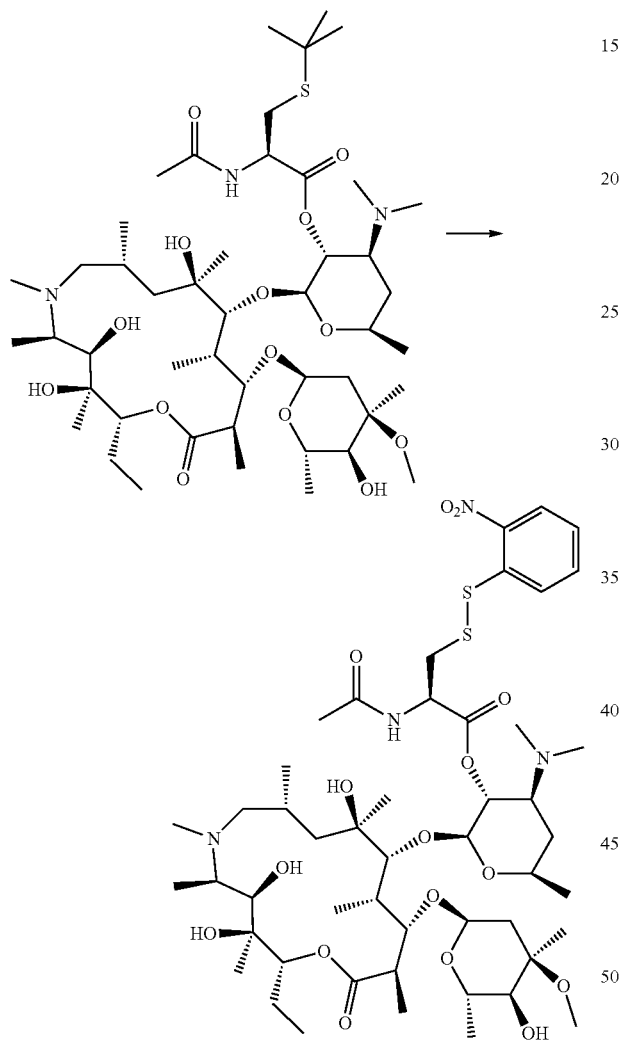

2-Nitrobenzenesulfenyl chloride (40.5 mg, 0.210 mmol) was suspended in anhydrous acetic acid (4.20 mL) and (2S,3R,4S,6R)-4-(dimethylamino)-2-(((2R,3S,4R,5R,8R, 10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl N-acetyl-S-(tert-butyl)-L-cysteinate (200-400 mg, 0.210-0.420 mmol) was added. The mixture was stirred at r.t. for 30 mins. The solvent was evaporated in vacuo to yield crude (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6, 8,10,12,14-heptamethyl-15-oxo-1-oxa-6-azacyclopenta-

158 decan-11-yl)oxy)-6-methyltetrahydro-2H-pyran-3-yl N-acetyl-S-((2-nitrophenyl)thio)-L-cysteinate (180-375 mg) as an orange oil. No purification was attempted. LCMS (Method A): Rt=1.62 mins; [M+H]+=1047.7.

Step 5: (2S,3R,4S,6R)-4-(Dimethylamino)-2-(((2R, 3S,4R,5R,8R,10R,11R,12S,13S,14R)-2- ethyl-3,4, 10-trihydroxy-13-(((2R,4R,5S,6S)-5-hydroxy-4-methoxy-4,6-dimethyltetrahydro-2H-pyran-2-yl) oxy)-3,5,6,8,10,12,14-heptamethyl-15-oxo-1-oxa-6-azacyclopentadecan-11-yl)oxy)-6-methyltetrahydro-2H-pyran-3-yl acetyl-L-cysteinate

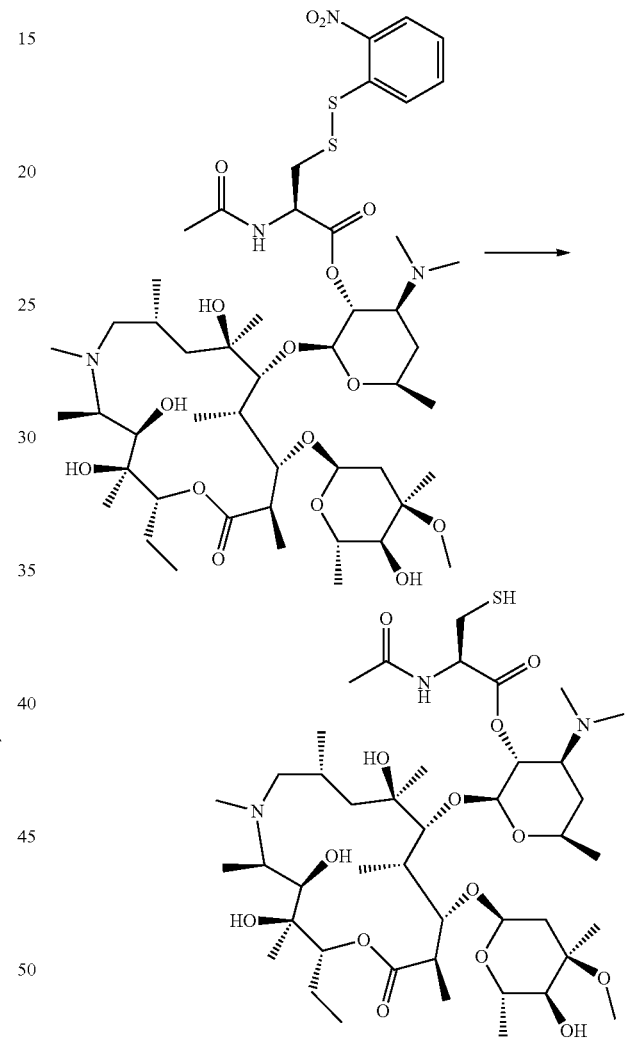

Method 1:

To a solution of thioglycolic acid (10.0 µL, 0.0900 mmol) in acetone (1 mL) was added crude (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3, 5,6,8,10,12,14-heptamethyl-15-oxo-1-oxa-6-azacyclopentadecan-11-yl)oxy)-6-methyltetrahydro-2H-pyran-3-yl N-acetyl-S-((2-nitrophenyl)thio)-L-cysteinate (180 mg, 0.0300 mmol) and DIPEA (10 µL, 0.0573 mmol). The resulting suspension was stirred at r.t. for 1 h. The solvent was evaporated in vacuo. The crude product purified by flash chromatography (Biotage Isolera Four; 10 g SNAP cartridge) eluting with 9:1 isohexane-acetone (1% TEA)→6:4 isohexane-acetone (1% TEA) to yield (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl acetyl-L-cysteinate (5.0 mg, 2%) as a yellow solid. LCMS (Method A): Rt=1.53 mins; [M+H]+=894.7.

Method 2: To a solution of thioglycolic acid (82.0 µL, 1.18 mmol) in anhydrous acetone (10 mL) was added (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl N-acetyl-S-((2-nitrophenyl)thio)-L-cysteinate (375 mg, 0.358 mmol) and TEA (110 µL, 0.789 mmol). The solvent was evaporated in vacuo and the resultant orange oil purified by reversed-phase preparative HPLC. To each fraction containing purified pure target material was immediately added water (10 mL), DCM (10 mL) and potassium acetate (0.300 g) and the layers separated. The organic phases were dried ($Na_2SO_4$), filtered, and the filtrates combined. The solvent was evaporated in vacuo to yield (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl acetyl-L-cysteinate (79 mg, 21%) as a white solid. LCMS (Method A): $R_t$=1.54 min; [M+H]+=894.6.

Chemical Synthesis Example 6

Step 1: ((R)-2-Methyl-3-(tris(4-methoxyphenyl)-14-sulfaneyl)propanoyl)-L-proline Captopril (0.500 g, 2.30 mmol) was dissolved in DCM (8 mL) and 4,4',4''-trimethoxytrityl chloride (0.850 g, 2.30 mmol) added under $N_2$. TEA (0.430 mL, 3.06 mmol) was added dropwise and the solution stirred at r.t. for 1.5 h. Water (5 mL) was added and the layers separated (phase separator). The aqueous phase was diluted with sat. $NH_4Cl_{(aq)}$ (15 mL) and extracted with dichloromethane (15 mL). The combined organics were dried ($MgSO_4$), filtered and the solvent evaporated in vacuo. The crude product was purified by flash chromatography (Biotage Isolera Four; 25 g Sfar cartridge) eluting with DCM→95:5 DCM-MeOH to yield ((R)-2-methyl-3-(tris(4-methoxyphenyl)-14-sulfaneyl)propanoyl)-L-proline (1.03 g, 88%) as an orange solid. LCMS (Method A): Rt=2.95 mins; [M−H]−=548.7.

Step 2: (2S,3R,4S,6R)-4-(Dimethylamino)-2-(((2R, 3S,4R,5R,8R,10R,11R,12S,13S,14R)-2- ethyl-3,4, 10-trihydroxy-13-(((2R,4R,5S,6S)-5-hydroxy-4-methoxy-4,6-dimethyltetrahydro-2H-pyran-2-yl) oxy)-3,5,6,8,10,12,14-heptamethyl-15-oxo-1-oxa-6-azacyclopentadecan-11-yl)oxy)-6-methyltetrahydro-2H-pyran-3-yl ((R)-2-methyl-3-(tris(4-methoxyphenyl)-14-sulfaneyl)propanoyl)-L-prolinate

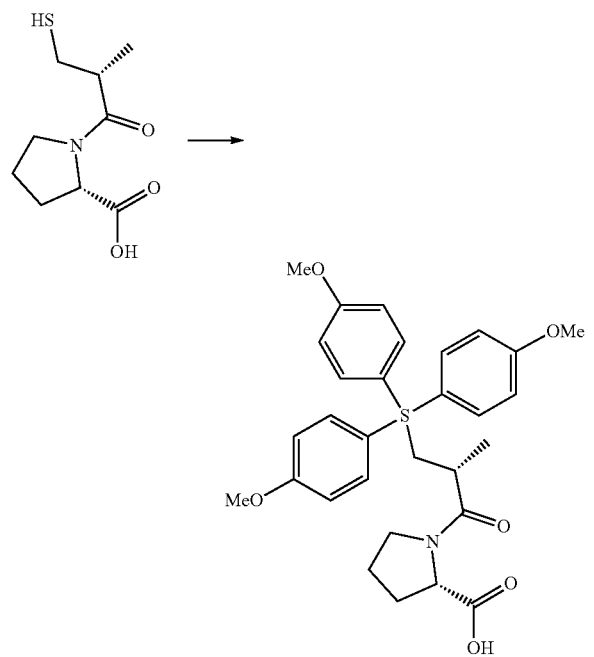

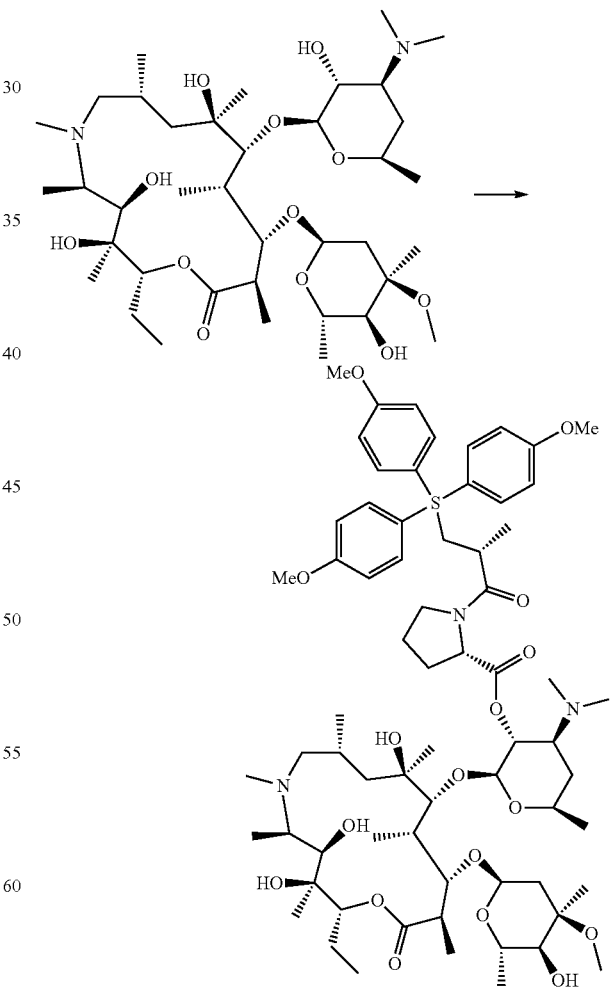

Azithromycin (681 mg, 0.910 mmol), COMU (1.36 g, 3.18 mmol) and DIPEA (0.950 mL, 5.46 mmol) were dissolved in anhydrous DCM (45 mL). ((R)-2-Methyl-3-(tris(4-methoxyphenyl)-14-sulfaneyl)propanoyl)-L-proline (500 mg, 0.910 mmol) was added and the mixture stirred at r.t. for 5 days. The mixture was diluted with DCM (25 mL) and the solution washed with sat. NH4Cl$_{(aq)}$ (2×30 mL). The organic phase was dried (Na$_2$SO$_4$), filtered and the solvent evaporated in vacuo. The crude product was purified by flash chromatography (Biotage Isolera Four; 25 g Sfar cartridge), eluting with 95:5 isohexane-acetone (1% TEA)→60:40 isohexane-acetone (1% TEA), to yield (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl ((R)-2-methyl-3-(tris(4-methoxyphenyl)-14-sulfaneyl)propanoyl)-L-prolinate (960 mg, 60%) as an orange solid. LCMS (Method A): Rt=2.06 mins; [M+H]+=1280.9.

Step 3: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl ((R)-3-mercapto-2-methylpropanoyl)-L-prolinate

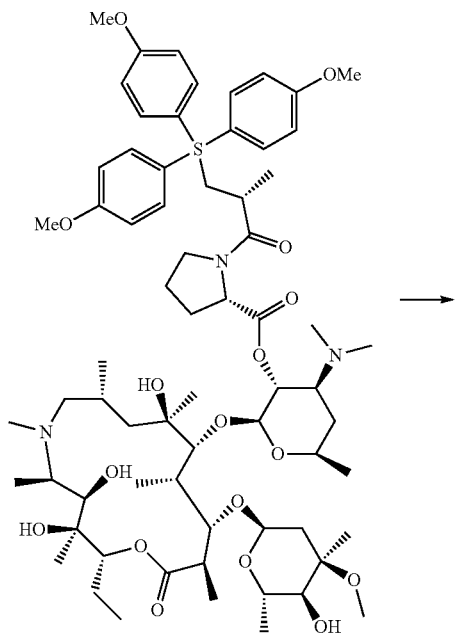

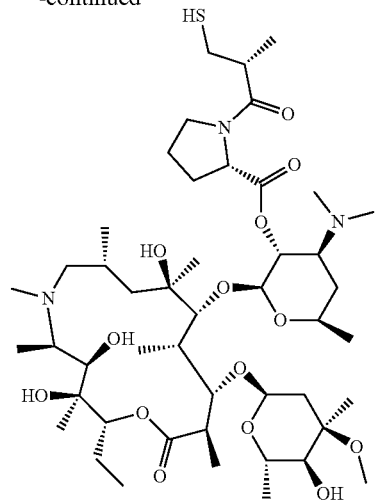

(2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl ((R)-2-methyl-3-(tris(4-methoxyphenyl)-14-sulfaneyl)propanoyl)-L-prolinate (960 mg, 0.570 mmol) and triethylsilane (0.270 mL, 1.71 mmol) were dissolved in anhydrous DCM (25 mL). Chloroacetic acid (3.95 g, 41.8 mmol) was added and the mixture stirred at r.t. for 14 h. The mixture was diluted with DCM (20 mL), water (25 mL) and triethylamine (5 mL) at 0° C. The organic phase was washed with dilute triethylamine in water (25 mL). The organic phase was dried (Na$_2$SO$_4$), filtered and the solvent evaporated in vacuo. The crude product was purified by flash chromatography (Biotage Isolera Four; 25 g SFar cartridge) eluting with 95:5 isohexane-acetone (1% TEA)→60:40 isohexane-acetone (1% TEA), to yield (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl ((R)-3-mercapto-2-methylpropanoyl)-L-prolinate (31 mg, 6%) as a white solid. LCMS (Method A): Rt=2.30 mins; [M+H]+=948.8. $^1$H-NMR (400 MHz, CDCl$_3$) δ 5.06 (d, J=4.8 Hz, 1H), 4.55-4.75 (m, 1H), 4.43 (d, J=7.3 Hz, 1H), 3.95-4.36 (m, 3H), 3.66 (t, J=6.6 Hz, 2H), 3.51 (dd, J=15.3, 6.2 Hz, 1H), 3.28-3.37 (m, 4H), 3.15-3.28 (m, 1H), 3.02 (t, J=10.1 Hz, 1H), 2.53-2.85 (m, 4H), 2.38-2.53 (m, 2H), 2.24-2.38 (m, 9H), 1.40-2.23 (m, 13H), 1.01-1.39 (m, 33H), 0.79-0.95 (m, 9H).

Chemical Synthesis Example 7

[(2S,3R,4S,6R)-4-(Dimethylamino)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-tetrahydropyran-2-yl]oxy-3,5,6,8,10,12,14-heptamethyl-15-oxo-1-oxa-6-azacyclopentadec-11-yl]oxy]-6-methyl-tetrahydropyran-3-yl] (2E,4E,6E,8E)-3,7-dimethyl-9-(2,6,6-trimethylcyclohexen-1-yl)nona-2,4,6,8-tetraenoate

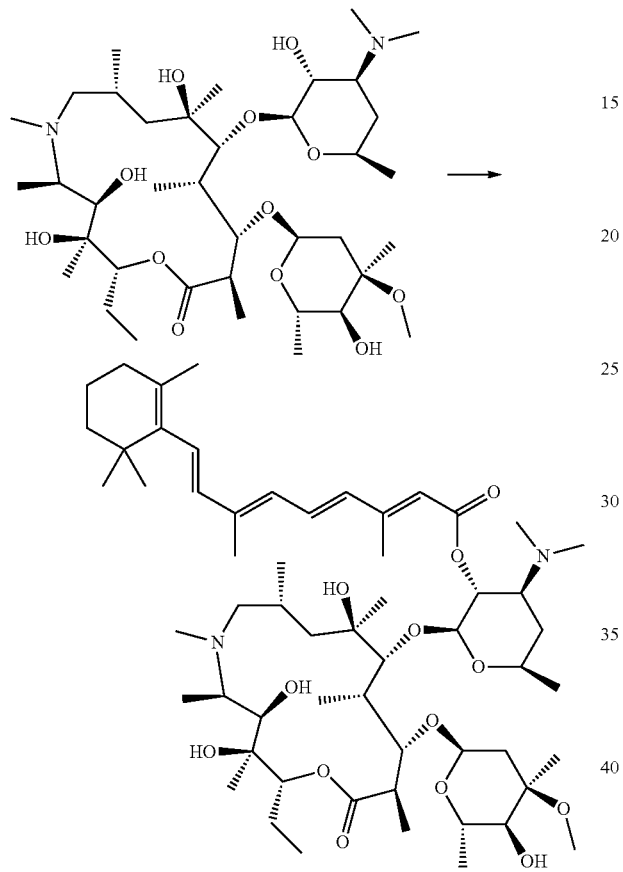

Azithromycin (500 mg, 0.668 mmol), COMU (1.00 g, 2.34 mmol) and DIPEA (0.700 mL, 4.02 mmol) were dissolved in anhydrous DCM (15 mL). Retinoic acid (all trans) (201 mg, 0.668 mmol) was added and the mixture stirred at 30° C. for 20 h. The mixture was diluted with DCM (15 mL) and washed with sat. $NH_4Cl_{(aq)}$ (2×15 mL). The organic phase was dried ($MgSO_4$), filtered and the solvent evaporated in vacuo. The crude product was purified by flash chromatography (Biotage Isolera Four; 25 g Sfar cartridge), eluting with 95:5 isohexane-acetone (1% TEA)→60:40 isohexane-acetone (1% TEA) and further purified by flash chromatography (Biotage Isolera Four; 10 g Sfar cartridge), eluting with 95:5 isohexane-acetone (1% TEA)→70:30 isohexane-acetone (1% TEA) to yield [(2S,3R,4S,6R)-4-(dimethylamino)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-tetrahydropyran-2-yl]oxy-3,5,6,8,10,12,14-heptamethyl-15-oxo-1-oxa-6-azacyclopentadec-11-yl]oxy]-6-methyl-tetrahydropyran-3-yl] (2E,4E,6E,8E)-3,7-dimethyl-9-(2,6,6-trimethylcyclohexen-1-yl)nona-2,4,6,8-tetraenoate (25 mg, 4%) as a yellow solid (25 mg, 4%). LCMS (Method A): Rt=2.30 mins; [M+H]+=1032.0.

Chemical Synthesis Example 8

Step 1: N-Acetyl-S-(pyridin-2-ylthio)-L-cysteine

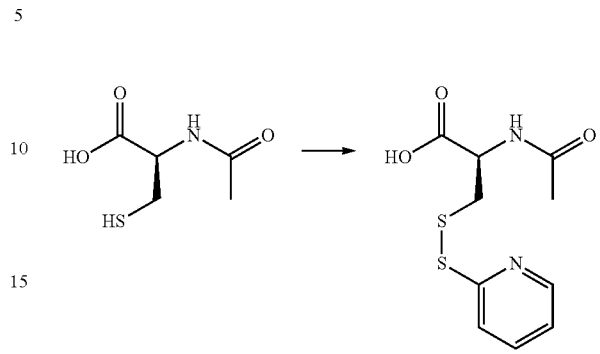

2,2'-Dipyridyl disulfide (1.10 g, 4.90 mmol) and N-acetyl-L-cysteine (400 mg, 2.45 mmol) were dissolved in 1:1 water-MeOH (6.8 mL). The solution was stirred for 16 h at r.t. The solvent was evaporated in vacuo and the crude product purified by flash chromatography eluting with DCM→75:25 DCM-MeOH to yield N-acetyl-S-(pyridin-2-ylthio)-L-cysteine (386 mg, 55%) as a yellow oil. LCMS (Method A): $R_t$=1.60 min; [M+H]+=273.2.

Step 2: S-(((R)-2-Acetamido-3-(((2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-3-oxopropyl)thio)-N-acetyl-L-cysteine

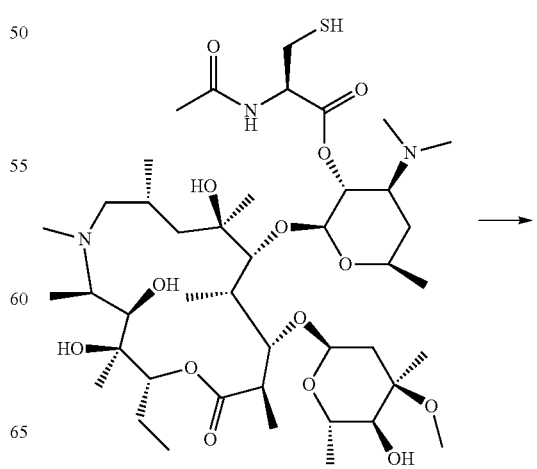

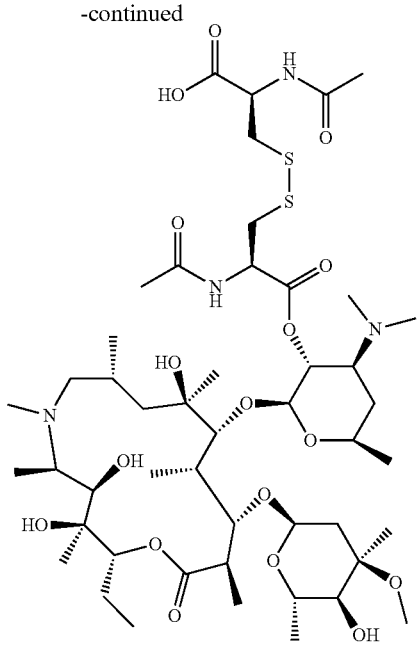

To a solution of N-acetyl-S-(pyridin-2-ylthio)-L-cysteine (15.2 mg, 0.0600 mmol) in chloroform (2 mL) was added TEA (10 mL, 0.060 mmol) and (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl acetyl-L-cysteinate (25.0 mg, 0.030 mmol). The mixture was stirred at r.t. for 1 h. The solvent was evaporated in vacuo and the crude product was purified by reversed-phase preparative HPLC. The fraction containing product was frozen (−78° C.) and the solvent evaporated in vacuo (lyophilisation) to yield S-(((R)-2-acetamido-3-(((2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-3-oxopropyl)thio)-N-acetyl-L-cysteine (10 mg, 34%) as a white solid. LCMS (Method A): $R_t$=2.20 min; $[M+H]^+$=1055.9.

Chemical Synthesis Example 9

Step 1: Ethyl N-acetyl-L-cysteinate

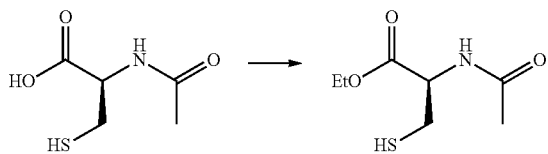

N-Acetyl-L-cysteine (470 mg, 2.88 mmol) was dissolved in ethanol (15 mL) and the reaction mixture degassed with $N_2$ before cooling to 0° C. Thionyl chloride (210 mL, 2.88 mmol) was added dropwise and the reaction mixture warmed to r.t. and stirred at this temperature for 4 h. The solvent was evaporated in vacuo and the mixture diluted with water and EtOAc. The layers were separated, and the aqueous phase extracted with EtOAc (3×10 mL). The combined organics were dried ($MgSO_4$), filtered and the solvent evaporated in vacuo. The crude product was purified by flash chromatography (Biotage Isolera Four, 100 g KPSil column) eluting with 75:25 isohexane-EtOAc→15:85 isohexane-EtOAc to yield ethyl N-acetyl-L-cysteinate as a pale yellow oil, which crystallised upon extended drying (vac. oven) to give a white solid (180 mg, 33%). $^1$H-NMR (400 MHz, $CHCl_3$): δ 6.47 (d, J=5.7 Hz, 1H), 4.79-4.85 (m, 1H), 4.28-4.16 (m, 2H), 2.78-3.22 (m, 2H), 2.03 (s, 3H), 1.36-1.17 (m, 4H).

Step 2: Ethyl N-acetyl-S-(pyridin-2-ylthio)-L-cysteinate

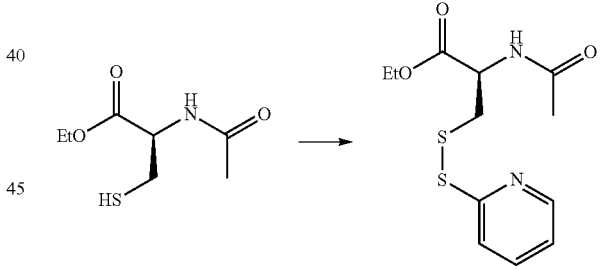

2,2'-Dipyridyl disulfide (1.98 g, 4.90 mmol) and ethyl (2R)-2-acetamido-3-sulfanyl-propanoate (0.195 g, 1.02 mmol) were dissolved in a mixture of 1:1 water-MeOH (6.8 mL). The solution was stirred for 16 h at r.t. The solvent was evaporated in vacuo and the crude product purified by reversed-phase preparative HPLC. Fractions containing product were concentrated under reduced pressure to give ethyl N-acetyl-S-(pyridin-2-ylthio)-L-cysteinate (135 mg, 43%) as a colourless oil. LCMS (Method A): $R_t$=1.96 min; $[M+H]^+$=301.1.

Step 3: (2S,3R,4S,6R)-4-(Dimethylamino)-2-(((2R,3S,4R,5R,8R,10R,11R,12S,13S,14R)-2- ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl S-(((R)-2-acetamido-3-ethoxy-3-oxopropyl)thio)-N-acetyl-L-cysteinate To a solution of ethyl N-acetyl-S-(pyridin-2-ylthio)-L-cysteinate (15.0 mg, 0.050 mmol) in chloroform (2.0 mL) was added TEA (10 mL, 0.060 mmol) and (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl acetyl-L-cysteinate (15.0 mg, 0.0168 mmol). The mixture was stirred at r.t. for 28 h. The solvent was evaporated in vacuo to yield the crude product as a yellow oil, which was purified by reversed-phase preparative HPLC. To each fraction containing desired product was added DCM (10 mL) and potassium acetate (0.50 g). The layers were separated and the combined organics dried (MgSO$_4$), filtered and the solvent evaporated in vacuo to yield (2S,3R,4S,6R)-4-(dimethylamino)-2-(((2R,3S,4R,5R,8R,10R,11R,12S,13S,14R)-2-ethyl-3,4,10- trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl S-(((R)-2-acetamido-3-ethoxy-3-oxopropyl)thio)-N-acetyl-L-cysteinate (3.5 mg, 19%) as a white solid. LCMS (Method A): R$_t$=1.57 min; [M+H]$^+$=1083.9.

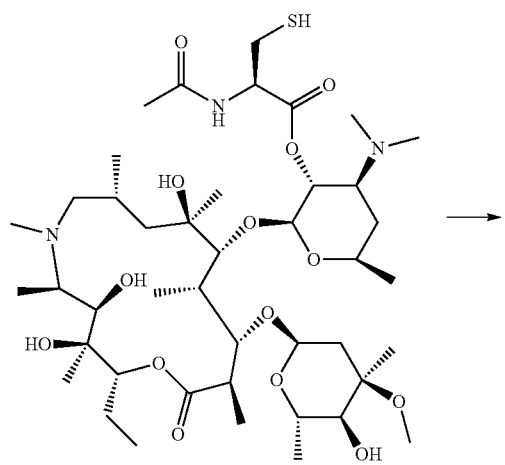

Chemical Synthesis Example 10

(2R,2'R)-3,3'-(((R)-8-(((2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5- hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-8-oxooctane-1,3-diyl)bis(disulfanediyl))bis(2-acetamidopropanoic acid)

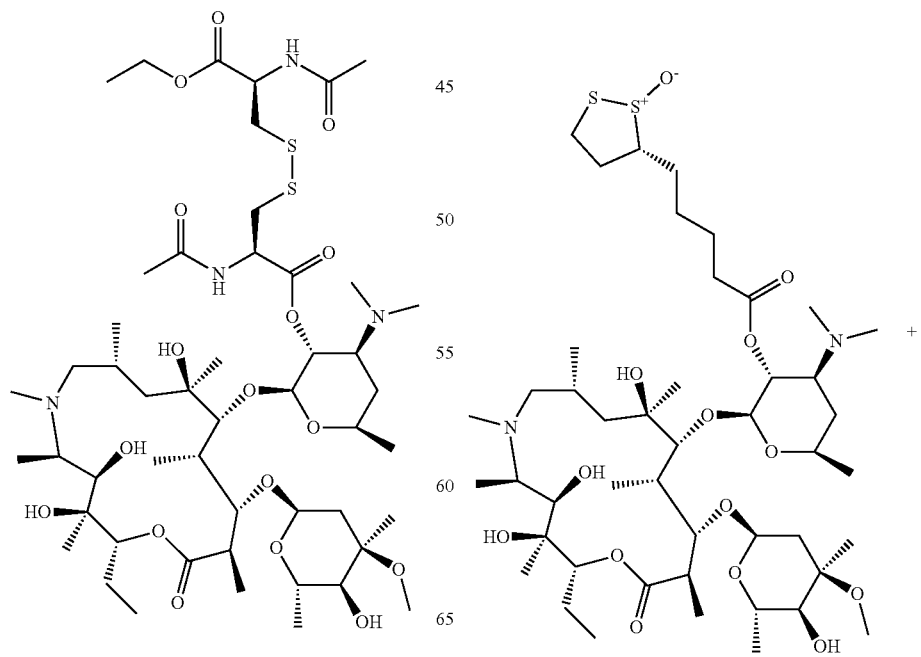

169
-continued

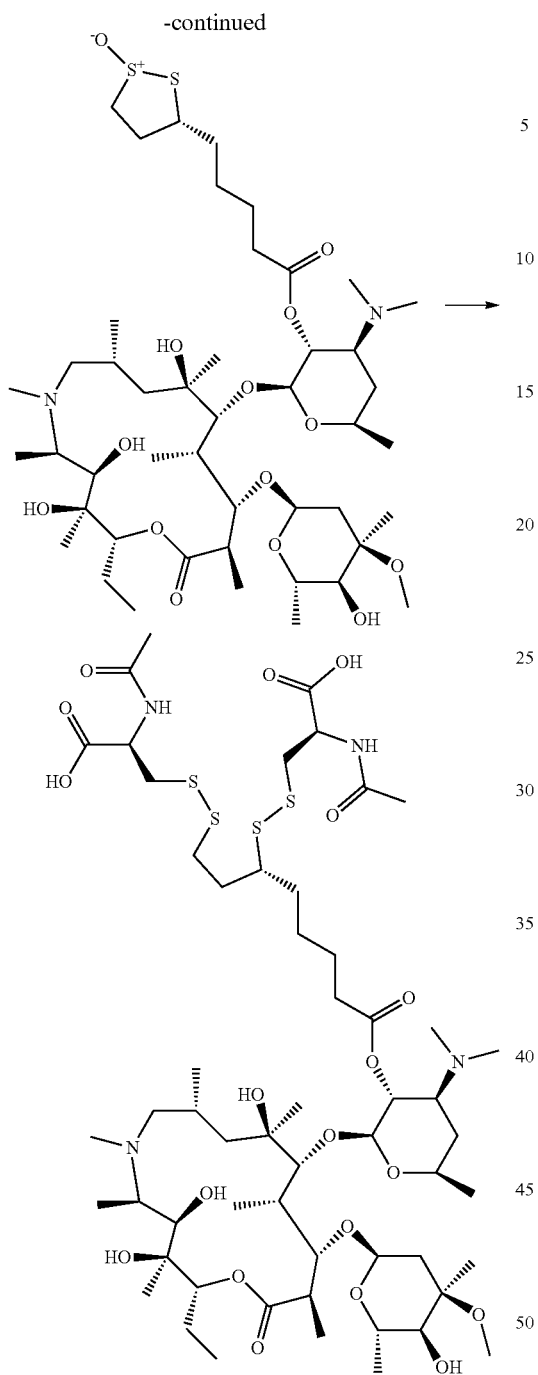

A mixture of (2S,3R,4S,6R)-4-(dimethylamino)-2-(((2R,3S,4R,5R,8R,10R,11R,12S,13S,14R)-2- ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((3R)-2-oxido-1,2-dithiolan-3-yl)pentanoate and (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5- hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((3R)-

170

1-oxido-1,2-dithiolan-3-yl)pentanoate (80.0 mg, 0.0600 mmol) were dissolved in THF (15 mL). N-Acetyl-L-cysteine (41.1 mg, 0.250 mmol) was added and the mixture stirred under $N_2$ at r.t. for 48 h. The solvent was evaporated in vacuo and the crude product purified by reversed-phase preparative HPLC. Fractions containing desired product were combined and the solution passed through a catch release cartridge (Biotage Isolute® NH2; 1 g) washing with MeCN (2 CV). The washings were passed through a second catch release cartridge (Biotage Isolute® NH2; 1 g) washing with MeCN (2 CV). Both cartridges were then eluted with 95:5 MeCN—AcOH (2 CV) and the solutions combined, frozen (−78° C.) and the solvent evaporated in vacuo (lyophilisation) to yield (2'S)-((2R,2'R)-3,3'-(((R)-8-(((2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5- hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-8-oxooctane-1,3-diyl)bis(disulfanediyl))bis(2-acetamidopropanoic acid) (14 mg, 15%) as a white solid. LCMS (Method A): $R_t$=1.66 min; [M+H]$^+$=1262.2.

Chemical Synthesis Example 11

(2'S)-((2R,2'R)-3,3'-(((R)-8-(((2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5- hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-8-oxooctane-1,3-diyl)bis(disulfanediyl))bis(2-methylpropanoyl))di-L-proline

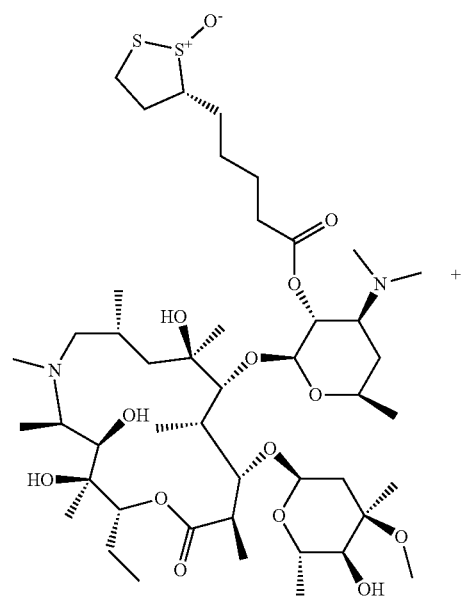

-continued

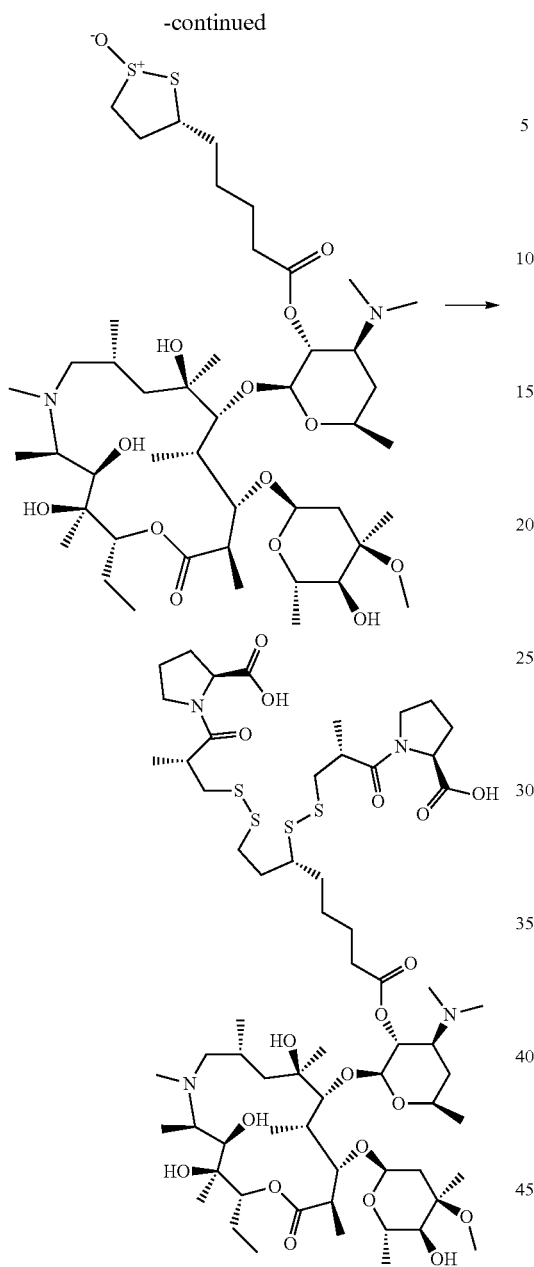

A mixture of (2S,3R,4S,6R)-4-(dimethylamino)-2-(((2R,3S,4R,5R,8R,10R,11R,12S,13S,14R)-2- ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((3R)-2-oxido-1,2-dithiolan-3-yl)pentanoate and (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5- hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((3R)-1-oxido-1,2-dithiolan-3-yl)pentanoate (80.0 mg, 0.0629 mmol)) were dissolved in anhydrous THF (15 mL).

Captopril (82 mg, 0.378 mmol) was added and the mixture stirred at r.t. for two weeks. The solvent was evaporated in vacuo and the crude product purified by reversed-phase preparative HPLC. Fractions containing desired product were combined and the solution passed through a catch release cartridge (Biotage Isolute NH2; 1 g) washing with MeCN (2 CV) and the product eluted with 95:5 MeCN—AcOH (2 CV). The eluent was frozen (−78° C.) and the solvent evaporated in vacuo (lyophilisation) to yield (2'S)-((2R,2'R)-3,3'-(((R)-8-(((2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-8-oxooctane-1,3-diyl)bis(disulfanediyl))bis(2-methylpropanoyl))di-L-proline (15.0 mg, 17%) as a white solid. LCMS (Method A): $R_t$=1.93 min; $[M+H]^+$=1369.8.

Chemical Synthesis Example 12

(2R,2'R)-3,3'-(((R)-8-(((2S,3R,4S,6R)-4-(Dimethyl-amino)-2-(((2R,3S,4R,5R,8R,10R,11R,12S,13S,14R)-2-ethyl-3,4,10-trihydroxy-13-(((2R,4R,5S,6S)-5- hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-8-oxooctane-1,3-diyl)bis(disulfanediyl))bis(2-(2-mercapto-2-methylpropanamido)propanoic acid)

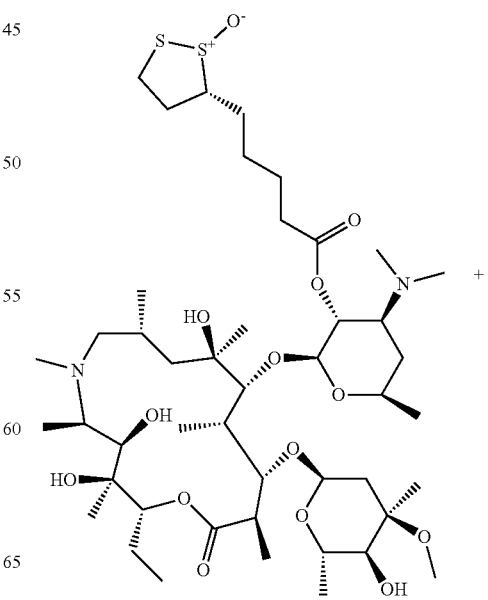

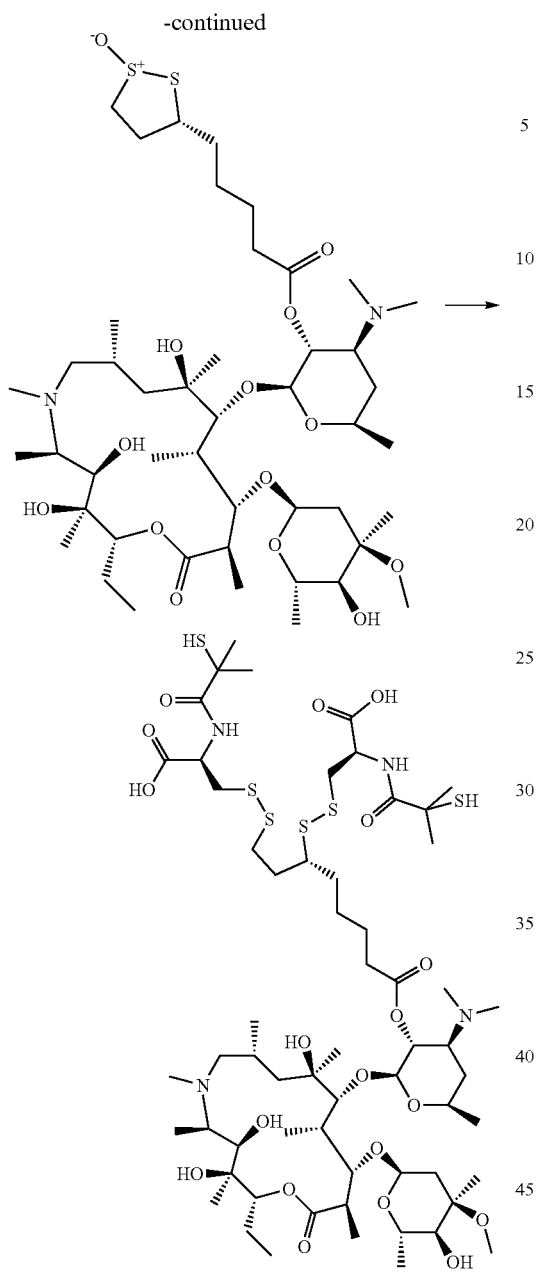

A mixture of (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((3R)-2-oxido-1,2-dithiolan-3-yl)pentanoate and (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((3R)-1-oxido-1,2-dithiolan-3-yl)pentanoate (80.0 mg, 0.0629 mmol) were dissolved in anhydrous THF (15 mL). Bucillamine (70.3 mg, 0.315 mmol) was added and the mixture stirred at r.t. for one week. The solvent was evaporated in vacuo and the crude product purified by reverse-phase preparative HPLC. Fractions containing desired product were combined and the solution passed through a catch release cartridge (Biotage Isolute NH2; 1 g) washing with MeCN (2 CV) and the product eluted with 95:5 MeCN—AcOH (2 CV). The solution was froze (−78° C.) and the solvent evaporated in vacuo (lyophilisation) to yield (2R, 2'R)-3,3'-(((R)-8-(((2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-8-oxooctane-1,3-diyl)bis(disulfanediyl))bis(2-(2-mercapto-2-methylpropanamido)propanoic acid) (5.0 mg, 17%) as a white solid. LCMS (Method F): $R_f$=5.02 min; [(M+H)/2]+=690.7; LCMS (Method A): $R_f$=2.00 min; [M+H]⁺=1379.8.

Chemical Synthesis Example 13

(4S,10R)-10-(5-(((2,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-5-oxopentyl)-7,7-dimethyl-6-oxo-1,2,8,9-tetrathia-5-azacyclododecane-4-carboxylic acid and (4S,12S)-12-(5-(((2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5- hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-5-oxopentyl)-7,7-dimethyl-6-oxo-1,2,8,9-tetrathia-5-azacyclododecane-4-carboxylic acid

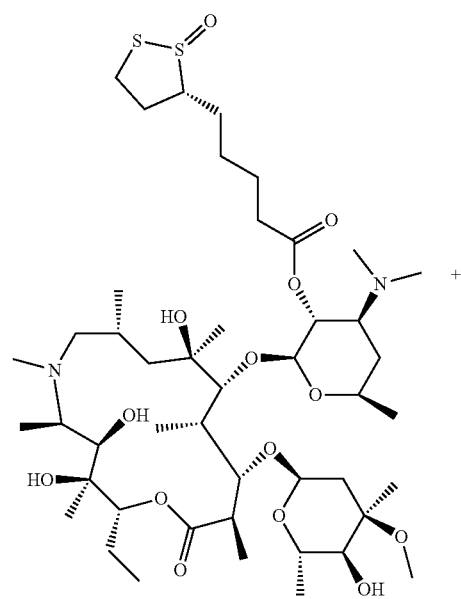

175
-continued

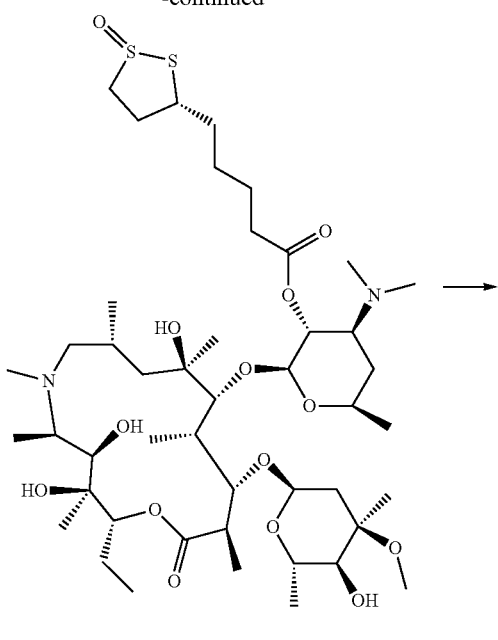

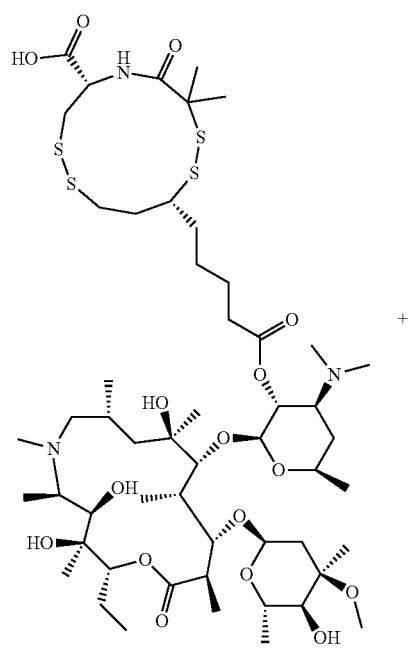

176
-continued

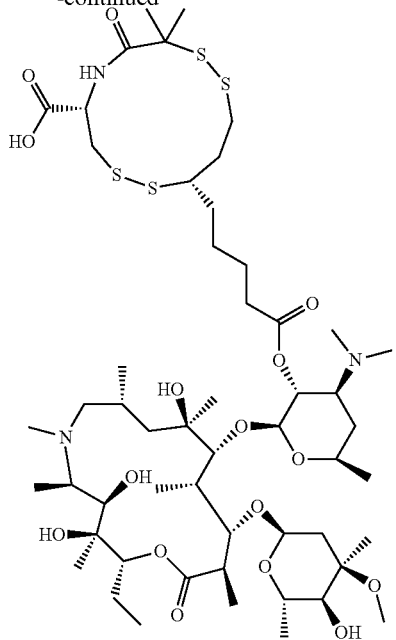

A mixture of (2S,3R,4S,6R)-4-(dimethylamino)-2-(((2R,3S,4R,5R,8R,10R,11R,12S,13S,14R)-2- ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((3R)-2-oxido-1,2-dithiolan-3-yl)pentanoate and (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5- hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((3R)-1-oxido-1,2-dithiolan-3-yl)pentanoate (80.0 mg, 0.0629 mmol) were dissolved in anhydrous THF (15 mL). Bucillamine (70.3 mg, 0.315 mmol) was added and the mixture stirred at r.t. for one week. The solvent was evaporated in vacuo and the crude mixture purified by reverse-phase preparative HPLC. Fractions containing desired product were passed through a catch release cartridge (Biotage Isolute NH2; 1 g) washing with MeCN (2 CV) and the product eluted with 95:5 MeCN—AcOH (2 CV). The solution was frozen (−78° C.) and the solvent evaporated in vacuo (lyophilisation) to yield the title compounds (7.0 mg, 1.5%) as a white solid. LCMS (Method E): $R_t$=4.81 min. $[(M+H)/2]^+$=580.1; LCMS(Method A) $R_t$=1.90 min. $[M+H]^+$=1158.7.

The compounds provided herein (e.g., in Table 1) are prepared according to a similar process as provided for any of the Chemical Synthesis Examples, such as, for example, Chemical Synthesis Example 1 hereinabove, such as, for example, starting from azithromycin dihydrate.

II. Biological Evaluation

Example 1: Rabbit Cornea Homogenate Stability Assay

Determining Rabbit Cornea Homogenate stability of the test compounds is performed using HPLC-MS. The assay is performed at two concentrations of Rabbit Cornea Homogenate (0.15 mg/ml and 0.45 mg/ml total protein) so that any hydrolysis observed can be assigned as esterase dependent or not.

Rabbit Cornea Homogenisation

Five rabbit corneas (e.g. New Zealand Whites) of approx. 50 mg each are sliced and scraped with a scalpel and tweezers until reduced to small (1-3 mm), thin pieces. These are transferred into a tared vial and accurately weighed, then diluted with 10 volumes aqueous PBS pH 7.4.

Sample is cooled intermittently on ice and shear homogenized for 3 minutes, then centrifuged for 3 min at 3000 rpm. The supernatant is pipetted off into a vial, and total protein concentration determined at 280 nm. Sample was stored at −78° C.

Rabbit Cornea Esterase Assay

Preparation of stock solutions:

10 mM Compound stocks are diluted to 100 µM in a 96 deep-well plate: 10 µl of 10 mM Compound stock is added to 990 µl 50 mM HEPES, pH7.5 buffer. Compounds are further diluted to 10 µM: 100 µl of 100 µM compound is added to 900 µl 50 mM HEPES, pH7.5 buffer. Esterase homogenate is diluted to 300 ng/µl and 900 ng/µl.

Assay Conditions:

A heater shaker is set to 37° C. Into a suitable 96 well plate (Run Plate), 75 µl of 300 or 900 ng/µl esterase homogenate is pipetted into each of the required wells (2 min, 5 min, 10 min, 20 min and 45 min). The plate is sealed and then warmed at 37° C. for 5 min.

Another 96 well PCR plate is put on ice (Kill Plate). To this is added 100 µl of MeCN to each well, labelled 0 min 2 min, 5 min, 10 min, 20 min and 45 min. The plate is covered to minimize evaporation.

For the T=0 sample only, to the 100 µl cold MeCN stop solution is added 50 µl of 300 or 900 ng/µl esterase homogenate followed by 50 µl of 10 µM compound solution. For the remaining timepoints, 75 µl of 10 µM compound solution is added to the Run Plate starting from T=45 min row and ending with T=2 min row. At the appropriate time point, 100 µl of the assay mixture is added to the matching kill plate well containing 100 µl of cold MeCN. Samples are analysed as soon as practicable by LCMS (Waters Xevo TQ-S or Micromass Ultima).

Parent conjugate and parent concentrations are determined against appropriate standard response curves and the half-life (T½) of the parent conjugate is calculated using the peak area of the parent conjugate at each time point in the linear region of the log-linear plot.

Example 2: Aqueous Hydrolysis Stability Assay

Determination of aqueous stability of the test compounds is performed using HPLC-MS. A test compound 10 mM stock solution is prepared in DMSO. 10 µl of the DMSO stock solution is dissolved in 990 µl of 50 mM HEPES pH 7.5 buffer or 1:1 (v/v) of Acetonitrile:Water to make a 100 µM solution. Final DMSO concentration is 1%. The solution is kept at room temperature and injected without delay into the LCMS (Waters Xevo TQ-S or Micromass Ultima). Additional injections are performed at appropriate time points.

Half-life ($T_{1/2}$) of the parent conjugate is calculated using the peak area of the parent conjugate at each time point in the linear region of the log-linear plot.

TABLE 2

| Comp | Hydrolytic % Azithromycin formation at [time] | Hydrolytic % keratolytic agent formation at [time] |
|---|---|---|
| 39 | C [25 min] | — |
| 6, 7, 8, and 9 | C [60 min] | C |
| 5 | A [82 min] | — |

A: percent active pharmaceutical ingredient (API) formation <15%;
B: percent API formation 15-30%;
C: percent API formation >30%.

Example 3: Aqueous Hydrolysis Stability Assay

Compounds with Slow Hydrolysis Rate

Determination of aqueous stability of the test compounds was performed using UPLC-MS. A test compound 10 mM stock solution was prepared in dry DMSO or DMF. 10 µL of the DMSO or DMF stock solution was dissolved in 990 µL of DPBS pH 7.4 buffer to make a 100 µM solution. This solution was used "as is" or immediately diluted further with DPBS to 25 µM. Final DMSO concentration was 1%. The solution was immediately placed in an autosampler maintained at 37° C. and injected without delay into the UPLCMS (Waters Xevo TQ-S or G2-XS). Additional injections were performed at appropriate time points. Half-life of the parent compound was determined from the MS response.

Compounds with Fast (<5 Minutes) Hydrolysis Rate

Determination of aqueous stability of the test compounds was performed using UPLC-MS. A test compound 10 mM stock solution was prepared in dry DMSO or DMF. 50 µL of the DMSO or DMF stock solution was further diluted with 150 µL of dry DMSO or DMF (as appropriate) to 2.5 mM. 10 µL of the 2.5 mM DMSO or DMF stock solution was dissolved in 990 µL of DPBS pH 7.4 buffer to make a 25 µM solution. Final DMSO concentration was 1%. The solution was immediately placed in an autosampler maintained at 37° C. and injected without delay into the UPLCMS (Waters Xevo TQ-S or G2-XS). Additional injections were performed at appropriate time points. Half-life of the parent compound was determined from the MS response.

TABLE 3

| Comp | Hydrolytic % Azithromycin formation at 45 Min | Aq $T_{1/2}$ (min) |
|---|---|---|
| 51 | C | 53.7 |
| 6, 7, 8, and 9 | C | 29.6 |
| 5 | C | 9.4 |
| 44 | C | <5 |
| 45 | C | <5 |
| 46 | B | 51.5 |
| 47 | C | 90.1 |
| 33 | C | 61.5 |
| 31 | A | >120 |
| 39 | C | <5 |

A: percent active pharmaceutical ingredient (API) formation <15%;
B: percent API formation 15-30%;
C: percent API formation >30%.

Example 4: Mouse Model of Experimental Dry Eye Disease

Female C57BL/6 mice (6-8 weeks old) or female HEL BCR Tg mice (6-8 weeks old) are commercially obtained. Experimental dry eye is induced as described by Niederkorn, et al. (J. Immunol. 2006, 176:3950-3957) and Dursun et al. (Invest. Ophthalmol. Vis. Sci. 2002, 43:632-638). In brief, mice are exposed to desiccating stress in perforated cages with constant airflow from fans positioned on both sides and room humidity maintained at 30% to 35%. Injection of scopolamine hydrobromide (0.5 mg/0.2 mL; Sigma-Aldrich, St. Louis, Mo.) is administered subcutaneously, three times a day (8:00 AM, 12:00 noon, and 5:00 PM), on alternating hind-flanks to augment disease. Mice are exposed to desiccating stress for 3 weeks. Untreated control mice are maintained in a nonstressed environment at 50% to 75% relative humidity without exposure to forced air. Test animals are exposed to test compound and subsequently tear samples are obtained to determine stability of test compounds, and tissue samples are taken to determine presence of pro-inflammatory biomarkers.

III. Preparation of Pharmaceutical Dosage Forms

Example 1: Solution for Topical Ophthalmic Use

The active ingredient is a compound of Table 1, or a pharmaceutically acceptable salt thereof, and is formulated as a solution with a concentration of from 0.1-1.5% w/v.

We claim:

1. A compound having a structure represented by Formula (Ia):

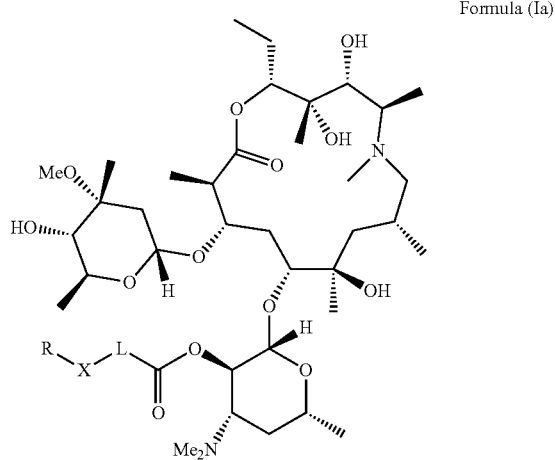

Formula (Ia)

or a pharmaceutically acceptable salt or solvate thereof, wherein,

L is bond, —(C=O)(OCR$^8$R$^9$)$_z$—, or —(C=O)(OCR$^8$R$^9$)$_z$O—;

each R$^8$ and R$^9$ is independently H, halogen, C$_1$-C$_3$-alkyl, C$_1$-C$_3$-haloalkyl, C$_1$-C$_3$-alkoxy, C$_3$-C$_5$-cycloalkyl, or R$^8$ and R$^9$ are taken together with the atoms to which they are attached to form a C$_3$-C$_5$-cycloalkyl;

z is 1-6;

X is absent or —O—; and

R is substituted alkyl, substituted heteroalkyl, or substituted heterocyclyl, the substituted alkyl being:

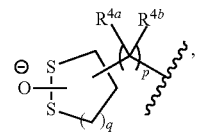

each R$^{4a}$ and R$^{4b}$ is independently H, halogen, or substituted or unsubstituted alkyl;

p is an integer from 1-10; and q is an integer from 1-3; and the substituted heteroalkyl being substituted with —COOH, —CH$_2$SH, and/or optionally substituted N-attached heterocyclyl, and being further substituted with one or more other substituent, each substituent being independently selected from the group consisting of acetamide, amino, C$_1$-C$_6$ alkyl, thiol, and oxo.

2. The compound of claim 1, wherein R is substituted heteroalkyl comprising two disulfide bonds within the heteroalkyl chain, the heteroalkyl being substituted with —COOH or substituted N-attached heterocyclyl, and being further substituted with one or more other substituent, each substituent being independently selected from the group consisting of acetamide and C$_1$-C$_6$ alkyl.

3. The compound of claim 1, wherein R is substituted heteroalkyl comprising one disulfide bond within the heteroalkyl chain, the heteroalkyl being substituted with acetamide, —COOH, and —SH.

4. The compound of claim 1, wherein R is heterocyclyl N-substituted with alkyl, the alkyl being further substituted with oxo and/or thiol.

5. The compound of claim 1, wherein q is 1 and p is an integer from 3-5.

6. The compound of claim 1, wherein each R$^{4a}$ and R$^{4b}$ is H.

7. The compound of claim 1, wherein R is:

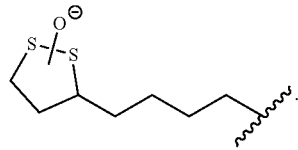

8. The compound of claim 1, wherein R is substituted heteroalkyl being substituted with —COOH, being further substituted with amino or acetamide, and having a structure represented by:

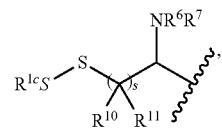

wherein:

R$^{1c}$ is:

substituted alkyl or substituted heteroalkyl, the alkyl being substituted with one or more alkyl substituent, each alkyl substituent being independently selected from the group consisting of carboxylic acid, —SH, thioalkyl, acetamide, amino, oxo, and optionally substituted heterocyclyl, and the heteroalkyl being substituted with one or more heteroalkyl substituent, each heteroalkyl substituent being independently selected from the group consisting of oxo, carboxylic acid, amino, thioalkyl, thiol, acetamide, and $C_1$-$C_3$ alkyl;

the substituted alkyl of $R^{1c}$ being substituted with the —COOH, or the substituted heteroalkyl of $R^{1c}$ being substituted with the —COOH:

$R^6$ and $R^7$ are each independently H, substituted or unsubstituted alkyl, or substituted or unsubstituted heteroalkyl;

each $R^{10}$ and $R^{11}$ is independently H, halogen, $C_1$-$C_3$-alkyl, $C_1$-$C_3$-haloalkyl, $C_1$-$C_3$-alkoxy, $C_3$-$C_5$-cycloalkyl, or two of $R^{10}$ and $R^{11}$ are taken together with the atoms to which they are attached to form a $C_3$-$C_5$-cycloalkyl; and s is an integer from 1-10.

9. The compound of claim 8, wherein $R^6$, $R^7$, $R^{10}$ and $R^{11}$ are each H, and s is 1-3.

10. The compound of claim 8, wherein $R^{1c}$ is heteroalkyl substituted with carboxylic acid.

11. The compound of claim 8, wherein $R^{1c}$ is alkyl substituted with carboxylic acid.

12. The compound of claim 8, wherein —S$R^{1c}$ is:

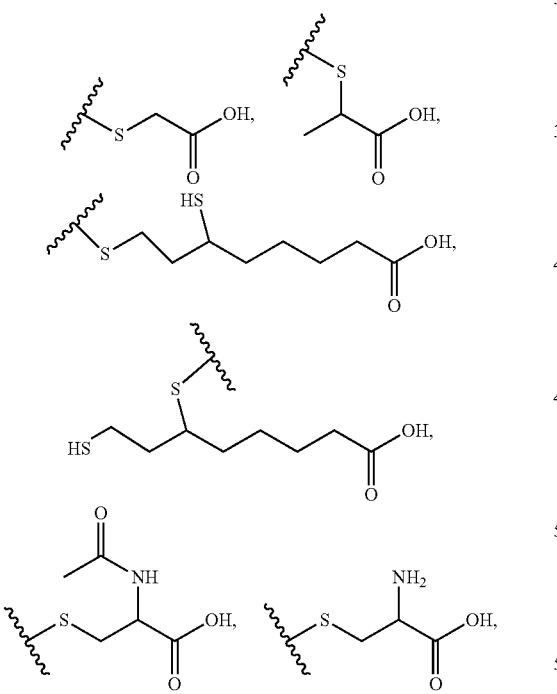

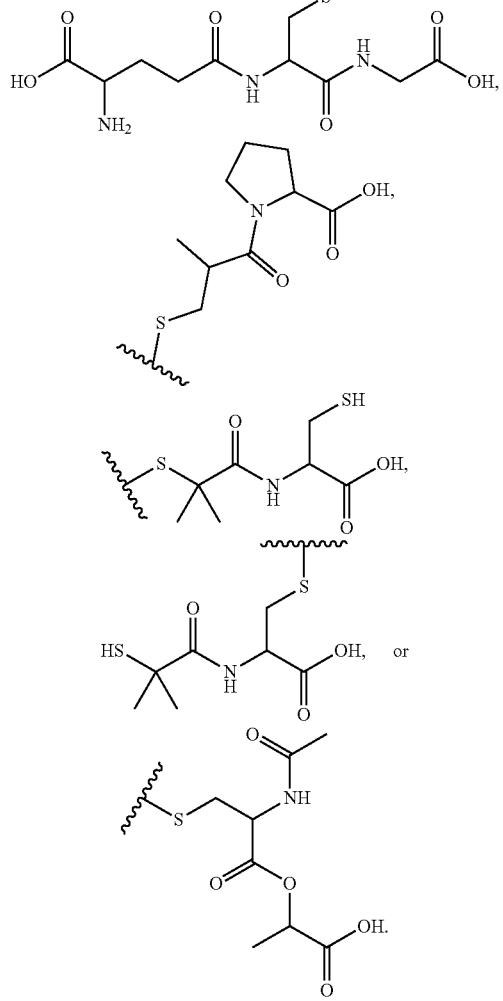

13. A pharmaceutical composition comprising a compound of claim 1, or a pharmaceutically acceptable salt thereof, and at least one pharmaceutically acceptable excipient.

14. The pharmaceutical composition of claim 13, wherein the pharmaceutical composition is suitable for topical ophthalmic administration.

15. A method of treating a dermal or an ocular disease or disorder in an individual, comprising administering to the individual a compound of claim 1.

16. The method of claim 15, wherein the dermal or the ocular disease or disorder is associated with keratosis, microbial infiltration, microbial infection, inflammation, or any combination thereof.

* * * * *